US010039821B2

(12) United States Patent
Burgard et al.

(10) Patent No.: US 10,039,821 B2
(45) Date of Patent: Aug. 7, 2018

(54) EUROPEAN PRRSV STRAIN

(71) Applicant: Boehringer Ingelheim Vetmedica GmbH, Ingelheim am Rhein (DE)

(72) Inventors: Kim Burgard, Wadgassen (DE); Jeremy Kroll, Urbandale, IA (US); Sarah M. Layton, Newton, IA (US); Volker Ohlinger, Havixbeck (DE); Francois-Xavier Orveillon, Mainz (DE); Stefan Pesch, Munster (DE); Michael Dennis Piontkowski, Perry, KS (US); Michael B. Roof, Ames, IA (US); Philip Utley, Slater, IA (US); Eric Martin Vaughn, Ames, IA (US)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 15/358,288

(22) Filed: Nov. 22, 2016

(65) Prior Publication Data

US 2017/0065709 A1 Mar. 9, 2017

Related U.S. Application Data

(62) Division of application No. 14/281,287, filed on May 19, 2014, now Pat. No. 9,534,207, which is a division of application No. 13/396,298, filed on Feb. 14, 2012, now Pat. No. 8,765,142.

(60) Provisional application No. 61/444,074, filed on Feb. 17, 2011.

(51) Int. Cl.
*A61K 39/12* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/5254* (2013.01); *A61K 2039/53* (2013.01); *A61K 2039/552* (2013.01); *A61K 2039/575* (2013.01); *C12N 2770/10021* (2013.01); *C12N 2770/10034* (2013.01); *C12N 2770/10064* (2013.01); *C12N 2770/10071* (2013.01)

(58) Field of Classification Search
CPC ............ C12N 7/00; C12N 2770/10034; C12N 2770/10031; C12N 2750/14321; C12N 2750/14322; C12N 2770/32034; A61K 39/12; A61K 2039/552; A61K 2039/53; A61K 39/23; A61K 2039/5252; A61K 39/0208; C07K 16/10; G01N 2333/015
See application file for complete search history.

(56) References Cited

U.S. PATENT DOCUMENTS

| | | | |
|---|---|---|---|
| 5,476,778 A | 12/1995 | Chladek et al. |
| 5,597,721 A | 1/1997 | Brun et al. |
| 5,620,691 A | 4/1997 | Wensvoort et al. |
| 5,674,500 A | 10/1997 | Peeters et al. |
| 5,677,429 A | 10/1997 | Benfield |
| 5,683,865 A | 11/1997 | Collins et al. |
| 5,698,203 A | 12/1997 | Visser et al. |
| 5,840,563 A | 11/1998 | Chladek et al. |
| 5,846,805 A | 12/1998 | Collins et al. |
| 5,858,729 A | 1/1999 | Van Woensel et al. |
| 5,866,401 A | 2/1999 | Hesse |
| 5,925,359 A | 7/1999 | Van Woensel et al. |
| 5,976,537 A | 11/1999 | Mengeling et al. |
| 5,989,563 A | 11/1999 | Chladek et al. |
| 5,998,601 A | 12/1999 | Murtaugh et al. |
| 6,001,370 A | 12/1999 | Burch et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,197,310 B1 | 3/2001 | Wensvoort et al. |
| 6,241,990 B1 | 6/2001 | Collins et al. |
| 6,268,199 B1 | 7/2001 | Meulenberg et al. |
| 6,455,245 B1 | 9/2002 | Wensvoort et al. |
| 6,498,008 B2 | 12/2002 | Collins et al. |
| 6,641,819 B2 | 11/2003 | Mengeling et al. |
| 6,660,513 B2 | 12/2003 | Mengeling et al. |
| 6,806,086 B2 | 10/2004 | Wensvoort et al. |
| 6,855,315 B2 | 2/2005 | Collins et al. |
| 6,982,160 B2 | 1/2006 | Collins et al. |
| 7,081,342 B2 | 7/2006 | Mengeling et al. |
| 7,122,347 B2 | 10/2006 | Verheije et al. |
| 7,132,106 B2 | 11/2006 | Calvert et al. |
| 7,232,680 B2 | 6/2007 | Calvert et al. |
| 7,264,804 B2 | 9/2007 | Collins et al. |
| 7,312,030 B2 | 12/2007 | van Rijn et al. |
| 7,335,473 B2 | 2/2008 | Wensvoort et al. |
| 7,368,117 B2 | 5/2008 | Fetzer et al. |
| 7,618,797 B2 | 11/2009 | Calvert et al. |
| 7,632,636 B2 | 12/2009 | Roof et al. |
| 7,691,389 B2 | 4/2010 | Calvert et al. |
| 7,722,878 B2 | 5/2010 | Vaughn et al. |
| 7,897,343 B2 | 3/2011 | Wensvoort et al. |
| 8,110,390 B2 | 2/2012 | Faaberg et al. |

(Continued)

FOREIGN PATENT DOCUMENTS

| | | |
|---|---|---|
| CA | 2103460 A1 | 12/1992 |
| EP | 587780 A1 | 3/1994 |

(Continued)

OTHER PUBLICATIONS

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

(Continued)

*Primary Examiner* — Bao Li
(74) *Attorney, Agent, or Firm* — Judy Jarecki-Black

(57) ABSTRACT

The present invention is related to improved modified live PRRS vaccines containing new PRRSV European strains of PRRSV and methods of use and manufacture of such vaccines.

5 Claims, 9 Drawing Sheets

(56) References Cited

U.S. PATENT DOCUMENTS

| | | |
|---|---|---|
| 2002/0012670 A1 | 1/2002 | Elbers et al. |
| 2002/0098573 A1 | 7/2002 | Meulenberg et al. |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |
| 2003/0157689 A1 | 8/2003 | Calvert et al. |
| 2003/0219732 A1 | 11/2003 | van Rijn et al. |
| 2004/0009190 A1 | 1/2004 | Elbers et al. |
| 2004/0132014 A1 | 7/2004 | Wensvoort et al. |
| 2004/0197872 A1 | 10/2004 | Meulenberg et al. |
| 2004/0224327 A1 | 11/2004 | Meulenberg et al. |
| 2004/0253270 A1 | 12/2004 | Meng et al. |
| 2006/0063151 A1 | 3/2006 | Roof et al. |
| 2006/0205033 A1 | 9/2006 | Meulenberg et al. |
| 2006/0240041 A1 | 10/2006 | Meulenberg et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0129398 A1 | 5/2010 | Klinge et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |
| 2012/0189655 A1 | 7/2012 | Wu et al. |
| 2012/0213741 A1 | 8/2012 | Berry et al. |
| 2012/0213810 A1 | 8/2012 | Burgard et al. |
| 2014/0271698 A1 | 9/2014 | Jordan et al. |
| 2014/0314808 A1 | 10/2014 | Fetzer et al. |
| 2015/0276737 A1 | 10/2015 | Collins et al. |

FOREIGN PATENT DOCUMENTS

| | | |
|---|---|---|
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| GB | 2282811 A | 4/1995 |
| GB | 2289279 A | 11/1995 |
| WO | 199221375 A1 | 12/1992 |
| WO | 199307898 A1 | 4/1993 |
| WO | 199314196 A1 | 7/1993 |
| WO | 1996036356 A1 | 11/1996 |
| WO | 1998018933 A1 | 5/1998 |
| WO | 199850426 A1 | 11/1998 |
| WO | 199855626 A2 | 12/1998 |
| WO | 2000053787 A1 | 9/2000 |
| WO | 200159077 A1 | 8/2001 |
| WO | 200190363 A1 | 11/2001 |
| WO | 2002095040 A1 | 11/2002 |
| WO | 2006002193 A2 | 1/2006 |
| WO | 2006034319 A2 | 3/2006 |
| WO | 2006074986 A2 | 7/2006 |
| WO | 2007002321 A2 | 1/2007 |
| WO | 2008121958 A1 | 10/2008 |
| WO | 2010025109 A1 | 3/2010 |
| WO | 20110128415 A1 | 10/2011 |
| WO | 2012110489 A2 | 8/2012 |
| WO | 2014150822 A2 | 9/2014 |
| WO | 2015092058 A1 | 6/2015 |

OTHER PUBLICATIONS

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.

Murtaugh et al., "Comparison of the structural protein coding sequences of the VR-2332 and Lelystad virus strains of the PRRS virus". Archives of Virology, vol. 140, No. 8, 1995, pp. 1451-1460.

Murtaugh et al., "Genetic Variation in the PRRS Virus". Coronaviruses and Arteriviruses, Plenum Press, New York, 1998, pp. 787-794.

Murtaugh et al., "Immunological Responses of Swine to Porcine Reproductive and Respiratory Syndrome Virus Infection". Viral Immunology, vol. 15, No. 4, 2002, pp. 533-547.

Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.

Nam et al. "Complete genomic characterization of a European type 1 porcine reproductive and respiratory syndrome virus isolate in Korea". Archives of Virology, vol. 154, No. 4, 2009, pp. 629-638.

NCBI: Accession No. AF046869. "Porcine reproductive and respiratory syndrome virus isolate 16244B, Feb. 18, 1997 (Nebraska) pass.3, complete genome." Mar. 17, 1999.

NCBI: Accession No. AF066183. "Porcine reproductive and respiratory syndrome virus RespPRRS MLV, complete genome." Feb. 22, 2001.

NCBI: Accession No. AF159149. "Porcine reproductive and respiratory syndrome virus isolate MLV RespPRRS/Repro, complete genome." Aug. 28, 2000.

NCBI: Accession No. AF176348. "Porcine reproductive and respiratory syndrome virus isolate PA8 complete genome." Sep. 3, 2002.

NCBI: Accession No. AF184212. "Porcine reproductive and respiratory syndrome virus strain SP, complete genome." Sep. 28, 2000.

NCBI: Accession No. AF325691. "Porcine reproductive and respiratory syndrome virus isolate NVSL 977985 IA 1-4-2, complete genome." Feb. 11, 2001.

NCBI: Accession No. AF331831. "Porcine reproductive and respiratory syndrome virus BJ-4, complete genome." Jan. 15, 2001.

(56) References Cited

OTHER PUBLICATIONS

NCBI: Accession No. B4ZWR2. "Porcine reproductive and respiratory syndrome virus (PRRSV)." May 2008, 1 page.
NCBI: Accession No. M96262.2. "Lelystad virus, complete genome." Nov. 8, 2000.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. U87392 AF030244 000153. "Porcine reproductive and respiratory syndrome virus strain VR-2332, complete genome." Nov. 17, 2000.
Nielsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Pesch et al., "New insights into the genetic diversity of European porcine reproductive and respiratory syndrome virus (PRRSV)". Veterinary Microbiology, vol. 107, 2005, pp. 31-48.
Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.
Porcine Reproductive and Respiratory Syndrome: A Report on the Seminar Held in Brussels on Nov. 4-5, 1991 and Organized by the European Commission, pp. 1-74.
Prieto et al., "Similarity of European porcine reproductive and respiratory syndrome virus strains to vaccine strain is not necessarily predictive of the degree of protective immunity conferred". The Veterinary Journal, vol. 175, No. 3, Mar. 2008, pp. 356-363.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.
Sun et al., "Crystal Structure of Porcine Reproductive and Respiratory Syndrome Virus Leader Protease Nsp1αÑ". Journal of Virology, vol. 83, No. 21, Nov. 2009, pp. 10931-10940.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Verheije et al., "Safety and protective efficacy of porcine reproductive and respiratory syndrome recombinant virus vaccines in young pigs". Vaccine, vol. 21, 2003, pp. 2556-2563.

Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
"Dutch Team Isolates Mystery Pig Disease Agent", Animal Pharm, vol. 230, Abstract No. 00278268, Jun. 21, 1991, p. 21.
Albina et al., "Immune responses in pigs infected with porcine reproductive and respiratory syndrome virus (PRRSV)". Veterinary Immunology and Immunopathology, vol. 61, 1998, pp. 49-66.
Allende et al., "Mutations in the genome of porcine reproductive and respiratory syndrome virus responsible for the attenuated phenotype". Archives of Virology, vol. 145, No. 6, Jun. 2000, pp. 1149-1161.
Allende et al., "North American and European porcine reproductive and respiratory syndrome viruses differ in non-structural protein coding regions". Journal of General Virology, vol. 80, 1999, pp. 307-315.
Allende et al., "Porcine Reproductive and Respiratory Syndrome Virus: Description of Persistence in Individual Pigs upon Experimental Infection†". Journal of Virology, vol. 74, No. 22, Nov. 2000, pp. 10834-10837.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Ansari et al., "Influence of N-Linked Glycosylation of Porcine Reproductive and Respiratory Syndrome Virus GP5 on Virus Infectivity, Antigenicity, and Ability to Induce Neutralizing Antibodies." Journal of Virology, vol. 80, No. 8, Apr. 2006, pp. 3994-4004.
Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 1, No. 4, Jul./Aug. 1992, pp. 19-21.
Brinton-Darnell, M. "Lactate Dehydrogenase-Elevating, Equine Arteritis and Lelystad Viruses". Encyclopedia of Virology, vol. 2, 1999, pp. 763-771.
Brockmeier et al., "Genomic sequence and virulence comparison of four Type 2 porcine reproductive and respiratory syndrome virus strains". Virus Research, vol. 169, No. 1, 2012, pp. 212-221.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.

(56) References Cited

OTHER PUBLICATIONS

Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Conzelmann et al., "Molecular Characterization of Porcine Reproductive and Respiratory Syndrome Virus, a Member of the Arterivirus Group". Virology, vol. 193, 1993, pp. 329-339.
Darwich et al., "Genetic and immunobiological diversities of porcine reproductive and respiratory syndrome genotype I strains". Veterinary Microbiology, vol. 150, 2011, pp. 49-62.
Database WPIL Week 8821, Derwent Publications Ltd., London, GB; AN 88-147502 [21] & WO,A,8 803 410 (INST PASTEUR) May 19, 1988, 1 page.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Drew, T., "Porcine Reproductive and Respiratory Syndrome Virus: A Review". Apr. 1996, 3 pages.
Fang et al., "Heterogeneity in nsp2 of European-like porcine reproductive and respiratory syndrome viruses isolated in The United States". Virus Research, vol. 100, 2004, pp. 229-235.
Flores-Mendoza et al., "Vaccines against porcine reproductive and respiratory syndrome virus (PRRSV): writing a history". Veterinaria Mexico, vol. 41, No. 2, pp. 139-159.
Gao et al., "Genomic characterization of two Chinese isolates of Porcine respiratory and reproductive syndrome virus". Archives of Virology, vol. 149, 2004, pp. 1341-1351.
Goyal, S., "Porcine Reproductive and Respiratory Syndrome", Journal of Veterinary Diagnostic Investigation, vol. 5, No. 4, 1993, pp. 656-664.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Hill, Howard, "Overview and History of Mystery Swine". Proceedings of the Mystery Swine Disease Committee Meeting, Denver, CO, Oct. 6, 1990, pp. 29-40.
Huang et al., "Novel strategies and approaches to develop the next generation of vaccines against porcine reproductive and respiratory syndrome virus (PRRSV)". Virus Research, vol. 154, 2010, pp. 141-149.
International Search Report and Written Opinion for PCT/EP2012/052475 dated Aug. 20, 2012.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Kimman et al., "Challenges for porcine reproductive and respiratory syndrome virus (PRRSV) vaccinology". Vaccine, vol. 27, No. 28, Jun. 2009, pp. 3704-3718.
Kvisgaard et al., "Genetic and antigenic characterization of complete genomes of Type 1 Porcine Reproductive and Respiratory Syndrome viruses (PRRSV) isolated in Denmark over a period of 10 years". Virus Research, vol. 178, 2013, pp. 197-205.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug. 2012, pp. 1199-1206.
Lesner et al., "Efficacy of Ingelvac® PRRS MLV against highly pathogenic PRRSV: a summary of three challenge trials". Virology & Viral Diseases—PRRS, 22nd International Pig Veterinary Society Congress, Korea, 2012, p. 958.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.
Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.
Mengeling et al., "Clinical Effects of porcine reproductive and respiratory syndrome virus on pigs during the early postnatal interval". American Journal of Veterinary Research, vol. 59, No. 1, Jan. 1998, pp. 52-55.
Mengeling et al., "Comparative safety and efficacy of attenuated single-strain and multi-strain vaccines for porcine reproductive and respiratory syndrome". Veterinary Microbiology, vol. 93, 2003, pp. 25-38.
Mengeling et al., "Comparison among strains of porcine reproductive and respiratory syndrome virus for their ability to cause reproductive failure". American Journal of Veterinary Research, vol. 57, No. 6, Jun. 1996, pp. 834-839.
Wensvoort et al., "The Porcine Reproductive and Respiratory Syndrome; Characteristics and diagnosis of the causative virus". Veterinary Biotechnology Newsletter, vol. 3, 1993, pp. 113-120.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains' [Virus Research 74 (2001) 99-110]". Virus Research, vol. 79, 2001, p. 187.

SEQUENCE LISTING

<160> NUMBER OF SEQ ID NOS: 34

<210> SEQ ID NO 1
<211> LENGTH: 14843
<212> TYPE: DNA
<213> ORGANISM: Porcine reproductive respiratory syndrome virus

<400> SEQUENCE: 1

```
tttgtgtacc ttggaggcgt gggtacagcc ctgccccacc ctttggtccc tgttctagcc      60
cgacaagtac ccttctctct cggggcgagc gcgccgcctg ctgctccctt gcggcgggaa     120
ggacctcccg agtatttccg gagagcacct gctttacggg atctccgccc tttaaccatg     180
tctgggatgt tctcccggtg catgtgcacc ccggctgccc gggtattttg gaacgccggc     240
caagtctatt gcacacggtg tctcagtgca cggtctcttc tctctccaga acttcaggac     300
acggacctcg tgcagttggg cttgtttcac aagcctaaag acaagctcca ttggaaagtt     360
cccattggta tcccccaggt ggaatgttct ccatctgggt gttgctggct gtcaaccatt     420
tttcctttag cgcgcatgac ctccggcaat acaacttcc ttcaacgact cgtgaaggtt      480
gctgatgtat tgtaccgtga cggttgctta accctagac acctccgtga actccaagtt      540
tacgagcgtg gttgcaattg gtatccgatt acggggcctg tgcctgggat ggctgtgtac     600
gcgaactcca tgcacgtgtc cgaccaaccg ttccctggtg ccactcatgt gttaacaaat     660
tccccttttgc ctcaacgggc ttgtcggcag ccgttctgtc cgttcgaaga ggcccattct     720
agcatataca ggtgggaaaa atttgtaatt tttatggatt cctcctccga cggtcgatct     780
cgcatgatgt ggactccgga atccgatgac tccacggctt ggaagttct gccgcccgag     840
ctagaacacc aggtcaaggt ccttgttcgg agctttcccg cccatcacct tgtcgacctt     900
gccgattggg agctcactga gtccctgat aacggttttt ccttcagcac gtcacatcct     960
tgcggctacc ttgttcggga cccggctgta tccgaaggca agtgttggct ttcctgcttt    1020
ttgagccagt cagccgaagt gctcagtcgc gaggcgcatc tggctaccgc ctatggttac    1080
caaaccaagt gggtgtgcc tggcaagtac atccagcgca gacttcaagt tcacggtctc    1140
cgtgctgtgg tcgaccctga tggtcccatt cacgttgaag cattgtcttg ccccagtct      1200
tggatcaggc acttgaccct gaatgatgat gtcaccccgg gattcgttcg cctaatgtct    1260
cttcgcattg tgccgaacac agagcctacc acacaccgga tctttcgttt tggagtgcac    1320
aagtggtatg gtgccgccgg caacgggcc cgtggcaagc gtgccgcaa aagtgagaaa       1380
gactcggctt ccaccctcaa ggttgcccga ccgacttcca ccagtggaat cgtcacctac   1440
```

```
tccccacctg cggacgggtc ttgtggttgg catgcccttg ccgccatact gaaccggatg    1500
attaataatg acttcacgtc ccctctgcct cggtacaaca ggccggagga cgattgggct    1560
tctgatggtg accttgctca ggccattcaa tgtttgcaac tacctgccgc catagctcgg    1620
aaccgcgcct gccctaacgc caaatacctc ataaaactca acggagttca ttgggaggta    1680
gaggtgaggc ctggaatggc tcctcgctcc ctctctcgtg agtgcgttgt tggcgtctgc    1740
tctgaaggct gtgtcgcgtc gccttacccg gaggacgggt tgcctaaacg tgcacttgag    1800
gccctggcgt ctgcttatag actgccttca gactgtgttt gtgatggtat tattgacttc    1860
cttgccaatc cacctcccca ggagttctgg actcttgaca aaatgttgac ttccccgtca    1920
ccggagcagt ccggcttctc tagtctgtat aaattgttgt tagagatctt gccgcagaaa    1980
tgcggatcca cagaagggga attcatctat actgttgaga ggatgttgaa ggattgtccg    2040
agctccaaac aggccatggc cctccttgca aaaattaagg tcccatcctc aaaggcccca    2100
tccgtgactc tgaacgagtg cttccccacg gatgttccag tcaactctga gttaatatct    2160
tgggaagagc ccaaagaccc tggcgctgct gttgtcctat gtccatcgga tgcaaaagaa    2220
tctaaggaaa cagcccctga agaagctcaa gcgagaaacc gtaaggtcct tcaccctgtg    2280
gtccttaccg aggaacttag cgagcaacag gtgcaggtgg ttgagggtga tcaggatatg    2340
ccactggatt tgacttggcc aaccttaacc gctacggcga cccctgttag agggccggta    2400
ccggacaatt tgagctctgg cattggtgcc cagcccgcta ccgttcaaga actcattctg    2460
gcgaggcctg cacccgtct tgttgagcgc tgtggcacgg agtcgaacgg cagcagttca    2520
tttctggatt tgcctgacgt gcagacctcg gaccagcctt tagacctgtc cctggccgcg    2580
tggcctgtaa gggctaccgc gtctgacccc ggttggatcc acgtaggcg tgagcctgtc    2640 tttgtgaagc ctcgaggtgt tttctctgat ggcgagtcgg cccttcagtt cggagagctt    2700
tccgaagcca gttctgtcgt cgatgaccgg acaaagaag ctccggtggt tgacgccccc    2760
atcgatttga caacttcgaa cgagacgctc tctgggtctg ccccctttga attcgccaaa    2820
ttcaggcgcc cgcgtttctc cgcgcaagct ttaatcgacc gaggtggtcc gcttgccgat    2880
gttcatgcaa agataaagag tcgggtatat gaacaatgcc ttcaagcttg tgaacctggt    2940
agtcgtgcga ccccagccac caagaagtgg ctcgacaaaa tgtgggacag ggtggacatg    3000
aaaacttggc gctgcacctc gcagttccaa gctggtcaca ttcttgagtc cctcaaattc    3060
ctccctgaca tgattcaaga cacaccgcct cctgttccca ggaagaaccg agctggtgac    3120
agtgccggcc tgaagcaact ggtggcgcag tgggatagga aatcgagtgt gacaccccc     3180 acaaaaccgg ttggaccggt gcttgaccag gccgtccctc tgcctatgga catccagcaa    3240
ggagatgcca tctccgctga caagccaccc cattcgcaaa acccttctag tcaagtagat    3300
gtgggtggag gttggaaaag ttttatgctc tccggcaccc gtttcgcggg gtccgttagt    3360
cagcgcctta cgacatgggt ttttgaggtt ctctcccatc tcccagcttt tatgctcaca    3420
cttttctcgc cacgggctc tatggctcca ggtgattggc tgtttgcagg tgctgttcta    3480
cttgctctcc tgctctgccg ttcttaccca atactcggat gccttccctt attgggtgtc    3540
ttttctggtt ctgtgcggtg tgttcgtttg ggtgttttg gttcttggat ggcttttgct    3600
gtatttttat tctcgactcc acccgaccca gtcggttctt cttgtgacca cgattcgccg    3660
gagtgtcatg ctgagctttt ggctcttgag cagcgccaac tttgggaacc tgtgcgcagc    3720
cttgtggtcg ggccatcggg cctcttatgc gtcattcttg gcaagttact cggtgggtca    3780
cgttgtctct ggtttgttct cctacgtata tgcatgctcg cagatttggc aatttctctt    3840
```

```
atttatgtgg tgtcccaagg gcgttgtcac aagtgttggg gaaagtgtat aaggacggct   3900
cctgcagaag tggcccttaa tgtgtttcct ttttcgcgcg ccacccgctc atctcttgtg   3960
tccttgtgtg atcggttcca agcgccaaaa ggagttgacc ccgtgcactt ggcgacaggc   4020
tggcgcgggt gctggtgtgg tgagagccct attcatcaat cacaccaaaa accgatagct   4080
tatgccaact tggatgaaaa gaagatatcc gcccagacgg tgattgctgt cccgtatgat   4140
cctagtcagg ccattaaatg cctgaaagtt ttgcaggcag gagggctat tgtgaccag    4200
cctacgcccg aggtcgtccg tgtgtctgag attcccttct cggcccatt ttttccgaag    4260
gtcccagtca acccagactg cagggttgtg gtagattcgg acactttgt ggctgcggtc    4320
cgctgcggtt attcgacagc acaactggtc cttggtcggg gcaactttgc caagctaaat   4380
cagaccccc tcaggaactc tgtccccacc aaaacaactg gtggggcctc atacacccttt  4440
gccgtggccc aggtatctgt gtggactctt gttcatttca tcctcggcct ttggttaacg   4500
tcacctcaag tgtgtggtcg agggacctct gacccgtggt gttcgaaccc ttttcgtat    4560
cctacttatg gccccggagt gtgtgttcc tctcgactct gcgtgtctgc cgacggagtt    4620
accctgccat tgttctcagc cgttgcccat ctttccggta gagaggtggg gatttttatt    4680
ttggtgcttg cctccttggg cgctttagcc caccgcttgg ctcttaaggc agacatgtca    4740
atggtctttt tggcgttttg tgcttacgcc tggcccatga gctcctggtt aatttgcttc    4800
tttcctatgc tcttgaggtg ggtaacccttt catcctctca ctatgctttg ggtgcactca    4860
tttttggtgt tttgcctacc agctgccggc gttctctcgc tgggaataac cggtcttctt    4920
tgggcagttg gccgtttcac ccaggttgcc ggaattatca caccttatga catccaccag    4980
tatacctccg gaccacgtgg tgcagctgct gtagcaacgg ctccagaagg tacttacatg    5040
gcggccgttc ggagagccgc tttgactgga cggactttga tcttcacacc atctgcagtc    5100
ggatcccttc ttgaaggtgc tttcagaact caaaagccct gccttaacac cgtgaatgtc    5160
gtaggctctt cccttggttc tggaggagtt ttcaccattg atggcagaag agtcatcgtc    5220
actgccaccc atgtgttgaa tggtaacaca gccagggtca ctggtgattc ctacaaccgc    5280
atgcacacgt tcaatactaa tggtgattat gcctggtccc atgctgatga ctggcaaggc    5340
gttgcccta tggttaagat cgctaagggg tatcgcggtc gtgcctactg gcaaacgtca     5400
accggagtcg aacctggcat catgggggaa ggattcgcct tctgtttcac taactgtggc    5460
gactcagggt cacctgtcat ttcagaagct ggtgacctta ttggagtcca taccggttca    5520
aacaaactcg gttctggtct tgtgacaacc cctgaagggg agacctgctc catcaaggaa    5580
actaggctct ctgacctttc tagacatttt gcaggtccaa gcgtccctct tggggacatt    5640
aagttgagcc cagccatcat ccctgatgtg acaactattc gagtgacttt ggcatcgctc    5700
cttgcttctg tccccgtgat ggaaggtggc ctctcaactg tccagctttt gtgcgtcttt    5760
ttccttctct ggcgcatgat gggccatgcc tggacaccca ttgttgccgt aggcttcttt    5820
ttgctgaatg aaattctccc agcagtcttg gtccgagctg tgttctcttt tgcactcttt    5880
gtacttgcat gggccacccc ctggtcggca caagtgttga tgattagact cctcacggcg    5940
gctctcaacc gcaacaggtt gtccctggcg ttctacgcat tcggaggtgt cgttggcctg    6000
gccacagaaa tcgggacttt tgctggtgga tggcctgaac tgtcccaagc cctctcgaca    6060
tactgcttcc tgcccaggtt ccttgctgtg actagttatg tccccaccat catcatcggt    6120
gggctccatg ccctcggcgt aattttgtgg ttattcaaat accgatgcct ccacaacatg    6180
```

```
ctggttggtg atgggagttt ctcaagcgct ttcttcctac ggtattttgc tgagggtaat    6240
cttaggaaag gcgtgtcgca gtcctgtggc atgaataacg aatccctgac agctgctttg    6300
gcttgcaagt tgtcgcaagc tgaccttgat tttttgtcca gtttaacgaa cttcaagtgc    6360
tttgtgtccg cttcaaacat gaaaaatgca gctggccaat acatcgaggc ggcgtatgct    6420
agagctctgc gtcaggagct ggcctccttg gttcaggttg acaagatgaa aggagtattg    6480
gccaagctcg aggctttcgc tgagacggcc actccgtcac ttgacacagg ggacgtgatt    6540
gttctgcttg ggcaacaccc ccatggatcc atcctcgaca ttaatgtggg gggtgaaagg    6600
aaaactgtgt ctgtgcaaga aacacgatgc ctgggtggtt ccaaattcag tgtctgcact    6660
gtcgtgtcca acacgcccgt ggataccttg accggtatcc cacttcagac gccaaccccg    6720 cttttttgaaa atggcccgcg ccatcgcagc gaggacgacg acctcaaagt tgagagaatg    6780
aaaaaacact gtgtatccct cggcttccac aaaatcaatg gtaaagttta ctgcaaaatt    6840
tgggacaagt ctaacggcga caccttttac acggatgatt cccgatacac tcaagaccat    6900
gcttttcagg acaggtcaac cgactataga gacaggatt atgaaggtgt acagaccgcc    6960
ccccaacagg gattcgatcc aaagtccgaa gcccctgttg cactgttgt aatcggtggc    7020 attacgtata acaggcatct ggtcaaaggt aaggaggtcc tagttcccaa acctgacaac    7080
tgccttgaag ctgccagact gtcccttgag caagctcttg ctgggatggg ccaaacttgt    7140
gaccttacag ctaccgaagt ggagaaacta agcgcatca ttagtcaact ccaaggtctg    7200
accactgaac aggctttaaa ctgctagccg ccagcggctt gacccgctgt ggccgcggcg    7260
gcctagttgt aactgaaacg gcggtaaaaa tcgtaaaata ccacagcaga actttcacct    7320
taggctcttt agacctaaaa gtcacctccg aggtggaggt gaagaaatca actgagcagg    7380
ggcacgctgt cgtggcgaac ttatgttccg gtgtcgtctt gatgaggcct cacccaccgt    7440
cccttgttga cgttctcctc aaacccggac ttgacacaac acccggcatt caaccagggc    7500
atggggccgg gaatatgggc gtgaacggtt ctatttggga ttttgaaact gcacccacaa    7560
aggtagaact agagttgtcc aagcaaataa tccaagcatg tgaagtcagg cgcggggacg    7620 cccctaaccct ccaactcccc tacaagcttt atcctgtcag gggggaccccc gagcggcgta    7680 aaggtcgcct tgtcaacact aggtttggag atttaccttta caaaactccc caagacacca    7740
agtccgcaat tcatgcggct tgttgcctgc atcccaatgg ggtcctcgtg tctgatggca    7800
aatccacgct gggtaccact cttcaacatg gtttcgagct ttatgtcccc actgtacctt    7860
atagtgtcat ggaatacctt gattcacgcc ctgacacccc tttttatgtgt actaaacatg    7920 gcacttccaa ggctgctgca gaggacctcc aaaaatatga cctatccact caagggtttg    7980
tcttgcctgg ggtcctacgc ctagtgcgca ggttcatctt tagccatgtt ggtaaggcgc    8040
caccactgtt ccttccatca acctaccctg ccaagaactc catggcaggg gtcaatggcc    8100
agaggttccc aacaaaggat gtccagagca tacctgaaat tgatgaaatg tgcgcccgtg    8160
ccgtcaagga aaattggcag actgtgacac cttgcaccct caaaaaacag tactgttcca    8220
aacctaaaac tagaaccatc ctaggtacca acaacttcat agccttggct cacaggtcag    8280
cactcagtgg tgtcacccag cgttcatga agaaggcctg gaagtcccca attgccttgg    8340
ggaaaaacaa gtttaaggaa ttgcattgca ctgtcgccgg cagatgcctt gaggctgacc    8400
tggcttcctg cgatcgcagc accccgccca ttgtgaggtg gtttgttgcc aacctcctgt    8460
atgaacttgc aggatgtgaa gagtacttgc ctagctacgt gctcaactgt tgccatgacc    8520
ttgtggcaac gcaggatggc gctttcacaa aacgcggtgg cctgtcgtcc ggggacccccg    8580
```

```
tcaccagtgt gtccaacacc gtctactcac tgataattta cgcccagcac atggtgcttt    8640
cggccttgaa gatgggtcat gaaattggtc tcaagttcct tgaggaacag ctcaaatttg    8700
aggaccttct tgaaatccag cccatgttag tgtattctga tgacctcgtc ttgtatgcgg    8760
aaagaccac ttttcccaac taccattggt gggtcgagca tcttgacctg atgttgggct     8820
ttaaaacgga cccaaagaaa actgtcataa ctgataaacc cagttttctc ggctgcagaa    8880
ttgaagcagg acggcagtta gtccccaatc gcgaccgtat tctggctgct cttgcatatc    8940
atatgaaggc gcagaacgcc tcagagtatt atgcgtccgc tgccgcaatt ctgatggatt    9000
cgtgtgcttg cattgaccat gaccccgagt ggtatgagga tcttatctgc ggcatcgccc    9060
ggtgtgctcg ccaggacggt taccgttttc caggcccggc attttcatg tccatgtggg     9120
agaagctgaa aagtcataat gaagggaaga atgccgtca ctgcggcatc tgcgacgcca     9180
aagccgacta tgcgtccgcc tgtggacttg atttgtgttt gttccattca cactttcatc    9240
aacactgccc agtcactctg agctgtggcc accatgccgg ttcaaaggaa tgttcgcagt    9300
gtcagtcacc tgtcggggct ggcaaatccc cccttgacgc tgtgctgaaa caaatcccgt    9360
acaaacctcc tcgtaccatt atcatgaagg tggacaacaa acaacgacc cttgacccgg     9420
gaagatatca gtcccgtcga ggtcttgttg cagtcaaaag aggtattgca ggtaatgagg    9480
ttgatctttc tgatggagac taccaagtgg tgcctctttt gccgacttgc aaagacataa    9540
acatggtgaa ggtggcttgc aacgtactac tcagcaagtt tatagtaggg ccgccaggtt    9600
ccggaaaaac cacctggcta ctgaaccaag tccaggacga tgatgtcatt tacacaccta    9660
ctcatcagac aatgtttgac atagtcagtg ctcttaaagt ttgcaggtat ccatcccag    9720
gagcctcagg actcccttt ccaccacctg ccaggtccgg gccgtgggtt aggctcatcg     9780
ccagcggaca tgtccctggc cgagtgtcat atctcgatga ggcaggatat tgcaatcatc    9840
tagacattct aaggctgctt tccaaaaacac cccttgtgtg tttgggtgac cttcagcaac    9900
ttcacccggt cggctttgat tcctattgtt atgtgttcga tcagatgcct cagaagcagc    9960
tgaccaccat ttatagattt ggccctaaca tctgtgcagc catccagcct tgttacaggg   10020
agaaacttga atccaaggcc aggaacacca gagtggtttt caccacccgg cctgtggcct   10080
ttggtcaggt cctgacaccg taccacaaag atcgtaccgg ctctgcaata actatagatt   10140
catcccaggg ggcgaccttc gacattgtga cattgcatct accatcgcca aagtccctaa   10200
acaaatcccg agcacttgta gccatcactc gggcaagaca tgggttgttc atttatgacc   10260
ctcatgacca actccaggag tttttcaact taaccccga gcgcactgat tgtaaccttg    10320
cgttcagccg tggggatgag ctggttgttt tgaatgtgga taatgcggtc acaactgtag   10380
cgaaggccct agagacaggt tcaccccgat ttcgagtatc ggaccgagg tgcaagtctc     10440
tcttagccgc ttgttcggcc agtctagaag ggagctgcat gccactacca caagtagcac   10500
ataacctggg gttttacttt tccccggaca gcccagcttt tgcacccctg ccaaaagagc   10560
tggcgccaca ttggccagtg gtcacccacc agaataatcg agcgtggcct gatcgacttg   10620
tcgctagtat gcgcccaatt gatgcccgct acagcaagcc aatggtcggt gcagggtatg   10680
tggtcgggcc atccattttt cttggcactc ctggtgtggt gtcatactat ctcacattat   10740
acatcggggg cgagcctcag gccctgccag aaacactcgt ttcaacagga cgtatagcca   10800
cagattgtcg ggaatatctc gacgcggctg aggaagaggc agcgagagaa cttccccacg   10860
catttattgg cgatgtcaaa ggcactacga tcgggggtg tcaccacatt acatcgaaat     10920
```

```
acctacctag gtccctgcct aaagactctg ttgctgtggt tggggtgagt tcgcccggta   10980
gggctgctaa agccgtgtgc actctcaccg atgtgtacct ccccgaactc cgaccatatt   11040
tgcaaccgga gacggcatca aaatgctgga aacttaaact ggatttcagg gatgttcgac   11100
tgatggtctg gaaaggcgcc acagcctatt tccagttgga agggctgaca tggtcagcgc   11160
tgcccgatta tgctaggttc attcagctac ccaaggatgc cgttgtgtac atcgatccgt   11220
gtatagggcc ggcaacagcc aatcgcaagg ttgtgcgaac cacagactgg cgggccgacc   11280
tggcagtgac accgtatgat tacggtgctc aggtcatttt gacaacagcc tggttcgagg   11340
accttgggcc gcagtggaag attttggggt tgcagccttt cagacgaaca tttggctttg   11400
agaacactga agattgggca attctcgcac gccgtatgaa tgacggcaaa gattacactg   11460
actataattg gcattgtgta cgagaacgcc cacacgcaat ttacgggcgc gcccgtgacc   11520
atacgtatca ttttgccctt ggcactgaac tgcaagtaga gctgggcaga ccccggctgc   11580
ctcctgagca agtgccgtga acgcggagtg atgcaatggg tttactgtgg agtaaaatca   11640
gtcagttgtt cgtggatgcc ttcactgagt tccttgttag tgtggttgac attgtcatct   11700
ttctcgccat attgtttggg ttcactgttg caggctggtt attggtcttc cttctcagag   11760
tggtttgctc cgcgtttctc cgttcgcgct ctgccattca ctcttccgaa ctatcgaagg   11820
tcctatgagg gcttgctacc caactgcaga ccggatgtcc cacaattcgc agttaagcac   11880
ccgttgggta tactttggca tatgcgagtc tcccacctaa ttgacgaaat ggtctctcgc   11940
cgcatttacc ggaccatgga acattcgggt caagcggcct ggaagcaggt tgttagtgaa   12000
gccactctca caaaactgtc aaggcttgac gtagtcactc atttccaaca cctggccgca   12060
gtggaggctg attcttgccg cttccttagc tcacgactcg cgatgctgaa aaaccttgcc   12120
gttggcaatg tgagcctgga gtacaacact actttggacc gcgttgagct catctttccc   12180
acaccaggta cgaggcccaa gttgaccgat tttaggcaat ggcttatcag cgtgcacgct   12240
tccatcttct cctctgtggc ttcgtctgtt accttgttca cagtgctttg gcttcgaatt   12300
ccagctctac gctatgtttt tggtttccat ggcccacgg caacacatca ttcgaactaa   12360
ctatcaatta cactatatgt aagccatgcc taccagtca agctgcccaa caaagactcg   12420
agcctggccg taacgtgtgg tgcaaaatag ggcacgacag gtgtgaggaa cgtgaccatg   12480
atgagttgtc aatgtccatt ccgtccgggt acgacaacct caaacttgag ggttattatg   12540
cttggctggc tttttttgtcc ttttcctacg cggcccaatt ccatccggag ctgttcggaa   12600
taggaaacgt gtcgcgcgtc tttgtggata agcgacacca gttcatttgc gccgagcatg   12660
atggacaaaa ttcaaccata tctgccagac acaacatctc cgcgtcgtat gcggtgtatt   12720
accatcatca aatagacggg ggcaattggt ttcatttgga atggctgcga ccattctttt   12780
cctcctggct ggtgctcaac atctcatggt ttctgaggcg ttcgcctgca gccctgctt   12840 ctcgacgcat ctatcagata ttaagaccaa cacgaccgcg gctgccggtt tcatggtcct   12900
tcagaacatc aattgttttcc aatctcacag ggcctcaaca gcgcaaggta ccactcccct   12960
caggaggtcg tcccaatgtc gtgaagccgt cggcattccc cagtacatca cgataacggc   13020
taatgtgacc gatgaatcgt atttgtacaa cgcggacttg ctgatgcttt ccgcgtgcct   13080
tttctacgcc tcggaaatga gcgagaaagg cttcaaagtc atctttggga atatttctgg   13140
cgttgtttcc gcttgtgtta atttcacaga ttatgtggcc catgtgaccc aacacactca   13200
gcagcaccat ttggtaattg atcacattcg gttactacac ttcttgacac cgtctacgat   13260
gaggtgggct acaaccattg cttgtttgct tgccattctt ttggcggtat gaaatgttct   13320
```

```
tgcaagttgg ggcatttctt gactcctcac tcttgcttct ggtggctttt tttgctgtgt   13380
accggcttgt cttggtcctt tgtcgatggc aacgacgaca gctcgacatc ccaatacata   13440
tataatttga cgatatgcga gctgaatggg accgaatggt tgtccggtca ttttgattgg   13500
gcagtcgaaa cctttgtgct ttacccagtt gccactcata tcatttcact gggttttctc   13560
acaacaagcc atttccttga tgcgctcggt ctcggcgctg tgtccgccac aggattcatt   13620
ggcgagcggt atgtacttag cagcatgtac ggcgtttgcg ccttcgcggc gttcgtatgt   13680
tttgtcatcc gtgctgctaa aaattgcatg gcttgccgct atgcccgcac ccggtttacc   13740
aacttcatcg tggacgaccg gggaagaatc catcgatgga agtcttcaat agtggtggag   13800
aaattgggca agctgaagt cggtggtgac cttgtcaaca ttaagcatgt tgtcctcgaa   13860
ggggttaaag ctcaaccttt gacgaggact tcggctgagc aatgggaagc ctagacgact   13920
tttgcaacga tcccaccgcc gcacaaaaac tcgtgctggc ctttagcatc acatatacac   13980
ccataatgat atacgccctt aaggtgtcac gcggccgact cctggggctg ttgcacatct   14040
tgatatttct gaattgttcc tttacttttg ggtacatgac atatgtgcat tttcaatcca   14100
ccaaccgtgt cgcattcact ctgggggctg tagtcgccct tttgtggggt gtttacagcc   14160
tcacagagtc atggaagttc atcacttcca gatgcagatt gtgttgccta ggccggcgat   14220
acattctggc ccctgcccat cacgtagaaa gtgctgcagg cctccattca atcccagcgt   14280
ctggtaaccg agcatacgct gtgagaaagc ccggactaac atcagtgaac ggcactctag   14340
tacctgggct tcggagcctc gtgctgggcg gcaaacgagc tgttaaacga ggagtggtta   14400
acctcgtcaa gtatggccgg taagaaccag agccagaaga aaagaagaaa tgcagctccg   14460
atggggaaag gccagccagt caatcaactg tgccagttgc tgggtacaat gataaagtcc   14520
cagcgccagc aatctagggg aggacaggcc aaaaagaaga agcctgagaa gccacatttt   14580
cccctagctg ctgaagatga cattcggcac catctcaccc aggccgaacg ttccctctgc   14640
ttgcaatcga tccagacggc tttcaatcaa ggcgcaggaa ctgcgtcgct ttcatccagc   14700
gggaaggtca gtttccaggt tgagttcatg ctgccggttg ctcatacagt gcgcctgatt   14760
cgcgtgactt ctacatccgc cagtcagggt gcaaattaat ttgacagtca ggtgaatggc   14820
cgcgattgac gtgtggcctc taa                                          14843
```

<210> SEQ ID NO 2
<211> LENGTH: 2349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Gly Met Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe His Lys Pro Lys Asp Lys Leu His Trp Lys Val Pro Ile Gly
    50                  55                  60

Ile Pro Gln Val Glu Cys Ser Pro Ser Gly Cys Cys Trp Leu Ser Thr
65                  70                  75                  80

```
Ile Phe Pro Leu Ala Arg Met Thr Ser Gly Asn His Asn Phe Leu Gln
             85                  90                  95

Arg Leu Val Lys Val Ala Asp Val Leu Tyr Arg Asp Gly Cys Leu Thr
            100                 105                 110

Pro Arg His Leu Arg Glu Leu Gln Val Tyr Glu Arg Gly Cys Asn Trp
            115                 120                 125

Tyr Pro Ile Thr Gly Pro Val Pro Gly Met Ala Val Tyr Ala Asn Ser
            130                 135                 140

Met His Val Ser Asp Gln Pro Phe Pro Gly Ala Thr His Val Leu Thr
145                 150                 155                 160

Asn Ser Pro Leu Pro Gln Arg Ala Cys Arg Gln Pro Phe Cys Pro Phe
            165                 170                 175

Glu Glu Ala His Ser Ser Ile Tyr Arg Trp Glu Lys Phe Val Ile Phe
            180                 185                 190

Met Asp Ser Ser Ser Asp Gly Arg Ser Arg Met Met Trp Thr Pro Glu
            195                 200                 205

Ser Asp Asp Ser Thr Ala Leu Glu Val Leu Pro Pro Glu Leu Glu His
            210                 215                 220

Gln Val Lys Val Leu Val Arg Ser Phe Pro Ala His His Leu Val Asp
225                 230                 235                 240

Leu Ala Asp Trp Glu Leu Thr Glu Ser Pro Asp Asn Gly Phe Ser Phe
            245                 250                 255

Ser Thr Ser His Pro Cys Gly Tyr Leu Val Arg Asp Pro Ala Val Ser
            260                 265                 270

Glu Gly Lys Cys Trp Leu Ser Cys Phe Leu Ser Gln Ser Ala Glu Val
            275                 280                 285

Leu Ser Arg Glu Ala His Leu Ala Thr Ala Tyr Gly Tyr Gln Thr Lys
            290                 295                 300

Trp Gly Val Pro Gly Lys Tyr Ile Gln Arg Arg Leu Gln Val His Gly
305                 310                 315                 320

Leu Arg Ala Val Val Asp Pro Asp Gly Pro Ile His Val Glu Ala Leu
            325                 330                 335

Ser Cys Pro Gln Ser Trp Ile Arg His Leu Thr Leu Asn Asp Asp Val
            340                 345                 350

Thr Pro Gly Phe Val Arg Leu Met Ser Leu Arg Ile Val Pro Asn Thr
            355                 360                 365

Glu Pro Thr Thr His Arg Ile Phe Arg Phe Gly Val His Lys Trp Tyr
            370                 375                 380

Gly Ala Ala Gly Lys Arg Ala Arg Gly Lys Arg Ala Ala Lys Ser Glu
385                 390                 395                 400

Lys Asp Ser Ala Ser Thr Leu Lys Val Ala Arg Pro Thr Ser Thr Ser
            405                 410                 415

Gly Ile Val Thr Tyr Ser Pro Pro Ala Asp Gly Ser Cys Gly Trp His
            420                 425                 430

Ala Leu Ala Ala Ile Leu Asn Arg Met Ile Asn Asn Asp Phe Thr Ser
            435                 440                 445

Pro Leu Pro Arg Tyr Asn Arg Pro Glu Asp Asp Trp Ala Ser Asp Gly
            450                 455                 460

Asp Leu Ala Gln Ala Ile Gln Cys Leu Gln Leu Pro Ala Ala Ile Ala
465                 470                 475                 480

Arg Asn Arg Ala Cys Pro Asn Ala Lys Tyr Leu Ile Lys Leu Asn Gly
            485                 490                 495

Val His Trp Glu Val Glu Val Arg Pro Gly Met Ala Pro Arg Ser Leu
```

-continued

```
            500                 505                 510
Ser Arg Glu Cys Val Gly Val Cys Ser Glu Gly Cys Val Ala Ser
        515                 520                 525
Pro Tyr Pro Glu Asp Gly Leu Pro Lys Arg Ala Leu Glu Ala Leu Ala
        530                 535                 540
Ser Ala Tyr Arg Leu Pro Ser Asp Cys Val Cys Asp Gly Ile Ile Asp
545                 550                 555                 560
Phe Leu Ala Asn Pro Pro Gln Glu Phe Trp Thr Leu Asp Lys Met
                565                 570                 575
Leu Thr Ser Pro Ser Pro Glu Gln Ser Gly Phe Ser Ser Leu Tyr Lys
                580                 585                 590
Leu Leu Leu Glu Ile Leu Pro Gln Lys Cys Gly Ser Thr Glu Gly Glu
                595                 600                 605
Phe Ile Tyr Thr Val Glu Arg Met Leu Lys Asp Cys Pro Ser Ser Lys
        610                 615                 620
Gln Ala Met Ala Leu Leu Ala Lys Ile Lys Val Pro Ser Ser Lys Ala
625                 630                 635                 640
Pro Ser Val Thr Leu Asn Glu Cys Phe Pro Thr Asp Val Pro Val Asn
                645                 650                 655
Ser Glu Leu Ile Ser Trp Glu Gly Pro Lys Asp Pro Gly Ala Ala Val
                660                 665                 670
Val Leu Cys Pro Ser Asp Ala Lys Glu Ser Lys Glu Thr Ala Pro Glu
        675                 680                 685
Glu Ala Gln Ala Arg Asn Arg Lys Val Leu His Pro Val Val Leu Thr
        690                 695                 700
Glu Glu Leu Ser Glu Gln Gln Val Gln Val Val Glu Gly Asp Gln Asp
705                 710                 715                 720
Met Pro Leu Asp Leu Thr Trp Pro Thr Leu Thr Ala Thr Ala Thr Pro
                725                 730                 735
Val Arg Gly Pro Val Pro Asp Asn Leu Ser Ser Gly Ile Gly Ala Gln
                740                 745                 750
Pro Ala Thr Val Gln Glu Leu Ile Leu Ala Arg Pro Ala Pro Arg Leu
        755                 760                 765
Val Glu Arg Cys Gly Thr Glu Ser Asn Gly Ser Ser Ser Phe Leu Asp
        770                 775                 780
Leu Pro Asp Val Gln Thr Ser Asp Gln Pro Leu Asp Leu Ser Leu Ala
785                 790                 795                 800
Ala Trp Pro Val Arg Ala Thr Ala Ser Asp Pro Gly Trp Ile His Gly
                805                 810                 815
Arg Arg Glu Pro Val Phe Val Lys Pro Arg Gly Val Phe Ser Asp Gly
                820                 825                 830
Glu Ser Ala Leu Gln Phe Gly Glu Leu Ser Glu Ala Ser Ser Val Val
                835                 840                 845
Asp Asp Arg Thr Lys Glu Ala Pro Val Val Asp Ala Pro Ile Asp Leu
                850                 855                 860
Thr Thr Ser Asn Glu Thr Leu Ser Gly Ser Asp Pro Phe Glu Phe Ala
865                 870                 875                 880
Lys Phe Arg Arg Pro Arg Phe Ser Ala Gln Ala Leu Ile Asp Arg Gly
                885                 890                 895
Gly Pro Leu Ala Asp Val His Ala Lys Ile Lys Ser Arg Val Tyr Glu
                900                 905                 910
Gln Cys Leu Gln Ala Cys Glu Pro Gly Ser Arg Ala Thr Pro Ala Thr
                915                 920                 925
```

-continued

```
Lys Lys Trp Leu Asp Lys Met Trp Asp Arg Val Asp Met Lys Thr Trp
    930                 935                 940
Arg Cys Thr Ser Gln Phe Gln Ala Gly His Ile Leu Glu Ser Leu Lys
945                 950                 955                 960
Phe Leu Pro Asp Met Ile Gln Asp Thr Pro Pro Val Pro Arg Lys
                965                 970                 975
Asn Arg Ala Gly Asp Ser Ala Gly Leu Lys Gln Leu Val Ala Gln Trp
                980                 985                 990
Asp Arg Lys Ser Ser Val Thr Pro Pro Thr Lys Pro Val Gly Pro Val
    995                 1000                1005
Leu Asp Gln Ala Val Pro Leu Pro Met Asp Ile Gln Gln Gly Asp
    1010                1015                1020
Ala Ile Ser Ala Asp Lys Pro Pro His Ser Gln Asn Pro Ser Ser
    1025                1030                1035
Gln Val Asp Val Gly Gly Gly Trp Lys Ser Phe Met Leu Ser Gly
    1040                1045                1050
Thr Arg Phe Ala Gly Ser Val Ser Gln Arg Leu Thr Thr Trp Val
    1055                1060                1065
Phe Glu Val Leu Ser His Leu Pro Ala Phe Met Leu Thr Leu Phe
    1070                1075                1080
Ser Pro Arg Gly Ser Met Ala Pro Gly Asp Trp Leu Phe Ala Gly
    1085                1090                1095
Ala Val Leu Leu Ala Leu Leu Leu Cys Arg Ser Tyr Pro Ile Leu
    1100                1105                1110
Gly Cys Leu Pro Leu Leu Gly Val Phe Ser Gly Ser Val Arg Cys
    1115                1120                1125
Val Arg Leu Gly Val Phe Gly Ser Trp Met Ala Phe Ala Val Phe
    1130                1135                1140
Leu Phe Ser Thr Pro Pro Asp Pro Val Gly Ser Ser Cys Asp His
    1145                1150                1155
Asp Ser Pro Glu Cys His Ala Glu Leu Leu Ala Leu Glu Gln Arg
    1160                1165                1170
Gln Leu Trp Glu Pro Val Arg Ser Leu Val Val Gly Pro Ser Gly
    1175                1180                1185
Leu Leu Cys Val Ile Leu Gly Lys Leu Leu Gly Gly Ser Arg Cys
    1190                1195                1200
Leu Trp Phe Val Leu Leu Arg Ile Cys Met Leu Ala Asp Leu Ala
    1205                1210                1215
Ile Ser Leu Ile Tyr Val Val Ser Gln Gly Arg Cys His Lys Cys
    1220                1225                1230
Trp Gly Lys Cys Ile Arg Thr Ala Pro Ala Glu Val Ala Leu Asn
    1235                1240                1245
Val Phe Pro Phe Ser Arg Ala Thr Arg Ser Ser Leu Val Ser Leu
    1250                1255                1260
Cys Asp Arg Phe Gln Ala Pro Lys Gly Val Asp Pro Val His Leu
    1265                1270                1275
Ala Thr Gly Trp Arg Gly Cys Trp Cys Gly Glu Ser Pro Ile His
    1280                1285                1290
Gln Ser His Gln Lys Pro Ile Ala Tyr Ala Asn Leu Asp Glu Lys
    1295                1300                1305
Lys Ile Ser Ala Gln Thr Val Ile Ala Val Pro Tyr Asp Pro Ser
    1310                1315                1320
```

```
Gln Ala Ile Lys Cys Leu Lys Val Leu Gln Ala Gly Gly Ala Ile
1325                1330                1335

Val Asp Gln Pro Thr Pro Glu Val Val Arg Val Ser Glu Ile Pro
1340                1345                1350

Phe Ser Ala Pro Phe Phe Pro Lys Val Pro Val Asn Pro Asp Cys
1355                1360                1365

Arg Val Val Val Asp Ser Asp Thr Phe Val Ala Ala Val Arg Cys
1370                1375                1380

Gly Tyr Ser Thr Ala Gln Leu Val Leu Gly Arg Gly Asn Phe Ala
1385                1390                1395

Lys Leu Asn Gln Thr Pro Leu Arg Asn Ser Val Pro Thr Lys Thr
1400                1405                1410

Thr Gly Gly Ala Ser Tyr Thr Leu Ala Val Ala Gln Val Ser Val
1415                1420                1425

Trp Thr Leu Val His Phe Ile Leu Gly Leu Trp Leu Thr Ser Pro
1430                1435                1440

Gln Val Cys Gly Arg Gly Thr Ser Asp Pro Trp Cys Ser Asn Pro
1445                1450                1455

Phe Ser Tyr Pro Thr Tyr Gly Pro Gly Val Val Cys Ser Ser Arg
1460                1465                1470

Leu Cys Val Ser Ala Asp Gly Val Thr Leu Pro Leu Phe Ser Ala
1475                1480                1485

Val Ala His Leu Ser Gly Arg Glu Val Gly Ile Phe Ile Leu Val
1490                1495                1500

Leu Ala Ser Leu Gly Ala Leu Ala His Arg Leu Ala Leu Lys Ala
1505                1510                1515

Asp Met Ser Met Val Phe Leu Ala Phe Cys Ala Tyr Ala Trp Pro
1520                1525                1530

Met Ser Ser Trp Leu Ile Cys Phe Phe Pro Met Leu Leu Arg Trp
1535                1540                1545

Val Thr Leu His Pro Leu Thr Met Leu Trp Val His Ser Phe Leu
1550                1555                1560

Val Phe Cys Leu Pro Ala Ala Gly Val Leu Ser Leu Gly Ile Thr
1565                1570                1575

Gly Leu Leu Trp Ala Val Gly Arg Phe Thr Gln Val Ala Gly Ile
1580                1585                1590

Ile Thr Pro Tyr Asp Ile His Gln Tyr Thr Ser Gly Pro Arg Gly
1595                1600                1605

Ala Ala Ala Val Ala Thr Ala Pro Glu Gly Thr Tyr Met Ala Ala
1610                1615                1620

Val Arg Arg Ala Ala Leu Thr Gly Arg Thr Leu Ile Phe Thr Pro
1625                1630                1635

Ser Ala Val Gly Ser Leu Leu Glu Gly Ala Phe Arg Thr Gln Lys
1640                1645                1650

Pro Cys Leu Asn Thr Val Asn Val Val Gly Ser Ser Leu Gly Ser
1655                1660                1665

Gly Gly Val Phe Thr Ile Asp Gly Arg Arg Val Ile Val Thr Ala
1670                1675                1680

Thr His Val Leu Asn Gly Asn Thr Ala Arg Val Thr Gly Asp Ser
1685                1690                1695

Tyr Asn Arg Met His Thr Phe Asn Thr Asn Gly Asp Tyr Ala Trp
1700                1705                1710

Ser His Ala Asp Asp Trp Gln Gly Val Ala Pro Met Val Lys Ile
```

```
                1715                1720                1725

Ala Lys Gly Tyr Arg Gly Arg Ala Tyr Trp Gln Thr Ser Thr Gly
        1730                1735                1740

Val Glu Pro Gly Ile Met Gly Glu Gly Phe Ala Phe Cys Phe Thr
        1745                1750                1755

Asn Cys Gly Asp Ser Gly Ser Pro Val Ile Ser Glu Ala Gly Asp
        1760                1765                1770

Leu Ile Gly Val His Thr Gly Ser Asn Lys Leu Gly Ser Gly Leu
        1775                1780                1785

Val Thr Thr Pro Glu Gly Glu Thr Cys Ser Ile Lys Glu Thr Arg
        1790                1795                1800

Leu Ser Asp Leu Ser Arg His Phe Ala Gly Pro Ser Val Pro Leu
        1805                1810                1815

Gly Asp Ile Lys Leu Ser Pro Ala Ile Ile Pro Asp Val Thr Thr
        1820                1825                1830

Ile Pro Ser Asp Leu Ala Ser Leu Leu Ala Ser Val Pro Val Met
        1835                1840                1845

Glu Gly Gly Leu Ser Thr Val Gln Leu Leu Cys Val Phe Phe Leu
        1850                1855                1860

Leu Trp Arg Met Met Gly His Ala Trp Thr Pro Ile Val Ala Val
        1865                1870                1875

Gly Phe Phe Leu Leu Asn Glu Ile Leu Pro Ala Val Leu Val Arg
        1880                1885                1890

Ala Val Phe Ser Phe Ala Leu Phe Val Leu Ala Trp Ala Thr Pro
        1895                1900                1905

Trp Ser Ala Gln Val Leu Met Ile Arg Leu Leu Thr Ala Ala Leu
        1910                1915                1920

Asn Arg Asn Arg Leu Ser Leu Ala Phe Tyr Ala Phe Gly Gly Val
        1925                1930                1935

Val Gly Leu Ala Thr Glu Ile Gly Thr Phe Ala Gly Gly Trp Pro
        1940                1945                1950

Glu Leu Ser Gln Ala Leu Ser Thr Tyr Cys Phe Leu Pro Arg Phe
        1955                1960                1965

Leu Ala Val Thr Ser Tyr Val Pro Thr Ile Ile Ile Gly Gly Leu
        1970                1975                1980

His Ala Leu Gly Val Ile Leu Trp Leu Phe Lys Tyr Arg Cys Leu
        1985                1990                1995

His Asn Met Leu Val Gly Asp Gly Ser Phe Ser Ser Ala Phe Phe
        2000                2005                2010

Leu Arg Tyr Phe Ala Glu Gly Asn Leu Arg Lys Gly Val Ser Gln
        2015                2020                2025

Ser Cys Gly Met Asn Asn Glu Ser Leu Thr Ala Ala Leu Ala Cys
        2030                2035                2040

Lys Leu Ser Gln Ala Asp Leu Asp Phe Leu Ser Ser Leu Thr Asn
        2045                2050                2055

Phe Lys Cys Phe Val Ser Ala Ser Asn Met Lys Asn Ala Ala Gly
        2060                2065                2070

Gln Tyr Ile Glu Ala Ala Tyr Ala Arg Ala Leu Arg Gln Glu Leu
        2075                2080                2085

Ala Ser Leu Val Gln Val Asp Lys Met Lys Gly Val Leu Ala Lys
        2090                2095                2100

Leu Glu Ala Phe Ala Glu Thr Ala Thr Pro Ser Leu Asp Thr Gly
        2105                2110                2115
```

```
Asp Val Ile Val Leu Leu Gly Gln His Pro His Gly Ser Ile Leu
    2120                2125                2130

Asp Ile Asn Val Gly Gly Glu Arg Lys Thr Val Ser Val Gln Glu
    2135                2140                2145

Thr Arg Cys Leu Gly Gly Ser Lys Phe Ser Val Cys Thr Val Val
    2150                2155                2160

Ser Asn Thr Pro Val Asp Thr Leu Thr Gly Ile Pro Leu Gln Thr
    2165                2170                2175

Pro Thr Pro Leu Phe Glu Asn Gly Pro Arg His Arg Ser Glu Asp
    2180                2185                2190

Asp Asp Leu Lys Val Glu Arg Met Lys Lys His Cys Val Ser Leu
    2195                2200                2205

Gly Phe His Lys Ile Asn Gly Lys Val Tyr Cys Lys Ile Trp Asp
    2210                2215                2220

Lys Ser Asn Gly Asp Thr Phe Tyr Thr Asp Asp Ser Arg Tyr Thr
    2225                2230                2235

Gln Asp His Ala Phe Gln Asp Arg Ser Thr Asp Tyr Arg Asp Arg
    2240                2245                2250

Asp Tyr Glu Gly Val Gln Thr Ala Pro Gln Gln Gly Phe Asp Pro
    2255                2260                2265

Lys Ser Glu Ala Pro Val Gly Thr Val Val Ile Gly Gly Ile Thr
    2270                2275                2280

Tyr Asn Arg His Leu Val Lys Gly Lys Glu Val Leu Val Pro Lys
    2285                2290                2295

Pro Asp Asn Cys Leu Glu Ala Ala Arg Leu Ser Leu Glu Gln Ala
    2300                2305                2310

Leu Ala Gly Met Gly Gln Thr Cys Asp Leu Thr Ala Thr Glu Val
    2315                2320                2325

Glu Lys Leu Lys Arg Ile Ile Ser Gln Leu Gln Gly Leu Thr Thr
    2330                2335                2340

Glu Gln Ala Leu Asn Cys
    2345
```

<210> SEQ ID NO 3
<211> LENGTH: 1463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Thr Gly Phe Lys Leu Leu Ala Ala Ser Gly Leu Thr Arg Cys Gly Arg
1               5                   10                  15

Gly Gly Leu Val Val Thr Glu Thr Ala Val Lys Ile Val Lys Tyr His
                20                  25                  30

Ser Arg Thr Phe Thr Leu Gly Ser Leu Asp Leu Lys Val Thr Ser Glu
        35                  40                  45

Val Glu Val Lys Lys Ser Thr Glu Gln Gly His Ala Val Val Ala Asn
    50                  55                  60

Leu Cys Ser Gly Val Val Leu Met Arg Pro His Pro Pro Ser Leu Val
65                  70                  75                  80

Asp Val Leu Leu Lys Pro Gly Leu Asp Thr Thr Pro Gly Ile Gln Pro
                85                  90                  95

Gly His Gly Ala Gly Asn Met Gly Val Asn Gly Ser Ile Trp Asp Phe
```

```
            100                 105                 110
Glu Thr Ala Pro Thr Lys Val Glu Leu Glu Leu Ser Lys Gln Ile Ile
            115                 120                 125
Gln Ala Cys Glu Val Arg Arg Gly Asp Ala Pro Asn Leu Gln Leu Pro
            130                 135                 140
Tyr Lys Leu Tyr Pro Val Arg Gly Asp Pro Glu Arg Arg Lys Gly Arg
145                 150                 155                 160
Leu Val Asn Thr Arg Phe Gly Asp Leu Pro Tyr Lys Thr Pro Gln Asp
            165                 170                 175
Thr Lys Ser Ala Ile His Ala Ala Cys Cys Leu His Pro Asn Gly Val
            180                 185                 190
Leu Val Ser Asp Gly Lys Ser Thr Leu Gly Thr Thr Leu Gln His Gly
            195                 200                 205
Phe Glu Leu Tyr Val Pro Thr Val Pro Tyr Ser Val Met Glu Tyr Leu
            210                 215                 220
Asp Ser Arg Pro Asp Thr Pro Phe Met Cys Thr Lys His Gly Thr Ser
225                 230                 235                 240
Lys Ala Ala Ala Glu Asp Leu Gln Lys Tyr Asp Leu Ser Thr Gln Gly
            245                 250                 255
Phe Val Leu Pro Gly Val Leu Arg Leu Val Arg Arg Phe Ile Phe Ser
            260                 265                 270
His Val Gly Lys Ala Pro Pro Leu Phe Leu Pro Ser Thr Tyr Pro Ala
            275                 280                 285
Lys Asn Ser Met Ala Gly Val Asn Gly Gln Arg Phe Pro Thr Lys Asp
            290                 295                 300
Val Gln Ser Ile Pro Glu Ile Asp Glu Met Cys Ala Arg Ala Val Lys
305                 310                 315                 320
Glu Asn Trp Gln Thr Val Thr Pro Cys Thr Leu Lys Lys Gln Tyr Cys
            325                 330                 335
Ser Lys Pro Lys Thr Arg Thr Ile Leu Gly Thr Asn Asn Phe Ile Ala
            340                 345                 350
Leu Ala His Arg Ser Ala Leu Ser Gly Val Thr Gln Ala Phe Met Lys
            355                 360                 365
Lys Ala Trp Lys Ser Pro Ile Ala Leu Gly Lys Asn Lys Phe Lys Glu
            370                 375                 380
Leu His Cys Thr Val Ala Gly Arg Cys Leu Glu Ala Asp Leu Ala Ser
385                 390                 395                 400
Cys Asp Arg Ser Thr Pro Ala Ile Val Arg Trp Phe Val Ala Asn Leu
            405                 410                 415
Leu Tyr Glu Leu Ala Gly Cys Glu Glu Tyr Leu Pro Ser Tyr Val Leu
            420                 425                 430
Asn Cys Cys His Asp Leu Val Ala Thr Gln Asp Gly Ala Phe Thr Lys
            435                 440                 445
Arg Gly Gly Leu Ser Ser Gly Asp Pro Val Thr Ser Val Ser Asn Thr
            450                 455                 460
Val Tyr Ser Leu Ile Ile Tyr Ala Gln His Met Val Leu Ser Ala Leu
465                 470                 475                 480
Lys Met Gly His Glu Ile Gly Leu Lys Phe Leu Glu Glu Gln Leu Lys
            485                 490                 495
Phe Glu Asp Leu Leu Glu Ile Gln Pro Met Leu Val Tyr Ser Asp Asp
            500                 505                 510
Leu Val Leu Tyr Ala Glu Arg Pro Thr Phe Pro Asn Tyr His Trp Trp
            515                 520                 525
```

```
Val Glu His Leu Asp Leu Met Leu Gly Phe Lys Thr Asp Pro Lys Lys
    530                 535                 540
Thr Val Ile Thr Asp Lys Pro Ser Phe Leu Gly Cys Arg Ile Glu Ala
545                 550                 555                 560
Gly Arg Gln Leu Val Pro Asn Arg Asp Arg Ile Leu Ala Ala Leu Ala
                    565                 570                 575
Tyr His Met Lys Ala Gln Asn Ala Ser Glu Tyr Tyr Ala Ser Ala Ala
                580                 585                 590
Ala Ile Leu Met Asp Ser Cys Ala Cys Ile Asp His Asp Pro Glu Trp
            595                 600                 605
Tyr Glu Asp Leu Ile Cys Gly Ile Ala Arg Cys Ala Arg Gln Asp Gly
    610                 615                 620
Tyr Arg Phe Pro Gly Pro Ala Phe Phe Met Ser Met Trp Glu Lys Leu
625                 630                 635                 640
Lys Ser His Asn Glu Gly Lys Lys Cys Arg His Cys Gly Ile Cys Asp
                    645                 650                 655
Ala Lys Ala Asp Tyr Ala Ser Ala Cys Gly Leu Asp Leu Cys Leu Phe
                660                 665                 670
His Ser His Phe His Gln His Cys Pro Val Thr Leu Ser Cys Gly His
            675                 680                 685
His Ala Gly Ser Lys Glu Cys Ser Gln Cys Gln Ser Pro Val Gly Ala
    690                 695                 700
Gly Lys Ser Pro Leu Asp Ala Val Leu Lys Gln Ile Pro Tyr Lys Pro
705                 710                 715                 720
Pro Arg Thr Ile Ile Met Lys Val Asp Asn Lys Thr Thr Thr Leu Asp
                    725                 730                 735
Pro Gly Arg Tyr Gln Ser Arg Arg Gly Leu Val Ala Val Lys Arg Gly
                740                 745                 750
Ile Ala Gly Asn Glu Val Asp Leu Ser Asp Gly Asp Tyr Gln Val Val
            755                 760                 765
Pro Leu Leu Pro Thr Cys Lys Asp Ile Asn Met Val Lys Val Ala Cys
    770                 775                 780
Asn Val Leu Leu Ser Lys Phe Ile Val Gly Pro Pro Gly Ser Gly Lys
785                 790                 795                 800
Thr Thr Trp Leu Leu Asn Gln Val Gln Asp Asp Val Ile Tyr Thr
                    805                 810                 815
Pro Thr His Gln Thr Met Phe Asp Ile Val Ser Ala Leu Lys Val Cys
                820                 825                 830
Arg Tyr Ser Ile Pro Gly Ala Ser Gly Leu Pro Phe Pro Pro Pro Ala
            835                 840                 845
Arg Ser Gly Pro Trp Val Arg Leu Ile Ala Ser Gly His Val Pro Gly
    850                 855                 860
Arg Val Ser Tyr Leu Asp Glu Ala Gly Tyr Cys Asn His Leu Asp Ile
865                 870                 875                 880
Leu Arg Leu Leu Ser Lys Thr Pro Leu Val Cys Leu Gly Asp Leu Gln
                    885                 890                 895
Gln Leu His Pro Val Gly Phe Asp Ser Tyr Cys Tyr Val Phe Asp Gln
                900                 905                 910
Met Pro Gln Lys Gln Leu Thr Thr Ile Tyr Arg Phe Gly Pro Asn Ile
            915                 920                 925
Cys Ala Ala Ile Gln Pro Cys Tyr Arg Glu Lys Leu Glu Ser Lys Ala
    930                 935                 940
```

```
Arg Asn Thr Arg Val Val Phe Thr Thr Arg Pro Val Ala Phe Gly Gln
945                 950                 955                 960

Val Leu Thr Pro Tyr His Lys Asp Arg Thr Gly Ser Ala Ile Thr Ile
            965                 970                 975

Asp Ser Ser Gln Gly Ala Thr Phe Asp Ile Val Thr Leu His Leu Pro
        980                 985                 990

Ser Pro Lys Ser Leu Asn Lys Ser Arg Ala Leu Val Ala Ile Thr Arg
        995                 1000                1005

Ala Arg His Gly Leu Phe Ile Tyr Asp Pro His Asp Gln Leu Gln
    1010                1015                1020

Glu Phe Phe Asn Leu Thr Pro Glu Arg Thr Asp Cys Asn Leu Ala
    1025                1030                1035

Phe Ser Arg Gly Asp Glu Leu Val Val Leu Asn Val Asp Asn Ala
    1040                1045                1050

Val Thr Thr Val Ala Lys Ala Leu Glu Thr Gly Ser Pro Arg Phe
    1055                1060                1065

Arg Val Ser Asp Pro Arg Cys Lys Ser Leu Leu Ala Ala Cys Ser
    1070                1075                1080

Ala Ser Leu Glu Gly Ser Cys Met Pro Leu Pro Gln Val Ala His
    1085                1090                1095

Asn Leu Gly Phe Tyr Phe Ser Pro Asp Ser Pro Ala Phe Ala Pro
    1100                1105                1110

Leu Pro Lys Glu Leu Ala Pro His Trp Pro Val Thr His Gln
    1115                1120                1125

Asn Asn Arg Ala Trp Pro Asp Arg Leu Val Ala Ser Met Arg Pro
    1130                1135                1140

Ile Asp Ala Arg Tyr Ser Lys Pro Met Val Gly Ala Gly Tyr Val
    1145                1150                1155

Val Gly Pro Ser Ile Phe Leu Gly Thr Pro Gly Val Val Ser Tyr
    1160                1165                1170

Tyr Leu Thr Leu Tyr Ile Gly Gly Glu Pro Gln Ala Leu Pro Glu
    1175                1180                1185

Thr Leu Val Ser Thr Gly Arg Ile Ala Thr Asp Cys Arg Glu Tyr
    1190                1195                1200

Leu Asp Ala Ala Glu Glu Ala Ala Arg Glu Leu Pro His Ala
    1205                1210                1215

Phe Ile Gly Asp Val Lys Gly Thr Thr Ile Gly Gly Cys His His
    1220                1225                1230

Ile Thr Ser Lys Tyr Leu Pro Arg Ser Leu Pro Lys Asp Ser Val
    1235                1240                1245

Ala Val Val Gly Val Ser Ser Pro Gly Arg Ala Ala Lys Ala Val
    1250                1255                1260

Cys Thr Leu Thr Asp Val Tyr Leu Pro Glu Leu Arg Pro Tyr Leu
    1265                1270                1275

Gln Pro Glu Thr Ala Ser Lys Cys Trp Lys Leu Lys Leu Asp Phe
    1280                1285                1290

Arg Asp Val Arg Leu Met Val Trp Lys Gly Ala Thr Ala Tyr Phe
    1295                1300                1305

Gln Leu Glu Gly Leu Thr Trp Ser Ala Leu Pro Asp Tyr Ala Arg
    1310                1315                1320

Phe Ile Gln Leu Pro Lys Asp Ala Val Val Tyr Ile Asp Pro Cys
    1325                1330                1335

Ile Gly Pro Ala Thr Ala Asn Arg Lys Val Val Arg Thr Thr Asp
```

```
                   1340                1345                1350

Trp  Arg  Ala  Asp  Leu  Ala  Val  Thr  Pro  Tyr  Asp  Tyr  Gly  Ala  Gln
          1355                1360                1365

Val  Ile  Leu  Thr  Thr  Ala  Trp  Phe  Glu  Asp  Leu  Gly  Pro  Gln  Trp
     1370                1375                1380

Lys  Ile  Leu  Gly  Leu  Gln  Pro  Phe  Arg  Arg  Thr  Phe  Gly  Phe  Glu
1385                1390                1395

Asn  Thr  Glu  Asp  Trp  Ala  Ile  Leu  Ala  Arg  Arg  Met  Asn  Asp  Gly
     1400                1405                1410

Lys  Asp  Tyr  Thr  Asp  Tyr  Asn  Trp  His  Cys  Val  Arg  Glu  Arg  Pro
1415                1420                1425

His  Ala  Ile  Tyr  Gly  Arg  Ala  Arg  Asp  His  Thr  Tyr  His  Phe  Ala
     1430                1435                1440

Leu  Gly  Thr  Glu  Leu  Gln  Val  Glu  Leu  Gly  Arg  Pro  Arg  Leu  Pro
1445                1450                1455

Pro  Glu  Gln  Val  Pro
     1460

<210> SEQ ID NO 4
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met  Gln  Trp  Val  Tyr  Cys  Gly  Val  Lys  Ser  Val  Ser  Cys  Ser  Trp  Met
1                   5                   10                  15

Pro  Ser  Leu  Ser  Ser  Leu  Leu  Val  Trp  Leu  Thr  Leu  Ser  Ser  Phe  Ser
               20                  25                  30

Pro  Tyr  Cys  Leu  Gly  Ser  Leu  Leu  Gln  Ala  Gly  Tyr  Trp  Ser  Ser  Phe
          35                   40                  45

Ser  Glu  Trp  Phe  Ala  Pro  Arg  Phe  Ser  Val  Arg  Ala  Leu  Pro  Phe  Thr
     50                   55                  60

Leu  Pro  Asn  Tyr  Arg  Arg  Ser  Tyr  Glu  Gly  Leu  Leu  Pro  Asn  Cys  Arg
65                   70                  75                  80

Pro  Asp  Val  Pro  Gln  Phe  Ala  Val  Lys  His  Pro  Leu  Gly  Ile  Leu  Trp
                85                   90                  95

His  Met  Arg  Val  Ser  His  Leu  Ile  Asp  Glu  Met  Val  Ser  Arg  Arg  Ile
               100                  105                 110

Tyr  Arg  Thr  Met  Glu  His  Ser  Gly  Gln  Ala  Ala  Trp  Lys  Gln  Val  Val
          115                  120                 125

Ser  Glu  Ala  Thr  Leu  Thr  Lys  Leu  Ser  Arg  Leu  Asp  Val  Val  Thr  His
     130                  135                 140

Phe  Gln  His  Leu  Ala  Ala  Val  Glu  Ala  Asp  Ser  Cys  Arg  Phe  Leu  Ser
145                  150                 155                 160

Ser  Arg  Leu  Ala  Met  Leu  Lys  Asn  Leu  Ala  Val  Gly  Asn  Val  Ser  Leu
                165                  170                 175

Glu  Tyr  Asn  Thr  Thr  Leu  Asp  Arg  Val  Glu  Leu  Ile  Phe  Pro  Thr  Pro
               180                  185                 190

Gly  Thr  Arg  Pro  Lys  Leu  Thr  Asp  Phe  Arg  Gln  Trp  Leu  Ile  Ser  Val
          195                  200                 205

His  Ala  Ser  Ile  Phe  Ser  Ser  Val  Ala  Ser  Ser  Val  Thr  Leu  Phe  Thr
     210                  215                 220
```

```
Val Leu Trp Leu Arg Ile Pro Ala Leu Arg Tyr Val Phe Gly Phe His
225                 230                 235                 240

Trp Pro Thr Ala Thr His His Ser Asn
                245

<210> SEQ ID NO 5
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Tyr Gln Arg Ala Arg Phe His Leu Leu Cys Gly Phe Val
1               5                   10                  15

Cys Tyr Leu Val His Ser Ala Leu Ala Ser Asn Ser Ser Thr Leu
                20                  25                  30

Cys Phe Trp Phe Pro Leu Ala His Gly Asn Thr Ser Phe Glu Leu Thr
            35                  40                  45

Ile Asn Tyr Thr Ile Cys Lys Pro Cys Pro Thr Ser Gln Ala Ala Gln
50                  55                  60

Gln Arg Leu Glu Pro Gly Arg Asn Val Trp Cys Lys Ile Gly His Asp
65                  70                  75                  80

Arg Cys Glu Glu Arg Asp His Asp Glu Leu Ser Met Ser Ile Pro Ser
                85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
            130                 135                 140

Ala Glu His Asp Gly Gln Asn Ser Thr Ile Ser Ala Arg His Asn Ile
145                 150                 155                 160

Ser Ala Ser Tyr Ala Val Tyr Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Ala Ser Pro Ala Ser
            195                 200                 205

Arg Arg Ile Tyr Gln Ile Leu Arg Pro Thr Arg Pro Arg Leu Pro Val
210                 215                 220

Ser Trp Ser Phe Arg Thr Ser Ile Val Ser Asn Leu Thr Gly Pro Gln
225                 230                 235                 240

Gln Arg Lys Val Pro Leu Pro Ser Gly Gly Arg Pro Asn Val Val Lys
                245                 250                 255

Pro Ser Ala Phe Pro Ser Thr Ser Arg
                260                 265

<210> SEQ ID NO 6
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

-continued

```
Met Ala Ala Thr Ile Leu Phe Leu Leu Ala Gly Ala Gln His Leu Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Gly Phe Met Val Leu Gln
        35                  40                  45

Asn Ile Asn Cys Phe Gln Ser His Arg Ala Ser Thr Ala Gln Gly Thr
50                  55                  60

Thr Pro Leu Arg Arg Ser Ser Gln Cys Arg Glu Ala Val Gly Ile Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Ile Ser Gly Val
            115                 120                 125

Val Ser Ala Cys Val Asn Phe Thr Asp Tyr Val Ala His Val Thr Gln
            130                 135                 140

His Thr Gln Gln His His Leu Val Ile Asp His Ile Arg Leu Leu His
145                 150                 155                 160

Phe Leu Thr Pro Ser Thr Met Arg Trp Ala Thr Thr Ile Ala Cys Leu
                165                 170                 175

Leu Ala Ile Leu Leu Ala Val
            180

<210> SEQ ID NO 7
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Cys Ser Cys Lys Leu Gly His Phe Leu Thr Pro His Ser Cys
1               5                   10                  15

Phe Trp Trp Leu Phe Leu Leu Cys Thr Gly Leu Ser Trp Ser Phe Val
            20                  25                  30

Asp Gly Asn Asp Asp Ser Ser Ser Gln Tyr Ile Tyr Asn Leu Thr
        35                  40                  45

Ile Cys Glu Leu Asn Gly Thr Glu Trp Leu Ser Gly His Phe Asp Trp
50                  55                  60

Ala Val Glu Thr Phe Val Leu Tyr Pro Val Ala Thr His Ile Ile Ser
65                  70                  75                  80

Leu Gly Phe Leu Thr Thr Ser His Phe Leu Asp Ala Leu Gly Leu Gly
                85                  90                  95

Ala Val Ser Ala Thr Gly Phe Ile Gly Glu Arg Tyr Val Leu Ser Ser
            100                 105                 110

Met Tyr Gly Val Cys Ala Phe Ala Ala Phe Val Cys Phe Val Ile Arg
            115                 120                 125

Ala Ala Lys Asn Cys Met Ala Cys Arg Tyr Ala Arg Thr Arg Phe Thr
            130                 135                 140

Asn Phe Ile Val Asp Asp Arg Gly Arg Ile His Arg Trp Lys Ser Ser
145                 150                 155                 160

Ile Val Val Glu Lys Leu Gly Lys Ala Glu Val Gly Gly Asp Leu Val
                165                 170                 175
```

Asn Ile Lys His Val Leu Glu Gly Val Lys Ala Gln Pro Leu Thr
            180                 185                 190

Arg Thr Ser Ala Glu Gln Trp Glu Ala
        195                 200

<210> SEQ ID NO 8
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Ser Leu Asp Asp Phe Cys Asn Asp Pro Thr Ala Ala Gln Lys
1               5                   10                  15

Leu Val Leu Ala Phe Ser Ile Thr Tyr Thr Pro Ile Met Ile Tyr Ala
            20                  25                  30

Leu Lys Val Ser Arg Gly Arg Leu Leu Gly Leu Leu His Ile Leu Ile
        35                  40                  45

Phe Leu Asn Cys Ser Phe Thr Phe Gly Tyr Met Thr Tyr Val His Phe
    50                  55                  60

Gln Ser Thr Asn Arg Val Ala Phe Thr Leu Gly Ala Val Val Ala Leu
65                  70                  75                  80

Leu Trp Gly Val Tyr Ser Leu Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Pro Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 9
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Gly Lys Asn Gln Ser Gln Lys Lys Arg Arg Asn Ala Ala Pro
1               5                   10                  15

Met Gly Lys Gly Gln Pro Val Asn Gln Leu Cys Gln Leu Leu Gly Thr
            20                  25                  30

Met Ile Lys Ser Gln Arg Gln Gln Ser Arg Gly Gly Gln Ala Lys Lys
        35                  40                  45

Lys Lys Pro Glu Lys Pro His Phe Pro Leu Ala Ala Glu Asp Asp Ile
    50                  55                  60

Arg His His Leu Thr Gln Ala Glu Arg Ser Leu Cys Leu Gln Ser Ile
65                  70                  75                  80

Gln Thr Ala Phe Asn Gln Gly Ala Gly Thr Ala Ser Leu Ser Ser Ser
                85                  90                  95

```
Gly Lys Val Ser Phe Gln Val Glu Phe Met Leu Pro Val Ala His Thr
            100                 105                 110
Val Arg Leu Ile Arg Val Thr Ser Thr Ser Ala Ser Gln Gly Ala Asn
                115                 120                 125
```

<210> SEQ ID NO 10
<211> LENGTH: 14843
<212> TYPE: DNA
<213> ORGANISM: Porcine reproductive respiratory syndrome virus

<400> SEQUENCE: 10

| | | | | | |
|---|---|---|---|---|---|
| tttgtgtacc | ttggaggcgt | gggtacagcc | ctgccccacc | ccttggcccc | tgttctagcc | 60 |
| cgacaggtac | ccttctctct | cggggcgagc | gcgccgcctg | ctgctcccct | gcggcgggaa | 120 |
| ggacctcccg | agtatttccg | gagagcacct | gctttacggg | atctccgccc | tttaaccatg | 180 |
| tctgggatgt | tctcccggtg | catgtgcacc | ccggctgccc | gggtattttg | gaacgccggc | 240 |
| caagtctatt | gcacacggtg | tctcagtgca | cggtctcttc | tctctccaga | acttcaggac | 300 |
| acggacctcg | gtgcagttgg | cttgtttcac | aagcctaaag | acaagctcca | ttggaaagtt | 360 |
| cccattggta | tcccccaggt | ggaatgttct | ccatctgggt | gttgctggct | gtcaaccatt | 420 |
| tttcctttag | cgcgcatgac | ctccggcaat | cacaacttcc | ttcaacgact | cgtgaaggtt | 480 |
| gctgacgtat | tgtaccgtga | cggttgctta | accctagac | acctccgtga | actccaagtt | 540 |
| tacgagcgtg | gttgcaattg | gtatccgatt | acggggcctg | tgcctgggat | ggctgtgtac | 600 |
| gcgaactcca | tgcacgtgtc | cgaccaaccg | ttccctggtg | ccactcatgt | gttaacaaat | 660 |
| tcccctttgc | ctcaacgggc | ttgtcggcag | ccgttctgtc | cgttcgaaga | ggcccattct | 720 |
| agcatataca | ggtgggaaaa | atttgtaatt | tttatggatt | cctcctccga | cggtcgatct | 780 |
| cgcatgatgt | ggactccgga | atccgatgac | tccacggctt | ggaagttct | gccgcccgag | 840 |
| ctagaacacc | aggtcaaggt | ccttgttcgg | agctttcccg | cccatcacct | tgtcgacctt | 900 |
| gccgattggg | agctcactga | gtcccctgag | aacggttttt | ccttcagcac | gtcacatcct | 960 |
| tgcggctacc | ttgttcggga | cccggctgta | tccgaaggca | agtgttggct | ttcctgcttt | 1020 |
| ttgagccagt | cagccgaagt | gctcagtcgc | gaggcgcatc | tggctaccgc | ctatggttac | 1080 |
| caaaccaagt | ggggtgtgcc | tggcaagtac | atccagcgca | gacttcaagt | tcacggtctc | 1140 |
| cgtgctgtgg | tcgaccctga | tggtcccatt | cacgttgaag | cattgtcttg | cccccagtct | 1200 |
| tggatcaggc | acttgaccct | gaatgatgat | gtcaccccgg | gattcgttcg | cctaatgtct | 1260 |
| cttcgcattg | tgccgaacac | agagcctacc | acacaccgga | tctttcgttt | tggagtgcac | 1320 |
| aagtggtatg | gtgccgccgg | caaacgggcc | cgtggcaagc | gtgccgccaa | aagtgagaaa | 1380 |
| gactcggctt | ccaccctcaa | ggttgcccga | ccgacttcca | ccagtggaat | cgtcacctac | 1440 |
| tccccacctg | cggacgggtc | ttgtggttgg | catgcccttg | ccgccatact | gaaccggatg | 1500 |
| attaataatg | acttcacgtc | ccctctgcct | cggtacaaca | ggccgagga | cgattgggct | 1560 |
| tctgatggtg | accttgctca | ggccattcaa | tgtttgcaac | tacctgccgc | catagctcgg | 1620 |
| aaccgcgcct | gccctaacgc | caaatacctc | gtaaaactca | acggagttca | ttgggaggta | 1680 |
| gaggtgaggc | ctggaatggc | tcctcgctcc | ctctctcgtg | agtgcgttgt | tggcgtctgc | 1740 |
| tctgaaggct | gtgtcgcgtc | gccttacccg | gaggacgggt | tgcctaaacg | tgcacttgag | 1800 |
| gccctggcgt | ctgcttatag | actgccttca | gactgtgttt | gtgatggtat | tattgacttc | 1860 |
| cttgccaatc | cacctcccca | ggagttctgg | actcttgaca | aaatgttgac | ttccccgtca | 1920 |

```
ccggagcagt ccggcttctc tagtctgtat aaattgttgt tagaggtctt gccgcagaaa    1980
tgcggatcca cagaaggggga attcatctat actgttgaga ggatgttgaa ggattgtccg    2040
agctccaaac aggccatggc cctccttgca aaaattaagg tcccatcctc aaaggcccca    2100
tccgtgactc tgaacgagtg cttccccacg gatgttccag tcaactctga gttaatatct    2160
tgggaagagc ccaaagaccc tggcgctgct gttgtcctat gtccatcgga tgcaaaagaa    2220
tctaaggaaa cagcccctga agaagctcaa gcgagaaacc gtaaggtcct ccaccctgtg    2280
gtccttaccg aggaacttag cgagcaacag gtgcaggtgg ttgagggtga tcaggatatg    2340
ccactggatt tgacttggcc aaccttaacc gctacggcga cccctgttag agggccggta    2400
ccggacaatt tgagctctgg cattggtgcc cagcccgcta ccgttcaaga actcattctg    2460
gcgaggcctg caccccgtct tgttgagcgc tgtggcacgg agtcgaacgg cagcagttca    2520
tttctggatt tgcctgacgt gcagacctcg gaccagcctt tagacctgtc cctggccgcg    2580
tggcctgtaa gggctaccgc gtctgacccc ggttggatcc acggtaggcg tgagcctgtc    2640
tttgtgaagc ctcgaggtgt tttctctgat ggcgagtcgg cccttcagtt cggagagctt    2700
tccgaagcca gttctgtcgt cgatgaccgg acaaaagaag ctccggtggt tgacgccccc    2760
atcgatttga caacttcgaa cgagacgctc tctgggtctg acccctttga attcgccaaa    2820
ttcaggcgcc cgcgtttctc cgcgcaagct ttaatcgacc gaggtggtcc gcttgccgat    2880
gttcatgcaa agataaagag tcgggtatat gaacaatgcc ttcaagcttg tgaacctggt    2940
agtcgtgcga ccccagccac caagaagtgg ctcgacaaaa tgtgggacag ggtggacatg    3000
aaaacttggc gctgcacctc gcagttccaa gctggtcaca ttcttgagtc cctcaaattc    3060
ctccctgaca tgattcaaga cacaccgcct cctgttccca ggaagaaccg agctggtgac    3120
agtgccggcc tgaagcaact ggtggcgcag tgggatagga aattgagtgt gacacccccc    3180
acaaaaccgg ttggaccggt gcttgaccag accgtccctc tgcctatgga catccagcaa    3240
gaagatgcca tctccgctga caagccaccc cattcgcaaa accttctag tcaagtagat    3300 gtgggtggag gttggaaaag ttttatgctc tccggcaccc gtttcgcggg gtccgttagt    3360
cagcgcctta cgacatgggt ttttgaggtt ctctcccatc tcccagcttt tatgctcaca    3420
cttttctcgc cacggggctc tatggctcca ggtgattggc tgtttgcagg tgctgttcta    3480
cttgctctcc tgctctgccg ttcttaccca atactcggat gccttccctt attgggtgtc    3540
ttttctggtt ctgtgcggtg tgttcgtttg ggtgtttttg gttcttggat ggcttttgct    3600 gtattttat tctcgactcc acccgaccca gtcggttctt cttgtgacca cgattcgccg    3660
gagtgtcatg ctgagctttt ggctcttgag cagcgccaac tttgggaacc tgtgcgcagc    3720
cttgtggtcg ggccatcggg cctcttatgc gtcattcttg gcaagttact cggtgggtca    3780
cgttgtctct ggtttgttct cctacgtata tgcatgctcg cagatttggc aatttctctt    3840
atttatgtgg tgtcccaagg cgttgtcac aagtgtggg gaaagtgtat aaggacggct    3900
cctgcagaag tgacccttaa tgtgtttcct ttttcgcgcg ccacccgctc atctcttgtg    3960
tccttgtgtg atcggttcca agcgccaaaa ggagttgacc ccgtgcactt ggcgacaggc    4020
tggcgcgggg ctggtgtgg tgagagcccct attcatcaat cacaccaaaa accgatagct    4080
tatgccaact tggatgaaaa gaagatatcc gcccagacgg tgattgctgt cccgtatgat    4140
cccagtcagg ccattaaatg cctgaaagtt ttgcaggcag agggggctat tgtggaccag    4200
cctacgcccg aggtcgtccg tgtgtctgag attcccttct cggccccatt ttttccgaag    4260
gtcccagtca cccagattg cagggttgtg gtagattcgg acactttgt ggctgcggtc    4320
```

```
cgctgcggtt attcgacagc acaactggtc cttggtcggg gcaactttgc caagctaaat    4380
cagacccccc tcaggaactc tgtccccacc aaaacaactg gtggggcctc atacacccct    4440
gccgtggccc aggtatctgt gtggactctt gttcatttca tcctcggcct ttggttaacg    4500
tcacctcaag tgtgtggtcg agggacctct gacccgtggt gttcgaaccc tttttcgtat    4560
cctacttatg gccccggagt tgtgtgttcc tctcgactct gcgtgtctgc cgacggagtt    4620
accctgccat tgttctcagc cgttgccat  ctttccggta gagaggtggg gattttatt     4680 ttggtgcttg cctccttggg cgctttagcc caccgcttgg ctcttaaggc agacatgtca    4740
atggtctttt tggcgttttg tgcttacgcc tggcccatga gctcctggtt aatttgcttc    4800
tttcctatgc tcttgaggtg ggtaaccctt catcctctca ctatgctttg ggtgcactca    4860
tttttggtgt tttgcctacc agctgccggc gttctctcgc tgggaataac cggtcttctt    4920
tgggcagttg gccgtttcac ccaggttgcc ggaattatca caccttatga catccaccag    4980
tatacctccg gaccacgtgg tgcagctgct gtagcaacgg ctccagaagg tacttacatg    5040
gcggccgttc ggagagccgc tttgactgga cggactttga tcttcacacc atctgcagtc    5100
ggatcccttc ttgaaggtgc tttcagaact caaaagccct gccttaacac cgtgaatgtc    5160
gtaggctctt cccttggttc tggaggagtt ttcaccattg atggcagaag agtcatcgtc    5220
actgccaccc atgtgttgaa tggtaacaca gccagggtca ctggtgattc ctacaaccgc    5280
atgcacacgt tcaatactaa tggtgattat gcctggtccc atgctgatga ctggcaaggc    5340 gttgcccta tggttaagat cgctaagggg tatcgcggtc gtgcctactg gcaaacgtca     5400
accggagtcg aacctggcat catgggggaa ggattcgcct tctgtttcac taactgtggc    5460
gactcagggt cacctgtcat ttcagaagct ggtgaccta ttggagtcca taccggttca      5520
aacaaactcg gttctggtct tgtgacaacc cctgaagggg agacctgctc catcaaggaa    5580
actaggctct ctgaccttc tagacatttt gcaggtccaa gcgtccctct tggggacatt     5640
aagttgagcc cagccatcat ccctgatgtg acaactattc cgagtgactt ggcatcgctc    5700
cttgcttctg tccccgtgat ggaaggtggc ctctcaactg tccagctttt gtgcgtcttt    5760
ttccttctct ggcgcatgat gggccatgcc tggacaccca ttgttgccgt aggcttcttt    5820
ttgctgaatg aaattctccc agcagtcttg gtccgagctg tgttctcttt tgcactcttt    5880
gtacttgcat gggccacccc ctggtcggca caagtgttga tgattagact cctcacggcg    5940
gctctcaacc gcaacaggtt gtccctggcg ttctacgcac tcggaggtgt cgttggcctg    6000
gccacagaaa tcgggacttt tgctggtgga tggcctgaac tgtcccaagc cctctcgaca    6060
tactgcttcc tgcccaggtt ccttgctgtg actagttatg tccccaccat catcatcggt    6120
gggctccatg ccctcggcgt aattttgtgg ttattcaaat accgatgcct ccacaacatg    6180
ctggttggtg atgggagttt ctcaagcgct ttcttcctac ggtattttgc tgagggtaat    6240
cttaggaaag gcgtgtcgca gtcctgtggc atgaataacg aatccctgac agctgctttg    6300
gcttgcaagt tgtcgcaagc tgaccttgat tttttgtcca gtttaacgaa cttcaagtgc    6360
tttgtgtccg cttcaaacat gaaaaatgca gctggccaat acatcgaggc ggcgtatgct    6420
agagctctgc gtcaggagct ggcctccttg gttcaggttg acaagatgaa aggagtattg    6480
gccaagctcg aggctttcgc tgagacggcc actccgtcac ttgacacagg tgacgtgatt    6540
gttctgcttg gcaacaccc ccatggatcc atcctgaca ttaatgtggg gggtgaaagg      6600
aaaactgtgt ctgtgcaaga aacacgatgc ctgggtggtt ccaaattcag tgtctgcact    6660
```

```
gtcgtgtcca acacgcccgt ggataccttg accggcatcc cacttcagac gccaacccca   6720
cttttttgaaa atggcccgcg ccatcgcagc gaggacgacg accttaaagt tgagagaatg   6780
aaaaaacact gtgtatccct cggcttccac aaaatcaatg gtaaagttta ctgcaaaatt   6840
tgggacaagt ctaacggcga caccttttac acggatgatt cccgatacac tcaagaccat   6900
gcttttcagg acaggtcaac cgactataga gacagggatt atgaaggtgt acagaccgcc   6960
ccccaacagg gattcgatcc aaagtccgaa gcccctgttg gcactgttgt aatcggtggc   7020
attacgtata acaggcatct ggtcaaaggt aaggaggtcc tagttcccaa acctgacaac   7080
tgccttgaag ctgccagact gtcccttgag caagctcttg ctgggatggg ccaaacttgt   7140
gaccttacag ctaccgaagt ggagaaacta aagcgcatca ttagtcaact ccaaggtctg   7200
accactgaac aggctttaaa ctgctagccg ccagcggctt gacccgctgt ggccgcggcg   7260
gcctagttgt aactgaaacg gcggtaaaaa tcgtaaaata ccacagcaga actttcacct   7320
taggctcttt agacctaaaa gtcacctccg aggtggaggt gaagaaatca actgagcagg   7380
ggcacgctgt cgtggcgaac ttatgttccg gtgtcgtctt gatgaggcct cacccaccgt   7440
cccttgttga cgttctcctc aaacccggac ttgacacaac accggcatt caaccagggc   7500
atggggccgg gaatatgggc gtgaacggtt ctatttggga ttttgaaact gcacccacaa   7560
aggtagaact agagttgtcc aagcaaataa tccaagcatg tgaagtcagg cgcggggacg   7620
cccctaacct ccaactcccc tacaagcttt atcctgtcag gggggacccc gagcggcgta   7680
aaggtcgcct tgtcaacact aggtttggag atttaccta caaaactccc caagacacca   7740
agtccgcaat tcatgcggct tgttgcctgc atcccaatgg ggtcctcgtg tctgatggta   7800
aatccacgct gggtaccact cttcaacatg gtttcgagct ttatgtcccc actgtacctt   7860
atagtgtcat ggaataccct gattcacgcc ctgacacccc ttttatgtgt actaaacatg   7920
gcacttccaa ggctgctgca gaggacctcc aaaaatatga cctatccact caagggtttg   7980
tcttgcctgg ggtcctacgc ctagtgcgca ggttcatctt tagccatgtt ggtaaggcgc   8040
caccactgtt ccttccatca acctaccctg ccaagaactc catggcaggg gtcaatggcc   8100
agaggttccc aacaaaggat gtccagagca tacctgaaat tgatgaaatg tgcgcccgtg   8160
ccgtcaagga aaattggcag actgtgacac cttgcaccct caaaaaacag tactgttcca   8220
aacctaaaac tagaaccatc ctaggtacca acaacttcat agccttggct cacaggtcag   8280
cactcagtgg tgtcacccag gcgttcatga agaaggcctg gaagtcccca attgccttgg   8340
ggaaaaacaa gtttaaggaa ttgcattgca ctgtcgccgg cagatgcctt gaggctgacc   8400
tggcttcctg cgatcgcagc accccgcca ttgtgaggtg gtttgttgcc aacctcctgt   8460
atgaacttgc aggatgtgaa gagtacttgc ctagctacgt gctcaactgt tgccatgacc   8520
ttgtggcaac gcaggatggc gctttcacaa aacgcggtgg cctgtcgtcc ggggaccccg   8580
tcaccagtgt gtccaacacc gtctactcac tgataattta cgcccagcac atggtgcttt   8640
cggccttgaa gatgggtcat gaaattggtc tcaagttcct tgaggaacag ctcaaatttg   8700
aggaccttct tgaaatccag cccatgttag tgtattctga tgacctcgtc ttgtatgcgg   8760
aaagaccac ttttcccaac taccattggt gggtcgagca tcttgacctg atgttgggct   8820
ttaaaacgga cccaaagaaa actgtcataa ctgataaacc cagttttctc ggctgcagaa   8880
ttgaagcagg acggcagtta gtccccaatc gcgaccgtat tctggctgct cttgcatatc   8940
atatgaaggc gcagaacgcc tcagagtatt atgcgtccgc tgccgcaatt ctgatggatt   9000
cgtgtgcttg cattgaccat gaccccgagt ggtatgagga ccttatctgc ggcatcgccc   9060
```

```
ggtgtgctcg ccaggacggt taccgttttc caggcccggc atttttcatg tccatgtggg    9120
agaagctgaa aagtcataac gaagggaaga aatgccgtca ctgcggcatc tgcgacgcca    9180
aagccgacta tgcgtccgcc tgtggacttg atttgtgttt gttccattca cactttcatc    9240
aacactgccc agtcactctg agctgtggcc accatgccgg ttcaaaggaa tgttcgcagt    9300
gtcagtcacc tgtcggggct ggcaaatccc cccttgacgc tgtgctgaaa caaatcccgt    9360
acaaacctcc tcgtaccatt atcatgaagg tggacaacaa acaacgacc cttgacccgg    9420 gaagatatca gtcccgtcga ggtcttgttg cagtcaaaag aggtattgca ggtaatgagg    9480
ttgatctttc tgatggagac taccaagtgg tgcctctttt gccgacttgc aaagacataa    9540
acatggtgaa ggtggcttgc aacgtactac tcagcaagtt tatagtaggg ccgccaggtt    9600
ccggaaaaac cacctggcta ctgaaccaag tccaggacga tgatgtcatt tacacaccta    9660
ctcatcagac aatgtttgac atagtcagtg ctcttaaagt ttgcaggtat tccatcccag    9720
gagcctcagg actcccttt ccaccacctg ccaggtccgg gccgtgggtt aggctcatcg    9780
ccagcggaca tgtccctggc cgagtgtcat atctcgatga ggcaggatat tgcaatcatc    9840
tagacattct aaggctgctt tccaaaacac cccttgtgtg tttgggtgac cttcagcaac    9900
ttcacccggt cggctttgat tcctattgtt atgtgttcga tcagatgcct cagaagcagc    9960
tgaccaccat ttatagattt ggccctaaca tctgtgcagc catccagcct tgttacaggg    10020
agaaacttga atccaaggcc aggaacacca gagtggtttt caccacccgg cctgtggcct    10080
ttggtcaggt cctgacaccg taccacaaag atcgtaccgg ctctgcaata actatagatt    10140
catcccaggg ggcgaccttc gacattgtga cattgcatct accatcgcca aagtccctaa    10200
acaaatcccg agcacttgta gccatcactc gggcaagaca tgggttgttc atttatgacc    10260
ctcatgacca actccaggag ttttcaact taaccccga gcgcactgat tgtaaccttg    10320
cgttcagccg tggggatgag ctggttgttt tgaatgtgga taatgcggtc acaactgtag    10380
cgaaggccct agagacaggt tcaccccgat ttcgagtatc ggacccgagg tgcaagtctc    10440
tcttagccgc ttgttcggcc agtctagaag ggagctgcat gccactacca caagtagcac    10500
ataacctggg gttttacttt tccccggaca gcccagcttt tgcaccctg ccaaaagagc    10560 tggcgccaca ttggccagtg gtcacccacc agaataatcg agcgtggcct gatcgacttg    10620
tcgctagtat gcgcccaatt gatgcccgct acagcaagcc aatggtcggt gcagggtatg    10680
tggtcgggcc atccattttt cttggcactc ctggtgtggt gtcatactat ctcacattat    10740
acatcggggg cgagcctcag gccctgccag aaacactcgt ttcaacagga cgtatagcca    10800
cagattgtcg ggaatatctc gacgcggctg aggaagaggc agcgagagaa cttccccacg    10860
catttattgg cgatgtcaaa ggcactacgg tcgggggtg tcaccacatt acatcgaaat    10920
acctacctag gtccctgcct aaagactctg ttgctgtggt tggggtgagt tcgcccggta    10980
gggctgctaa agccgtgtgc actctcaccg atgtgtacct ccccgaactc cgaccatatt    11040
tgcaaccgga gacggcatca aaatgctgga aacttaaact ggatttcagg gatgttcgac    11100
tgatggtctg gaaaggcgcc acagcctatt tccagttgga agggctgaca tggtcagcgc    11160
tgcccgatta tgctaggttc attcagctac ccaaggatgc cgttgtgtac atcgatcgt    11220 gtatagggcc ggcaacagcc aatcgcaagg ttgtgcgaac cacagactgg cgggccgacc    11280
tggcagtgac accgtatgat tacggtgctc aggtcatttt tgacaacagcc tggttcgagg    11340 accttgggcc gcagtggaag attttgggt tgcagccttt cagacgaaca tttggctttg    11400
```

```
agaacactga agattgggca attctcgcac gccgtatgaa tgacggcaaa gattacactg    11460
actataattg gcattgtgta cgagaacgcc cacacgcaat ttacgggcgc gcccgtgacc    11520
atacgtatca ttttgcccett ggcactgaac tgcaagtaga gctgggcaga ccccggctgc   11580
ctcctgagca agtgccgtga acgcggagtg atgcaatggg ttcactgtgg agtaaaatca    11640
gtcagttgtt cgtggatgcc ttcactgagt tccttgttag tgtggttgac attgtcatct    11700
ttctcgccat attgtttggg ttcactgttg caggctggtt attggtcttc cttctcagag    11760
tggtttgctc cgcgtttctc cgttcgcgct ctgccattca ctctcccgaa ctatcgaagg    11820
tcctatgagg gcttgctacc caactgcaga ccggatgtcc cacaattcgc agttaagcac    11880
ccgttgggta ctttggca tatgcgagtc tcccacctaa ttgacgaaat ggtctctcgc      11940
cgcatttacc ggaccatgga acattcgggt caagcggcct ggaagcaggt tgttagtgaa    12000
gccactctca caaaactgtc aaggcttgac gtagtcactc atttccaaca cctggccgca    12060
gtggaggctg attcttgccg cttccttagc tcacgactcg cgatgctgaa aaaccttgcc    12120
gttggcaatg tgagcctgga gtacaacact actttggacc cgttgagct catctttccc     12180
acaccaggta cgaggcccaa gttgaccgat tttaggcaat ggcttatcag cgtgcacgct    12240
tccatcttct cctctgtggc ttcgtctgtt accttgttca cagtgctttg gcttcgaatt    12300
ccagctctac gctatgtttt tggtttccat tgcccacgg caacacatca ttcgaactaa    12360
ctatcaatta cactatatgt aagccatgcc ctaccagtca agctgcccaa caagactcg     12420
agcctggccg taacgtgtgg tgcaaaatag ggcacgacag gtgtgaggaa cgtgaccatg    12480
atgagttgtc aatgtccatt ccgtccgggt acgacaacct caaacttgag ggttattatg    12540
cttggctggc ttttttgtcc ttttcctacg cggcccaatt ccatccggag ctgttcggaa    12600
taggaaacgt gtcgcgcgtc tttgtggata agcgacacca gttcatttgc gccgagcatg    12660
atggacaaaa ttcaaccata tctgccagac acaacatctc cgcgtcgtat cggtgtatt    12720
accatcatca aatagacggg ggcaattggt ttcatttgga atggctgcga ccattctttt    12780
cctcctggct ggtgctcaac atctcatggt ttctgaggcg ttcgcctgca agccctgctt    12840
ctcgacgcat ctatcagata ttaagaccaa cacgaccgcg gctgccggtt tcatggtcct    12900
tcagaacatc aattgttttcc aatctcacag ggcctcaaca gcgcaaggta ccactcccct   12960
caggaggtcg tcccaatgtc gtgaagccgt cggcattccc cagtacatca cgataacggc    13020
taatgtgacc gatgaatcgt atttgtacaa cgcggacttg ctgatgcttt ccgcgtgcct    13080
tttctacgcc tcgaaatga gcgagaaagg cttcaaagtc atctttggga atatttctgg     13140
cgttgtttcc gcttgtgtta atttcacaga ttatgtggcc catgtgaccc aacacactca    13200
gcagcaccat ttggtaattg atcacattcg gttactacac ttcttgacac cgtctacgat    13260
gaggtgggct acaaccattg cttgtttgtt tgccattctt ttggcggtat gaaatgttct    13320
tgcaagttgg ggcatttctt gactcctcac tcttgcttct ggtggctttt tttgctgtgt    13380
accggcttgt cttggtcctt tgtcgatggc aacgacaaca gctcgacatc ccaatacata    13440
tataatttga cgatatgcga gctgaatggg accgaatggt tgtccggtca ttttgattgg    13500
gcagtcgaaa cctttgtgct ttacccagtt gccactcata tcatttcact gggttttctc    13560
acaacaagcc atttccttga tgcgctcggt ctcggcgctg tgtccgccac aggattcatt    13620
ggcgagcggt atgtacttag cagcatgtac ggcgtttgcg ccttcgcggc gctcgtatgt    13680
tttgtcatcc gtgctgctaa aaattgcatg gcttgccgct atgcccgcac ccggtttacc    13740
aacttcatcg tggacgaccg gggaagaatc catcgatgga agtcttcaat agtggtggag    13800
```

-continued

```
aaattgggca aagctgaagt cggtggtgac cttgtcaaca ttaagcatgt tgtcctcgaa    13860 gggggttaaag ctcaacccctt gacgaggact tcggctgagc aatgggaagc ctagacgact   13920
tttgcaacga tcccaccgcc gcacaaaaac tcgtgctggc ctttagcatc acatatacac    13980
ccataatgat atacgcccctt aaggtgtcac gcggccgact cctggggctg ttgcacatct    14040
tgatatttct gaattgttcc tttacttttg ggtacatgac atatgtgcat tttcaatcca    14100
ccaaccgtgt cgcactcact ctgggggctg tagtcgccct tttgtggggt gtttacagcc    14160
tcacagagtc atggaagttc atcacttcca gatgcagatt gtgttgccta ggccggcgat    14220
acattctggc ccctgcccat cacgtagaaa gtgctgcagg cctccattca atcccagcgt    14280
ctggtaaccg agcatacgct gtgagaaagc ccggactaac atcagtgaac ggcactctag    14340
tacctgggct tcggagcctc gtgctgggcg caaacgagc tgttaaacga ggagtggtta    14400
acctcgtcaa gtatggccgg taagaaccag agccagaaga aagaagaaa tgcagctccg    14460 atggggaaag gccagccagt caatcaactg tgccagttgc tgggtacaat gataaagtcc    14520
cagcgccagc aatctagggg aggacaggcc aaaaagaaga agcctgagaa gccacatttt    14580
cccctagctg ctgaagatga cattcggcac catctcaccc aggccgaacg ttccctctgc    14640
ttgcaatcga tccagacggc tttcaatcaa ggcgcaggaa ctgcgtcgct ttcatccagc    14700
gggaaggtca gtttccaggt tgagttcatg ctgccggttg ctcatacagt gcgcctgatt    14760
cgcgtgactt ctacatccgc cagtcagggt gcaaattaat ttgacagtca ggtgaatggc    14820
cgcgattgac gtgtggcctc taa                                            14843
```

<210> SEQ ID NO 11
<211> LENGTH: 2349
<212> TYPE: PRT
<213> ORGANISM: Porcine reproductive respiratory syndrome virus

<400> SEQUENCE: 11

```
Met Ser Gly Met Phe Ser Arg Cys Met Cys Thr Pro Ala Ala Arg Val
 1               5                  10                  15

Phe Trp Asn Ala Gly Gln Val Tyr Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe His Lys Pro Lys Asp Lys Leu His Trp Lys Val Pro Ile Gly
    50                  55                  60

Ile Pro Gln Val Glu Cys Ser Pro Ser Gly Cys Cys Trp Leu Ser Thr
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
           100                 105                 110

Pro Arg His Leu Arg Glu Leu Gln Val Tyr Glu Arg Gly Cys Asn Trp
       115                 120                 125

Tyr Pro Ile Thr Gly Pro Val Pro Gly Met Ala Val Tyr Ala Asn Ser
   130                 135                 140

Met His Val Ser Asp Gln Pro Phe Pro Gly Ala Thr His Val Leu Thr
145                 150                 155                 160

Asn Ser Pro Leu Pro Gln Arg Ala Cys Arg Gln Pro Phe Cys Pro Phe
                165                 170                 175

Glu Glu Ala His Ser Ser Ile Tyr Arg Trp Glu Lys Phe Val Ile Phe
```

```
                180                 185                 190
Met Asp Ser Ser Asp Gly Arg Ser Arg Met Met Trp Thr Pro Glu
                195                 200                 205

Ser Asp Ser Thr Ala Leu Glu Val Leu Pro Pro Glu Leu Glu His
        210                 215                 220

Gln Val Lys Val Leu Val Arg Ser Phe Pro Ala His His Leu Val Asp
225                 230                 235                 240

Leu Ala Asp Trp Glu Leu Thr Glu Ser Pro Glu Asn Gly Phe Ser Phe
                245                 250                 255

Ser Thr Ser His Pro Cys Gly Tyr Leu Val Arg Asp Pro Ala Val Ser
                260                 265                 270

Glu Gly Lys Cys Trp Leu Ser Cys Phe Leu Ser Gln Ser Ala Glu Val
        275                 280                 285

Leu Ser Arg Glu Ala His Leu Ala Thr Ala Tyr Gly Tyr Gln Thr Lys
        290                 295                 300

Trp Gly Val Pro Gly Lys Tyr Ile Gln Arg Arg Leu Gln Val His Gly
305                 310                 315                 320

Leu Arg Ala Val Val Asp Pro Asp Gly Pro Ile His Val Glu Ala Leu
                325                 330                 335

Ser Cys Pro Gln Ser Trp Ile Arg His Leu Thr Leu Asn Asp Asp Val
                340                 345                 350

Thr Pro Gly Phe Val Arg Leu Met Ser Leu Arg Ile Val Pro Asn Thr
                355                 360                 365

Glu Pro Thr Thr His Arg Ile Phe Arg Phe Gly Val His Lys Trp Tyr
        370                 375                 380

Gly Ala Ala Gly Lys Arg Ala Arg Gly Lys Arg Ala Ala Lys Ser Glu
385                 390                 395                 400

Lys Asp Ser Ala Ser Thr Leu Lys Val Ala Arg Pro Thr Ser Thr Ser
                405                 410                 415

Gly Ile Val Thr Tyr Ser Pro Pro Ala Asp Gly Ser Cys Gly Trp His
                420                 425                 430

Ala Leu Ala Ala Ile Leu Asn Arg Met Ile Asn Asn Asp Phe Thr Ser
                435                 440                 445

Pro Leu Pro Arg Tyr Asn Arg Pro Glu Asp Asp Trp Ala Ser Asp Gly
        450                 455                 460

Asp Leu Ala Gln Ala Ile Gln Cys Leu Gln Leu Pro Ala Ala Ile Ala
465                 470                 475                 480

Arg Asn Arg Ala Cys Pro Asn Ala Lys Tyr Leu Val Lys Leu Asn Gly
                485                 490                 495

Val His Trp Glu Val Glu Val Arg Pro Gly Met Ala Pro Arg Ser Leu
                500                 505                 510

Ser Arg Glu Cys Val Val Gly Val Cys Ser Glu Gly Cys Val Ala Ser
        515                 520                 525

Pro Tyr Pro Glu Asp Gly Leu Pro Lys Arg Ala Leu Glu Ala Leu Ala
        530                 535                 540

Ser Ala Tyr Arg Leu Pro Ser Asp Cys Val Cys Asp Gly Ile Ile Asp
545                 550                 555                 560

Phe Leu Ala Asn Pro Pro Gln Glu Phe Trp Thr Leu Asp Lys Met
                565                 570                 575

Leu Thr Ser Pro Ser Pro Glu Gln Ser Gly Phe Ser Ser Leu Tyr Lys
                580                 585                 590

Leu Leu Leu Glu Val Leu Pro Gln Lys Cys Gly Ser Thr Glu Gly Glu
                595                 600                 605
```

```
Phe Ile Tyr Thr Val Glu Arg Met Leu Lys Asp Cys Pro Ser Ser Lys
    610                 615                 620
Gln Ala Met Ala Leu Leu Ala Lys Ile Lys Val Pro Ser Ser Lys Ala
625                 630                 635                 640
Pro Ser Val Thr Leu Asn Glu Cys Phe Pro Thr Asp Val Pro Val Asn
                645                 650                 655
Ser Glu Leu Ile Ser Trp Glu Glu Pro Lys Asp Pro Gly Ala Ala Val
            660                 665                 670
Val Leu Cys Pro Ser Asp Ala Lys Glu Ser Lys Glu Thr Ala Pro Glu
        675                 680                 685
Glu Ala Gln Ala Arg Asn Arg Lys Val Leu His Pro Val Val Leu Thr
690                 695                 700
Glu Glu Leu Ser Glu Gln Gln Val Gln Val Val Glu Gly Asp Gln Asp
705                 710                 715                 720
Met Pro Leu Asp Leu Thr Trp Pro Thr Leu Thr Ala Thr Ala Thr Pro
                725                 730                 735
Val Arg Gly Pro Val Pro Asp Asn Leu Ser Ser Gly Ile Gly Ala Gln
            740                 745                 750
Pro Ala Thr Val Gln Glu Leu Ile Leu Ala Arg Pro Ala Pro Arg Leu
        755                 760                 765
Val Glu Arg Cys Gly Thr Glu Ser Asn Gly Ser Ser Ser Phe Leu Asp
770                 775                 780
Leu Pro Asp Val Gln Thr Ser Asp Gln Pro Leu Asp Leu Ser Leu Ala
785                 790                 795                 800
Ala Trp Pro Val Arg Ala Thr Ala Ser Asp Pro Gly Trp Ile His Gly
                805                 810                 815
Arg Arg Glu Pro Val Phe Val Lys Pro Arg Gly Val Phe Ser Asp Gly
            820                 825                 830
Glu Ser Ala Leu Gln Phe Gly Glu Leu Ser Glu Ala Ser Ser Val Val
        835                 840                 845
Asp Asp Arg Thr Lys Glu Ala Pro Val Val Asp Ala Pro Ile Asp Leu
850                 855                 860
Thr Thr Ser Asn Glu Thr Leu Ser Gly Ser Asp Pro Phe Glu Phe Ala
865                 870                 875                 880
Lys Phe Arg Arg Pro Arg Phe Ser Ala Gln Ala Leu Ile Asp Arg Gly
                885                 890                 895
Gly Pro Leu Ala Asp Val His Ala Lys Ile Lys Ser Arg Val Tyr Glu
            900                 905                 910
Gln Cys Leu Gln Ala Cys Glu Pro Gly Ser Arg Ala Thr Pro Ala Thr
        915                 920                 925
Lys Lys Trp Leu Asp Lys Met Trp Asp Arg Val Asp Met Lys Thr Trp
930                 935                 940
Arg Cys Thr Ser Gln Phe Gln Ala Gly His Ile Leu Glu Ser Leu Lys
945                 950                 955                 960
Phe Leu Pro Asp Met Ile Gln Asp Thr Pro Pro Val Pro Arg Lys
                965                 970                 975
Asn Arg Ala Gly Asp Ser Ala Gly Leu Lys Gln Leu Val Ala Gln Trp
            980                 985                 990
Asp Arg Lys Leu Ser Val Thr Pro Pro Thr Lys Pro Val Gly Pro Val
        995                 1000                1005
Leu Asp Gln Thr Val Pro Leu Pro Met Asp Ile Gln Gln Glu Asp
        1010                1015                1020
```

Ala Ile Ser Ala Asp Lys Pro Pro His Ser Gln Asn Pro Ser Ser
1025                1030                1035

Gln Val Asp Val Gly Gly Trp Lys Ser Phe Met Leu Ser Gly
1040                1045                1050

Thr Arg Phe Ala Gly Ser Val Ser Gln Arg Leu Thr Thr Trp Val
1055                1060                1065

Phe Glu Val Leu Ser His Leu Pro Ala Phe Met Leu Thr Leu Phe
1070                1075                1080

Ser Pro Arg Gly Ser Met Ala Pro Gly Asp Trp Leu Phe Ala Gly
1085                1090                1095

Ala Val Leu Leu Ala Leu Leu Leu Cys Arg Ser Tyr Pro Ile Leu
1100                1105                1110

Gly Cys Leu Pro Leu Leu Gly Val Phe Ser Gly Ser Val Arg Cys
1115                1120                1125

Val Arg Leu Gly Val Phe Gly Ser Trp Met Ala Phe Ala Val Phe
1130                1135                1140

Leu Phe Ser Thr Pro Pro Asp Pro Val Gly Ser Ser Cys Asp His
1145                1150                1155

Asp Ser Pro Glu Cys His Ala Glu Leu Leu Ala Leu Glu Gln Arg
1160                1165                1170

Gln Leu Trp Glu Pro Val Arg Ser Leu Val Val Gly Pro Ser Gly
1175                1180                1185

Leu Leu Cys Val Ile Leu Gly Lys Leu Leu Gly Gly Ser Arg Cys
1190                1195                1200

Leu Trp Phe Val Leu Leu Arg Ile Cys Met Leu Ala Asp Leu Ala
1205                1210                1215

Ile Ser Leu Ile Tyr Val Val Ser Gln Gly Arg Cys His Lys Cys
1220                1225                1230

Trp Gly Lys Cys Ile Arg Thr Ala Pro Ala Glu Val Thr Leu Asn
1235                1240                1245

Val Phe Pro Phe Ser Arg Ala Thr Arg Ser Ser Leu Val Ser Leu
1250                1255                1260

Cys Asp Arg Phe Gln Ala Pro Lys Gly Val Asp Pro Val His Leu
1265                1270                1275

Ala Thr Gly Trp Arg Gly Cys Trp Cys Gly Glu Ser Pro Ile His
1280                1285                1290

Gln Ser His Gln Lys Pro Ile Ala Tyr Ala Asn Leu Asp Glu Lys
1295                1300                1305

Lys Ile Ser Ala Gln Thr Val Ile Ala Val Pro Tyr Asp Pro Ser
1310                1315                1320

Gln Ala Ile Lys Cys Leu Lys Val Leu Gln Ala Gly Gly Ala Ile
1325                1330                1335

Val Asp Gln Pro Thr Pro Glu Val Val Arg Val Ser Glu Ile Pro
1340                1345                1350

Phe Ser Ala Pro Phe Phe Pro Lys Val Pro Val Asn Pro Asp Cys
1355                1360                1365

Arg Val Val Val Asp Ser Asp Thr Phe Val Ala Ala Val Arg Cys
1370                1375                1380

Gly Tyr Ser Thr Ala Gln Leu Val Leu Gly Arg Gly Asn Phe Ala
1385                1390                1395

Lys Leu Asn Gln Thr Pro Leu Arg Asn Ser Val Pro Thr Lys Thr
1400                1405                1410

Thr Gly Gly Ala Ser Tyr Thr Leu Ala Val Ala Gln Val Ser Val

```
                1415                1420                1425
Trp Thr Leu Val His Phe Ile Leu Gly Leu Trp Leu Thr Ser Pro
    1430                1435                1440
Gln Val Cys Gly Arg Gly Thr Ser Asp Pro Trp Cys Ser Asn Pro
    1445                1450                1455
Phe Ser Tyr Pro Thr Tyr Gly Pro Gly Val Val Cys Ser Ser Arg
    1460                1465                1470
Leu Cys Val Ser Ala Asp Gly Val Thr Leu Pro Leu Phe Ser Ala
    1475                1480                1485
Val Ala His Leu Ser Gly Arg Glu Val Gly Ile Phe Ile Leu Val
    1490                1495                1500
Leu Ala Ser Leu Gly Ala Leu Ala His Arg Leu Ala Leu Lys Ala
    1505                1510                1515
Asp Met Ser Met Val Phe Leu Ala Phe Cys Ala Tyr Ala Trp Pro
    1520                1525                1530
Met Ser Ser Trp Leu Ile Cys Phe Phe Pro Met Leu Leu Arg Trp
    1535                1540                1545
Val Thr Leu His Pro Leu Thr Met Leu Trp Val His Ser Phe Leu
    1550                1555                1560
Val Phe Cys Leu Pro Ala Ala Gly Val Leu Ser Leu Gly Ile Thr
    1565                1570                1575
Gly Leu Leu Trp Ala Val Gly Arg Phe Thr Gln Val Ala Gly Ile
    1580                1585                1590
Ile Thr Pro Tyr Asp Ile His Gln Tyr Thr Ser Gly Pro Arg Gly
    1595                1600                1605
Ala Ala Ala Val Ala Thr Ala Pro Glu Gly Thr Tyr Met Ala Ala
    1610                1615                1620
Val Arg Arg Ala Ala Leu Thr Gly Arg Thr Leu Ile Phe Thr Pro
    1625                1630                1635
Ser Ala Val Gly Ser Leu Leu Glu Gly Ala Phe Arg Thr Gln Lys
    1640                1645                1650
Pro Cys Leu Asn Thr Val Asn Val Val Gly Ser Ser Leu Gly Ser
    1655                1660                1665
Gly Gly Val Phe Thr Ile Asp Gly Arg Arg Val Ile Val Thr Ala
    1670                1675                1680
Thr His Val Leu Asn Gly Asn Thr Ala Arg Val Thr Gly Asp Ser
    1685                1690                1695
Tyr Asn Arg Met His Thr Phe Asn Thr Asn Gly Asp Tyr Ala Trp
    1700                1705                1710
Ser His Ala Asp Asp Trp Gln Gly Val Ala Pro Met Val Lys Ile
    1715                1720                1725
Ala Lys Gly Tyr Arg Gly Arg Ala Tyr Trp Gln Thr Ser Thr Gly
    1730                1735                1740
Val Glu Pro Gly Ile Met Gly Glu Gly Phe Ala Phe Cys Phe Thr
    1745                1750                1755
Asn Cys Gly Asp Ser Gly Ser Pro Val Ile Ser Glu Ala Gly Asp
    1760                1765                1770
Leu Ile Gly Val His Thr Gly Ser Asn Lys Leu Gly Ser Gly Leu
    1775                1780                1785
Val Thr Thr Pro Glu Gly Glu Thr Cys Ser Ile Lys Glu Thr Arg
    1790                1795                1800
Leu Ser Asp Leu Ser Arg His Phe Ala Gly Pro Ser Val Pro Leu
    1805                1810                1815
```

-continued

Gly Asp Ile Lys Leu Ser Pro Ala Ile Ile Pro Asp Val Thr Thr
1820            1825            1830

Ile Pro Ser Asp Leu Ala Ser Leu Leu Ala Ser Val Pro Val Met
1835            1840            1845

Glu Gly Gly Leu Ser Thr Val Gln Leu Leu Cys Val Phe Phe Leu
1850            1855            1860

Leu Trp Arg Met Met Gly His Ala Trp Thr Pro Ile Val Ala Val
1865            1870            1875

Gly Phe Phe Leu Leu Asn Glu Ile Leu Pro Ala Val Leu Val Arg
1880            1885            1890

Ala Val Phe Ser Phe Ala Leu Phe Val Leu Ala Trp Ala Thr Pro
1895            1900            1905

Trp Ser Ala Gln Val Leu Met Ile Arg Leu Leu Thr Ala Ala Leu
1910            1915            1920

Asn Arg Asn Arg Leu Ser Leu Ala Phe Tyr Ala Leu Gly Gly Val
1925            1930            1935

Val Gly Leu Ala Thr Glu Ile Gly Thr Phe Ala Gly Gly Trp Pro
1940            1945            1950

Glu Leu Ser Gln Ala Leu Ser Thr Tyr Cys Phe Leu Pro Arg Phe
1955            1960            1965

Leu Ala Val Thr Ser Tyr Val Pro Thr Ile Ile Gly Gly Leu
1970            1975            1980

His Ala Leu Gly Val Ile Leu Trp Leu Phe Lys Tyr Arg Cys Leu
1985            1990            1995

His Asn Met Leu Val Gly Asp Gly Ser Phe Ser Ser Ala Phe Phe
2000            2005            2010

Leu Arg Tyr Phe Ala Glu Gly Asn Leu Arg Lys Gly Val Ser Gln
2015            2020            2025

Ser Cys Gly Met Asn Asn Glu Ser Leu Thr Ala Ala Leu Ala Cys
2030            2035            2040

Lys Leu Ser Gln Ala Asp Leu Asp Phe Leu Ser Ser Leu Thr Asn
2045            2050            2055

Phe Lys Cys Phe Val Ser Ala Ser Asn Met Lys Asn Ala Ala Gly
2060            2065            2070

Gln Tyr Ile Glu Ala Ala Tyr Ala Arg Ala Leu Arg Gln Glu Leu
2075            2080            2085

Ala Ser Leu Val Gln Val Asp Lys Met Lys Gly Val Leu Ala Lys
2090            2095            2100

Leu Glu Ala Phe Ala Glu Thr Ala Thr Pro Ser Leu Asp Thr Gly
2105            2110            2115

Asp Val Ile Val Leu Leu Gly Gln His Pro His Gly Ser Ile Leu
2120            2125            2130

Asp Ile Asn Val Gly Gly Glu Arg Lys Thr Val Ser Val Gln Glu
2135            2140            2145

Thr Arg Cys Leu Gly Gly Ser Lys Phe Ser Val Cys Thr Val Val
2150            2155            2160

Ser Asn Thr Pro Val Asp Thr Leu Thr Gly Ile Pro Leu Gln Thr
2165            2170            2175

Pro Thr Pro Leu Phe Glu Asn Gly Pro Arg His Arg Ser Glu Asp
2180            2185            2190

Asp Asp Leu Lys Val Glu Arg Met Lys Lys His Cys Val Ser Leu
2195            2200            2205

Gly Phe His Lys Ile Asn Gly Lys Val Tyr Cys Lys Ile Trp Asp
2210                2215                2220

Lys Ser Asn Gly Asp Thr Phe Tyr Thr Asp Asp Ser Arg Tyr Thr
    2225                2230                2235

Gln Asp His Ala Phe Gln Arg Ser Thr Asp Tyr Arg Asp Arg
2240                2245                2250

Asp Tyr Glu Gly Val Gln Thr Ala Pro Gln Gln Gly Phe Asp Pro
    2255                2260                2265

Lys Ser Glu Ala Pro Val Gly Thr Val Val Ile Gly Gly Ile Thr
2270                2275                2280

Tyr Asn Arg His Leu Val Lys Gly Lys Glu Val Leu Val Pro Lys
    2285                2290                2295

Pro Asp Asn Cys Leu Glu Ala Ala Arg Leu Ser Leu Glu Gln Ala
2300                2305                2310

Leu Ala Gly Met Gly Gln Thr Cys Asp Leu Thr Ala Thr Glu Val
    2315                2320                2325

Glu Lys Leu Lys Arg Ile Ile Ser Gln Leu Gln Gly Leu Thr Thr
2330                2335                2340

Glu Gln Ala Leu Asn Cys
    2345

<210> SEQ ID NO 12
<211> LENGTH: 1463
<212> TYPE: PRT
<213> ORGANISM: Porcine reproductive respiratory syndrome virus

<400> SEQUENCE: 12

Thr Gly Phe Lys Leu Leu Ala Ala Ser Gly Leu Thr Arg Cys Gly Arg
1               5                   10                  15

Gly Gly Leu Val Val Thr Glu Thr Ala Val Lys Ile Val Lys Tyr His
            20                  25                  30

Ser Arg Thr Phe Thr Leu Gly Ser Leu Asp Leu Lys Val Thr Ser Glu
        35                  40                  45

Val Glu Val Lys Lys Ser Thr Glu Gln Gly His Ala Val Val Ala Asn
    50                  55                  60

Leu Cys Ser Gly Val Val Leu Met Arg Pro His Pro Pro Ser Leu Val
65                  70                  75                  80

Asp Val Leu Leu Lys Pro Gly Leu Asp Thr Thr Pro Gly Ile Gln Pro
                85                  90                  95

Gly His Gly Ala Gly Asn Met Gly Val Asn Gly Ser Ile Trp Asp Phe
            100                 105                 110

Glu Thr Ala Pro Thr Lys Val Glu Leu Glu Leu Ser Lys Gln Ile Ile
        115                 120                 125

Gln Ala Cys Glu Val Arg Arg Gly Asp Ala Pro Asn Leu Gln Leu Pro
    130                 135                 140

Tyr Lys Leu Tyr Pro Val Arg Gly Asp Pro Glu Arg Lys Gly Arg
145                 150                 155                 160

Leu Val Asn Thr Arg Phe Gly Asp Leu Pro Tyr Lys Thr Pro Gln Asp
                165                 170                 175

Thr Lys Ser Ala Ile His Ala Ala Cys Cys Leu His Pro Asn Gly Val
            180                 185                 190

Leu Val Ser Asp Gly Lys Ser Thr Leu Gly Thr Thr Leu Gln His Gly
        195                 200                 205

Phe Glu Leu Tyr Val Pro Thr Val Pro Tyr Ser Val Met Glu Tyr Leu
    210                 215                 220

```
Asp Ser Arg Pro Asp Thr Pro Phe Met Cys Thr Lys His Gly Thr Ser
225                 230                 235                 240

Lys Ala Ala Ala Glu Asp Leu Gln Lys Tyr Asp Leu Ser Thr Gln Gly
                245                 250                 255

Phe Val Leu Pro Gly Val Leu Arg Leu Val Arg Arg Phe Ile Phe Ser
            260                 265                 270

His Val Gly Lys Ala Pro Pro Leu Phe Leu Pro Ser Thr Tyr Pro Ala
        275                 280                 285

Lys Asn Ser Met Ala Gly Val Asn Gly Gln Arg Phe Pro Thr Lys Asp
    290                 295                 300

Val Gln Ser Ile Pro Glu Ile Asp Glu Met Cys Ala Arg Ala Val Lys
305                 310                 315                 320

Glu Asn Trp Gln Thr Val Thr Pro Cys Thr Leu Lys Lys Gln Tyr Cys
                325                 330                 335

Ser Lys Pro Lys Thr Arg Thr Ile Leu Gly Thr Asn Asn Phe Ile Ala
                340                 345                 350

Leu Ala His Arg Ser Ala Leu Ser Gly Val Thr Gln Ala Phe Met Lys
            355                 360                 365

Lys Ala Trp Lys Ser Pro Ile Ala Leu Gly Lys Asn Lys Phe Lys Glu
        370                 375                 380

Leu His Cys Thr Val Ala Gly Arg Cys Leu Glu Ala Asp Leu Ala Ser
385                 390                 395                 400

Cys Asp Arg Ser Thr Pro Ala Ile Val Arg Trp Phe Val Ala Asn Leu
                405                 410                 415

Leu Tyr Glu Leu Ala Gly Cys Glu Glu Tyr Leu Pro Ser Tyr Val Leu
                420                 425                 430

Asn Cys Cys His Asp Leu Val Ala Thr Gln Asp Gly Ala Phe Thr Lys
            435                 440                 445

Arg Gly Gly Leu Ser Ser Gly Asp Pro Val Thr Ser Val Ser Asn Thr
        450                 455                 460

Val Tyr Ser Leu Ile Ile Tyr Ala Gln His Met Val Leu Ser Ala Leu
465                 470                 475                 480

Lys Met Gly His Glu Ile Gly Leu Lys Phe Leu Glu Glu Gln Leu Lys
                485                 490                 495

Phe Glu Asp Leu Leu Glu Ile Gln Pro Met Leu Val Tyr Ser Asp Asp
                500                 505                 510

Leu Val Leu Tyr Ala Glu Arg Pro Thr Phe Pro Asn Tyr His Trp Trp
            515                 520                 525

Val Glu His Leu Asp Leu Met Leu Gly Phe Lys Thr Asp Pro Lys Lys
        530                 535                 540

Thr Val Ile Thr Asp Lys Pro Ser Phe Leu Gly Cys Arg Ile Glu Ala
545                 550                 555                 560

Gly Arg Gln Leu Val Pro Asn Arg Asp Arg Ile Leu Ala Ala Leu Ala
                565                 570                 575

Tyr His Met Lys Ala Gln Asn Ala Ser Glu Tyr Tyr Ala Ser Ala Ala
                580                 585                 590

Ala Ile Leu Met Asp Ser Cys Ala Cys Ile Asp His Asp Pro Glu Trp
            595                 600                 605

Tyr Glu Asp Leu Ile Cys Gly Ile Ala Arg Cys Ala Arg Gln Asp Gly
        610                 615                 620

Tyr Arg Phe Pro Gly Pro Ala Phe Phe Met Ser Met Trp Glu Lys Leu
625                 630                 635                 640
```

-continued

```
Lys Ser His Asn Glu Gly Lys Lys Cys Arg His Cys Gly Ile Cys Asp
                 645                 650                 655
Ala Lys Ala Asp Tyr Ala Ser Ala Cys Gly Leu Asp Leu Cys Leu Phe
            660                 665                 670
His Ser His Phe His Gln His Cys Pro Val Thr Leu Ser Cys Gly His
        675                 680                 685
His Ala Gly Ser Lys Glu Cys Ser Gln Cys Gln Ser Pro Val Gly Ala
    690                 695                 700
Gly Lys Ser Pro Leu Asp Ala Val Leu Lys Gln Ile Pro Tyr Lys Pro
705                 710                 715                 720
Pro Arg Thr Ile Ile Met Lys Val Asp Asn Lys Thr Thr Thr Leu Asp
                725                 730                 735
Pro Gly Arg Tyr Gln Ser Arg Arg Gly Leu Val Ala Val Lys Arg Gly
            740                 745                 750
Ile Ala Gly Asn Glu Val Asp Leu Ser Asp Gly Asp Tyr Gln Val Val
        755                 760                 765
Pro Leu Leu Pro Thr Cys Lys Asp Ile Asn Met Val Lys Val Ala Cys
    770                 775                 780
Asn Val Leu Leu Ser Lys Phe Ile Val Gly Pro Pro Gly Ser Gly Lys
785                 790                 795                 800
Thr Thr Trp Leu Leu Asn Gln Val Gln Asp Asp Val Ile Tyr Thr
                805                 810                 815
Pro Thr His Gln Thr Met Phe Asp Ile Val Ser Ala Leu Lys Val Cys
            820                 825                 830
Arg Tyr Ser Ile Pro Gly Ala Ser Gly Leu Pro Phe Pro Pro Ala
        835                 840                 845
Arg Ser Gly Pro Trp Val Arg Leu Ile Ala Ser Gly His Val Pro Gly
    850                 855                 860
Arg Val Ser Tyr Leu Asp Glu Ala Gly Tyr Cys Asn His Leu Asp Ile
865                 870                 875                 880
Leu Arg Leu Leu Ser Lys Thr Pro Leu Val Cys Leu Gly Asp Leu Gln
                885                 890                 895
Gln Leu His Pro Val Gly Phe Asp Ser Tyr Cys Tyr Val Phe Asp Gln
            900                 905                 910
Met Pro Gln Lys Gln Leu Thr Thr Ile Tyr Arg Phe Gly Pro Asn Ile
        915                 920                 925
Cys Ala Ala Ile Gln Pro Cys Tyr Arg Glu Lys Leu Glu Ser Lys Ala
    930                 935                 940
Arg Asn Thr Arg Val Val Phe Thr Thr Arg Pro Val Ala Phe Gly Gln
945                 950                 955                 960
Val Leu Thr Pro Tyr His Lys Asp Arg Thr Gly Ser Ala Ile Thr Ile
                965                 970                 975
Asp Ser Ser Gln Gly Ala Thr Phe Asp Ile Val Thr Leu His Leu Pro
            980                 985                 990
Ser Pro Lys Ser Leu Asn Lys Ser Arg Ala Leu Val Ala Ile Thr Arg
        995                 1000                1005
Ala Arg His Gly Leu Phe Ile Tyr Asp Pro His Asp Gln Leu Gln
    1010                1015                1020
Glu Phe Phe Asn Leu Thr Pro Glu Arg Thr Asp Cys Asn Leu Ala
    1025                1030                1035
Phe Ser Arg Gly Asp Glu Leu Val Val Leu Asn Val Asp Asn Ala
    1040                1045                1050
Val Thr Thr Val Ala Lys Ala Leu Glu Thr Gly Ser Pro Arg Phe
```

-continued

```
            1055                1060                1065
Arg Val Ser Asp Pro Arg Cys Lys Ser Leu Leu Ala Ala Cys Ser
        1070                1075            1080
Ala Ser Leu Glu Gly Ser Cys Met Pro Leu Pro Gln Val Ala His
        1085                1090            1095
Asn Leu Gly Phe Tyr Phe Ser Pro Asp Ser Pro Ala Phe Ala Pro
        1100                1105            1110
Leu Pro Lys Glu Leu Ala Pro His Trp Pro Val Val Thr His Gln
        1115                1120            1125
Asn Asn Arg Ala Trp Pro Asp Arg Leu Val Ala Ser Met Arg Pro
        1130                1135            1140
Ile Asp Ala Arg Tyr Ser Lys Pro Met Val Gly Ala Gly Tyr Val
        1145                1150            1155
Val Gly Pro Ser Ile Phe Leu Gly Thr Pro Gly Val Val Ser Tyr
        1160                1165            1170
Tyr Leu Thr Leu Tyr Ile Gly Gly Glu Pro Gln Ala Leu Pro Glu
        1175                1180            1185
Thr Leu Val Ser Thr Gly Arg Ile Ala Thr Asp Cys Arg Glu Tyr
        1190                1195            1200
Leu Asp Ala Ala Glu Glu Glu Ala Ala Arg Glu Leu Pro His Ala
        1205                1210            1215
Phe Ile Gly Asp Val Lys Gly Thr Thr Val Gly Gly Cys His His
        1220                1225            1230
Ile Thr Ser Lys Tyr Leu Pro Arg Ser Leu Pro Lys Asp Ser Val
        1235                1240            1245
Ala Val Val Gly Val Ser Ser Pro Gly Arg Ala Ala Lys Ala Val
        1250                1255            1260
Cys Thr Leu Thr Asp Val Tyr Leu Pro Glu Leu Arg Pro Tyr Leu
        1265                1270            1275
Gln Pro Glu Thr Ala Ser Lys Cys Trp Lys Leu Lys Leu Asp Phe
        1280                1285            1290
Arg Asp Val Arg Leu Met Val Trp Lys Gly Ala Thr Ala Tyr Phe
        1295                1300            1305
Gln Leu Glu Gly Leu Thr Trp Ser Ala Leu Pro Asp Tyr Ala Arg
        1310                1315            1320
Phe Ile Gln Leu Pro Lys Asp Ala Val Val Tyr Ile Asp Pro Cys
        1325                1330            1335
Ile Gly Pro Ala Thr Ala Asn Arg Lys Val Val Arg Thr Thr Asp
        1340                1345            1350
Trp Arg Ala Asp Leu Ala Val Thr Pro Tyr Asp Tyr Gly Ala Gln
        1355                1360            1365
Val Ile Leu Thr Thr Ala Trp Phe Glu Asp Leu Gly Pro Gln Trp
        1370                1375            1380
Lys Ile Leu Gly Leu Gln Pro Phe Arg Arg Thr Phe Gly Phe Glu
        1385                1390            1395
Asn Thr Glu Asp Trp Ala Ile Leu Ala Arg Arg Met Asn Asp Gly
        1400                1405            1410
Lys Asp Tyr Thr Asp Tyr Asn Trp His Cys Val Arg Glu Arg Pro
        1415                1420            1425
His Ala Ile Tyr Gly Arg Ala Arg Asp His Thr Tyr His Phe Ala
        1430                1435            1440
Leu Gly Thr Glu Leu Gln Val Glu Leu Gly Arg Pro Arg Leu Pro
        1445                1450            1455
```

Pro Glu Gln Val Pro
        1460

<210> SEQ ID NO 13
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gln Trp Val His Cys Gly Val Lys Ser Val Ser Cys Ser Trp Met
1               5                   10                  15

Pro Ser Leu Ser Ser Leu Leu Val Trp Leu Thr Leu Ser Ser Phe Ser
            20                  25                  30

Pro Tyr Cys Leu Gly Ser Leu Leu Gln Ala Gly Tyr Trp Ser Ser Phe
        35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Gly Ile Leu Trp
                85                  90                  95

His Met Arg Val Ser His Leu Ile Asp Glu Met Val Ser Arg Arg Ile
            100                 105                 110

Tyr Arg Thr Met Glu His Ser Gly Gln Ala Ala Trp Lys Gln Val Val
        115                 120                 125

Ser Glu Ala Thr Leu Thr Lys Leu Ser Arg Leu Asp Val Val Thr His
    130                 135                 140

Phe Gln His Leu Ala Ala Val Glu Ala Asp Ser Cys Arg Phe Leu Ser
145                 150                 155                 160

Ser Arg Leu Ala Met Leu Lys Asn Leu Ala Val Gly Asn Val Ser Leu
                165                 170                 175

Glu Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Thr
    210                 215                 220

Val Leu Trp Leu Arg Ile Pro Ala Leu Arg Tyr Val Phe Gly Phe His
225                 230                 235                 240

Trp Pro Thr Ala Thr His His Ser Asn
                245

<210> SEQ ID NO 14
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Tyr Gln Arg Ala Arg Phe His Leu Leu Leu Cys Gly Phe Val
1               5                   10                  15

Cys Tyr Leu Val His Ser Ala Leu Ala Ser Asn Ser Ser Thr Leu
            20                  25                  30

Cys Phe Trp Phe Pro Leu Ala His Gly Asn Thr Ser Phe Glu Leu Thr
             35                  40                  45

Ile Asn Tyr Thr Ile Cys Lys Pro Cys Pro Thr Ser Gln Ala Ala Gln
 50                  55                  60

Gln Arg Leu Glu Pro Gly Arg Asn Val Trp Cys Lys Ile Gly His Asp
 65                  70                  75                  80

Arg Cys Glu Glu Arg Asp His Asp Glu Leu Ser Met Ser Ile Pro Ser
                 85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
        130                 135                 140

Ala Glu His Asp Gly Gln Asn Ser Thr Ile Ser Ala Arg His Asn Ile
145                 150                 155                 160

Ser Ala Ser Tyr Ala Val Tyr Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Ala Ser Pro Ala Ser
        195                 200                 205

Arg Arg Ile Tyr Gln Ile Leu Arg Pro Thr Arg Pro Arg Leu Pro Val
210                 215                 220

Ser Trp Ser Phe Arg Thr Ser Ile Val Ser Asn Leu Thr Gly Pro Gln
225                 230                 235                 240

Gln Arg Lys Val Pro Leu Pro Ser Gly Gly Arg Pro Asn Val Val Lys
                245                 250                 255

Pro Ser Ala Phe Pro Ser Thr Ser Arg
                260                 265

<210> SEQ ID NO 15
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Ala Thr Ile Leu Phe Leu Leu Ala Gly Ala Gln His Leu Met
 1               5                  10                  15

Val Ser Glu Ala Phe Ala Cys Lys Pro Cys Phe Ser Thr His Leu Ser
                20                  25                  30

Asp Ile Lys Thr Asn Thr Thr Ala Ala Ala Gly Phe Met Val Leu Gln
             35                  40                  45

Asn Ile Asn Cys Phe Gln Ser His Arg Ala Ser Thr Ala Gln Gly Thr
 50                  55                  60

Thr Pro Leu Arg Arg Ser Ser Gln Cys Arg Glu Ala Val Gly Ile Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Ile Ser Gly Val

```
              115                 120                 125
Val Ser Ala Cys Val Asn Phe Thr Asp Tyr Val Ala His Val Thr Gln
        130                 135                 140

His Thr Gln Gln His His Leu Val Ile Asp His Ile Arg Leu Leu His
145                 150                 155                 160

Phe Leu Thr Pro Ser Thr Met Arg Trp Ala Thr Thr Ile Ala Cys Leu
                165                 170                 175

Phe Ala Ile Leu Leu Ala Val
            180

<210> SEQ ID NO 16
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Lys Cys Ser Cys Lys Leu Gly His Phe Leu Thr Pro His Ser Cys
1               5                   10                  15

Phe Trp Trp Leu Phe Leu Leu Cys Thr Gly Leu Ser Trp Ser Phe Val
            20                  25                  30

Asp Gly Asn Asp Asn Ser Ser Thr Ser Gln Tyr Ile Tyr Asn Leu Thr
        35                  40                  45

Ile Cys Glu Leu Asn Gly Thr Glu Trp Leu Ser Gly His Phe Asp Trp
    50                  55                  60

Ala Val Glu Thr Phe Val Leu Tyr Pro Val Ala Thr His Ile Ile Ser
65                  70                  75                  80

Leu Gly Phe Leu Thr Thr Ser His Phe Leu Asp Ala Leu Gly Leu Gly
                85                  90                  95

Ala Val Ser Ala Thr Gly Phe Ile Gly Glu Arg Tyr Val Leu Ser Ser
            100                 105                 110

Met Tyr Gly Val Cys Ala Phe Ala Ala Leu Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Ile His Arg Trp Lys Ser Ser
145                 150                 155                 160

Ile Val Val Glu Lys Leu Gly Lys Ala Glu Val Gly Gly Asp Leu Val
                165                 170                 175

Asn Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 17
<211> LENGTH: 173
<212> TYPE: PRT
<213> ORGANISM: Porcine reproductive respiratory syndrome virus

<400> SEQUENCE: 17

Met Gly Ser Leu Asp Asp Phe Cys Asn Asp Pro Thr Ala Ala Gln Lys
1               5                   10                  15

Leu Val Leu Ala Phe Ser Ile Thr Tyr Thr Pro Ile Met Ile Tyr Ala
            20                  25                  30

Leu Lys Val Ser Arg Gly Arg Leu Leu Gly Leu Leu His Ile Leu Ile
```

```
                35                  40                  45
Phe Leu Asn Cys Ser Phe Thr Phe Gly Tyr Met Thr Tyr Val His Phe
        50                  55                  60
Gln Ser Thr Asn Arg Val Ala Leu Thr Leu Gly Ala Val Ala Leu
 65                  70                  75                  80
Leu Trp Gly Val Tyr Ser Leu Thr Glu Ser Trp Lys Phe Ile Thr Ser
                85                  90                  95
Arg Cys Arg Leu Cys Cys Leu Gly Arg Arg Tyr Ile Leu Ala Pro Ala
                100                 105                 110
His His Val Glu Ser Ala Ala Gly Leu His Ser Ile Pro Ala Ser Gly
                115                 120                 125
Asn Arg Ala Tyr Ala Val Arg Lys Pro Gly Leu Thr Ser Val Asn Gly
                130                 135                 140
Thr Leu Val Pro Gly Leu Arg Ser Leu Val Leu Gly Gly Lys Arg Ala
145                 150                 155                 160
Val Lys Arg Gly Val Val Asn Leu Val Lys Tyr Gly Arg
                165                 170

<210> SEQ ID NO 18
<211> LENGTH: 128
<212> TYPE: PRT
<213> ORGANISM: Porcine reproductive respiratory syndrome virus

<400> SEQUENCE: 18

Met Ala Gly Lys Asn Gln Ser Gln Lys Lys Arg Arg Asn Ala Ala Pro
 1               5                  10                  15
Met Gly Lys Gly Gln Pro Val Asn Gln Leu Cys Gln Leu Leu Gly Thr
                20                  25                  30
Met Ile Lys Ser Gln Arg Gln Gln Ser Arg Gly Gly Gln Ala Lys Lys
                35                  40                  45
Lys Lys Pro Glu Lys Pro His Phe Pro Leu Ala Ala Glu Asp Asp Ile
        50                  55                  60
Arg His His Leu Thr Gln Ala Glu Arg Ser Leu Cys Leu Gln Ser Ile
 65                  70                  75                  80
Gln Thr Ala Phe Asn Gln Gly Ala Gly Thr Ala Ser Leu Ser Ser Ser
                85                  90                  95
Gly Lys Val Ser Phe Gln Val Glu Phe Met Leu Pro Val Ala His Thr
                100                 105                 110
Val Arg Leu Ile Arg Val Thr Ser Thr Ser Ala Ser Gln Gly Ala Asn
                115                 120                 125

<210> SEQ ID NO 19
<211> LENGTH: 7050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgtctggga tgttctcccg gtgcatgtgc accccggctg cccgggtatt ttggaacgcc      60
ggccaagtct attgcacacg tgtctcagtg cacggtctc ttctctctcc agaacttcag     120
gacacggacc tcggtgcagt tggcttgttt cacaagccta agacaagct ccattggaaa     180 gttcccattg gtatccccca ggtggaatgt tctccatctg ggtgttgctg gctgtcaacc     240
atttttcctt tagcgcgcat gacctccggc aatcacaact ccttcaacg actcgtgaag     300
```

```
gttgctgatg tattgtaccg tgacggttgc ttaaccccta gacacctccg tgaactccaa    360
gtttacgagc gtggttgcaa ttggtatccg attacgggc ctgtgcctgg gatggctgtg    420
tacgcgaact ccatgcacgt gtccgaccaa ccgttcctg gtgccactca tgtgttaaca    480
aattccctt tgcctcaacg ggcttgtcgg cagccgttct gtccgttcga agaggcccat    540
tctagcatat acaggtggga aaaatttgta atttttatgg attcctcctc cgacggtcga    600
tctcgcatga tgtggactcc ggaatccgat gactccacgg cttggaagt tctgccgccc    660
gagctagaac accaggtcaa ggtccttgtt cggagctttc ccgcccatca ccttgtcgac    720
cttgccgatt gggagctcac tgagtcccct gataacggtt tttccttcag cacgtcacat    780
ccttgcggct accttgttcg ggacccggct gtatccgaag gcaagtgttg gctttcctgc    840
tttttgagcc agtcagccga agtgctcagt cgcgaggcgc atctggctac cgcctatggt    900
taccaaaacca gtggggtgt gcctggcaag tacatccagc gcagacttca agttcacggt    960
ctccgtgctg tggtcgaccc tgatggtccc attcacgttg aagcattgtc ttgccccag    1020
tcttggatca ggcacttgac cctgaatgat gatgtcaccc cggggattcgt tcgcctaatg   1080
tctcttcgca ttgtgccgaa cacagagcct accacacacc ggatctttcg ttttggagtg    1140
cacaagtggt atggtgccgc cggcaaacgg gcccgtggca agcgtgccgc caaaagtgag    1200
aaagactcgg cttccaccct caaggttgcc cgaccgactt ccaccagtgg aatcgtcacc    1260
tactccccac ctgcggacgg gtcttgtggt tggcatgccc ttgccgccat actgaaccgg    1320
atgattaata tgacttcac gtccctctg cctcggtaca acaggccgga ggacgattgg    1380
gcttctgatg gtgaccttgc tcaggccatt caatgtttgc aactacctgc cgccatagct    1440
cggaaccgcg cctgccctaa cgccaaatac ctcataaaac tcaacggagt tcattgggag    1500
gtagaggtga ggcctggaat ggctcctcgc tccctctctc gtgagtgcgt tgttggcgtc    1560
tgctctgaag gctgtgtcgc gtcgccttac ccggaggacg ggttgcctaa acgtgcactt    1620
gaggccctgg cgtctgctta tagactgcct tcagactgtg tttgtgatgg tattattgac    1680
ttccttgcca atccacctcc ccaggagttc tggactcttg acaaaatgtt gacttccccg    1740
tcaccggagc agtccggctt ctctagtctg tataaattgt tgttagagat cttgccgcag    1800
aaatgcggat ccacagaagg ggaattcatc tatactgttg agaggatgtt gaaggattgt    1860
ccgagctcca acaggccat ggccctcctt gcaaaaatta aggtcccatc ctcaaaggcc    1920
ccatccgtga ctctgaacga gtgcttcccc acggatgttc cagtcaactc tgagttaata    1980
tcttgggaag agcccaaaga ccctggcgct gctgttgtcc tatgtccatc ggatgcaaaa    2040
gaatctaagg aaacagcccc tgaagaagct caagcgagaa accgtaaggt ccttcaccct    2100
gtggtccttta ccgaggaact tagcgagcaa caggtgcagg tggttgaggg tgatcaggat    2160
atgccactgg atttgacttg gccaaccta accgctacgg cgaccctgt tagagggccg    2220
gtaccggaca atttgagctc tggcattggt gcccagcccg ctaccgttca agaactcatt    2280
ctggcgaggc ctgcaccccg tcttgttgag cgctgtggca cggagtcgaa cggcagcagt    2340
tcatttctgg atttgcctga cgtgcagacc tcggaccagc cttagacct gtccctggcc    2400
gcgtggcctg taagggctac cgcgtctgac cccggttgga tccacggtag gcgtgagcct    2460
gtctttgtga agcctcgagg tgttttctct gatggcgagt cggcccttca gttcggagag    2520
ctttccgaag ccagttctgt cgtcgatgac cggacaaaag aagctccggt ggttgacgcc    2580
cccatcgatt tgaacaacttc gaacgagacg ctctctgggg ctgaccccctt tgaattcgcc    2640
aaattcaggc gcccgcgttt ctccgcgcaa gctttaatcg accgaggtgg tccgcttgcc    2700
```

```
gatgttcatg caaagataaa gagtcgggta tatgaacaat gccttcaagc ttgtgaacct    2760
ggtagtcgtg cgaccccagc caccaagaag tggctcgaca aaatgtggga cagggtggac    2820
atgaaaactt ggcgctgcac ctcgcagttc caagctggtc acattcttga gtccctcaaa    2880
ttcctccctg acatgattca agacacaccg cctcctgttc ccaggaagaa ccagctggt     2940
gacagtgccg gcctgaagca actggtggcg cagtgggata ggaaatcgag tgtgacaccc    3000
cccacaaaac cggttggacc ggtgcttgac caggccgtcc ctctgcctat ggacatccag    3060
caaggagatg ccatctccgc tgacaagcca ccccattcgc aaaacccttc tagtcaagta    3120
gatgtgggtg gaggttggaa aagttttatg ctctccggca cccgtttcgc ggggtccgtt    3180
agtcagcgcc ttacgacatg gttttttgag gttctctccc atctcccagc ttttatgctc    3240
acacttttct cgccacgggg ctctatggct ccaggtgatt ggctgtttgc aggtgctgtt    3300
ctacttgctc tcctgctctg ccgttcttac ccaatactcg gatgccttcc cttattgggt    3360
gtcttttctg gttctgtgcg gtgtgttcgt ttgggtgttt ttggttcttg gatggctttt    3420
gctgtatttt tattctcgac tccacccgac ccagtcggtt cttcttgtga ccacgattcg    3480
ccggagtgtc atgctgagct tttggctctt gagcagcgcc aactttggga acctgtgcgc    3540
agccttgtgg tcgggccatc gggcctctta tgcgtcattc ttggcaagtt actcggtggg    3600
tcacgttgtc tctggtttgt tctcctacgt atatgcatgc tcgcagattt ggcaatttct    3660
cttatttatg tggtgtccca agggcgttgt cacaagtgtt ggggaaagtg tataaggacg    3720
gctcctgcag aagtggccct taatgtgttt ccttttcgc gcgccacccg ctcatctctt     3780
gtgtccttgt gtgatcggtt ccaagcgcca aaaggagttg accccgtgca cttggcgaca    3840
ggctggcgcg ggtgctggtg tggtgagagc cctattcatc aatcacacca aaaccgata     3900
gcttatgcca acttggatga aaagaagata tccgcccaga cggtgattgc tgtcccgtat    3960
gatcctagtc aggccattaa atgcctgaaa gttttgcagg caggaggggc tattgtggac    4020
cagcctacgc ccgaggtcgt ccgtgtgtct gagattccct tctcggcccc attttttccg    4080
aaggtcccag tcaacccaga ctgcagggtt gtggtagatt cggacacttt tgtggctgcg    4140
gtccgctgcg gttattcgac agcacaactg gtccttggtc ggggcaactt tgccaagcta    4200
aatcagaccc ccctcaggaa ctctgtcccc accaaaacaa ctggtggggc ctcatacacc    4260
cttgccgtgg cccaggtatc tgtgtggact cttgttcatt tcatcctcgg cctttggtta    4320
acgtcacctc aagtgtgtgg tcgagggacc tctgacccgt ggtgttcgaa ccctttttcg    4380
tatcctactt atggccccgg agttgtgtgt cctctcgac tctgcgtgtc tgccgacgga     4440
gttaccctgc cattgttctc agccgttgcc catctttccg gtagagaggt ggggattttt    4500
attttggtgc ttgcctcctt gggcgcttta gcccaccgct ggctcttaa ggcagacatg     4560
tcaatggtct ttttggcgtt ttgtgcttac gcctggccca tgagctcctg gttaatttgc    4620
ttctttccta tgctcttgag gtgggtaacc cttcatcctc tcactatgct tgggtgcac     4680
tcattttttgg tgttttgcct accagctgcc ggcgttctct cgctgggaat aaccggtctt    4740
ctttgggcag ttggccgttt cacccaggtt gccggaatta tcacaccta tgacatccac    4800
cagtatacct ccggaccacg tggtgcagct gctgtagcaa cggctccaga aggtacttac    4860
atggcggccg ttcggagagc cgctttgact ggacggactt tgatcttcac accatctgca    4920
gtcggatccc ttcttgaagg tgctttcaga actcaaaagc cctgccttaa caccgtgaat    4980
gtcgtaggct cttcccttgg ttctggagga gttttcacca ttgatggcag aagagtcatc    5040
```

| | | | | | |
|---|---|---|---|---|---|
| gtcactgcca | cccatgtgtt | gaatggtaac | acagccaggg | tcactggtga | ttcctacaac | 5100
| cgcatgcaca | cgttcaatac | taatggtgat | tatgcctggt | cccatgctga | tgactggcaa | 5160
| ggcgttgccc | ctatggttaa | gatcgctaag | gggtatcgcg | gtcgtgccta | ctggcaaacg | 5220
| tcaaccggag | tcgaacctgg | catcatgggg | gaaggattcg | ccttctgttt | cactaactgt | 5280
| ggcgactcag | ggtcacctgt | catttcagaa | gctggtgacc | ttattggagt | ccataccggt | 5340
| tcaaacaaac | tcggttctgg | tcttgtgaca | acccctgaag | gggagacctg | ctccatcaag | 5400
| gaaactaggc | tctctgacct | ttctagacat | tttgcaggtc | aagcgtccc | tcttggggac | 5460
| attaagttga | gcccagccat | catccctgat | gtgacaacta | ttccgagtga | cttggcatcg | 5520
| ctccttgctt | ctgtccccgt | gatggaaggt | ggcctctcaa | ctgtccagct | tttgtgcgtc | 5580
| ttttccttc | tctggcgcat | gatgggccat | gcctggacac | ccattgttgc | cgtaggcttc | 5640
| ttttgctga | atgaaattct | cccagcagtc | ttggtccgag | ctgtgttctc | ttttgcactc | 5700
| tttgtacttg | catgggccac | cccctggtcg | gcacaagtgt | tgatgattag | actcctcacg | 5760
| gcggctctca | accgcaacag | gttgtccctg | gcgttctacg | cattcggagg | tgtcgttggc | 5820
| ctggccacag | aaatcgggac | ttttgctggt | ggatggcctg | aactgtccca | agccctctcg | 5880
| acatactgct | tcctgcccag | gttccttgct | gtgactagtt | atgtccccac | catcatcatc | 5940
| ggtgggctcc | atgccctcgg | cgtaattttg | tggttattca | ataccgatg | cctccacaac | 6000
| atgctggttg | gtgatgggag | tttctcaagc | gctttcttcc | tacggtattt | tgctgagggt | 6060
| aatcttagga | aaggcgtgtc | gcagtcctgt | ggcatgaata | acgaatccct | gacagctgct | 6120
| ttggcttgca | agttgtcgca | agctgacctt | gattttttgt | ccagtttaac | gaacttcaag | 6180
| tgctttgtgt | ccgcttcaaa | catgaaaaat | gcagctggcc | aatacatcga | ggcggcgtat | 6240
| gctagagctc | tgcgtcagga | gctggcctcc | ttggttcagg | ttgacaagat | gaaaggagta | 6300
| ttggccaagc | tcgaggcttt | cgctgagacg | gccactccgt | cacttgacac | aggggacgtg | 6360
| attgttctgc | ttgggcaaca | ccccatgga | tccatcctcg | acattaatgt | gggggtgaa | 6420
| aggaaaactg | tgtctgtgca | agaaacacga | tgcctgggtg | gttccaaatt | cagtgtctgc | 6480
| actgtcgtgt | ccaacacgcc | cgtggatacc | ttgaccggta | tcccacttca | gacgccaacc | 6540
| ccacttttg | aaaatggccc | gcgccatcgc | agcgaggacg | acgacctcaa | agttgagaga | 6600
| atgaaaaaac | actgtgtatc | cctcggcttc | cacaaaatca | atggtaaagt | ttactgcaaa | 6660
| atttgggaca | agtctaacgg | cgacaccttt | tacacggatg | attcccgata | cactcaagac | 6720
| catgcttttc | aggacaggtc | aaccgactat | agagacaggg | attatgaagg | tgtacagacc | 6780
| gcccccaac | agggattcga | tccaaagtcc | gaagcccctg | ttggcactgt | tgtaatcggt | 6840
| ggcattacgt | ataacaggca | tctggtcaaa | ggtaaggagg | tcctagttcc | caaacctgac | 6900
| aactgccttg | aagctgccag | actgtcccctt | gagcaagctc | ttgctgggat | gggccaaact | 6960
| tgtgaccttta | cagctaccga | agtggagaaa | ctaaagcgca | tcattagtca | actccaaggt | 7020
| ctgaccactg | aacaggcttt | aaactgctag | | | 7050

<210> SEQ ID NO 20
<211> LENGTH: 4392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
acaggcttta aactgctagc cgccagcggc ttgacccgct gtggccgcgg cggcctagtt      60
gtaactgaaa cggcggtaaa aatcgtaaaa taccacagca gaactttcac cttaggctct     120
ttagacctaa aagtcacctc cgaggtggag gtgaagaaat caactgagca ggggcacgct     180
gtcgtggcga acttatgttc cggtgtcgtc ttgatgaggc ctcacccacc gtcccttgtt     240
gacgttctcc tcaaacccgg acttgacaca acacccggca ttcaaccagg gcatgggcc      300
gggaatatgg gcgtgaacgg ttctatttgg gattttgaaa ctgcacccac aaaggtagaa     360
ctagagttgt ccaagcaaat aatccaagca tgtgaagtca ggcgcgggga cgcccctaac     420
ctccaactcc cctacaagct ttatcctgtc aggggggacc ccgagcggcg taaaggtcgc     480
cttgtcaaca ctaggtttgg agatttacct tacaaaactc cccaagacac caagtccgca     540
attcatgcgg cttgttgcct gcatcccaat ggggtcctcg tgtctgatgg caaatccacg     600
ctgggtacca ctcttcaaca tggtttcgag ctttatgtcc ccactgtacc ttatagtgtc     660
atggaatacc ttgattcacg ccctgacacc ccttttatgt gtactaaaca tggcacttcc     720
aaggctgctg cagaggacct ccaaaaatat gacctatcca ctcaagggtt tgtcttgcct     780
ggggtcctac gcctagtgcg caggttcatc tttagccatg ttggtaaggc gccaccactg     840
ttccttccat caacctaccc tgccaagaac tccatggcag gggtcaatgg ccagaggttc     900
ccaacaaagg atgtccagag catacctgaa attgatgaaa tgtgcgcccg tgccgtcaag     960
gaaaattggc agactgtgac accttgcacc ctcaaaaaac agtactgttc caaacctaaa    1020
actagaacca tcctaggtac caacaacttc atagccttgg ctcacaggtc agcactcagt    1080
ggtgtcaccc aggcgttcat gaagaaggcc tggaagtccc caattgcctt ggggaaaaac    1140
aagtttaagg aattgcattg cactgtcgcc ggcagatgcc ttgaggctga cctggcttcc    1200
tgcgatcgca gcaccccgc cattgtgagg tggtttgttg ccaacctcct gtatgaactt     1260
gcaggatgtg aagagtactt gcctagctac gtgctcaact gttgccatga ccttgtggca    1320
acgcaggatg gcgcttttca caaaacgcggt ggcctgtcgt ccggggaccc cgtcaccagt    1380
gtgtccaaca ccgtctactc actgataatt tacgcccagc acatggtgct ttcggccttg    1440
aagatgggtc atgaaattgg tctcaagttc cttgaggaac agctcaaatt tgaggacctt    1500
cttgaaatcc agcccatgtt agtgtattct gatgacctcg tcttgtatgc ggaaagaccc    1560
acttttccca actaccattg gtgggtcgag catcttgacc tgatgttggg ctttaaaacg    1620
gacccaaaga aaactgtcat aactgataaa cccagttttc tcggctgcag aattgaagca    1680
ggacggcagt tagtccccaa tcgcgaccgt attctggctg ctcttgcata tcatatgaag    1740
gcgcagaacg cctcagagta ttatgcgtcc gctgccgcaa ttctgatgga ttcgtgtgct    1800
tgcattgacc atgaccccga gtggtatgag gatcttatct gcggcatcgc ccggtgtgct    1860
cgccaggacg gttaccgttt tccaggcccg gcattttca tgtccatgtg ggagaagctg     1920
aaaagtcata tgaagggaa gaaatgccgt cactgcggca tctgcgacgc caaagccgac    1980
tatgcgtccg cctgtggact tgatttgtgt ttgttccatt cacactttca tcaacactgc    2040
ccagtcactc tgagctgtgg ccaccatgcc ggttcaaagg aatgttcgca gtgtcagtca    2100
cctgtcgggg ctggcaaatc ccccttgac gctgtgctga acaaatccc gtacaaacct      2160
cctcgtacca ttatcatgaa ggtggacaac aaaacaacga cccttgaccc gggaagatat    2220
cagtcccgtc gaggtcttgt tgcagtcaaa agaggtattg caggtaatga ggttgatctt    2280
tctgatggag actaccaagt ggtgcctctt ttgccgactt gcaaagacat aaacatggtg    2340
aaggtggctt gcaacgtact actcagcaag tttatagtag ggccgccagg ttccggaaaa    2400
```

```
accacctggc tactgaacca agtccaggac gatgatgtca tttacacacc tactcatcag   2460
acaatgtttg acatagtcag tgctcttaaa gtttgcaggt attccatccc aggagcctca   2520
ggactcccttt tccaccacc tgccaggtcc gggccgtggg ttaggctcat cgccagcgga   2580
catgtccctg gccgagtgtc atatctcgat gaggcaggat attgcaatca tctagacatt   2640
ctaaggctgc tttccaaaac accccttgtg tgtttgggtg accttcagca acttcacccg   2700
gtcggctttg attcctattg ttatgtgttc gatcagatgc ctcagaagca gctgaccacc   2760
atttatagat ttggccctaa catctgtgca gccatccagc cttgttacag ggagaaactt   2820
gaatccaagg ccaggaacac cagagtggtt ttcaccaccc ggcctgtggc ctttggtcag   2880
gtcctgacac cgtaccacaa agatcgtacc ggctctgcaa taactataga ttcatcccag   2940
ggggcgacct tcgacattgt gacattgcat ctaccatcgc caaagtccct aaacaaatcc   3000
cgagcacttg tagccatcac tcgggcaaga catgggttgt tcatttatga ccctcatgac   3060
caactccagg agttttttcaa cttaaccccc gagcgcactg attgtaacct tgcgttcagc   3120
cgtggggatg agctggttgt tttgaatgtg gataatgcgg tcacaactgt agcgaaggcc   3180
ctagagacag gttcaccccg atttcgagta tcggacccga ggtgcaagtc tctcttagcc   3240
gcttgttcgg ccagtctaga agggagctgc atgccactac cacaagtagc acataacctg   3300
gggttttact tttccccgga cagcccagct tttgcacccc tgccaaaaga gctggcgcca   3360
cattggccag tggtcaccca ccagaataat cgagcgtggc ctgatcgact tgtcgctagt   3420
atgcgcccaa ttgatgcccg ctacagcaag ccaatggtcg gtgcaggta tgtggtcggg   3480
ccatccattt ttcttggcac tcctggtgtg gtgtcatact atctcacatt atacatcggg   3540
ggcgagcctc aggccctgcc agaaacactc gtttcaacag gacgtatagc cacagattgt   3600
cgggaatatc tcgacgcggc tgaggaagag gcagcgagag aacttcccca cgcatttatt   3660
ggcgatgtca aaggcactac gatcgggggg tgtcaccaca ttacatcgaa ataccctacct   3720
aggtccctgc ctaaagactc tgttgctgtg gttggggtga gttcgcccgg tagggctgct   3780
aaagccgtgt gcactctcac cgatgtgtac ctcccccgaac tccgaccata tttgcaaccg   3840
gagacggcat caaaatgctg gaaacttaaa ctggatttca gggatgttcg actgatggtc   3900
tggaaaggcg ccacagccta tttccagttg gaagggctga catggtcagc gctgcccgat   3960
tatgctaggt tcattcagct acccaaggat gccgttgtgt acatcgatcc gtgtataggg   4020
ccggcaacag ccaatcgcaa ggttgtgcga accacagact ggcgggccga cctggcagtg   4080
acaccgtatg attacggtgc tcaggtcatt ttgacaacag cctggttcga ggaccttggg   4140
ccgcagtgga agatttttggg gttgcagcct ttcagacgaa catttggctt tgagaacact   4200
gaagattggg caattctcgc acgccgtatg aatgacggca aagattacac tgactataat   4260
tggcattgtg tacgagaacg cccacacgca atttacgggc gcgcccgtga ccatacgtat   4320
cattttgccc ttggcactga actgcaagta gagctgggca gaccccggct gcctcctgag   4380
caagtgccgt ga                                                        4392
```

<210> SEQ ID NO 21
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atgcaatggg tttactgtgg agtaaaatca gtcagttgtt cgtggatgcc ttcactgagt    60
tccttgttag tgtggttgac attgtcatct ttctcgccat attgtttggg ttcactgttg   120
caggctggtt attggtcttc cttctcagag tggtttgctc cgcgtttctc cgttcgcgct   180
ctgccattca ctcttccgaa ctatcgaagg tcctatgagg gcttgctacc caactgcaga   240
ccggatgtcc cacaattcgc agttaagcac ccgttgggta tactttggca tatgcgagtc   300
tcccacctaa ttgacgaaat ggtctctcgc cgcatttacc ggaccatgga acattcgggt   360
caagcggcct ggaagcaggt tgttagtgaa gccactctca caaaactgtc aaggcttgac   420
gtagtcactc atttccaaca cctggccgca gtggaggctg attcttgccg cttccttagc   480
tcacgactcg cgatgctgaa aaaccttgcc gttggcaatg tgagcctgga gtacaacact   540
actttggacc gcgttgagct catctttccc acaccaggta cgaggcccaa gttgaccgat   600
tttaggcaat ggcttatcag cgtgcacgct tccatcttct cctctgtggc ttcgtctgtt   660
accttgttca cagtgctttg gcttcgaatt ccagctctac gctatgtttt tggtttccat   720
tggcccacgg caacacatca ttcgaactaa                                    750
```

<210> SEQ ID NO 22
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggcttatc agcgtgcacg cttccatctt ctcctctgtg gcttcgtctg ttaccttgtt    60
cacagtgctt tggcttcgaa ttccagctct acgctatgtt tttggtttcc attggcccac   120
ggcaacacat cattcgaact aactatcaat tacactatat gtaagccatg ccctaccagt   180
caagctgccc aacaaagact cgagcctggc cgtaacgtgt ggtgcaaaat agggcacgac   240
aggtgtgagg aacgtgacca tgatgagttg tcaatgtcca ttccgtccgg gtacgacaac   300
ctcaaacttg agggttatta tgcttggctg gcttttttgt cctttttccta cgcggcccaa   360 ttccatccgg agctgttcgg aataggaaac gtgtcgcgcg tctttgtgga taagcgacac   420
cagttcattt gcgccgagca tgatggacaa aattcaacca tatctgccag acacaacatc   480
tccgcgtcgt atgcggtgta ttaccatcat caaatagacg ggggcaattg gtttcatttg   540
gaatggctgc gaccattctt ttcctcctgg ctggtgctca acatctcatg gtttctgagg   600
cgttcgcctg caagccctgc ttctcgacgc atctatcaga tattaagacc aacacgaccg   660
cggctgccgg tttcatggtc cttcagaaca tcaattgttt ccaatctcac agggcctcaa   720
cagcgcaagg taccactccc ctcaggaggt cgtcccaatg tcgtgaagcc gtcggcattc   780
cccagtacat cacgataa                                                 798
```

<210> SEQ ID NO 23
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggctgcga ccattctttt cctcctggct ggtgctcaac atctcatggt ttctgaggcg    60
```

```
ttcgcctgca agccctgctt ctcgacgcat ctatcagata ttaagaccaa cacgaccgcg      120
gctgccggtt tcatggtcct tcagaacatc aattgtttcc aatctcacag ggcctcaaca      180
gcgcaaggta ccactcccct caggaggtcg tcccaatgtc gtgaagccgt cggcattccc      240
cagtacatca cgataacggc taatgtgacc gatgaatcgt atttgtacaa cgcggacttg      300
ctgatgcttt ccgcgtgcct tttctacgcc tcggaaatga gcgagaaagg cttcaaagtc      360
atctttggga atatttctgg cgttgtttcc gcttgtgtta atttcacaga ttatgtggcc      420
catgtgaccc aacacactca gcagcaccat ttggtaattg atcacattcg gttactacac      480
ttcttgacac cgtctacgat gaggtgggct acaaccattg cttgtttgct tgccattctt      540
ttggcggtat ga                                                          552
```

<210> SEQ ID NO 24
<211> LENGTH: 606
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 24

```
atgaaatgtt cttgcaagtt ggggcatttc ttgactcctc actcttgctt ctggtggctt       60
tttttgctgt gtaccggctt gtcttggtcc tttgtcgatg caacgacga cagctcgaca      120 tcccaataca tatataattt gacgatatgc gagctgaatg ggaccgaatg gttgtccggt      180
cattttgatt gggcagtcga aacctttgtg ctttacccag ttgccactca tatcatttca      240
ctgggttttc tcacaacaag ccatttcctt gatgcgctcg gtctcggcgc tgtgtccgcc      300
acaggattca ttggcgagcg gtatgtactt agcagcatgt acggcgtttg cgccttcgcg      360
gcgttcgtat gttttgtcat ccgtgctgct aaaaattgca tggcttgccg ctatgcccgc      420
acccggttta ccaacttcat cgtggacgac cggggaagaa tccatcgatg gaagtcttca      480
atagtggtgg agaaattggg caaagctgaa gtcggtggtg accttgtcaa cattaagcat      540
gttgtcctcg aagggggttaa agctcaacct ttgacgagga cttcggctga gcaatgggaa      600
gcctag                                                                 606
```

<210> SEQ ID NO 25
<211> LENGTH: 522
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 25

```
atgggaagcc tagacgactt tgcaacgat cccaccgccg cacaaaaact cgtgctggcc        60
tttagcatca catatacacc cataatgata tacgcccta aggtgtcacg cggccgactc      120
ctggggctgt tgcacatctt gatatttctg aattgttcct ttactttttgg gtacatgaca      180 tatgtgcatt tcaatccac caaccgtgtc gcattcactc tgggggctgt agtcgccctt      240
ttgtggggtg tttacagcct cacagagtca tggaagttca tcacttccag atgcagattg      300
tgttgcctag gccggcgata cattctggcc cctgcccatc acgtagaaag tgctgcaggc      360
ctccattcaa tccagcgtc tggtaaccga gcatacgctg tgagaaagcc cggactaaca      420
tcagtgaacg gcactctagt acctgggctt cggagcctcg tgctgggcgg caaacgagct      480
gttaaacgag gagtggttaa cctcgtcaag tatggccggt aa                         522
```

<210> SEQ ID NO 26
<211> LENGTH: 431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggccggta agaaccagag ccagaagaaa agaagaaatg cagctccgat ggggaaaggc      60
cagccagtca atcaactgtg ccagttgctg ggtacaatga taaagtccca gcgccagcaa     120
tctaggggag acaggccaa aaagaagaag cctgagaagc acattttcc cctagctgct       180 gaagatgaca ttcggcacca tctcacccag gccgaacgtt ccctctgctt gcaatcgatc     240
cagacggctt tcaatcaagg cgcaggaact gcgtcgcttt catccagcgg aaggtcagt     300 ttccaggttg agttcatgct gccggttgct catacagtgc gcctgattcg cgtgacttct     360
acatccgcca gtcagggtgc aaattaattt gacagtcagg tgaatggccg cgattgacgt     420
gtggcctcta a                                                          431
```

<210> SEQ ID NO 27
<211> LENGTH: 7083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgtctggga tgttctcccg gtgcatgtgc accccggctg cccgggtatt ttggaacgcc     60
ggccaagtct attgcacacg tgtctcagt gcacggtctc ttctctctcc agaacttcag    120
gacacggacc tcggtgcagt tggcttgttt cacaagccta agacaagct ccattggaaa    180 gttcccattg gtatccccca ggtggaatgt tctccatctg ggtgttgctg gctgtcaacc    240
atttttcctt tagcgcgcat gacctccggc aatcacaact tccttcaacg actcgtgaag    300
gttgctgacg tattgtaccg tgacggttgc ttaaccccta gacacctccg tgaactccaa    360
gtttacgagc gtggttgcaa ttggtatccg attacggggc ctgtgcctgg gatggctgtg    420
tacgcgaact ccatgcacgt gtccgaccaa ccgttccctg gtgccactca tgtgttaaca    480 aattccccctt tgcctcaacg ggcttgtcgg cagccgttct gtccgttcga agaggcccat    540
tctagcatat acaggtggga aaaatttgta atttttatgg attcctcctc cgacggtcga    600
tctcgcatga tgtggactcc ggaatccgat gactccacgg ctttggaagt tctgccgccc    660
gagctagaac accaggtcaa ggtccttgtt cggagctttc ccgcccatca ccttgtcgac    720
cttgccgatt gggagctcac tgagtccct gagaacggtt tttccttcag cacgtcacat    780
ccttgcggct accttgttcg ggaccccggct gtatccgaag caagtgttg ctttcctgc     840 tttttgagcc agtcagccga agtgctcagt cgcgaggcgc atctggctac cgcctatggt    900
taccaaacca gtgggggtgt gcctggcaag tacatccagc gcagacttca agttcacggt    960
ctccgtgctg tggtcgaccc tgatggtccc attcacgttg aagcattgtc ttgccccag     1020 tcttggatca ggcacttgac cctgaatgat gatgtcaccc cggattcgt tcgcctaatg    1080 tctcttcgca ttgtgccgaa cacagagcct accacacacc ggatctttcg ttttggagtg    1140
cacaagtggt atggtgccgc cggcaaacgg gcccgtggca agcgtgccgc caaaagtgag    1200
```

```
aaagactcgg cttccaccct caaggttgcc cgaccgactt ccaccagtgg aatcgtcacc    1260
tactccccac ctgcggacgg gtcttgtggt tggcatgccc ttgccgccat actgaaccgg    1320
atgattaata atgacttcac gtcccctctg cctcggtaca acaggccgga ggacgattgg    1380
gcttctgatg gtgaccttgc tcaggccatt caatgtttgc aactacctgc cgccatagct    1440
cggaaccgcg cctgccctaa cgccaaatac ctcgtaaaac tcaacggagt tcattgggag    1500
gtagaggtga ggcctggaat ggctcctcgc tccctctctc gtgagtgcgt tgttggcgtc    1560
tgctctgaag gctgtgtcgc gtcgccttac ccggaggacg ggttgcctaa acgtgcactt    1620
gaggccctgg cgtctgctta tagactgcct tcagactgtg tttgtgatgg tattattgac    1680
ttccttgcca atccacctcc ccaggagttc tggactcttg acaaaatgtt gacttccccg    1740
tcaccggagc agtccggctt ctctagtctg tataaattgt tgttagaggt cttgccgcag    1800
aaatgcggat ccacagaagg ggaattcatc tatactgttg agaggatgtt gaaggattgt    1860
ccgagctcca acaggccat ggccctcctt gcaaaaatta aggtcccatc ctcaaaggcc    1920
ccatccgtga ctctgaacga gtgcttcccc acgatgttca cagtcaactc tgagttaata    1980
tcttgggaag agcccaaaga ccctggcgct gctgttgtcc tatgtccatc ggatgcaaaa    2040
gaatctaagg aaacagcccc tgaagaagct caagcgagaa accgtaaggt cctccaccct    2100
gtggtcctta ccgaggaact tagcgagcaa caggtgcagg tggttgaggg tgatcaggat    2160
atgccactgg atttgacttg gccaaccta accgctacgg cgaccctgt tagagggccg    2220 gtaccggaca atttgagctc tggcattggt gcccagcccg ctaccgttca agaactcatt    2280
ctggcgaggc ctgcaccccg tcttgttgag cgctgtggca cggagtcgaa cggcagcagt    2340
tcatttctgg atttgcctga cgtgcagacc tcggaccagc ctttagacct gtccctggcc    2400
gcgtggcctg taagggctac cgcgtctgac cccggttgga tccacggtag gcgtgagcct    2460
gtctttgtga agcctcgagg tgttttctct gatggcgagt cggcccttca gttcggagag    2520 cttttccgaag ccagttctgt cgtcgatgac cggacaaaag aagctccggt ggttgacgcc    2580
cccatcgatt tgacaacttc gaacgagacg ctctctgggt ctgacccctt gaattcgcc    2640 aaattcaggc gcccgcgttt ctccgcgcaa gctttaatcg accgaggtgg tccgcttgcc    2700
gatgttcatg caaagataaa gagtcgggta tatgaacaat gccttcaagc ttgtgaacct    2760
ggtagtcgtg cgaccccagc caccaagaag tggctcgaca aaatgtggga cagggtggac    2820
atgaaaactt ggcgctgcac ctcgcagttc caagctggtc acattcttga gtccctcaaa    2880
ttcctccctg acatgattca agacacaccg cctcctgttc ccaggaagaa ccgagctggt    2940
gacagtgccg gcctgaagca actggtggcg cagtgggata ggaaattgag tgtgacaccc    3000
cccacaaaac cggttggacc ggtgcttgac cagaccgtcc ctctgcctat ggacatccag    3060
caagaagatg ccatctccgc tgacaagcca ccccattcgc aaaaccttc tagtcaagta    3120 gatgtgggtg gaggttggaa aagtttatg ctctccggca cccgtttcgc ggggtccgtt    3180
agtcagcgcc ttacgacatg ggttttgag gttctctccc atctcccagc ttttatgctc    3240
acacttttct cgccacgggg ctctatggct ccaggtgatt ggctgtttgc aggtgctgtt    3300
ctacttgctc tcctgctctg ccgttcttac ccaatactcg gatgcttcc cttattgggt    3360 gtcttttctg gttctgtgcg gtgtgttcgt ttgggtgttt ttggttcttg gatggctttt    3420
gctgtatttt tattctcgac tccacccgac ccagtcggtt cttcttgtga ccacgattcg    3480
ccggagtgtc atgctgagct tttggctctt gagcagcgcc aactttggga acctgtgcgc    3540
agccttgtgg tcgggccatc gggcctctta tgcgtcattc ttggcaagtt actcggtggg    3600
```

```
tcacgttgtc tctggtttgt tctcctacgt atatgcatgc tcgcagattt ggcaatttct   3660
cttatttatg tggtgtccca agggcgttgt cacaagtgtt ggggaaagtg tataaggacg   3720
gctcctgcag aagtgaccct taatgtgttt ccttttcgc gcgccacccg ctcatctctt    3780
gtgtccttgt gtgatcggtt ccaagcgcca aaaggagttg accccgtgca cttggcgaca   3840
ggctggcgcg ggtgctggtg tggtgagagc cctattcatc aatcacacca aaaaccgata   3900
gcttatgcca acttggatga aaagaagata tccgcccaga cggtgattgc tgtcccgtat   3960
gatcccagtc aggccattaa atgcctgaaa gttttgcagg caggagggc tattgtggac    4020 cagcctacgc ccgaggtcgt ccgtgtgtct gagattccct tctcggcccc attttttccg   4080
aaggtcccag tcaacccaga ttgcagggtt gtggtagatt cggacacttt tgtggctgcg   4140
gtccgctgcg gttattcgac agcacaactg gtccttggtc ggggcaactt tgccaagcta   4200
aatcagaccc ccctcaggaa ctctgtcccc accaaaacaa ctggtggggc ctcatacacc   4260
cttgccgtgg cccaggtatc tgtgtggact cttgttcatt tcatcctcgg cctttggtta   4320
acgtcacctc aagtgtgtgg tcgagggacc tctgacccgt ggtgttcgaa cccttttcg   4380 tatcctactt atggccccgg agttgtgtgt cctctcgac tctgcgtgtc tgccgacgga    4440
gttaccctgc cattgttctc agccgttgcc catctttccg gtagagaggt ggggattttt   4500
attttggtgc ttgcctcctt gggcgcttta gcccaccgct tggctcttaa ggcagacatg   4560
tcaatggtct ttttggcgtt ttgtgcttac gcctggccca tgagctcctg gttaatttgc   4620
ttctttccta tgctcttgag gtgggtaacc cttcatcctc tcactatgct ttgggtgcac   4680 tcattttgg tgttttgcct accagctgcc ggcgttctct cgctgggaat aaccggtctt    4740
ctttgggcag ttggccgttt cacccaggtt gccggaatta tcacacctta tgacatccac   4800
cagtatacct ccggaccacg tggtgcagct gctgtagcaa cggctccaga aggtacttac   4860
atggcggccg ttcggagagc cgctttgact ggacggactt tgatcttcac accatctgca   4920
gtcggatccc ttcttgaagg tgctttcaga actcaaaagc cctgccttaa caccgtgaat   4980
gtcgtaggct cttcccttgg ttctggagga gttttcacca ttgatggcag aagagtcatc   5040
gtcactgcca cccatgtgtt gaatggtaac acagccaggg tcactggtga ttcctacaac   5100
cgcatgcaca cgttcaatac taatggtgat tatgcctggt cccatgctga tgactggcaa   5160
ggcgttgccc ctatggttaa gatcgctaag gggtatcgcg tcgtgccta ctggcaaacg    5220 tcaaccggag tcgaacctgg catcatgggg gaaggattcg ccttctgttt cactaactgt   5280
ggcgactcag ggtcacctgt catttcagaa gctggtgacc ttattggagt ccataccggt   5340
tcaaacaaac tcggttctgg tcttgtgaca accccctgaag gggagacctg ctccatcaag   5400
gaaactaggc tctctgacct ttctagacat tttgcaggtc caagcgtccc tcttggggac   5460
attaagttga gcccagccat catccctgat gtgacaacta ttccgagtga cttggcatcg   5520
ctccttgctt ctgtccccgt gatggaaggt ggcctctcaa ctgtccagct tttgtgcgtc   5580 ttttttccttc tctggcgcat gatgggccat gcctggacac ccattgttgc cgtaggcttc   5640
tttttgctga atgaaattct cccagcagtc ttggtccgag ctgtgttctc ttttgcactc   5700
tttgtacttg catgggccac cccctggtcg gcacaagtgt tgatgattag actcctcacg   5760
gcggctctca accgcaacag gttgtccctg gcgttctacg cactcggagg tgtcgttggc   5820
ctggccacag aaatcgggac ttttgctggt ggatggcctg aactgtccca agccctctcg   5880
acatactgct tcctgcccag gttccttgct gtgactagtt atgtccccac catcatcatc   5940
```

| | |
|---|---|
| ggtgggctcc atgccctcgg cgtaattttg tggttattca ataccgatg cctccacaac | 6000 |
| atgctggttg gtgatgggag tttctcaagc gctttcttcc tacggtattt tgctgagggt | 6060 |
| aatcttagga aaggcgtgtc gcagtcctgt ggcatgaata acgaatccct gacagctgct | 6120 |
| ttggcttgca agttgtcgca agctgacctt gattttttgt ccagtttaac gaacttcaag | 6180 |
| tgctttgtgt ccgcttcaaa catgaaaaat gcagctggcc aatacatcga ggcggcgtat | 6240 |
| gctagagctc tgcgtcagga gctggcctcc ttggttcagg ttgacaagat gaaaggagta | 6300 |
| ttggccaagc tcgaggcttt cgctgagacg gccactccgt cacttgacac aggtgacgtg | 6360 |
| attgttctgc ttgggcaaca cccccatgga tccatcctcg acattaatgt gggggggtgaa | 6420 |
| aggaaaactg tgtctgtgca agaaacacga tgcctgggtg gttccaaatt cagtgtctgc | 6480 |
| actgtcgtgt ccaacacgcc cgtggatacc ttgaccggca tcccacttca gacgccaacc | 6540 |
| ccactttttg aaaatggccc cgcgccatcgc agcgaggacg acgaccttaa agttgagaga | 6600 |
| atgaaaaaac actgtgtatc cctcggcttc cacaaaatca atggtaaagt ttactgcaaa | 6660 |
| atttgggaca gtctaacgg cgacaccttt tacacgatg attcccgata cactcaagac | 6720 |
| catgcttttc aggacaggtc aaccgactat agagacaggg attatgaagg tgtacagacc | 6780 |
| gcccccaac agggattcga tccaaagtcc gaagcccctg ttggcactgt tgtaatcggt | 6840 |
| ggcattacgt ataacaggca tctggtcaaa ggtaaggagg tcctagttcc caaacctgac | 6900 |
| aactgccttg aagctgccag actgtcccctt gagcaagctc ttgctgggat gggccaaact | 6960 |
| tgtgacctta cagctaccga agtggagaaa ctaaagcgca tcattagtca actccaaggt | 7020 |
| ctgaccactg aacaggcttt aaactgctag ccgccagcgg cttgacccgc tgtggccgcg | 7080 |
| gcg | 7083 |

<210> SEQ ID NO 28
<211> LENGTH: 4392
<212> TYPE: DNA
<213> ORGANISM: Porcine reproductive respiratory syndrome virus

<400> SEQUENCE: 28

| | |
|---|---|
| acaggcttta aactgctagc cgccagcggc ttgacccgct gtggccgcgg cggcctagtt | 60 |
| gtaactgaaa cggcggtaaa aatcgtaaaa taccacagca gaactttcac cttaggctct | 120 |
| ttagacctaa aagtcacctc cgaggtggag gtgaagaaat caactgagca ggggcacgct | 180 |
| gtcgtggcga acttatgttc cggtgtcgtc ttgatgaggc ctcacccacc gtcccttgtt | 240 |
| gacgttctcc tcaaacccgg acttgacaca acacccggca ttcaaccagg catgggggcc | 300 |
| gggaatatgg gcgtgaacgg ttctatttgg gattttgaaa ctgcacccac aaaggtagaa | 360 |
| ctagagttgt ccaagcaaat aatccaagca tgtgaagtca ggcgcgggga cgcccctaac | 420 |
| ctccaactcc cctacaagct ttatcctgtc agggggggacc ccgagcggcg taaaggtcgc | 480 |
| cttgtcaaca ctaggtttgg agatttacct tacaaaactc cccaagacac caagtccgca | 540 |
| attcatgcgg cttgttgcct gcatcccaat ggggtcctcg tgtctgatgg taaatccacg | 600 |
| ctgggtacca ctcttcaaca tggtttcgag ctttatgtcc ccactgtacc ttatagtgtc | 660 |
| atggaatacc ttgattcacg ccctgacacc cctttatgt gtactaaaca tggcacttcc | 720 |
| aaggctgctg cagaggacct ccaaaaatat gacctatcca ctcaagggtt tgtcttgcct | 780 |
| ggggtcctac gcctagtgcg caggttcatc tttagccatg ttggtaaggc gccaccactg | 840 |
| ttccttccat caacctaccc tgccaagaac tccatggcag gggtcaatgg ccagaggttc | 900 |
| ccaacaaagg atgtccagag cataccctgaa attgatgaaa tgtgcgcccg tgccgtcaag | 960 |

```
gaaaattggc agactgtgac accttgcacc ctcaaaaaac agtactgttc caaacctaaa    1020
actagaacca tcctaggtac caacaacttc atagccttgg ctcacaggtc agcactcagt    1080
ggtgtcaccc aggcgttcat gaagaaggcc tggaagtccc caattgcctt ggggaaaaac    1140
aagtttaagg aattgcattg cactgtcgcc ggcagatgcc ttgaggctga cctggcttcc    1200
tgcgatcgca gcaccccgc cattgtgagg tggtttgttg ccaacctcct gtatgaactt    1260
gcaggatgtg aagagtactt gcctagctac gtgctcaact gttgccatga ccttgtggca    1320
acgcaggatg gcgctttcac aaaacgcggt ggcctgtcgt ccggggaccc cgtcaccagt    1380
gtgtccaaca ccgtctactc actgataatt tacgcccagc acatggtgct ttcggccttg    1440
aagatgggtc atgaaattgg tctcaagttc cttgaggaac agctcaaatt tgaggacctt    1500
cttgaaatcc agcccatgtt agtgtattct gatgacctcg tcttgtatgc ggaaagaccc    1560
acttttccca actaccattg gtgggtcgag catcttgacc tgatgttggg ctttaaaacg    1620
gacccaaaga aaactgtcat aactgataaa cccagttttc tcggctgcag aattgaagca    1680
ggacggcagt tagtccccaa tcgcgaccgt attctggctg ctcttgcata tcatatgaag    1740
gcgcagaacg cctcagagta ttatgcgtcc gctgccgcaa ttctgatgga ttcgtgtgct    1800
tgcattgacc atgaccccga gtggtatgag gaccttatct gcggcatcgc ccggtgtgct    1860
cgccaggacg gttaccgttt tccaggcccg gcattttttca tgtccatgtg ggagaagctg    1920
aaaagtcata acgaagggaa gaaatgccgt cactgcggca tctgcgacgc caaagccgac    1980
tatgcgtccg cctgtggact tgatttgtgt ttgttccatt cacactttca tcaacactgc    2040
ccagtcactc tgagctgtgg ccaccatgcc ggttcaaagg aatgttcgca gtgtcagtca    2100
cctgtcgggg ctggcaaatc ccccttgac gctgtgctga acaaatccc gtacaaacct    2160 cctcgtacca ttatcatgaa ggtggacaac aaaacaacga cccttgaccc gggaagatat    2220
cagtcccgtc gaggtcttgt tgcagtcaaa agaggtattg caggtaatga ggttgatctt    2280
tctgatggag actaccaagt ggtgcctctt ttgccgactt gcaaagacat aaacatggtg    2340
aaggtggctt gcaacgtact actcagcaag tttatagtag ggccgccagg ttccggaaaa    2400
accacctggc tactgaacca agtccaggac gatgatgtca tttacacacc tactcatcag    2460
acaatgtttg acatagtcag tgctcttaaa gtttgcaggt attccatccc aggagcctca    2520 ggactcccctt ttccaccacc tgccaggtcc gggccgtggg ttaggctcat cgccagcgga    2580
catgtccctg gccgagtgtc atatctcgat gaggcaggat attgcaatca tctagacatt    2640
ctaaggctgc tttccaaaac accccttgtg tgtttgggtg accttcagca acttcacccg    2700
gtcggctttg attcctattg ttatgtgttc gatcagatgc ctcagaagca gctgaccacc    2760
atttatagat ttggccctaa catctgtgca gccatccagc cttgttacag ggagaaactt    2820
gaatccaagg ccaggaacac cagagtggtt tcaccaccc ggcctgtggc ctttggtcag    2880
gtcctgacac cgtaccacaa agatcgtacc ggctctgcaa taactataga ttcatcccag    2940
ggggcgacct tcgacattgt gacattgcat ctaccatcgc caaagtccct aaacaaatcc    3000
cgagcacttg tagccatcac tcgggcaaga catgggttgt tcatttatga ccctcatgac    3060
caactccagg agtttttcaa cttaaccccc gagcgcactg attgtaacct tgcgttcagc    3120 cgtgggatg agctggttgt tttgaatgtg gataatgcgg tcacaactgt agcgaaggcc    3180
ctagagacag gttcaccccg atttcgagta tcggacccga ggtgcaagtc tctcttagcc    3240
gcttgttcgg ccagtctaga agggagctgc atgccactac cacaagtagc acataaccctg    3300
```

```
gggttttact tttccccgga cagcccagct tttgcacccc tgccaaaaga gctggcgcca      3360
cattggccag tggtcaccca ccagaataat cgagcgtggc ctgatcgact tgtcgctagt      3420
atgcgcccaa ttgatgcccg ctacagcaag ccaatggtcg gtgcagggta tgtggtcggg      3480
ccatccattt ttcttggcac tcctggtgtg gtgtcatact atctcacatt atacatcggg      3540
ggcgagcctc aggccctgcc agaaacactc gtttcaacag gacgtatagc cacagattgt      3600
cgggaatatc tcgacgcggc tgaggaagag gcagcgagag aacttcccca cgcatttatt      3660
ggcgatgtca aaggcactac ggtcgggggg tgtcaccaca ttacatcgaa ataccctacct      3720 aggtccctgc ctaaagactc tgttgctgtg gttggggtga gttcgcccgg tagggctgct      3780
aaagccgtgt gcactctcac cgatgtgtac ctccccgaac tccgaccata tttgcaaccg      3840
gagacggcat caaaatgctg gaaacttaaa ctggatttca gggatgttcg actgatggtc      3900
tggaaaggcg ccacagccta tttccagttg aagggctga catggtcagc gctgcccgat      3960
tatgctaggt tcattcagct acccaaggat gccgttgtgt acatcgatcc gtgtataggg      4020
ccggcaacag ccaatcgcaa ggttgtgcga accacagact ggcgggccga cctggcagtg      4080
acaccgtatg attacggtgc tcaggtcatt ttgacaacag cctggttcga ggaccttggg      4140
ccgcagtgga agattttggg gttgcagcct ttcagacgaa catttggctt tgagaacact      4200
gaagattggg caattctcgc acgccgtatg aatgacggca agattacac tgactataat      4260 tggcattgtg tacgagaacg cccacacgca atttacgggc gcgcccgtga ccatacgtat      4320
cattttgccc ttggcactga actgcaagta gagctgggca gaccccggct gcctcctgag      4380
caagtgccgt ga                                                         4392

<210> SEQ ID NO 29
<211> LENGTH: 750
<212> TYPE: DNA
<213> ORGANISM: Porcine reproductive respiratory syndrome virus

<400> SEQUENCE: 29
atgcaatggg ttcactgtgg agtaaaatca gtcagttgtt cgtggatgcc ttcactgagt        60
tccttgttag tgtggttgac attgtcatct ttctcgccat attgtttggg ttcactgttg       120
caggctggtt attggtcttc cttctcagag tggtttgctc cgcgtttctc cgttcgcgct       180
ctgccattca ctctcccgaa ctatcgaagg tcctatgagg gcttgctacc caactgcaga       240
ccggatgtcc cacaattcgc agttaagcac ccgttgggta ctttggca tatgcgagtc        300 tcccacctaa ttgacgaaat ggtctctcgc cgcatttacc ggaccatgga acattcgggt       360
caagcggcct ggaagcaggt tgttagtgaa gccactctca caaaactgtc aaggcttgac       420
gtagtcactc atttccaaca cctggccgca gtggaggctg attcttgccg cttccttagc       480
tcacgactcg cgatgctgaa aaaccttgcc gttggcaatg tgagcctgga gtacaacact       540
actttggacc gcgttgagct catctttccc acaccaggta cgaggcccaa gttgaccgat       600
tttaggcaat ggcttatcag cgtgcacgct tccatcttct cctctgtggc ttcgtctgtt       660
accttgttca cagtgctttg gcttcgaatt ccagctctac gctatgtttt tggtttccat       720
tggcccacgg caacacatca ttcgaactaa                                        750

<210> SEQ ID NO 30
<211> LENGTH: 798
<212> TYPE: DNA
<213> ORGANISM: Porcine reproductive respiratory syndrome virus

<400> SEQUENCE: 30
```

```
atggcttatc agcgtgcacg cttccatctt ctcctctgtg gcttcgtctg ttaccttgtt      60
cacagtgctt tggcttcgaa ttccagctct acgctatgtt tttggtttcc attggcccac     120
ggcaacacat cattcgaact aactatcaat tacactatat gtaagccatg ccctaccagt     180
caagctgccc aacaaagact cgagcctggc cgtaacgtgt ggtgcaaaat agggcacgac     240
aggtgtgagg aacgtgacca tgatgagttg tcaatgtcca ttccgtccgg gtacgacaac     300
ctcaaacttg agggttatta tgcttggctg gcttttttgt cctttttccta cgcggcccaa    360
ttccatccgg agctgttcgg aataggaaac gtgtcgcgcg tctttgtgga taagcgacac    420
cagttcattt gcgccgagca tgatggacaa aattcaacca tatctgccag acacaacatc    480
tccgcgtcgt atgcggtgta ttaccatcat caaatagacg ggggcaattg gtttcatttg    540
gaatggctgc gaccattctt ttcctcctgg ctggtgctca acatctcatg gtttctgagg    600
cgttcgcctg caagccctgc ttctcgacgc atctatcaga tattaagacc aacacgaccg    660
cggctgccgg tttcatggtc cttcagaaca tcaattgttt ccaatctcac agggcctcaa    720
cagcgcaagg taccactccc ctcaggaggt cgtcccaatg tcgtgaagcc gtcggcattc    780
cccagtacat cacgataa                                                  798

<210> SEQ ID NO 31
<211> LENGTH: 552
<212> TYPE: DNA
<213> ORGANISM: Porcine reproductive respiratory syndrome virus

<400> SEQUENCE: 31
atggctgcga ccattctttt cctcctggct ggtgctcaac atctcatggt ttctgaggcg     60
ttcgcctgca gccctgcttc tcgacgcat ctatcagata ttaagaccaa cacgaccgcg    120
gctgccggtt tcatggtcct tcagaacatc aattgtttcc aatctcacag gcctcaaca    180
gcgcaaggta ccactcccct caggaggtcg tcccaatgtc gtgaagccgt cggcattccc    240
cagtacatca cgataacggc taatgtgacc gatgaatcgt atttgtacaa cgcggacttg    300
ctgatgcttt ccgcgtgcct tttctacgcc tcggaaatga gcgagaaagg cttcaaagtc    360
atctttggga atatttctgg cgttgtttcc gcttgtgtta atttcacaga ttatgtggcc    420
catgtgaccc aacacactca gcagcaccat ttggtaattg atcacattcg gttactacac    480
ttcttgacac cgtctacgat gaggtgggct acaaccattg cttgtttgtt tgccattctt    540
ttggcggtat ga                                                        552

<210> SEQ ID NO 32
<211> LENGTH: 606
<212> TYPE: DNA
<213> ORGANISM: Porcine reproductive respiratory syndrome virus

<400> SEQUENCE: 32
atgaaatgtt cttgcaagtt ggggcatttc ttgactcctc actcttgctt ctggtggctt     60
tttttgctgt gtaccggctt gtcttggtcc tttgtcgatg caacgacaa cagctcgaca    120
tcccaataca tatataattt gacgatatgc gagctgaatg ggaccgaatg gttgtccggt    180
cattttgatt gggcagtcga aacctttgtg ctttacccag ttgccactca tatcatttca    240
ctgggttttc tcacaacaag ccatttcctt gatgcgctcg gtctcggcgc tgtgtccgcc    300
acaggattca ttggcgagcg gtatgtactt agcagcatgt acggcgtttg cgccttcgcg    360
gcgctcgtat gttttgtcat ccgtgctgct aaaaattgca tggcttgccg ctatgcccgc    420
```

-continued

```
acccggttta ccaacttcat cgtggacgac cggggaagaa tccatcgatg gaagtcttca      480
atagtggtgg agaaattggg caaagctgaa gtcggtggtg accttgtcaa cattaagcat      540
gttgtcctcg aagggttaa agctcaaccc ttgacgagga cttcggctga gcaatgggaa       600
gcctag                                                                 606

<210> SEQ ID NO 33
<211> LENGTH: 522
<212> TYPE: DNA
<213> ORGANISM: Porcine reproductive respiratory syndrome virus

<400> SEQUENCE: 33
atgggaagcc tagacgactt tgcaacgat cccaccgccg cacaaaaact cgtgctggcc       60
tttagcatca catatacacc cataatgata tacgcccta aggtgtcacg cggccgactc      120
ctggggctgt tgcacatctt gatatttctg aattgttcct ttactttgg gtacatgaca      180 tatgtgcatt ttcaatccac caaccgtgtc gcactcactc tggggctgt agtcgccctt      240 ttgtggggtg tttacagcct cacagagtca tggaagttca tcacttccag atgcagattg      300
tgttgcctag gccggcgata cattctggcc cctgcccatc acgtagaaag tgctgcaggc      360
ctccattcaa tcccagcgtc tggtaaccga gcatacgctg tgagaaagcc cggactaaca      420
tcagtgaacg gcactctagt acctgggctt cggagcctcg tgctgggcgg caaacgagct      480
gttaaacgag gagtggttaa cctcgtcaag tatggccggt aa                        522

<210> SEQ ID NO 34
<211> LENGTH: 387
<212> TYPE: DNA
<213> ORGANISM: Porcine reproductive respiratory syndrome virus

<400> SEQUENCE: 34
atggccggta agaaccagag ccagaagaaa agaagaaatg cagctccgat ggggaaaggc       60
cagccagtca atcaactgtg ccagttgctg ggtacaatga taaagtccca gcgccagcaa      120
tctaggggag gacaggccaa aagaagaag cctgagaagc cacattttcc cctagctgct      180
gaagatgaca ttcggcacca tctcacccag gccaacgtt ccctctgctt gcaatcgatc       240
cagacggctt tcaatcaagg cgcaggaact gcgtcgcttt catccagcgg gaaggtcagt      300
ttccaggttg agttcatgct gccggttgct catacagtgc gcctgattcg cgtgacttct      360
acatccgcca gtcagggtgc aaattaa                                         387
```

EUROPEAN PRRSV STRAIN

SEQUENCE LISTING

This application contains a sequence listing in accordance with 37 C.F.R. 1.821-1.825. The sequence listing accompanying this application is hereby incorporated by reference in its entirety.

FIELD OF THE INVENTION

The present invention relates to a live attenuated strain of a European Porcine Reproductive and Respiratory Syndrome Virus (PRRSV), methods for the production of such strains, vaccines based thereon and methods for the production of such vaccines and the use thereof in the treatment of swine.

BACKGROUND OF THE INVENTION

Porcine reproductive and respiratory syndrome (PRRS) is viewed by many as the most important disease currently affecting the pig industry worldwide. The syndrome first was described in 1987 in the United States as "mystery swine disease" and rapidly spread across the globe. It causes severe reproduction losses, is associated with increased mortality due to secondary infections, and is linked to reduced feed conversion and average daily weight gain. Unfortunately, control of the virus that causes PRRS has proven to be difficult.

PRRS virus (PRRSV) is an enveloped single stranded RNA virus classified in the family Arteriviridae (Cavanaugh, 1997). It causes a widespread disease of swine that was first described as 'mystery swine disease' in the USA in 1987 (Hill, 1990). The disease manifests as respiratory illness in all age groups of swine leading to death in some younger pigs and severe reproductive problems in breeding age females.

Transmission of the PRRSV can, and often does, occur through direct contact between infected and susceptible pigs. Transmission over very short distances by air or through semen also may occur. Once infected, the virus can remain in the blood of adults for about two weeks, and in infected pigs for one to two months or more. Infected boars may shed the virus in the semen for more than 100 days. This long period of viremia significantly increases the possibility of transmission. In addition, the PRRS virus can cross the placenta during the last third of the gestation period to infect piglets in utero and cause stillbirth or weak-born piglets.

All types and sizes of herds, including those with high or ordinary health status or from either indoor or outdoor units, can be infected with PRRS virus. Infected herds may experience severe reproductivity losses, as well as, increased levels of post weaning pneumonia with poor growth. The reproductive phase typically lasts for two to three months; however, post weaning problems often become endemic. The reproductive disease is characterized by an abortion outbreak that affects both sows and gilts in the last term of gestation. Premature farrowings around 109 and 112 days of gestation occur. The number of stillbirths and weak-born piglets increases and results in a considerable increase in pre-weaning mortality.

The respiratory phase traditionally has been seen in the nursery, especially in continuous flow nurseries. However, respiratory problems caused by PRRS virus can also be seen in the finisher as part of the porcine respiratory disease complex (PRDC). A reduction in growth rate, an increase in the percentage of unmarketable pigs, and elevated post weaning mortality can occur. Diagnostic findings indicate high levels of pneumonia that associate with the PRRS virus together with a wide variety of other microbials commonly seen as secondary infectious agents. Bacterial isolates may include *Streptococcus suis*, *Haemophilus suis*, *Actinobacillus pleuropneumoniae*, *Actinobacillus suis*, *Mycoplasma hyopneumoniae*, and *Pasteurella multocida* among others. Viral agents commonly involved include swine influenza virus and porcine respiratory corona virus. Affected pigs rarely respond to high levels of medication, and all-in/all-out systems have failed to control the disease.

PRRSV virus exists as two genotypes referred to as "US" and "EU" type which share about 50% sequence homology (Dea S et al. (2000). Arch Virol 145:659-88). These two genotypes can also be distinguished by their immunological properties. Most sequencing information on various isolates is based on the structural proteins, namely the envelope protein GP5 which accounts for only about 4% of the viral genome, while only little is known on the non-structural proteins (nsp). Isolation of PRRSV and manufacture of vaccines have been described in a number of publications (WO 92/21375, WO 93/06211, WO93/03760, WO 93/07898, WO 96/36356, EP 0 676 467, EP 0 732 340, EP 0 835 930).

Vaccination is the key method for alleviating the burden of PRRS as pigs that recover from a PRRS infection will develop an immune response, which under normal circumstances will protect them from being infected again by the same virus strain. However, PRRS virus has the ability to change (by mutation or recombination); and therefore, new viral strains may arise. In such cases, cross protection between strains may not exist, and new outbreaks may be observed in farms that had been infected previously. Thus there is a continuing need for additional vaccines.

BRIEF SUMMARY OF THE INVENTION

The present invention is related to improved modified live PRRS vaccines of European genotype and new PRRSV strains which can be used for the manufacture of such vaccines. In particular, the invention provides improved PRRS virus strains that have been deposited with the European Collection of Cell Cultures (ECACC) under the Accession Numbers ECACC 11012501 and ECACC 11012502 each deposited on Jan. 25, 2011 in accordance with the provisions of the Budapest Treaty, or any descendant or progeny of one of the aforementioned strains.

In particular embodiments, the present invention describes a Porcine Reproductive and Respiratory Syndrome Virus (PRRSV) of a European type, which is of the strain deposited with European Collection of Cell Cultures (ECACC) under the Accession Numbers ECACC 11012501 or Accession Numbers ECACC 11012502.

The PRRSV is characterized in that the virus is attenuated by passaging at least 36 times in cell culture such that when the modified virus is administered to a swine or other mammal prone to PRRSV, it fails to cause clinical signs of PRRSV disease but is capable of inducing an immune response that immunizes the mammal against pathogenic forms of PRRSV.

Also contemplated is a method for the preparation of the live attenuated PRRSV deposited with European Collection of Cell Cultures (ECACC) under the Accession Numbers ECACC 11012502 or one attenuated from a parental strain deposited at Accession Numbers ECACC 11012501, comprising adapting an MA 104-grown PRRSV of a European type to non-MA 104 mammalian cells.

Another aspect of the invention contemplates a vaccine for the protection of pigs against PRRSV infection, comprising the live attenuated PRRSV deposited with European Collection of Cell Cultures (ECACC) under the Accession Numbers ECACC 11012502 or one attenuated from a parental strain deposited at Accession Numbers ECACC 11012501 and a pharmaceutically acceptable carrier. Such a vaccine may advantageously further comprise one or more non-PRRSV attenuated or inactivated pathogens or antigenic material thereof. For example, the non-PRRSV pathogens may be selected from Pseudorabies virus, Porcine influenza virus, Porcine parvovirus, Transmissible gastroenteritis virus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

In other embodiments, the vaccine may further comprise one or more additional European PRRSV strains selected from the group consisting of a PRRSV strain deposited under the Accession Numbers Lelystad virus strain (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108 or indeed may be a U.S. strain such as North American PRRS virus, pT7P129A; ATCC deposit VR-2332, ATCC deposit VR-2368; ATCC VR-2495; ATCC VR 2385, ATCC VR 2386, ATCC VR 2429, ATCC VR 2474, and ATCC VR 2402.

It is contemplated that the vaccine may comprise a carrier that is suitable for intradermal or intramuscular application. In some embodiments, the vaccine is in freeze-dried form. In specific embodiments, the vaccine comprises at least about $10^7$ virus particles.

Another aspect of the invention relates to a method for the preparation of a live attenuated vaccine for combating PRRS, comprising admixing a live attenuated PRRSV virus deposited with European Collection of Cell Cultures (ECACC) under the Accession Number ECACC 11012502 or one attenuated from a parental strain deposited at Accession Numbers ECACC 11012501 with a pharmaceutically acceptable carrier. In such methods the live attenuated PRRSV may preferably further comprise one or more additional European PRRSV strains selected from the group consisting of a PRRSV strain deposited under the Accession Numbers ECACC 04102703, ECACC 04102702, ECACC 04102704, CNCM Accession No. I-1140, CNCM Accession No I-1387, and CNCM Accession No I-1388.

In some embodiments, the live attenuated PRRSV may further comprise an adjuvant.

Also contemplated is a method of immunizing swine against porcine reproductive and respiratory syndrome (PRRS), the method comprising the step of administering to swine a vaccine composition including a live porcine reproductive and respiratory syndrome virus mixed with a pharmacologically compatible carrier agent, the virus comprising PRRS 94881 virus passaged at least 36 times in cell culture to modify the virus such that when the modified virus is administered to a swine or other mammal prone to PRRS, it fails to cause clinical signs of PRRS disease but is capable of inducing an immune response that immunizes the mammal against pathogenic forms of PRRS.

In some embodiments, the method is performed wherein the swine presents no lung lesions after vaccination. In other embodiments, the swine presents fewer lung lesions after vaccination as compared to vaccination with Porcilis vaccine.

Another aspect of the invention relates to a PRRS virus having a nucleotide sequence that is at least 95% homologous with the sequence set forth in either SEQ ID NO:1 or SEQ ID NO:10.

Also contemplated is a PRRS virus that comprises at least one ORF that encodes a protein that is at least 98% identical to any of the sequences set forth in SEQ ID NO: 2 to 9 or SEQ ID NO:11 to SEQ ID NO:18.

Also contemplated is a PRRS virus that has a nucleotide sequence of SEQ ID NO:1 or SEQ ID NO:10 or a fragment of either SEQ ID NO:1 or SEQ ID NO:2 wherein the fragment encodes an ORF selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

The invention further relates to a subunit vaccine for vaccination of a porcine animal wherein the vaccine comprises one or more nucleotides selected from the group consisting of a nucleotide that encodes an ORF selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

Another aspect of the invention relates to a subunit vaccine for vaccination of a porcine animal wherein the vaccine comprises one or more nucleotides selected from the group consisting of SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; and SEQ ID NO:34.

Also contemplated is a composition comprising one or more proteins selected from the group consisting of a protein having the sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

Also contemplated is an isolated nucleic acid comprising a sequence selected from the group consisting of SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34.

The invention further relates to a recombinant expression vector and/or vaccine comprising such expression vectors, wherein said vectors comprise a nucleic acid sequence that encodes one or more PRRSV ORFs selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 operably linked to a promoter. In such embodiments, the nucleic acid encoding the ORFs may preferably be selected from the group consisting of SEQ ID NO:19; SEQ ID NO:20; SEQ ID NO:21;

SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; and SEQ ID NO:34.

BRIEF DESCRIPTION OF SEVERAL VIEWS OF THE DRAWINGS

FIG. 7A shows means macroscopic lung lesions; FIG. 7B shows control animal histopathology; FIG. 7B shows PRRS infected animal histopathology.

DETAILED DESCRIPTION OF THE INVENTION

Figure 1A:
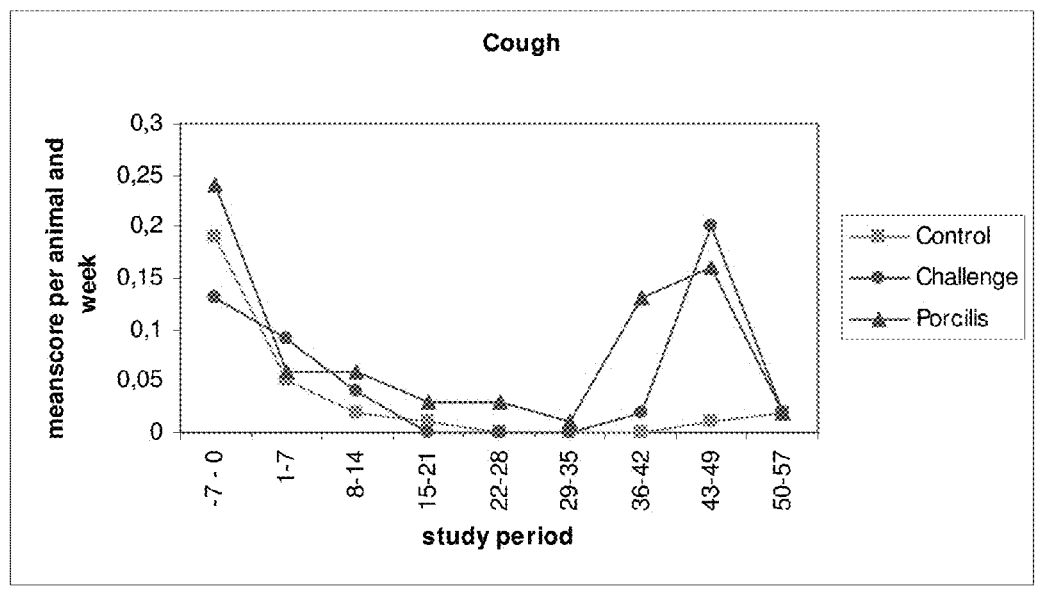
FIG. 1A: Clinical observation of cough score in respiratory challenge model using European challenge strain.

The present invention provides methods of treating or reducing the severity of porcine reproductive and respiratory syndrome virus (PRRSV) infection, as well as, methods of preventing PRRSV infection. Generally, the method is for treating or reducing the severity of or incidence of porcine reproductive and respiratory syndrome virus (PRRSV) infection. "Treating or reducing the severity of or incidence of" refers to a reduction in the severity of clinical signs, symptoms, and/or pathological signs normally associated with infection, up to and including prevention of any such signs or symptoms. "Pathological signs" refers to evidence of infection that is found microscopically or during necropsy (e.g. lung lesions).

The method generally includes the step of administering a therapeutic amount of a PRRSV antigen to a swine of a defined age or age range. For example, in one aspect of the invention, one therapeutic amount of a PRRSV antigen may be administered to a piglet about three-weeks-old or younger, and different therapeutic amounts of the antigen may be administered to a pig between about 3 weeks of age and 4 weeks of age. Similarly, an even different therapeutic amount might be administered to a pig between about four weeks and sixteen weeks of age (or any age within this range, e.g. five weeks to six weeks of age, nine weeks to fifteen weeks of age, seven weeks to ten weeks of age, etc.), or to pig older than sixteen weeks, such as an adult sow.

In specific embodiments, the present invention relates to an attenuated, atypical PRRSV strain and corresponding improved modified-live vaccines which confer effective immunity to this newly discovered typical PRRSV strain. "Effective immunity" refers to the ability of a vaccine to prevent swine PRRSV infections, including atypical PRRSV infections, which result in substantial clinical signs of the disease. It should be understood that the immunized swine may or may not be serologically positive for PRRSV, but the swine do not exhibit any substantial clinical symptoms.

In preferred forms, the vaccine of the invention includes a live European type PRRS live virus which has been attenuated in virulence. The resulting attenuated virus has been shown to be avirulent in challenged controlled host animal studies and to confer effective immunity. This particular strain of EU PRRS is not as virulent as others and hence, it is an attractive option as a vaccine candidate. The PRRSV 94881 parental strain does not cause severe, atypical PRRS disease in the pregnant sow nor severe lung lesions in young pigs. This strain was initially isolated from in the North Rhine Westphalia, Germany from a 3 week old piglet with severe respiratory disorder. The strain was subsequently attenuated via continuous passage in MA 104 cells. The attenuated strain was deposited in the European Collection of Cell Cultures (ECACC), Porton Down, Salisbury, Wiltshire, SP4 0JG, Great Britain, on Jan. 25, 2011 and was accorded Accession No. 11012502. This attenuated virus is a preferred Master Seed Virus (MSV) which has been subsequently passaged and developed as an effective PRRSV vaccine. The virulent parent strain denominated 94881 also was deposited in accordance with the Budapest Treaty at the European Collection of Cell Cultures (ECACC), Porton Down, Salisbury, Wiltshire, SP4 0JG, Great Britain, on Jan. 25, 2011 and was accorded Accession No. 11012501.

In certain exemplary embodiments the modified live virus vaccine was tested at a dosage of 1 ml for pigs and 2 ml for sows via intramuscular injection and was shown to be efficacious in producing protective immunity.

Passaging of the virus to attenuation was accomplished using classical virology methods. Specifically, the parental isolate PRRS 94881 was attenuated in vitro through continuous passing in MA 104 cells to achieve a maximum passage of 108 passes past initial isolation. Briefly, the material was passed at roughly 1 to 2 passes per week for a total of 108 passes in T-25 $cm^2$ or T-75 $cm^2$ flasks. Confluent MA 104 cell cultures with approximately 12-30 mL of Minimal Essential Medium (MEM) supplemented with 6% fetal bovine serum (FBS) were inoculated with 100 to 300 μl of the virus. Cultures were incubated for 3-7 days in a humidified chamber incubator at 37° C. with 4-6% $CO_2$. Once cultures reached >25% cytopathic effect (CPE), the flask was harvested by extracting the supernatant. A portion of the supernatant was passed into a new flask and 2 mL of the harvest was aliquoted for storage at −60° C. to −80° C.

The skilled person using standard techniques in the art will be able to determine the underlying nucleic acid sequence of the attenuated virus has been deposited ECACC under Accession No. 11012502. The present invention therefore further embraces a nucleic acid sequence specific for the attenuated PRRSV 94481 deposited at ECACC under Accession No. 11012502. Preferably, the invention further embraces PRRS virus nucleic acid sequences that share at least 95% sequence homology with the sequence of SEQ ID NO:1 or SEQ ID NO:10 as such viruses may likely be effective at conferring immunity upon animals vaccinated with attenuated viruses containing such homologous sequences. The sequence shown in SEQ ID NO:1 is the full length sequence of the attenuated PRRS 94881 MSV and has a full length sequence of 14843 bp. The ORFS 1 through 7 have been annotated for this sequence as follows:

| ORF Number | CDS in SEQ ID NO: 1 | Protein encoded |
|---|---|---|
| ORF1a | 178 to 7227 | SEQ ID NO: 2 |
| ORF1b | 7209 to 11600 | SEQ ID NO: 3 |
| ORF2 | 11611 to 12360 | SEQ ID NO: 4 |
| ORF3 | 12219 to 13016 | SEQ ID NO: 5 |
| ORF4 | 12761 to 13312 | SEQ ID NO: 6 |
| ORF5 | 13309 to 13914 | SEQ ID NO: 7 |
| ORF6 | 13902 to 14423 | SEQ ID NO: 8 |
| ORF7 | 14413 to 14799 | SEQ ID NO: 9 |

The sequence shown in SEQ ID NO:10 is the full length sequence of the parental PRRSV 94881 strain, passage 5 and has a full length sequence of 14843 bp. The ORFS 1 through 7 have been annotated for this sequence as follows:

| ORF Number | CDS in SEQ ID NO: 10 | Protein encoded |
|---|---|---|
| ORF1a | 178 to 7227 | SEQ ID NO: 11 |
| ORF1b | 7209 to 11600 | SEQ ID NO: 12 |
| ORF2 | 11611 to 12360 | SEQ ID NO: 13 |
| ORF3 | 12219 to 13016 | SEQ ID NO: 14 |
| ORF4 | 12761 to 13312 | SEQ ID NO: 15 |
| ORF5 | 13309 to 13914 | SEQ ID NO: 16 |
| ORF6 | 13902 to 14423 | SEQ ID NO: 17 |
| ORF7 | 14413 to 14799 | SEQ ID NO: 18 |

With the isolation of this new attenuated European PRRS virus strain it is possible to produce improved PRRS vaccines containing a most recent PRRS strain that is reflective of virulent PRRS strains found currently in the field. In particular, the new attenuated European PRRS virus may be used to prepare modified live vaccines (MLV). A modified live vaccine is characterized in that it contains live virus which can replicate in pigs, but does not exert clinical disease of PRRS. Furthermore, upon administration it induces an immunological response in pigs which generally leads to a significant extent of protection against subsequent infection with pathogenic PRRS virus. Virus showing such characteristics is usually called attenuated virus. In addition, the present invention provides details of the sequences of the ORFs of both the parental and the attenuated strains of PRRSV 94881. Thus, it is contemplated that the skilled person may employ the sequences of any one or more of the ORFs shown herein in a subunit vaccine.

As noted above, in general, attenuation of virus may be generated from pathogenic virus isolates by repeated passaging in suitable host cells that are permissive to the virus until the virus shows the desired properties (WO 92/21375, WO 93/06211, WO93/03760, WO 93/07898, WO 96/36356, EP 0 676 467, EP 0 732 340, EP 0 835 930). Alternatively, it may be generated by genetic reengineering through use of an infectious clone, normally a full-length complementary DNA transcript of the viral genome (WO 98/18933, EP 1 018 557, WO 03/062407, Nielsen et al, J Virol 2003, 77:3702-371 1). In a preferred embodiment, the present invention relates to a MLV containing attenuated PRRS virus of European genotype 94481 that is attenuated from a parental virus that is deposited at ECACC under Accession No. 11012501. A preferred MLV contains the attenuated virus of the present invention that is deposited at ECACC under Accession No. 11012502.

In another aspect, the present invention contemplates preparation and isolation of a progeny or descendant of a PPRS virus that has been deposited on Jan. 25, 2011 with the European Collection of Cell Cultures (ECACC), Porton Down, Salisbury, Wiltshire, SP4 0JG, Great Britain, under the Accession Numbers ECACC 11012502 (attenuated strain for MLV) and 11012501 (parental strain). The invention therefore extends to PRRS virus strains which are derived from the deposited strains through propagation or multiplication in an identical or divergent form, in particular descendants which possess the essential characteristics of the deposited strains. Upon continued propagation, the strains may acquire mutations most of which will not alter the properties of these strains significantly.

The strains of the invention may also be further modified to impart further desirable properties to them. This may be achieved by classical propagation and selection techniques, like continued propagation in suitable host cells to extend the attenuated phenotype. Alternatively, the strains may be genetically modified by directed mutation of the nucleic acid sequence of the genome of these strains by suitable genetic engineering techniques. The genome of PRRSV was completely or partly sequenced (Conzelmann et al., 1993; Meulenberg et al., 1993a, Murtaugh et al, 1995) and encodes, besides the RNA dependent RNA polymerase (ORFs 1a and 1b), six structural proteins of which four envelope glycoproteins named GP2 (ORF2), GP3 (ORF3), GP4 (ORF4) and GP5 (ORFS), a non-glycosylated membrane protein M (ORF6) and the nucleocapsid protein N (ORF7) (Meulenberg et al. 1995, 1996; van Nieuwstadt et al., 1996). Immunological characterization and nucleotide sequencing of European and US strains of PRRSV has identified minor antigenic differences within strains of PRRSV located in the structural viral proteins (Nelson et al., 1993; Wensvoort et al., 1992; Murtaugh et al., 1995). The PRRS 94881 MSV of the present invention has been compared with the European Reference Virus strain Lelystad Virus (LV) revealed nucleotide homologies ranging from 85.40 to 95.09 percent in the 8 different viral genes and amino acid identities from 86.39 to 97.27 percent between both virus strains. Two deletions in the ORF 1a of 94881 MSV could be identified compared to LV. For example, ORF1a of 94881 MSV has 85.40% nucleotide homology to Lelystad Virus resulting in an amino acid identity of 86.39%; ORF1b of 94881 MSV has 92.12% nucleotide homology to Lelystad Virus resulting in an amino acid identity of 97.27%; ORF2 of 94881 MSV has 91.07% nucleotide homology to Lelystad Virus resulting in an amino acid identity of 90.76%; ORF3 of 94881 MSV has 90.98% nucleotide homology to Lelystad Virus resulting in an amino acid identity of 89.43%; ORF4 of 94881 MSV has 90.58% nucleotide homology to Lelystad Virus resulting in an amino acid identity of 87.43%; ORF5 of 94881 MSV has 90.43% nucleotide homology to Lelystad Virus resulting in an amino acid identity of 88.56%; ORF6 of 94881 MSV has 95.02% nucleotide homology to Lelystad Virus resulting in an amino acid identity of 97.11%; ORF7 of 94881 MSV has 95.09% nucleotide homology to Lelystad Virus resulting in an amino acid identity of 92.97%;

Indeed, the PRRS 94881 virus of the present invention may be made into a chimeric virus wherein the backbone of the PRRS virus under ECACC Accession No. 11012502 or indeed the parent strain deposited under ECACC Accession No 11012501 is modified to replace the endogenous sequence of one or more of ORF 1a, ORF 1b, ORF 2, ORF 3, ORF 4, ORF 5, ORF 6, or ORF 7 with the corresponding ORF from a different strain of PRRS virus. For example, the different strain of the PRRS virus may be a different European strain such as Lelystad virus strain (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108 or indeed may be a U.S. strain such as North American PRRS virus, pT7P129A; ATCC deposit VR-2332, ATCC deposit VR-2368; ATCC VR-2495; ATCC VR 2385, ATCC VR 2386, ATCC VR 2429, ATCC VR 2474, and ATCC VR 2402.

Recombinant techniques for preparing modified sequences are well known to those of skill in the art and usually employ construction of a full-length complementary DNA copies (infectious clones) of the viral genome which may then be modified by DNA recombination and manipulation methods (like site-directed mutagenesis etc.). This way, for example antigenic sites or enzymatic properties of viral proteins may be modified. Infectious clones of PRRS virus strains of European and North American genotype have been reported in the literature.

The PRRS virus strains of the present invention are suitable for vaccines of the invention can be grown and harvested by methods known in the art, e.g. by propagating in suitable host cells like the simian cell line MA-104, Vero cells, or porcine alveolar macrophages. PRRSV preferentially grows in alveolar lung macrophages (Wensvoort et al., 1991). A few cell lines, such as CL2621 and other cell lines cloned from the monkey kidney cell line MA-104 (Benfield et al., 1992; Collins et al., 1992; Kim et al., 1993) are also susceptible to the virus.

Figure 9:
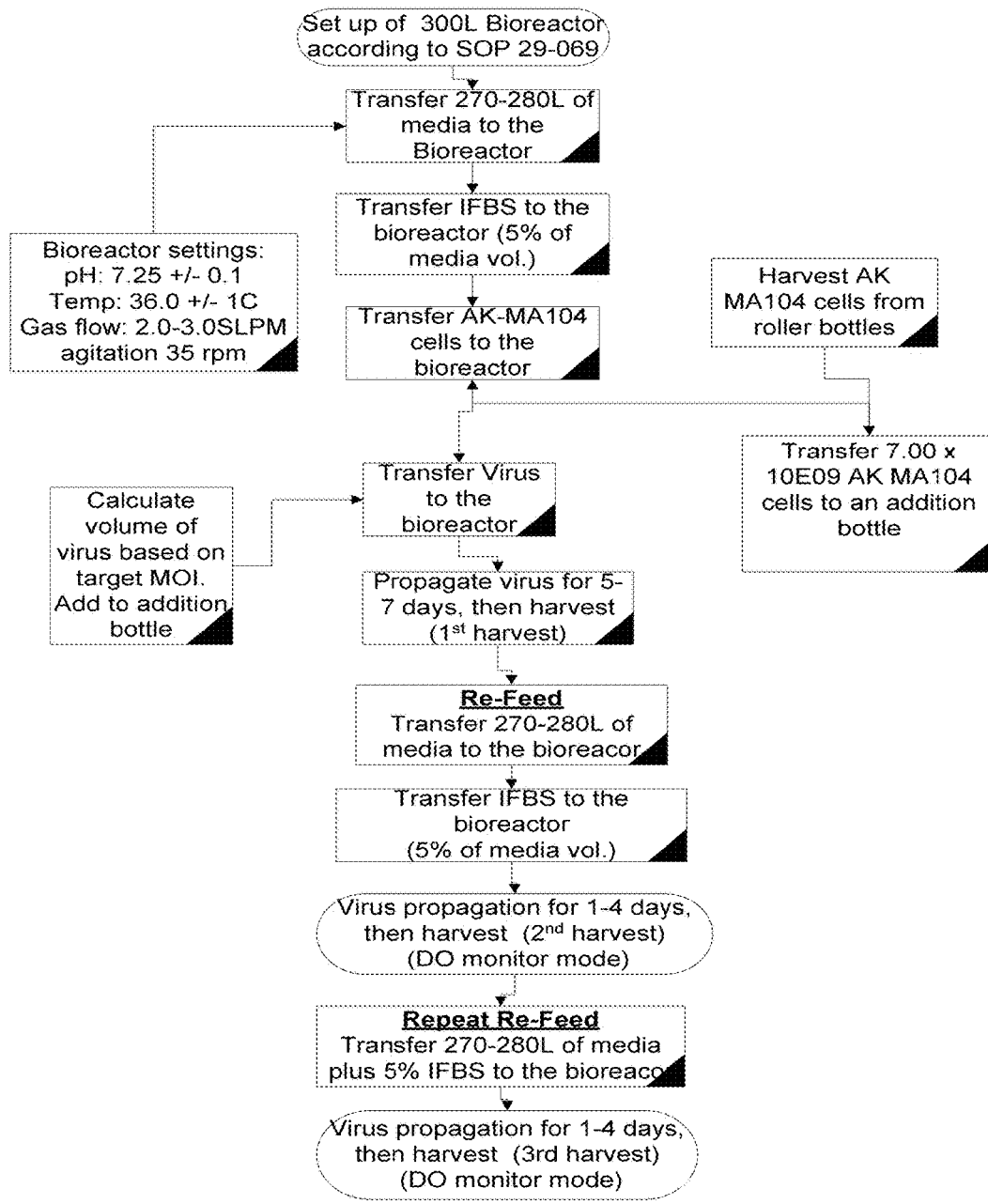
FIG. 9: Concurrent process for large-scale production of EU PRRS 94881.

Vaccines comprising any one of PRRSV strain PRRS virus under ECACC Accession No. 11012501, 11012501 Accession Numbers ECACC 04102703, ECACC 04102702, ECACC 04102704, CNCM Accession No. I-1140, CNCM Accession No I-1387, and CNCM Accession No I-1388 as well as any combination of these strains or their descendants are thus preferred embodiments of the present invention. In specific embodiments, the PRRS virus 94881 is grown in a process wherein there is a concurrent seeding of the virus and the host cells together on the same day into a bioreactor as shown in FIG. 9. Additional features of a method of production of PRRS virus 94881 may be as described in concurrently filed herewith as U.S. Provisional entitled "A Commercial scale process for production of PRRSV" filed concurrently with the instant application under application No. 61/444,071. While this is one method of growing the PRRSV 94881, it should be understood that the virus may be propagated according to any conventional method known to those of skill in the art.

Preferably, vaccines according to the present invention are modified live vaccines comprising one or more of these strains alive in a suitable carrier, but inactivated virus may also be used to prepare killed vaccine (KV). MLV are typically formulated to allow administration of $10^1$ to $10^7$ viral particles per dose, preferably $10^3$ to $10^5$ particles per dose, more preferably $10^4$ to $10^5$ particles per dose (4.0-5.0 $\log_{10}$ TCID$_{50}$). KV may be formulated based on a pre-inactivation titer of $10^3$ to $10^{10}$ viral particles per dose. The vaccine may comprise a pharmaceutically acceptable carrier, for example a physiological salt-solution.

Pigs can be infected by PRRSV via the oronasal route. Virus in the lungs is taken up by lung alveolar macrophages and in these cells replication of PRRSV is completed within 9 hours. PRRSV travels from the lungs to the lung lymph nodes within 12 hours and to peripheral lymph nodes, bone marrow and spleen within 3 days. At these sites, only a few cells stain positive for viral antigen. The virus is present in the blood during at least 21 days and often much longer. After 7 days, antibodies to PRRSV are found in the blood. The combined presence of virus and antibody in PRRS infected pigs shows that the virus infection can persist for a long time, albeit at a low level, despite the presence of antibody. During at least 7 weeks, the population of alveolar cells in the lungs is different from normal SPF lungs.

A vaccine according to the present invention may be presented in form of a freeze-dried preparation of the live virus, to be reconstituted with a solvent, to result in a solution for injection. The solvent may e.g. be water, physiological saline, or buffer, or an adjuvanting solvent. The solvent may contain adjuvants. The reconstituted vaccine may then be injected into the a pig, for example as an intramuscular or intradermal injection into the neck. For intramuscular injection, a volume of 2 ml may be applied, for an intradermal injection it is typically 0.2 ml. In a further aspect, the present invention therefore is a vaccine product, comprising in separate containers a freeze-dried composition of the virus, and a solvent for reconstitution, and optionally further containing a leaflet or label comprising instructions of use.

A vaccine according to the present invention may not only comprise one or more of the aforementioned strains, but may include further components active against PRRS or other porcine viral or bacterial diseases, like porcine circovirus or classical swine fever virus. Therefore, the invention further relates to a vaccine as described, characterized in that it contains at least one further antigen active against a porcine disease which is not PRRS. For example, such further antigens may include *Mycoplasma hyopneumoniae*, PCV2, SIV, *H. parasuis, E. rhusiopathiae, S. suis, A. suis, Leptospira* sp. Parvovirus and the like. In addition, the vaccine may comprise certain pharmaceutically or veterinary acceptable adjuvants. The invention provides new vaccine compositions, in particular, PRRS virus vaccines comprising PRRSV 94881 that further comprise adjuvants that enhance the efficacy of the vaccine such that a better clinical response/outcome is seen with the administration of the combination of the adjuvant and the vaccine as compared to administration of the vaccine alone. For example, the vaccine compositions of the invention may comprise a PRRSV 94881 virus vaccine and an adjuvant selected from the group consisting of MCP-1, α-tocopherol (e.g., α-tocopherol acetate, an exemplary version of which is sold as DILUVAC FORTE®), *Haemophilus somnus* fractions, carbopol and combinations thereof. In some embodiments, the virus vaccine comprising PRRS 94881 virus vaccine, which may be a recombinant subunit vaccine or alternatively may be a live attenuated virus vaccine. An exemplary live vaccine that exists is INGELVAC® PRRS MLV and the PRRS 94881 may be formulated in a manner similar to INGELVAC® PRRS MLV.

In addition to the above, the immunogenic compositions of the invention may contain other ingredients so long as the other ingredients do not interfere with the adjuvants or the underlying virus vaccine. Such other ingredients include, for example, binders, colorants, desiccants, antiseptics, wetting agents, stabilizers, excipients, adhesives, plasticizers, tackifiers, thickeners, patch materials, ointment bases, keratin removers, basic substances, absorption promoters, fatty acids, fatty acid ester, higher alcohols, surfactants, water, and buffer agents. Preferred other ingredients include buffer agents, ointment bases, fatty acids, antiseptics, basic substances, or surfactants.

The content or amount of the adjuvants used in the invention may vary and can be determined by taking into consideration, for example, the properties of the PRRS virus vaccine being used, and the dosage form. The adjuvant may comprise, for example, 1 to 100% by weight. The PRRSV 94881-based compositions of the invention are produced by mixing together the adjuvant component and the virus vaccine component, either alone or with various other ingredients. The compositions may be such that the virus vaccine and the adjuvant are presented as one formulation or alternatively, the adjuvant and the vaccine are presented in distinct formulations that can be administered simultaneously or sequentially.

The adjuvant component of the immunogenic compositions of the invention thus may be administered separately from the virus vaccine in the administration to organisms. Alternatively, the adjuvant according to the present invention, together with the virus vaccine, can be administered as a single vaccine composition. The virus vaccine may be any virus vaccine. More specific embodiments contemplate the use of a PRRS virus vaccine comprising PRRSV 94881. In addition such a vaccine may be combined with other vaccines such as INGELVAC® PRRS MLV and/or Porcilis®. This is merely one exemplary PRRS virus combination vaccine and other such vaccine combinations can be readily prepared.

The immunogenic compositions described herein are particularly advantageous in the induction of the production of an antibody response to PRRS virus. Administration of the vaccines preferably will produce a lessening of the severity of one or more clinical symptoms, such as lung lesions, anorexia, skin discolorations, lethargy, respiratory signs, mummified piglets, coughing, diarrhea and combinations thereof, that are associated with PRRSV infection.

The compositions thus particularly enhance the clinical outcome in a diseased animal as compared to the outcome from administration of PRRS virus vaccine alone. In specific embodiments, the enhanced clinical outcome is a reduction of the percentage of lung lesions by at least 50% when compared to animals not receiving the immunogenic composition in combination with said adjuvant. In other embodiments, the enhance clinical outcome is a reduction of viremia in animals by at least 45% when compared to animals not receiving the immunogenic composition in combination with said adjuvant.

Thus, in one aspect, the invention relates to an improved vaccine, more particularly and improved PRRS virus vaccine, wherein the improvement comprises admixing with the virus vaccine an adjuvant selected from the group consisting of MCP-1, *Haemophilus sonmus* fractions, carbopol and combinations thereof. The vaccine composition of the invention may further comprise a pharmaceutically acceptable carrier.

The vaccine compositions of the invention may be formulated by any method known in the art of formulation, for example, into liquid preparations, suspensions, ointments, powders, lotions, W/O emulsions, 0/W emulsions, emulsions, creams, cataplasms, patches, and gels and is preferably used as medicaments. Thus, according to another aspect of the present invention, there is provided a pharmaceutical composition comprising the above vaccine composition. The vaccine composition according to the present invention, when dermally administered, can significantly induce antibody production. Accordingly, in another preferred embodiment of the present invention, the vaccine composition can be provided as a transdermal preparation.

Further, as described above, the virus and adjuvant in the present invention may be administered, to an organism, together as a single vaccine composition, or as an adjuvant preparation separate and distinct from the antigenic PRRS virus component of the vaccine, whereby the adjuvant acts in a manner such that amount of an antibody produced in the organism in response to the PRRS virus vaccine can be significantly increased as compared to administration of the PRRS virus vaccine alone.

When the adjuvant and the PRRS virus vaccine are administered to an organism, the clinical outcome of the animal is enhanced. The effective amount of the adjuvant and the immunologically effective amount of the PRRS virus vaccine may be readily determined by a person having ordinary skill in the art by taking into consideration, for example, the type and properties of the antigenic substance, the species of organisms, age, body weight, severity of diseases, the type of diseases, the time of administration, and administration method and further using the amount of an antibody produced against the antigenic substance in the organism as an index.

The PRRS virus vaccine, the adjuvant, or combinations thereof can be administered to organisms by any suitable method selected depending, for example, upon the condition of animals and properties of diseases. Examples of such methods include intraperitoneal administration, dermal administration for example, subcutaneous injection, intramuscular injection, intradermal injection, and patching, nasal administration, oral administration, mucosal administration (for example, rectal administration, vaginal administration, and corneal administration). Among them, intramuscular administration is preferred.

An exemplary therapeutic dose of PRRSV MLV is about two milliliters (2 mLs). Skilled artisans will recognize that the dosage amount may be varied based on the breed, size, and other physical factors of the individual subject, as well as, the specific formulation of PRRSV MLV and the route of administration. Preferably, the PRRSV MLV is administered in a single dose; however, additional doses may be useful. Again, the skilled artisan will recognize through the present invention that the dosage and number of doses is influenced by the age and physical condition of the subject pig, as well as, other considerations common to the industry and the specific conditions under which the PRRSV MLV is administered.

In certain other embodiments, the vaccine may be a multivalent vaccine that comprises two or more PRRS viruses where at least one of the PRRS viruses is the attenuated 94881 virus deposited under ECACC Accession No. 11012502. The other PRRS viruses may be one or more selected from the group consisting of PRRSV strain Lelystad virus (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108 or indeed may be a U.S. strain such as North American PRRS virus, pT7P129A; ATCC deposit VR-2332, ATCC deposit VR-2368; ATCC VR-2495; ATCC VR 2385, ATCC VR 2386, ATCC VR 2429, ATCC VR 2474, and ATCC VR 2402.

The vaccines based on PRRS viruses may be used to vaccinate both piglets and sows. In one aspect of the invention, a particular dose regimen is selected based on the age of the pig and antigen selected for administration. This will permit pigs of any age to receive the most efficacious dose. In a preferred method, a therapeutic amount of PRRSV 94881 MLV is administered to a pig or piglet that is about two weeks old ±5 days of age. The amount selected will vary depending upon the age of the pig. Alternatively, a different therapeutic amount of such an MLV is administered to a pig or piglet that is older than about 3 weeks, and this amount will also change as the pig receiving such an administration ages or becomes older. Accordingly, pigs about four weeks old, six weeks old, eight weeks old, ten weeks old, twelve weeks old, fourteen weeks old, sixteen weeks old, a gilt, or a sow will all receive different amounts. Therapeutic dose to be used will be optimized in the field and is typically, determined in clinical studies in which a minimal immunizing dose is defined based on protection against a virulent heterologous PRRSV challenge in susceptible swine. Preferably, the PRRSV MLV produced according to the methods described herein is administered intramuscular administration; however, other methods of administration such as intradermal, intranasal, intraretinal, oral, subcutaneous, and the like, that are well-known and used in the art may be used.

The skilled person will recognize that the vaccination methods may involve determining the proper timing and dosage for vaccination of a pig against PRRSV. Such methods generally comprises the steps of determining at least one variable selected from the group consisting of age, health status, innate immunity level and active immunity level, of the pig, and adjusting a standard dosage level to account for these variables. Generally, the innate immunity level and active immunity level will be determined by referring to a standard comprised of average levels from a population of pigs of similar age and health status. In a particularly preferred method, all variable are considered prior to determining the optimum dosage level and timing of administration.

In preferred embodiments, the present invention also relates to isolated nucleic acids that code specific open reading frames of attenuated 94881 virus deposited under ECACC Accession No. 11012502 and the parent virulent 94881 virus deposited under ECACC Accession No. 11012501. For example, the complete nucleotide sequence of the attenuated 94881 virus deposited under ECACC Accession No. 11012502 has a sequence of SEQ ID NO:1 which encodes ORF1a, ORF1b, ORF2, ORF3, ORF4, ORF5, ORF6, ORF7 protein sequences of SEQ ID NO:2, SEQ ID NO:3, SEQ ID NO:4, SEQ ID NO:5, SEQ ID NO:6, SEQ ID NO:7, SEQ ID NO:8, and SEQ ID NO:9, respectively. The complete nucleotide sequence of the parent virulent 94881 virus deposited under ECACC Accession No. 11012501 has a sequence of SEQ ID NO:10 which encodes ORF1a, ORF1b, ORF2, ORF3, ORF4, ORF5, ORF6, ORF7 protein sequences of SEQ ID NO:11, SEQ ID NO:12, SEQ ID NO:13, SEQ ID NO:14, SEQ ID NO:15, SEQ ID NO:16, SEQ ID NO:17, and SEQ ID NO:18, respectively.

The PRRSV 94881 vaccine can be administered in any conventional fashion and in some preferred methods the administration is intramuscularly. It is preferred that the administered PRRSV vaccine provide its benefits of treating or reducing the severity of or incidence of PRRSV infection after a single dose, as with INGELVAC®, however, if other antigens or combination or multivalent vaccines are selected, it should be understood that they can be administered in their conventional fashion, which may include one or more booster doses after the initial administration. Those of skill in the art will be able to determine appropriate dosing levels based on the PRRSV vaccine selected and the age range of the animal to which the antigen will be administered.

In specific examples presented herein below pigs and sows were challenged with a new European derived strain of PRRSV that was able to reproducibly produce respiratory disease in piglets. Historically, European-derived PRRSV strains have been unable to reproduce respiratory disease in piglet model and hence respiratory challenge models relied on infection with non-European strains. Because of high genetic diversity there is a demand in Europe for a new vaccine based on an European strain. In additional examples, the animals were challenged with a strain that produced reproductive failure in gilts/sows challenge models. It has been found that the efficacy of the MLV vaccines based on attenuated 94881 virus deposited under ECACC Accession No 11012502 or any virus prepared from this strain or from the parental strain deposited at ECACC Accession No 11012501 can be shown using a variety of challenge models because this strain also is effective in other models of PRRS virus-induced respiratory or reproductive failure.

EXAMPLES

Example 1: Description of PRRSV Respiratory Challenge Model

As noted above, historically, EU-derived PRRSV strains are unable to reproduce respiratory disease in piglet model. Because of the high genetic diversity there is a demand in Europe for a new vaccine based on a European strain and a good, reproducible respiratory challenge model utilizing virulent a European-derived PRRSV strain is necessary for the conduction of the studies. In the following example, the inventors show that challenge of pigs with low passage European challenge strain (passage 4) reliably produced respiratory symptoms.

In this study, 3 groups with 12 animals, 3 weeks of age at allocation and appr. 10 weeks of age at challenge were used:
  Group 1: Control group
  Group 2: Challenge group (SD 35)
  Group 3: Vaccinated with PORCILIS® PRRSV (SD 0) and then challenged (SD 35).

The study was conducted over a 56 day period necropsy of 6 animals from each group was measured 10 days after challenge; necropsy of all remaining animals 21 days after challenge. Daily investigated parameters included: rectal temperature, respiratory and other clinical signs. Further parameters investigated included: body weight, mortality, viremia, seroconversion, pathological and histological examination of the lungs.

At study day −7 the groups of pigs were allocated to each group. At study day 0, Group 3 was vaccinated with POR-CILIS® PRRSV. At study day 35 group 2 and group 3 were challenged with a European challenge strain. At day 45 6 animals from each group were euthanized. The remaining animals were euthanized at day 56.

Figure 1B:
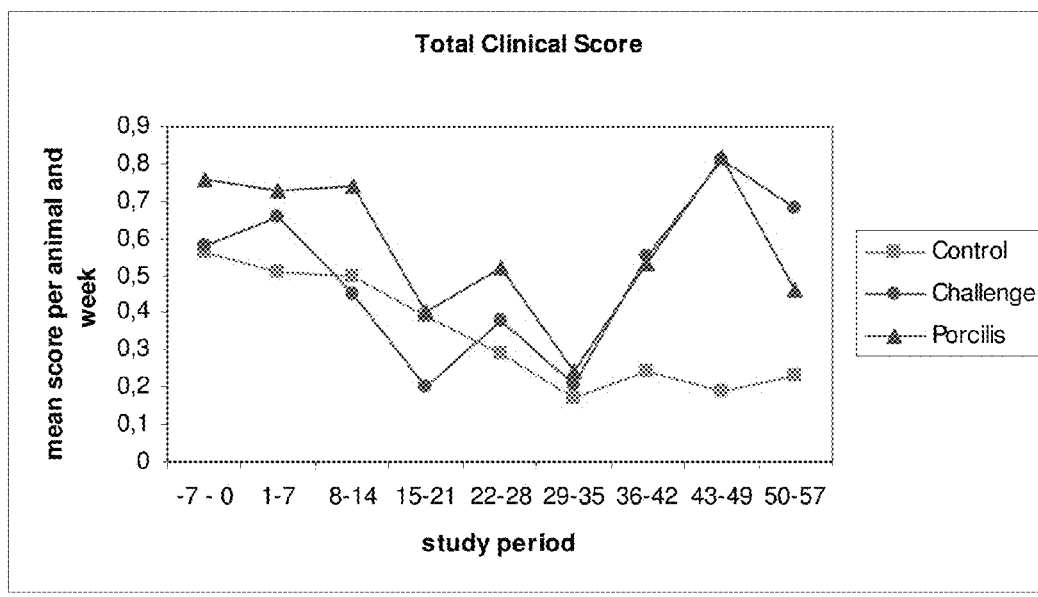
FIG. 1B: Clinical observation of total clinical score in respiratory challenge model using a European challenge strain.
Figure 2:
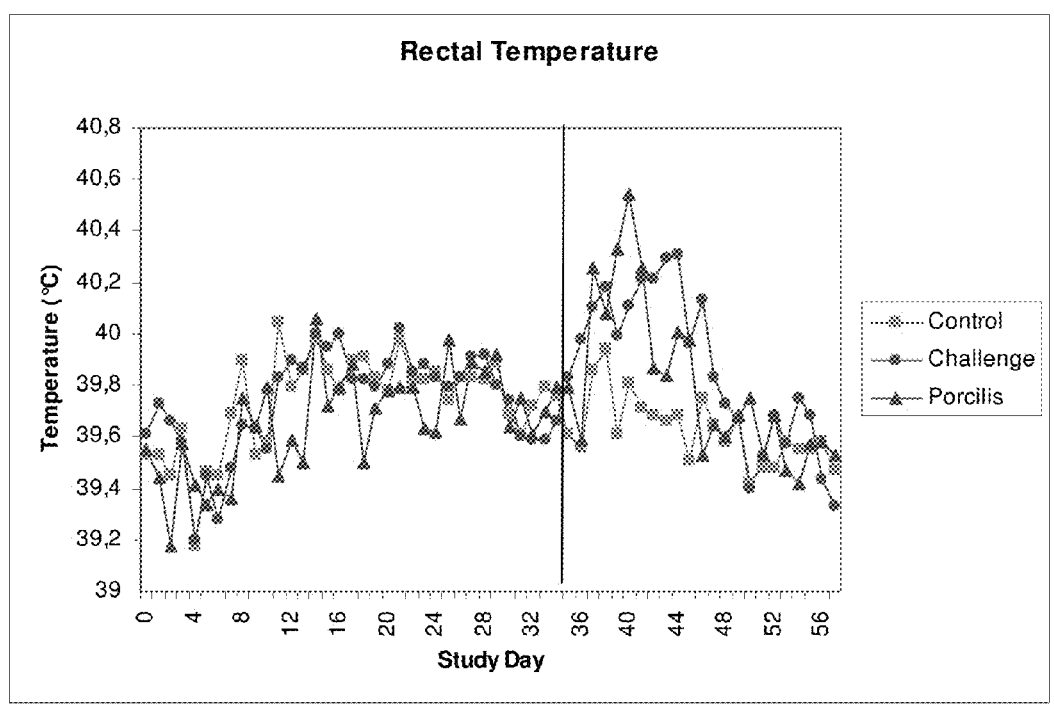
FIG. 2: Rectal temperature measurements in respiratory challenge model using a European challenge strain.

FIG. 1A shows coughing measurements as a meanscore per animal and week. It was seen that there was an increase in coughing after challenge in both the challenge alone (Group 2) and the Porcilis group (Group 3). FIG. 1B shows the total clinical score which was taken from dyspnea, coughing, nasal and eye discharge and behavior. These data showed that there was an overall increase in total clinical score after challenge in the challenge and Porcilis group. Rectal temperature of the animals was monitored before and after challenge and shows that there was an increase rectal temperature in the challenge and Porcilis group after Challenge (SD>35 group 1-2 $p \leq 0.001$; group 1-3 $p \leq 0.001$) (FIG. 2).

Figure 3:
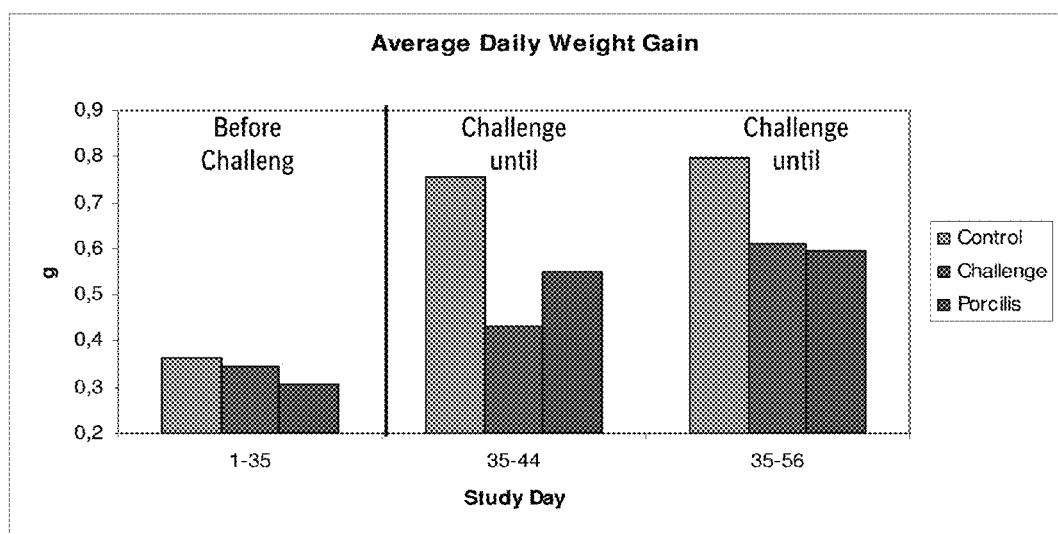
FIG. 3: Average daily weight gain measurements in respiratory challenge model using a European challenge strain.

Measurement of average daily weight (FIG. 3) showed that after challenge until first and until second necropsy the ADW was significantly less in the challenge (SD35-44 p≤0.001 and SD35-56 p≤0.01) and in the Porcilis vaccinated group (SD35-44 p≤0.05 and SD35-56 p≤0.05).

Figure 4:
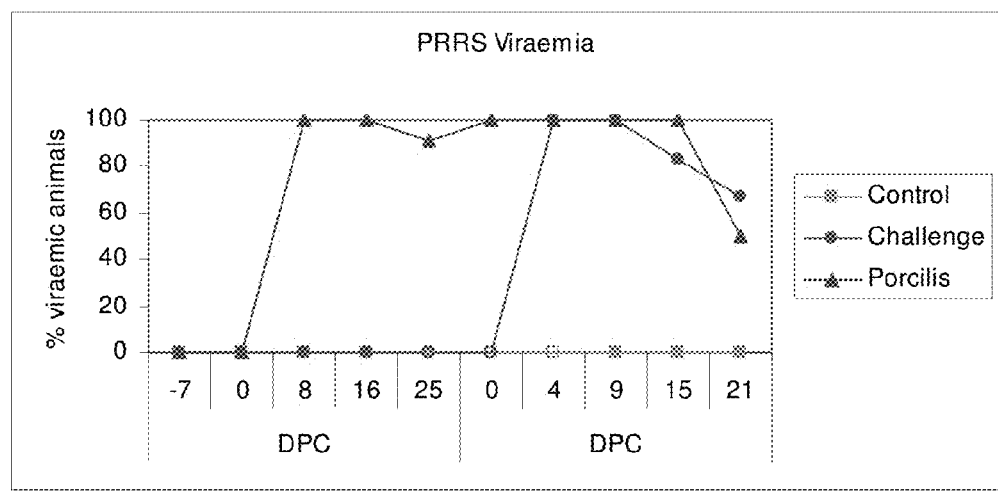
FIG. 4: PRRS viremia as indicated through quantitative PCR in respiratory challenge model using a European challenge strain.
Figure 5:
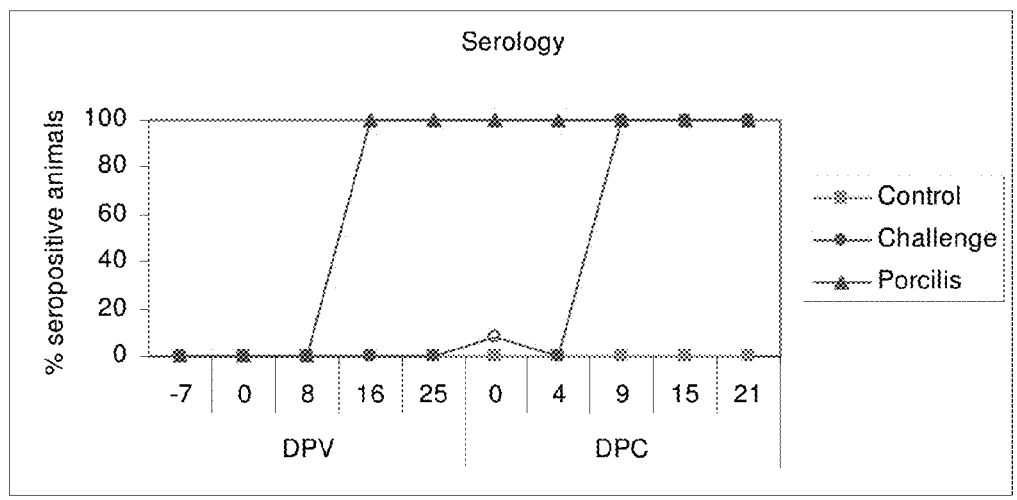
FIG. 5: PRSS Serology as indicated by ELISA in respiratory challenge model using a European challenge strain.

Viremia was monitored using PCR (FIG. 4) and ELISA assays (FIG. 5). PCR showed that in Group 1: all animals from the control group remained negative. In Group 2: all animals were positive for PRRSV after challenge; in Group 3: all animals were positive for PRRSV after vaccination. ELISA revealed: that in Group 1: all animals remained negative; in Group 2: all animals were positive for PRRSV AB after challenge in Group 3: all animals were positive for PRRSV AB after vaccination.

Figure 6:
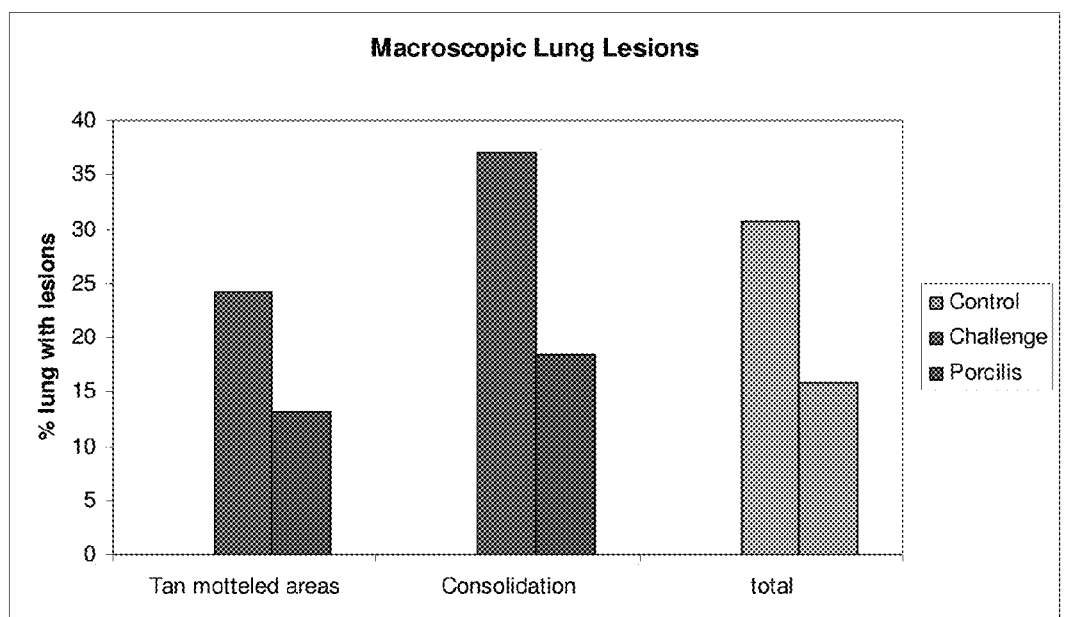
FIG. 6: Macroscopic examination of lung lesions in in respiratory challenge model using a European challenge strain.
Figure 7A:
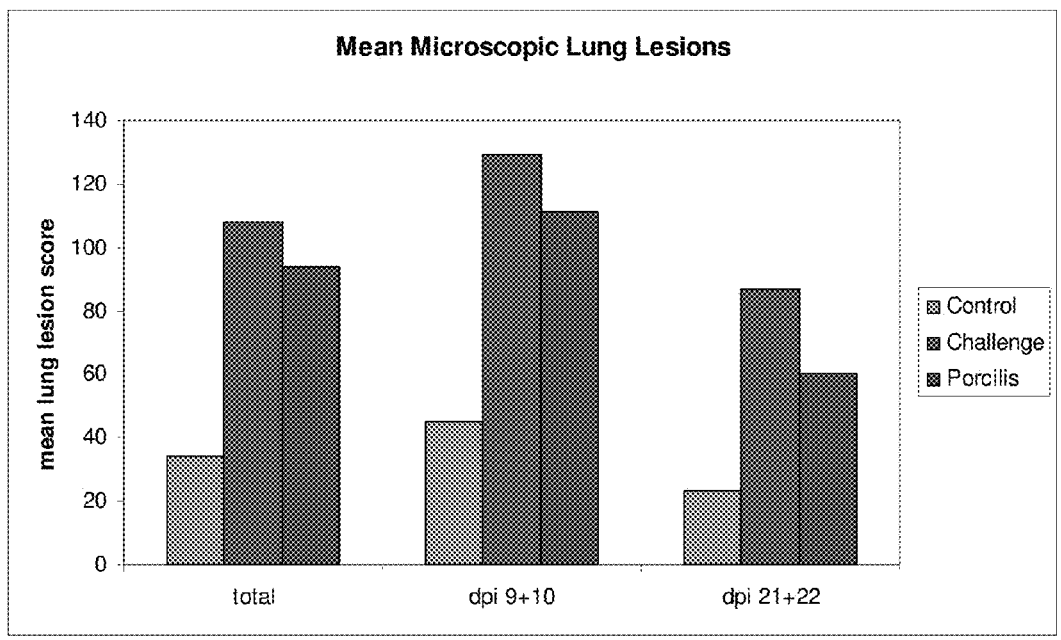
FIG. 7A-C: Histopathology measurements.
Figure 7B:
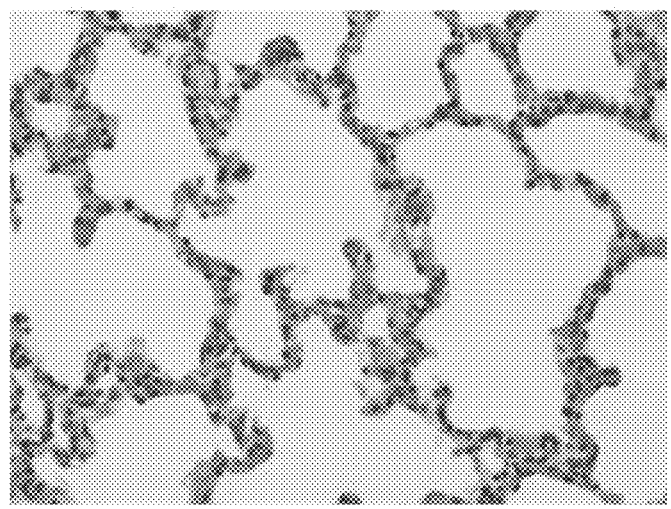
Figure 7C:
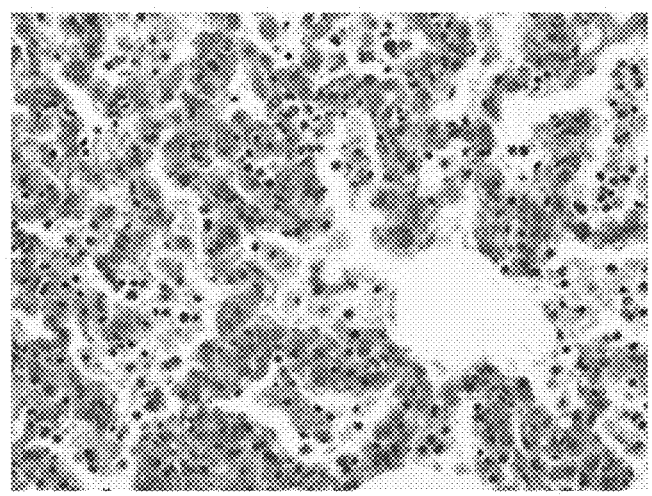

Macroscopic examination of the lungs was also performed (FIG. 6) where lungs were evaluated for tan mottled areas and areas of consolidation: In comparison to the control group significant macroscopic changes could be observed in the challenge and Porcilis group (group 1-2 p≤0.001; group 1-3 p≤0.05). In histopathological examination, the data also showed efficacy of vaccination (FIG. 7A through 7C). Mean lung lesion score was significantly higher in the challenge and Porcilis group in comparison to the control group (group 1-2 p≤0.001; group 1-3 p≤0.001). Microscopic lesions were stronger 10 days post infection.

In summary, coughing, total clinical scores and rectal temperatures increased after challenge in the challenge controls and Porcilis vaccinated groups. Body weight was significantly (p<0.05) less in the challenge controls and Porcilis group in comparison to the negative control group. All animals from the Porcilis group were positive for PRRS virus and antibodies after vaccination. All animals from the challenge controls were positive for PRRS virus and antibodies after challenge. Macroscopical and histological analysis of the lungs showed severe macroscopic and microscopic lung lesions in the challenge controls and Porcilis group in comparison to the negative control group.

This study thus confirmed that the European challenge strain used does induce significant (p<0.05) disease when compared to the negative control group: fever, coughing, reduced weight and severe macroscopic and microscopic lung lesions.

In addition, the European challenge strain has successfully demonstrated consistent and reproducible PRRSV-specific respiratory disease in the pig challenge model and therefore, is suitable for use as a challenge virus in future efficacy studies. Porcilis PRRS shows a lack of efficiency against the European challenge strain within the parameters of this study.

Example 2: Evaluation of Minimum Immunizing Dose of Attenuated PRRS Virus 94881 in Susceptible 2 Week Old Piglets Following Challenge with Heterologous European PRRS Isolate A vaccination-challenge study was performed to evaluate the minimum immunizing dose (MID) of Porcine Reproductive and Respiratory Syndrome Vaccine European-derived isolate 94881, Modified Live Virus (PRRS 94881 MLV) at three different titer levels, administered to Porcine Reproductive and Respiratory Syndrome (PRRS) susceptible piglets, that were approximately 14 days of age, to provide relevant reduction in lung lesions following challenge with a heterologous European isolate of PRRS. Fifteen piglets were included in each vaccinated group (Groups 1-3) as well as in the challenge control group (Group 4). Ten piglets were included in the negative control group (Group 5).

The vaccine groups and the challenge control groups were monitored for a number of parameters including: viremia post-challenge, clinical assessments post-vaccination, PRRS serology, viremia post-vaccination, clinical observations post-challenge, average daily weight gain (ADWG), rectal temperatures and PRRS virus detection in the lungs. A negative control group (Group 5), which was not challenged, was also included in the study for study validation purposes by demonstrating that biosecurity was not breached throughout the duration of the study.

The challenge control and negative control groups were PRRS negative up to the day of challenge (D28) and the negative control group remained PRRS negative for the remainder of the study (D38), thus validating the study.

Challenge was at 4 weeks post-vaccination. At this time, only 2 animals in low titer vaccine group, 1 animal in the medium titer vaccine group and 3 animals in the high titer vaccine group were PRRS qPCR positive in serum.

The challenge control group exhibited significant lung lesions typical of PRRS post-challenge. Post-challenge, the low, medium and high titer vaccine groups had median total lung lesion scores of 0.13%, 0.55%, and 0.40%, respectively; while the challenge control group had a median total lung lesion score of 33.40%. The median total lung lesion scores for the three vaccine titer groups were significantly lower than the challenge control group (p<0.0001). There were no statistical differences between vaccine titer groups (p≤0.1484) for total lung lesion scores. The negative control group had a median total lung lesion score of 0.00%.

On study Days 31, 35 and 38 of the post-challenge period, the three vaccine titer groups had significantly less viremia than the challenge control group (p≤0.0093). There were no statistical differences between vaccine titer groups for viremia post-challenge except on D35, when the high titer vaccine group exhibited significantly lower viremia than the medium titer vaccine group (p=0.0442). Negative control piglets were negative for viremia on D31, D35 and D38.

Clinically, severity (p≤0.0082) and frequency (p≤0.0268) of coughing was less severe in the three vaccine titer groups than the challenge control group during the post-challenge period; Day 29-Day 38. Pyrexia was more prominent in the challenge control group than in the three vaccine titer groups post-challenge. ADWG was significantly higher for the three vaccine titer groups compared with the challenge control group (p≤0.0027).

The MID of PRRS 94881 MLV as determined in this study is associated with the low titer vaccine level of $1 \times 10^{2.77}$ $TCID_{50}$/mL, based on a relevant reduction in gross lung lesions for all three titer levels in comparison to the challenge controls after receiving a virulent heterologous European-derived PRRS challenge. When secondary parameters were examined, all three vaccine titer levels were associated with efficacy and no clear distinctions between titer groups were evident.

General Design of Study:

This was a blinded randomized design study conducted in 70 weaned, PRRS susceptible piglets, 14-16 days of age on Day 0 (D0). A description of treatment groups is shown below in Table 2.1:

TABLE 2.1

Treatment Groups

| Group | No. of Animals on D 0 | Treatment on Day 0 |
|---|---|---|
| 1 | 15 | IVP No. 1 (mean titer of $1 \times 10^{2.77}$ of PRRS 94881 MLV) |
| 2 | 15 | IVP No. 2 (mean titer of $1 \times 10^{4.42}$ of PRRS 94881 MLV) |
| 3 | 15 | IVP No. 3 (mean titer of $1 \times 10^{5.84}$ of PRRS 94881 MLV) |
| 4 | 15 | CP (Placebo matched product without PRRS 94881 MLV) |
| 5 | 10 | CP (Placebo matched product without PRRS 94881 MLV) |

Eighty-three piglets met the study inclusion criteria, of which the first 70 numerical numbers were randomly assigned to one of five groups on D-3 by a biostatistician. Piglets were assigned 15 per group to Groups 1-4 and ten piglets to Group 5. All 83 piglets were PRRS seronegative.

Piglets were observed from D-1 to D26 for clinical assessments post-vaccination and observations will be recorded on the Clinical Assessment Record form.

Serology:

Venous whole blood was collected from piglets on D0, D7, D14, D21, D28. Sample collections were recorded. Blood samples were spun down and serum was harvested from each tube, split and transferred to appropriately labeled tubes. One set of serum samples were held at 2-8° C. and the other set of serum samples were held at −70±10° C. The set of serum samples collected on days 0, 7, 14, 21, 28 and 38 and held at 2-8° C. were tested for PRRS antibodies. Results were reported as negative (ELISA S/P ratio of <0.4) or positive (ELISA S/P ratio of ≥0.4).

PRRS Viremia:

The set of serum samples collected on days 0, 7, 14, 21, 28, 31, 35, and 38 and held at −70±10° C. were tested for PRRSv RNA by qPCR (Addendum 1, Attachment 7). Results were reported as n.d. (not detected), positive (EU PRRSv detected, but not quantifiable, GE/mL (genome equivalent)=<3.3 log) or a reported value (log GE/mL). For statistical purposes, "not detected" was assigned a value of 0 log GE/mL and a "positive" value was assigned a value of 3.0 log GE/mL.

Average Daily Weight Gain (ADWG):

Each pig was weighed on a calibrated scale and individual body weights were recorded. The average daily gain was determined from the D0 to D28 and from D28 to D38.

Clinical Observations Post-Challenge:

Piglets were observed by the Study Investigator or designees for clinical signs of disease from D27 to D38 and were recorded on the Clinical Observation Record form. Observations included respiration, behavior and cough based on the clinical observation scoring system as shown below in Table 2.2

TABLE 2.2

Clinical Observation Scoring System

| Respiration Score | Behavior Score | Cough Score |
|---|---|---|
| 0 = normal respiration | 0 = normal | 0 = no coughing |
| 1 = panting/rapid respiration | 1 = mild to moderate lethargy | 1 = soft or intermittent cough |
| 2 = dyspnea | 2 = severely | 2 = harsh or severe, |
| 3 = dead | lethargic or recumbent 3 = dead | repetitive cough 3 = dead |

A daily total clinical observation score for each piglet was determined by the summation of its daily respiration, behavior and cough scores.

Rectal temperatures were collected from D27 to D38.

Total Lung Lesion Score:

All piglets that died before D38 and remaining piglets that were euthanized on D38 were necropsied. Each set of lungs was examined for any gross lung pathology and determination of the % pathology for each lung lobe. If pathology of other organs were noted, these were described and noted as well.

Lung qPCR for PRRSV:

For each set of lungs, two samples from the Left and Right Apical lobes, the Left and Right Cardiac lobes, the Left and Right Diaphragmatic lobes and the Intermediate lobe, were retained. For one set of lung samples, all three samples from the left side were combined into one container; while all three samples from the right side and the Intermediate lung lobe sample were combined into another container. Each container was filled with a sufficient amount of 10% formalin solution. For the other set of lung samples, all three lung samples from the left side were combined into one WHIRLPAK®; while all three samples from the right side and the Intermediate lung lobe sample were combined into another WHIRLPAK®.

Frozen lung tissue samples were held at −70±10° C. until further analysis. For each piglet, all left lung samples were homogenized and tested as a single combined sample; and all right lung tissues and the intermediate lung lobe sample were homogenized and tested as a single combined sample. Results were reported as n.d. (not detected), positive (EU PRRSv detected, but not quantifiable, GE/mL (genome equivalent)=<3.3 log) or a test value (log GE/mL) for left and right lung samples. For analysis purposes for each piglet, the mean of left and right lung sample qPCR results were noted. For statistical purposes, "not detected" was assigned a value of 0 log GE/mL and a "positive" value was assigned a value of 3.0 log GE/mL.

Results

Total Lung Lesion Score Post-Challenge:

A summary of group minimum, maximum, median, 95% confidence interval, Q range and mean for total lung lesion scores showed that the low, medium and high titer vaccine groups had median total lung lesion scores of 0.13%, 0.55%, and 0.40%, respectively; while the challenge control group had a median total lung lesion score of 33.40%. The median total lung lesion scores for the three vaccine titer groups were significantly lower than the challenge control group (p<0.0001). There were no statistical differences between vaccine titer groups (p≥0.1484) for total lung lesion scores. The negative control group had a median total lung lesion score of 0.00%.

For one of the animals (high titer vaccine group), histologically mild suppurative interstitial pneumonia with copious fibrinopurulent pleuritis was noted. Airways and alveoli were relatively unremarkable except for scattered neutrophils. Lung tissue was IHC negative for M. hyo, PCV2, PRRSv and SIV antigens. Lung lesions were consistent with serositis generally associated with bacterial agents (Addendum 12; Accession 2009030254). Several pure bacterial cultures from lung tissue were isolated and identified as *Bordetella bronchiseptica* and a coagulase negative *Staphylococcus*. Although two types of bacteria were isolated from lung tissues, this piglet was not removed from Group 3 total lung lesion score analyses.

Two of 10 negative control piglets exhibited very minor lung lesions (No. 1767, 0.55%; No. 1789, 0.61%). These lesions were considered insignificant and not indicative of PRRS. Two of 10 negative control piglets exhibited very minor lung lesions (No. 1767, 0.55%; No. 1789, 0.61%). These lesions were considered insignificant and not indicative of PRRS.

PRRS Viremia Post-Challenge:

Individual PRRS viremia post-challenge results (D31-D38) were tabulated and it was found that all piglets were viremic post-challenge in the three vaccine titer groups and the challenge control group. At all three time points post-challenge, the three vaccine titer groups had significantly less viremia than the challenge control group ($p \leq 0.0093$). There were no differences between vaccine titer groups for viremia post-challenge except on D35, when the high titer vaccine group exhibited a lower mean viremia than the medium titer vaccine group (p=0.0442). Negative control piglets were negative for viremia on D31, D35 and D38. Area under curve (AUC) represents both the quantity and duration of viral load and is a good assessment tool for examining viremia. Significant differences were also detected between the three vaccine titer groups and the challenge control group with respect to AUC at both D28 to D38 ($p \leq 0.0162$), and D31 to D38 (p<0.0001). No differences were detected between vaccine titer groups with respect to AUC ($p \leq 0.3669$) at both time intervals.

The group frequency of viremic positive piglets was also summarized for D31 to D28 and is shown in Table 2.3. Since all vaccine and challenge control piglets were viremia positive post-challenge, the frequency viremia positive piglets was 100% for each group at each time point. Hence, no analyses were conducted on post-challenge frequency for viremia.

TABLE 2.3

Summary of Group Frequency of Viremic Positive Piglets - D 31 to D 38

| Study Day | Group* | No. Positive | % Positive | 95% CI | | Total No. |
|---|---|---|---|---|---|---|
| 31 | 1 | 14 | 100 | 76.8 | 100.0 | 14 |
| | 2 | 15 | 100 | 78.2 | 100.0 | 15 |
| | 3 | 15 | 100 | 78.2 | 100.0 | 15 |
| | 4 | 14 | 100 | 76.8 | 100.0 | 14 |
| | 5 | 0 | 0 | 0.0 | 30.8 | 10 |
| 35 | 1 | 14 | 100 | 76.8 | 100.0 | 14 |
| | 2 | 15 | 100 | 78.2 | 100.0 | 15 |
| | 3 | 15 | 100 | 78.2 | 100.0 | 15 |
| | 4 | 14 | 100 | 76.8 | 100.0 | 14 |
| | 5 | 0 | 0 | 0.0 | 30.8 | 10 |
| 38 | 1 | 14 | 100 | 76.8 | 100.0 | 14 |
| | 2 | 15 | 100 | 78.2 | 100.0 | 15 |
| | 3 | 15 | 100 | 78.2 | 100.0 | 15 |
| | 4 | 14 | 100 | 76.8 | 100.0 | 14 |
| | 5 | 0 | 0 | 0.0 | 30.8 | 10 |

*Group 1 = Low titer PRRS 94881 MLV; Group 2 = Medium titer PRRS 94881 MLV; Group 3 = High titer PRRS MLV; Group 4 = Challenge control group; Group 5 = Negative control group Lung qPCR Results:

Individual lung virus isolation results post-challenge were summarized as was the frequency of qPCR positive lung sample test results (p-values) for differences between groups. Lung tissues from piglets in all three vaccine titer groups and the challenge control group were qPCR positive for PRRSv post-challenge. There were no significant differences detected between vaccine titer groups and the challenge control group (p=1.0000). Since all vaccine titer piglets were qPCR positive for PRRSv, no tests were conducted between vaccine titer groups.

Although no differences were detected between vaccine titer groups and the challenge control group for frequency of qPCR positive lung tissues, differences were evident for viral load in lung tissues. Indeed, the low, medium and high titer vaccine groups had median lung qPCR values of 6.88, 6.80 and 6.81 $\log_{10}$ GE/mL, respectively; while the challenge control group had a median lung qPCR value of 8.13 $\log_{10}$ GE/mL. The differences between the vaccine titer groups and the challenge control group were significant ($p \leq 0.0001$). Conversely, no differences were detected between vaccine titer groups for median lung qPCR values ($p \leq 0.7379$).

Clinical Observation Scores Post-Challenge:

Abnormal respiration and behavior were not severe post-challenge, as evidenced by median maximum clinical scores of 0 (a score of 0 represented normal respiration or normal behavior) for all five groups. In addition, no significant differences were detected between vaccine titer groups and the challenge control group for both abnormal respiration and behavior ($p \leq 0.0996$).

Coughing was noted in all three vaccine titer groups and the challenge control, but was more severe in the challenge control group. For the three vaccine titer groups, each group had a maximum cough score of 1, which represented soft or intermittent coughing and median maximum cough score of 0. Conversely, the challenge control group had a maximum cough score of 2, which represented harsh or severe, repetitive coughing, and a median maximum cough score of 1. The three vaccine titer groups had significantly less severe coughing than the challenge control group ($p \leq 0.0082$). Coughing was not noted in the negative control group.

All three vaccine titer groups had maximum total scores of 1 and median maximum scores of zero. Conversely, the challenge control group had a maximum total score of 4 and a median maximum score of 1. The three vaccine groups had significantly lower maximum total clinical scores than the challenge control group ($p \leq 0.0047$). Again, the negative control group had a maximum total clinical score of zero and a median maximum total clinical score of zero.

The frequency of abnormal respiration or behavior for at least one day from D29 to D38 was low for all groups. Indeed, no abnormal respiration was noted in low and medium vaccine titer groups from D29 to D38. The high titer vaccine group had one of 15 (7%) piglets and the challenge control group had 3 of 14 (21%) piglets with abnormal respiration. Abnormal behavior was not noted in any vaccine titer group; while 2 of 14 (14%) challenge control piglets exhibited abnormal behavior for at least one day post-challenge. No significant differences were detected between vaccine titer groups and the challenge control group for frequency of abnormal respiration or behavior for at least one day post-challenge ($p \leq 0.0996$). Abnormal respiration or behavior was not noted in the negative control group.

The frequency of coughing was much higher in the challenge control than in the three vaccine titer groups. Indeed, the frequency of coughing for at least one day post-challenge was 14%, 13% and 27% for the low, medium and high titer vaccine groups, respectively. Conversely, the frequency of coughing for at least one day post-challenge for the challenge control group was 71%. The three vaccine titer groups had significantly less frequency of coughing than the challenge control group (p≤0.0268).

The frequency of any clinical sign post-challenge, as represented by a total clinical score >0, was higher in the challenge control group than in the three vaccine titer groups. Similar to the frequency of cough, the frequency of any clinical sign for at least one day post challenge was 14%, 13%, and 33% for the low, medium, and high titer vaccine groups, respectively; while 79% of piglets in the challenge control group had a least one clinical sign post-challenge. The three vaccine groups had significantly lower frequency of any clinical sign post-challenge than the challenge control group (p≤0.0253). No clinical signs were noted in the negative control group during this same time period.

Mean scores for abnormal respiration or behavior from D29 to D38 were low for all groups. Indeed, the mean respiration scores for the low and medium vaccine titer groups were 0.00 (normal), the high titer vaccine had a mean respiration score of 0.01 and the challenge control had a mean respiration score of 0.03. The mean score for behavior was 0.00 for all three vaccine titer groups; while the challenge control had a mean behavior score of 0.01. No significant differences were detected between vaccine titer groups and the challenge control group for mean respiration and behavior scores (p≤0.0996). Respiration and behavior mean scores for the negative control group were 0.00.

The challenge control group had a higher mean cough score than the three vaccine titer groups. Indeed, the mean cough scores were 0.01, 0.01 and 0.04 for the low, medium and high titer vaccine groups, respectively. Conversely, the mean cough score for the challenge control group was 0.28. The three vaccine titer groups had significantly lower mean cough scores than the challenge control group (p≤0.0077).

The mean total score was higher in the challenge control group than in the three vaccine titer groups. Similar to the mean cough scores, the mean total scores post challenge were 0.01, 0.01, and 0.04 for the low, medium, and high titer vaccine groups, respectively; while the mean total score for the challenge control group was 0.32. The three vaccine groups had significantly lower mean total scores than the challenge control group (p≤0.0025).

Rectal Temperatures Post-Challenge:

The maximum group mean rectal temperatures for low, medium, and high titer vaccine groups between D29 to D38 were 40.20° C. (D33), 40.33° C. (D35), and 40.20° C. (D37), respectively. The maximum group mean rectal temperature for the challenge control group and the negative control group between D29 and D38 were 40.51° C. (D33) and 39.95° C. (D33), respectively.

The low titer vaccine group had significantly lower rectal temperatures than the challenge control group on D29 (39.47 vs. 39.90° C.), D31 (39.85 vs. 40.20° C.), D35 (39.80 vs. 40.22° C.) and D38 (39.86 vs. 40.32° C.) (p≤0.0317); while the low titer vaccine had a significantly higher rectal temperature than the challenge control group on D30 (40.08 vs. 39.58° C.; p=0.0003). No significant differences were detected between the low titer vaccine group and the challenge control group on D32-D34 and D36-D37 (p≤0.0545).

The medium titer vaccine group had significantly lower rectal temperatures than the challenge control group on D31 (39.62 vs. 40.20° C.), D33 (40.15 vs. 40.51° C.), and D38 (39.58 vs. 40.32° C.) (p≤0.0227). No significant differences were detected between the medium titer vaccine group and the challenge control group on D29-D30, D32, and D34-D37 (p≤0.0580).

The high titer vaccine group had a significantly lower rectal temperature than the challenge control group on D33 (40.12 vs. 40.51° C.), D35 (39.79 vs. 40.22° C.), and D38 (39.55 vs. 40.32° C.) (p≤0.0147); while the high titer vaccine group had a significantly higher rectal temperature than the challenge control group on D32 (40.31 vs. 39.90° C.; p=0.0063). No significant differences were detected between the high titer vaccine group the challenge control group on D29-D31, D34 and D36-37 (p≥0.0708).

There was less frequency of pyrexia in the three vaccine titer groups post-challenge compared with the challenge control group. The frequency of pyrexia was low overall and similar between vaccine titer groups.

Average Daily Weight Gain (ADWG):

The least square mean ADWG from D0 to D28 for the low, medium and high titer vaccine groups were 0.4, 0.3, and 0.4 kg/day, respectively. The least square mean ADWG during this same time period for the challenge control group was 0.3 kg/day. The low titer vaccine group had a significantly higher least square mean ADWG than the challenge control group from D0 to D28 (p=0.0292); while no other significant differences were detected between vaccine titer groups and the challenge control group (p≥0.1262), or between vaccine titer groups (p≥0.1293), for least square mean ADWG. During this same time period, the negative control group had mean ADWG of 0.5 kg/day.

The least square mean ADWG from D28 to D38 for the low, medium and high titer vaccine groups were 0.5, 0.5 and 0.4 kg/day, respectively. The least square mean ADWG during this same time period for the challenge control group was 0.3 kg/day. The three vaccine titer groups significantly out gained the challenge control group post-challenge (p≤0.0027). During this same time period, the negative control group had a mean ADWG of 0.6 kg/day.

Clinical Assessments Post-Vaccination:

In the low titer vaccine group, one piglet (1735) was noted as thin from D0 to D10. In addition, one piglet beginning on D6 was noted as thin for 16 days, exhibited cough for 2 days and depression for 9 days, and was euthanized on D21 for animal welfare reasons due to poor health. Piglet 1727 had a total lung lesion score of 10.8%. Since this value was determined pre-challenge, it was not included in post-challenge total lung lesion analysis. In addition, areas of red/purple consolidation in the cranioventral areas of the lungs were noted, the liver was pale and kidneys had multiple red/purple areas in the renal pelvis. The pathologist noted fatty infiltration in central lobules in the liver, commonly seen in cases of negative energy balance and consequent lipolysis. No other lesions were observed in sections of liver, kidney and lung. Lung tissue was positive for EU PRRS by PCR. No growth was detected for routine bacterial culture.

In the medium titer vaccine group, one piglet was excluded from the study on D0 prior to treatment due to poor health and was replaced by another piglet. Two Piglets exhibited coughing for one and three days, respectively, beginning on D12. Four piglets were noted as thin on D2, D3 or both D2 and D3.

In the high titer vaccine group, one piglet (1728) exhibited lameness or lameness and swelling in one leg from D7 to D26. Beginning 18 days post-vaccination, one piglet was noted as thin for 6 days, and exhibited coughing for one day and rough hair coat for 4 days. Another Piglet was noted as thin on D2. Two Piglets exhibited coughing for two days and one day, respectively, beginning on D9. One piglet exhibited diarrhea for one day (D14).

In the challenge control group, six piglets exhibited periodic coughing for a cumulative of one to six days, beginning with a first piglet on D7 and ending with three piglets on D21. Two piglets were noted as thin for two and 11 days, respectively, beginning on D1 for one of these piglets. The second of these two Piglets also exhibited depression and rough hair coat for 4 days, weak on legs for one day and was found dead on D15. At necropsy for this piglet there were no lung lesions (lung lesion score of 0%) noted, no feed in the stomach and no abdominal fat, and diagnosed starvation as the cause of death. Since this lung lesion score was determined pre-challenge, it was not included in post-challenge lung lesion analysis.

The group test results (p-values) were summarized for any abnormal clinical assessment for at least one day from D1 to D26. No significant differences were detected between vaccine titer groups and the challenge control group (p≥0.0502); nor between vaccine titer groups (p≥0.3898). No piglets in the negative control group exhibited an abnormal clinical assessment from D-1 to D26.

PRRS Serology:

Individual piglet PRRS ELISA serology results were summarized. Piglets in the negative control group remained PRRS seronegative throughout the study. Seroconversion could be observed in the 3 vaccine titer groups by 14 days post-vaccination; while the challenge control group remained PRRS seronegative until post-challenge. Ten days post-challenge (D38) all piglets in the low and high titer vaccine groups and the challenge control group were PRRS seropositive; while 14 of 15 piglets in the medium titer vaccine groups were PRRS seropositive.

PRRS ELISA positive serology test results (p-values) were determined for differences between groups. The three vaccine titer groups had significantly higher frequencies of PRRS ELISA positive piglets than the challenge control group on D14, D21 and D28 (p<0.0001). No significant differences were detected between the three vaccine titer groups and challenge control on D38 (p=1.0000 or no test conducted) nor between the three vaccine titer groups at any time point (p=1.0000 or no test conducted).

PRRS Viremia Post-Vaccination:

Individual PRRS viremia results post-vaccination were determined. For statistical purposes, a "not detected" result was assigned a value of 0 log GE/mL and a "positive" value was assigned a value of 3.0 log GE/mL. All groups were PRRS viremia negative on D0. The group viremia (qPCR)-D7 to D28 post-vaccination titer (log GE/mL) data was assessed. Piglets in the three vaccine titer groups reached peak mean viremia on D7, after which titers levels for all three groups slowly declined prior to challenge (SD28). Conversely, the challenge control group and the negative control group remained negative for viremia during the pre-challenge phase of the study. From the group test results (p-values) for D7, D14, D21 and D28 qPCR results it was seen that all three vaccine titer groups had significantly higher median qPCR values than the challenge control group for D7-D28 (p≤0.0159). The medium vaccine titer group had a significantly higher qPCR median value than the low titer vaccine group (p=0.0193); otherwise, no differences were detected for qPCR median values between vaccine groups pre-challenge (p≤0.0594).

Four weeks post-vaccination, the frequency of viremia was low in the three vaccine titer groups.

The following conclusions can be made based upon these study results:

The absence of any break of biosecurity during the study and the confirmation of piglet's susceptibility to PRRS confirmed the validation of the study and its suitability for interpretation Substantial PRRS clinical disease was evident in the challenge control group, thus validating this challenge model as an adequate laboratory tool to evaluate PRRS vaccine efficacy and more specifically, the MID of PRRS 94881 MLV All three dose levels of PRRS 94881 MLV were associated with significant reduction in lung lesions, as well as significant reduction in viremia post-challenge, viral load in lung tissues, coughing, total clinical observation scores, pyrexia and ADWG The MID of PRRS 94881 MLV as determined in this study is associated with the low titer vaccine level of $1\times10^{2.77}$ TCID$_{50}$/mL, based on a relevant reduction in gross lung lesions for all three titer levels in comparison to the challenge controls after receiving a virulent heterologous European-derived PRRS challenge.

Further Depiction of Results

Clinical observations were taken every day. Quantitative RT-PCR was performed using PRRSV European specific primers for samples form blood, oral, fecal, and nasal swab, as well as lung lavages.

From these studies data showed that the piglets showed normal health except for a few pigs that were lame. Postmortem there were no abnormalities at necropsy except that 1-2 animal showed signs of mildly enlarged inguinal lymph nodes. Importantly, it was seen that there were no lung lesions observed with the vaccinated group.

Figure 8:
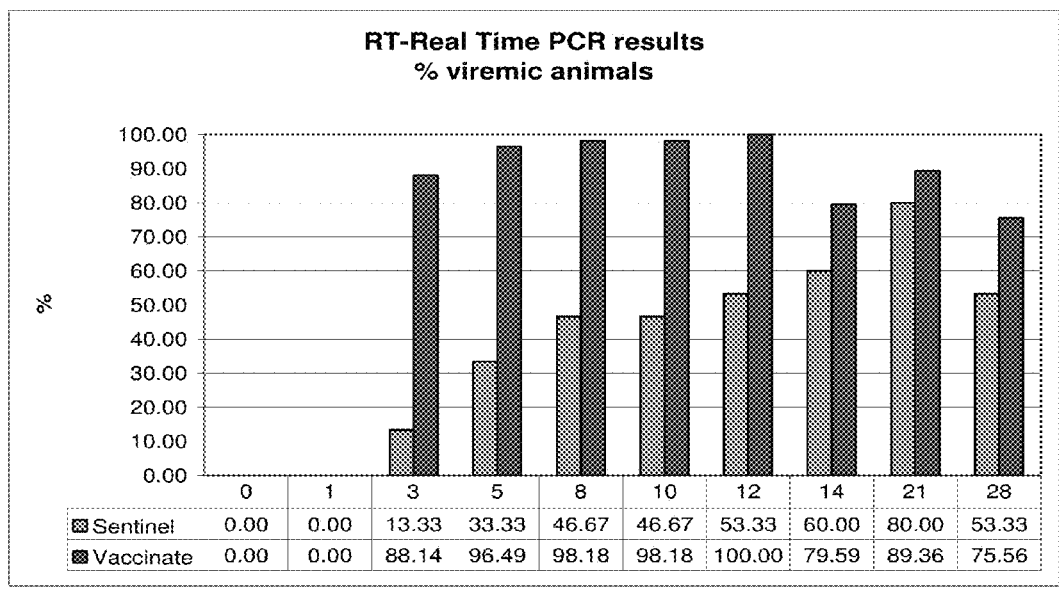
FIG. 8: Shows RT-PCT Time PCR results depicting % viremia in animals vaccinated with EU PRRS 94881.

FIG. 8 shows the percentage of viremic animals in the sentinel group as compared to the group vaccinated with a composition containing the attenuated PRRS virus strain deposited at ECACC Accession No. 11012502. This Figure shows the spread of the vaccine strain from vaccinated animals to sentinels. At the peak of PRRS viremia (SD21) as detected by quantitative RT-PCR, the viral load was 78.47% lower in sentinel infected pigs (mean viral load of 3.347 GE/ml) than in vaccinated animals (mean viral load of 4.014 GE/ml). In the room where the PRRS naïve sows were commingled with their vaccinated offspring, only 3 sows out of 8 were tested positive for PRRSV in blood by RT-PCR thus confirming limited and ineffective PRRS MLV vaccine exposure to naïve adult animals. The vaccine virus 94881 MLV was primarily excreted in the feces in this study. Indeed, in feces, the virus could be detected from one day to 21 days post vaccination. At five days post vaccination, almost 30% of the vaccinated animals excreted virus in feces. The PRRS virus was not detected in nasal secretions and in only a few animals via oral secretions (2 out of the 56 sampled animals at 5 days post vaccination).

Example 3: Exemplary Materials and Methods for Use in Testing Vaccine Efficacy Using PORCILIS® PRRS as an Example A selected number, for example, fourteen healthy pregnant sows from a confirmed PRRSV negative herd (tested virologically and serologically) were used in this study. Sows faced first or second parturition and were confirmed to be pregnant at the time of vaccination/challenge infection on day 94 of gestation. The sows were divided into three treatment groups. The first group was treated with a commercial dose of Porcilis™ PRRS of 2 ml containing at least $10^{4.0}$TCID$_{50}$ via intramuscular administration at day 94 of gestation. The challenge control group (group 2) received a dose of $10^{4.72}$ TCID$_{50}$ in 2 ml cell culture medium of the pathogenic European field isolate (passage 4) intranasally. Group 3 was vaccinated with a dose of 2 ml containing $10^{7.6}$TCID$_{50}$ i.m. PRRS MLV containing attenuated PRRS strain deposited at ECACC Accession No. 11012502 on Jan. 25, 2011 seven days before insemination and was challenged with the European field isolate (passage 4) ($10^{4.72}$ $TCID_{50}$ in 2 ml cell culture medium i.n.) at day 94 of gestation.

Animals from group 1 were monitored until day 5 post-farrowing. Animals from group 2 and 3 were monitored until day 28 post farrowing.

Animal Phase: All sows were accustomed to the animal facilities 1 week before vaccination. Sows and piglets were observed for their general health status by the investigator on a daily basis. Every animal that died or was euthanized was subjected to post-mortem examination and subsequent laboratory analysis.

Pregnancy was confirmed with ultrasound examination. Serum from sows was obtained on study days 0, 7, 14 and at farrowing for PCR and ELISA investigations. Any material that was associated with abortion was subjected to laboratory investigations.

Routine gross pathology was performed on all deadborn piglets. Lung tissue samples from all lung lobes were collected from deadborn piglets and from mummies. Samples for PCR testing were stored at −70° C. 2 ml of precolostral blood from each piglet was collected on the day of birth. Serum was prepared and aliquots were stored at −70° C. Serum was used to test for viremia to evaluate the transplacental infection. All piglets of group 1 that survived until day 5 were euthanized at 5 days of age.

Clinical and Reproductive Performance Parameters: The following criteria are exemplary criteria that may be investigated (priority order): number of live born piglets per litter, number of stillborn piglets per litter, number of mummified fetuses per litter and number of piglets surviving through day 5 or 28 of age, respectively. The number of piglets born viremic was determined using pre-colostral serum. The frequency of PCR positive blood and tissue samples from sows and/or piglets was investigated to evaluate the epidemiology and course of infection.

Field Samples: The field samples investigated in this study were taken from routine PRRSV diagnostics and consisted of blood, serum and various organ materials, mostly lungs and lymph nodes, from different European countries. The samples were stored at −20° C. for a maximum of 3 days before RNA preparation and residual material was subsequently transferred to −70° C. for long term storage. RNA and RT-PCR products were stored at −20° C.

Cell Culturing: MA104 cells (clone CL2621) were grown in MEM (Dulbecco, Germany) supplemented with 10% FCS and antibiotics.

Porcine alveolar macrophages were harvested using a method described by Wensvoort et al. (Wensvoort, G. et al. Vet. Quat. 1991, 13:121-130) and modified as follows: each lung lobe was infused with 50-100 ml PBS and subsequently massaged for 3 to 5 min. Then the fluid was rescued from the lobe and passed through a gaze filter. This procedure was repeated until the lavage fluid was clear. The pooled lavage fluid was centrifuged at 500 g for 15 min at room temperature. The pellet was washed in PBS and aliquots of $1 \times 10^7$ cells in 50% RPMI 1640 (Biochrom), 40% FCS and 10% DMSO were frozen at −196° C. For further use the PAMs were cultured in RPMI 1640 medium supplemented with 10% FCS and antibiotics.

Preparation of Organ Material for Virus Isolation in Cell Culture: About 0.5 $cm^3$ of tissue material was transferred into a tube containing one steel homogenizer ballet in 1.8 ml of sterile PBS. The tubes were agitated for 10 min until the organ material was homogenized. Cell debris was pelleted by centrifugation for 2 min at 450 g and room temperature. The supernatant was passed through a 0.45 .mu.m pore sterile filter and stored at −70° C. Aliquots of 30 μl were used to inoculate one semiconfluent cell culture monolayer using 24 well microtiter plates.

RNA Isolation: RNA from organ material was extracted with the RNeasy Mini Kit and from serum, plasma, cell culture supernatant and vaccine solution with the QTAamp Viral RNA Mini Kit (both Qiagen) according to the manufacturer's recommendations, using approximately 100 mg organ material and 140 μl fluid material, respectively, for each preparation. The RNA was finally eluted in 65 μl buffer as recommended by the manufacturer.

Plaque Purification of Virus: Confluent monolayers of Ma104 cells in cell culture dishes of 10 cm seeded 48 hours before were infected with the respective virus at tenfold dilutions from $10^{-1}$ to $10^{-4}$. The cells were incubated for 1 hour with the virus dilutions which were then removed, and the cells were overlaid with 30 ml of Ma104 medium containing 5% methylcellulose (Sigma). Plaques were picked after five to seven days and were transferred to Ma104 monolayers in 24 well plates. Virus from these plates was harvested at about 50% CPE and was subjected to further analysis.

Immunofluorescence Assay: Cells were fixed at −20° C. for 15 min using ice-cold aceton:methanol (1:1) and air-dried thereafter. After rehydration in PBS, cells were incubated with the PRRSV specific monoclonal antibody SDOW17 (Rural Technologies Inc., USA) diluted 1:1000 in PBS for 1 hour. After 3 washes with PBS, cells were incubated with goat anti-mouse FITC conjugated secondary antibody (Dianova, Hamburg, Germany) (1:150 in PBS) for another hour. After 3 final washes with PBS, cells were overlaid with glycerine:PBS solution (1:1) and subjected to immunofluorescence microscopy.

Diagnostic nRT-PCR: A diagnostic RT-nPCR can be carried out to check the samples for the presence of PRRSV-EU virus.

An exemplary diagnostic RT-nPCR can be carried out with the Titan One Tube Kit (Roche Molecular Biochemicals) as follows: [5 μl total RNA preparation, 1*RT-PCR buffer, 0.4 mM dNTPs, 20 pmol of primers PLS and PLR, 5 mM dithiothreitol, 1 mM $MgCl_2$, 2.5-5 U RNasin (Promega Ltd), 1-2.5 U enzyme mixture, adjusted to a final volume of 25 μl with DEPC treated aqua dest]. Routine cycling conditions used can be: 45° C. for 1 hour, 94° C. for 2 min and 30 cycles of 94° C. for 30 sec, 58° C. for 45 sec and 68° C. for 45 sec, final elongation step at 68° C. for 5 min. The nested PCR reaction was carried out with Qiagen Taq (Qiagen AG) as follows: [1 μl RT-PCR product, 1*PCR buffer, 10 μl Q-solution, 3.5 mM $MgCl_2$, 0.3 mM dNTPs, 20 pmol of each EU-7-n-s and EU-7-n-as primers, 2.5 U Taq polymerase, adjusted to a final volume of 50 μl with aqua dest]. Cycling conditions were as follows: 7 cycles with 94° C. for 1 min, 58° C. for 1 min and 72° C. for 1 min, followed by 30 cycles with 94° C. for 1 min and 70° C. for 1.5 min (no annealing step), final elongation step at 70° C. for 5 min.

Nucleotide Sequencing: Nucleotide sequencing can be performed on the nested PCR products which had been generated with primers that contained an M13 tag, either directly from the PCR reaction or from PCR products that had been excised from agarose gels and purified with the JETsorb gel extraction kit (Genomed). Sequencing was done using the automated sequencer LI-COR DNA Analyzer GENE READIR 4200® (LI-COR Inc., Lincoln, Nebr., USA). Nucleotide and deduced amino acid sequences can be analyzed with ALIGNIR®, vs1.1 (LI-COR Inc., Lincoln, Nebr., USA) and the DNASIS® 2.6 software package (Hitachi Software Genetic Systems Inc., San Francisco, USA).

Example 4: Determination of the Full Length Genome Sequence PRRSV 94881

The present example shows the determination of the full length genome nucleotide sequences of the attenuated 94881 strain and its parental strain 94881, passage 5. These sequences did not show any unclear nucleotide position what indicates the presence of a homogeneous viral content. The comparison of the 94881 Master Seed Virus with the European Reference Virus strain Lelystad Virus (LV) revealed nucleotide homologies ranging from 85.40 to 95.09 percent in the 8 different viral genes and amino acid identities from 86.39 to 97.27 percent between both virus strains. Two deletions in the ORF 1a of 94881 MSV could be identified compared to LV. The comparison between 94881 Master Seed Virus and its parental strain, passage 5, showed 26 nucleotide exchanges between both resulting in a total number of 14 amino acid exchanges.

other indication on a mixed sequence. After translation into amino acids clear amino acid sequences without any questionable amino acid were available for sequence comparison of 94881 MSV with the LV and with the parental strain 94881 passage 5. The alignments and comparisons of the nucleotide sequences between 94881 MSV and Lelystad virus were performed and showed that there were substantial differences at the nucleotide and amino acid level. Alignments also were performed between 94881 MSV and its parental strain, passage 5.

Sequence comparisons with LV resulted in nucleotide homologies from 85.40 to 95.09 percent in the 8 different viral genes and amino acid identities from 86.39 to 97.27 percent between both virus strains. Two deletions in the ORF 1a of 94881 MSV can be identified compared to LV. One deletion of 138 nucleotides is located at position 2154 to 2292 of LV and results in 46 missing amino acids. At position 2686 to 2688 a further triplet is deleted resulting in the missing amino acid Phenylalanine. An arrangement of all nucleotide homologies and amino acid identities between LV and both 94881 strains is shown in Table 4.1.

TABLE 4.1

Arrangement of nucleotide and amino acid sequence comparisons of the 94881 Master Seed Virus to the European Reference Virus Lelystad Virus

| ORF | length of the viral gene/protein nn/aa | no. of nucleotide deviations to Lelystad Virus | genetic homology to Lelystad Virus in percent | no. of amino acid deviations to Lelystad Virus | amino acid identity to Lelystad Virus in |
|---|---|---|---|---|---|
| 5'NTR | 177*/— | 9 | 94.92 | — | — |
| 1a | 7050**/2349 | 1050 | 85.40 | 326 | 86.39 |
| 1b | 4392/1463 | 346 | 92.12 | 40 | 97.27 |
| 2 | 750/249 | 67 | 91.07 | 23 | 90.76 |
| 3 | 798/265 | 72 | 90.98 | 28 | 89.43 |
| 4 | 552/183 | 52 | 90.58 | 23 | 87.43 |
| 5 | 606/201 | 58 | 90.43 | 23 | 88.56 |
| 6 | 522/173 | 26 | 95.02 | 5 | 97.11 |
| 7 | 387/128 | 19 | 95.09 | 9 | 92.97 |
| 3'NTR | 44***/— | 2 | 95.45 | — | — |

NTR: non translated region
*Only 177 nucleotides were compared between Lelystad Virus and 94881 MSV. The remaining 44 nucleotides, located upstream, had not been determined.
**The isolate 94881 MSV shows two deletions in the ORF 1a, one with 138 nucleotides and one with 3 nucleotides, respectively. The complete nucleotide and amino acid sequences of the Reference virus LV were used for the homology and identity calculations, deletions are assessed as deviations. The length of the corresponding viral gene of LV is 7191 nucleotides and the corresponding polyprotein 2396 amino acids, calculations of genetic homology and amino acid identity refer to the numbers of 7191 nucleotides and 2396 amino acids, respectively.
***Only 44 nucleotides were compared between Lelystad Virus and 94881 MSV. The remaining 83 nucleotides, located downstream, had not been determined For the full length genome sequence determination of the 94881 Master Seed Virus a total number of 1 reverse transcription, 17 external PCRs and 58 internal PCRs was performed, resulting in 40 PCR products which were used for sequencing. In case of 94881, passage 5, 1 reverse transcription, 17 external PCRs and 67 internal PCRs were performed, resulting in 40 PCR products, also, used for sequencing.

Overlapping sequence alignment analyses resulted in a full length sequence of 14843 nucleotides for both virus isolates comprising the complete open reading frames (ORFs) 1a to 7, each. Additionally, 177 nucleotides of the 5'-non translated region (5'NTR) and 43 nucleotides of the 3'-non translated region (3'NTR) could be determined, each. Compared with the European PRRSV reference virus isolate Lelystad (LV) (GenBank Assession no. M96262) 44 nucleotides of the 5'NTR and 83 nucleotides of the 3'NTR could not be determined as those regions were used for primer annealing regions.

The sequencing reactions resulted for both virus strains in a clear nucleotide sequence without any wobbles or any The sequence comparison of the full length nucleotide sequences of 94881 Master Seed Virus and 94881 Parental Strain, passage 5, revealed a total number of 26 nucleotide exchanges between both. The nucleotide exchanges were distributed as follows: 15 in the ORF 1a, 4 in the ORF 1b, 2 in the ORF 2, none in the ORF 3, 1 in the ORF 4, 3 in the ORF 5, 1 in the ORF 6 and none in the ORF 7. These nucleotide exchanges resulted in a total number of 14 amino acid exchanges which were distributed as follows: 8 in the polyprotein 1 a, 1 in the polyprotein 1b, 1 in the glycoprotein 2, none in the glycoprotein 3, 1 in the glycoprotein 4, 2 in the glycoprotein 5 and 1 in the matrix protein. Both strains showed the same deletions compared to Lelystad Virus in ORF 1a. An arrangement of all nucleotide exchanges and resulting amino acid exchanges including the positions in the viral genes and corresponding proteins is shown in detail in Table 4.2.

Example 5—Culture of Deposited Virus and MSV

As noted above, PARENT (low passage) 94881 is deposited at European Collection of Cell Cultures (ECACC) under the Accession Numbers ECACC 11012501, 94881 Master Seed Virus (MSV) is deposited at European Collection of Cell Cultures (ECACC) under the Accession Numbers ECACC 11012502. The growth and culture conditions for the parent virus and the MSV are provided in the present example.

Parent 94881:

This is a virus of a genotype which is PRRSV type 1, as such it is a European genotype PRRSV. The virus has a porcine host. The parent virus deposited at 11012501 was deposited at a titer of 5.81 Log 10 $TCID_{50}$/mL. Host cells for virus propagation are MA 104 cells. These cells are cultured Minimal Essential Medium (MEM) with 3.7 g/L sodium bicarbonate containing 6% irradiated Fetal Bovine Serum at 37±1° C. The cells are plated in T-flasks (75 cm$^2$) with a plating density of $2\times10^4$ to $2\times10^5$ cells/cm$^2$ and cultivated for 3 to 7 days until 100% confluent prior to passage. For virus growth, the virus is added to the cells at a MOI of 0.001-0.01 in T-flasks. The cells infected are at a confluency of about 80-100%, typically 1-3 days post cell planting. The infected cells are cultivated at 37±1° C. for 3-10 days post infection and the virus is then harvested. The harvest is performed when monolayer cells exhibit approximately 80-100% cytopathic effect (CPE) at 3-10 days post infection. The supernatant of infected MA104 tissue cultures (spent media+PRRSV from a culture with 80-100% CPE) is harvested and contains the virus that has been propagated. This supernatant may be stored at −70° C./−80° C. for several months until use. The virus is assessed for $TCID_{50}$ with Spearman and Kaerber calculation to determine log 10 $TCID_{50}$/mL of sample.

Vaccine (high passage) 94881 Master Seed Virus (MSV): This is a virus of a genotype which is PRRSV type 1, as such it is a European genotype PRRSV. The virus has a porcine host. The MSV deposited at 11012502 was deposited at a titer of 6.43 Log 10 TCID50/mL. Host cells used for the propagation of the MSV are MA 104 cells. These cells are cultured Minimal Essential Medium (MEM) with 1.4 g/L sodium bicarbonate and containing 10% irradiated Fetal Bovine Serum at 36±2° C. The cells are plated in T-flasks (75-150 cm2) or 850 cm2 roller bottles with a planting density of 1×104 to 1×105 cells/cm2 and cultivated for 3 to 7 days until 100% confluent prior to passage. For virus growth, the virus is added to the cells at a MOI of 0.001-0.01 in T-flasks or roller bottles. The cells infected are at a confluency of about 80-100%, typically 1-3 days post cell planting. The infected cells are cultivated at 36±2° C. for 3-14 days post infection and the virus is then harvested. The harvest is performed when monolayer cells exhibit approximately 80-100% cytopathic effect (CPE) at 3-14 days post infection. The supernatant of infected MA104 tissue cultures (spent media+PRRS from a culture with 80-100% CPE) is harvested and contains the virus that has been propagated. This supernatant may be stored at 2-8° C. for 5-10 days, −70° C. for several months until use. The MSV is assessed for TCID50 with Reed and Muench calculation to determine log 10 TCID50/mL of sample.

TABLE 4.2

Arrangement of nucleotide and amino acid sequence comparisons of the 94881 Master Seed Virus to 94881 Parental strain

| ORF | no. of deviating nucleotides | position in viral gene | exchange (nn) from parental strain to MSV | synonymous/ non synonymous | no. of deviating amino acids | position in viral protein | exchange (aa) from parental strain to MSV |
|---|---|---|---|---|---|---|---|
| 1a | 15 | 309 | C to T | synonymous | 8 | — | — |
|  |  | 753 | G to T | non synonymous |  | 251 | E to D |
|  |  | 1474 | G to A | non synonymous |  | 492 | V to I |
|  |  | 1789 | G to A | non synonymous |  | 597 | V to I |
|  |  | 2094 | C to T | synonymous |  | — | — |
|  |  | 2987 | T to C | non synonymous |  | 996 | L to S |
|  |  | 3034 | A to G | non synonymous |  | 1012 | T to A |
|  |  | 3065 | A to G | non synonymous |  | 1022 | E to G |
|  |  | 3736 | A to G | non synonymous |  | 1246 | T to A |
|  |  | 3966 | C to T | synonymous |  | — | — |
|  |  | 4101 | T to C | synonymous |  | — | — |
|  |  | 5803 | C to T | non synonymous |  | 1935 | L to F |
|  |  | 6354 | T to G | synonymous |  | — | — |
|  |  | 6519 | C to T | synonymous |  | — | — |
|  |  | 6588 | T to C | synonymous |  | — | — |
| 1b | 4 | 591 | T to C | synonymous | 1 | — | — |
|  |  | 1833 | C to T | synonymous |  | — | — |
|  |  | 1932 | C to T | synonymous |  | — | — |
|  |  | 3682 | G to A | non synonymous |  | 1228 | V to I |
| 2 | 2 | 13 | C to T | non synonymous | 1 | 5 | H to Y |
|  |  | 195 | C to T | synonymous |  | — | — |
| 3 | 0 | — | — | — | 0 | — | — |
| 4 | 1 | 529 | T to C | non synonymous | 1 | 177 | F to L |

TABLE 4.2-continued

Arrangement of nucleotide and amino acid sequence comparisons of the 94881 Master Seed Virus to 94881 Parental strain

| ORF | no. of deviating nucleotides | position in viral gene | exchange (nn) from parental strain to MSV | synonymous/non synonymous | no. of deviating amino acids | position in viral protein | exchange (aa) from parental strain to MSV |
|---|---|---|---|---|---|---|---|
| 5 | 3 | 109 | A to G | non synonymous | 2 | 37 | N to D |
|   |   | 364 | C to T | non synonymous |   | 122 | L to F |
|   |   | 570 | C to T | synonymous |   | — | — |
| 6 | 1 | 214 | C to T | non synonymous | 1 | 72 | L to F |
| 7 | 0 | — | — | — | 0 | — | — |

Example 6: PRRS 94881 $_{ML}$V Gilt MID Stud

Summary

The objective of this vaccination-challenge study was to evaluate the minimum immunizing dose (MID) of Porcine Reproductive and Respiratory Syndrome Vaccine European-derived Isolate 94881, Modified Live Virus, Code 19T1.U__ (PRRS 94881 MLV) in gilts. Two different titer levels were administered to PRRS seronegative gilts approximately 28 days pre-breeding (Day 0; D0), gilts were challenged with a heterologous European isolate of PRRSv at approximately 90 days of gestation (D118) and gilts were evaluated for the total number of live born piglets or percentages of live born piglets and weaned piglets at 20 days of age to determine the MID. At the time of challenge on Day 118 (D118), the challenge control group consisted of 8 pregnant gilts (Group 1, Placebo), the low titer group consisted of 8 pregnant gilts (Group 2, $1\times10^{2.43}$ TCID$_{50}$/dose), the high titer group consisted of 8 pregnant gilts (Group 3, $1\times10^{3.90}$ TCID$_{50}$/dose), and the negative control group consisted of 5 pregnant gilts (Group 4, Placebo, not challenged).

Both the low titer and the high titer groups were associated with higher percentages of live piglets per litter at farrowing (P≤0.0455) and higher percentages and numbers of live piglets per litter at weaning (P≤0.0203) in comparison to the challenge control group.

With regard to supportive efficacy parameters, the high dose group was associated with a higher percentage and number of healthy piglets per gilt at farrowing (P≤0.0211), a lower percentage and number of weak and mummified feti (P≤0.0090), a lower percentage of qPCR positive gilts and lower viral load in gilts post-challenge on D125, DOF 0 and DOF+13 (P≤0.0155), a lower percentage of piglets per gilt qPCR positive and lower piglet viral load on DOF 0 (P≤0.0030), a lower percentage of piglets per gilt with clinical disease (P≤<0.0001), and higher piglet body weights on DOF+20 and ADWG (P<0.0013), in comparison with the challenge control group.

The low dose group was associated with a higher percentage of healthy piglets per gilt at farrowing (P=0.0138), a lower percentage and number of mummified feti (P≤0.0190), a lower percentage of qPCR positive gilts and lower viral load in gilts post-challenge on D125, D132, DOF 0 and DOF+13 (P≤0.0290), a lower percentage of piglets per gilt qPCR positive on DOF 0 (P=0.0381), a lower percentage of piglets per gilt with clinical disease (P<0.0001), and higher piglet body weight on DOF+20 and ADWG (P<0.0028), in comparison to the challenge control group.

In conclusion, the study objective was met and data from this study establishes the MID of PRRS 94881 MLV in gilts as $1\times10^{2.43}$ TCID$_{50}$/2 mL. In addition, this study establishes duration of immunity (DOI) in gilts of approximately 4 months.

Objective(s)/Purpose of the Study

The objective of this vaccination-challenge study was to evaluate the minimum immunizing dose (MID) of Porcine Reproductive and Respiratory Syndrome Vaccine European-derived Isolate 94881, Modified Live Virus, Code 19T1.U__ (PRRS 94881 MLV), at two different titer levels (Group 2, low titer; Group 3, high titer), administered to PRRS sero-negative gilts pre-breeding to provide higher percentages of live born piglets and weaned piglets at 21 days of age, following challenge of gilts with a heterologous European isolate of Porcine Reproductive and Respiratory Syndrome virus (PRRSv) at approximately 90 days of gestation. The primary criteria to satisfy this objective was that one or both vaccine groups must demonstrate relevantly higher percentage or number of live born piglets and weaned piglets at 20 days of age (DOF+20), compared with the challenge control group (Group 1).

Other parameters analyzed between the vaccine groups and the challenge control group included gilt clinical assessments post-vaccination, gilt PRRS serology, gilt viremia, gilt clinical observations, piglet viremia, total piglets per litter, healthy live piglets per litter, weak live piglets per litter, mummies per litter, stillborns per litter, crushed/mortalities piglets per litter, piglet clinical observations, and piglet average daily weight gain (ADWG). These parameters were analyzed as supportive parameters and did not serve as primary parameters to satisfy the study objective.

Schedule of Events

TABLE 6.1

Gilt Schedule of Events

| Study Day(s) | Dates | Key Study Event |
|---|---|---|
| −2 or −1 | 20 Jul. 2010 to 21 Jul. 2010 | Health examination |
| −1 to 21 | 21 Jul. 2010 to 12 Aug. 2010 | Groups 1-4: Daily Clinical Assessments |

TABLE 6.1-continued

Gilt Schedule of Events

| Study Day(s) | Dates | Key Study Event |
|---|---|---|
| 0 | 22 Jul. 2010 | Groups 1-4: Blood collection; Vaccinated Groups 1 and 4 with Control Product (CP); Vaccinated Group 2 with Investigational Veterinary Product (IVP) No. 1 (low titer vaccine group); and vaccinated Group 3 with IVP No. 2 (high titer vaccine group) |
| 8 to 21 | 30 Jul. 2010 to 12 Aug. 2010 | Groups 1-4: Treated gilts once daily with Matrix ™ to synchronize estrus cycles |
| 7, 14, 21, 56 and 84 | 29 Jul. 2010, 5 Aug. 2010, 12 Aug. 2010, 16 Sep. 2010, 14 Oct. 2010 | Groups 1-4: Blood collection |
| 22 to 113 | 13 Aug. 2010 to 12 Nov. 2010 | Groups 1-4: Clinical Assessments at least three times a week |
| 26 to 32 | 17 Aug. 2010 to 23 Aug. 2010 | Groups 1-4: Observed for heat detection and bred gilts by artificial insemination (AI) |
| 84 | 14 Oct. 2010 | Groups 1-4: Pregnancy check by ultrasound |
| 116 to 20 days after farrowing | 15 Nov. 2010 to 5 Jan. 2011 | Groups 1-4: Clinical Observations, recorded abortions, stillbirths, mummies, live piglets, weak born piglets |
| 118 (approx. 90 days of gestation) | 17 Nov. 2010 | Groups 1-4: Blood collection Groups 1-3: Challenged with PRRSv isolate 190136 |
| 125, 132, farrowing/ abortion (DOF*), DOF +7, DOF +13 | 24 Nov. 2010, 1 Dec. 2010, 3 Dec. 2010 to 16 Dec. 2010, 10 Dec. 2010 to 23 Dec. 2010, 16 Dec. 2010 to 29 Dec. 2010 | Groups 1-4: Blood collection |
| DOF +20 | 23 Dec. 2010 to 5 Jan. 2011 | Groups 1-4: Blood collection from remaining gilts; Euthanized remaining gilts; Disposal |
| DOF +20 or later | 25 Dec. 2010 to 5 Jan. 2011 | Groups 1-4: Euthanized remaining gilts; Disposal |

*DOF = Day of Farrowing

TABLE 6.2

Piglet Schedule of Events

| Study Day(s) | Dates | Key Study Event |
|---|---|---|
| DOF | 3 Dec. 2010 to 16 Dec. 2010 | All dead piglets: Weighed; Necropsied; Collected blood/body fluid if possible; Collect lung samples All live piglets: Weighed; Blood collection (pre-colostral or peri-natal (within 12 hours of birth)) |
| DOF +1 to DOF +20 | 4 Dec. 2010 to 5 Jan. 2011 | All live piglets: Clinical Observations Dead piglets: Weighed; Necropsied; Collected blood/body fluid if possible; Collected lung samples |
| DOF +7 | 10 Dec. 2010 to 23 Dec. 2010 | All live piglets: Blood collection |
| DOF +13 | 16 Dec. 2010 to 29 Dec. 2010 | All live piglets: Blood collection |
| DOF +20 | 23 Dec. 2010 to 5 Jan. 2011 | All live piglets: Weighed; Blood collection; |
| DOF +20 or later | 25 Dec. 2010 to 5 Jan. 2011 | Group 1-3 piglets: Euthanized remaining piglets, Disposal; Group 4 piglets: Assigned to another BIVI project |

Study Design

TABLE 6.3

Study Design

| Group | Number of gilts on D 0 | Treatment on D 0 (approximately 28 days prior to breeding) | Number of gilts on D 118 | Challenged on D 118 with 6.0 mL (2 mL/nostril; 2 mL IM) of $1 \times 10^{6.30}$ TCID$_{50}$ of PRRSv 190136 |
|---|---|---|---|---|
| 1 (Challenge control group) | 28 | 2.0 mL IM of Control Product (Placebo matched product without PRRS 94881 MLV) | 16 | Yes |

TABLE 6.3-continued

Study Design

| Group | Number of gilts on D 0 | Treatment on D 0 (approximately 28 days prior to breeding) | Number of gilts on D 118 | Challenged on D 118 with 6.0 mL (2 mL/nostril; 2 mL IM) of $1 \times 10^{6.30}$ $TCID_{50}$ of PRRSv 190136 |
|---|---|---|---|---|
| 2 (Low titer group) | 28 | 2.0 mL IM of IVP No. 1 ($1 \times 10^{2.43}$ $TCID_{50}$ of PRRS 94881 MLV) | 16 | Yes |
| 3 (High titer group) | 28 | 2.0 mL IM of IVP No. 2 ($1 \times 10^{3.90}$ $TCID_{50}$ of PRRS 94881 MLV) | 16 | Yes |
| 4 (Negative control group) | 10 | 2.0 mL IM of Control Product | 5 | No |

Blinding Criteria

The Study Investigator and designees were blinded with regard to gilts assigned to Groups 1-4. To maintain blinding of the Study Investigator and designees, a person not collecting data administered the IVPs and CP to assigned gilts on D0. Laboratory personnel were blinded to the treatment each gilt received while conducting their respective tasks.

Materials

Investigational Veterinary Products (IVP) and Control Product (CP)

TABLE 6.4

Investigational Veterinary Products (IVPs)

| | |
|---|---|
| Generic Product Name: | Porcine Reproductive and Respiratory Syndrome, Modified Live Virus |
| Isolate: | Isolate 94881 |
| Formulation: | The Manufacturer's Batch Protocol (MBP) for PRRS 94881 MLV vaccine, Lot 390-005 (cake) is presented in Appendix 1. The MBP for Sterile Carbopol Adjuvanted Diluent, Lot 808-002 (diluent) is presented in Section 15.1, Appendix 1. D 0 just prior to vaccination, BIVI-Ames reconstituted/diluted PRRS 94881 MLV vaccine, Lot 390-005 with Sterile Carbopol Adjuvanted Diluent, Lot 808-002 to formulate the two IVPs. IVP No. 1 was formulated to a targeted titer level of approximately $1 \times 10^{3.0}$ $TCID_{50}/2$ mL and IVP No. 2 was formulated to a targeted titer level of approximately $1 \times 10^{4.5}$ $TCID_{50}/2$ mL. An adequate volume of each IVP was formulated for vaccination and testing. |
| IVP Lot/Serial Nos.: | IVP No. 1: N270-142<br>IVP No. 2: N270-143 |
| Manufacturer: | Boehringer Ingelheim Vetmedica, Inc.<br>2621 North Belt Highway<br>St. Joseph, MO 64506 |
| Expiration Date: | An expiration date of 22 Jul. 2010 was assigned to each IVP for study purposes only. |
| Storage Requirements: | Rehydrated/diluted IVP was stored at 2-8° C. or on ice |
| Testing: | PRRS 94881 MLV, Serial 390-005 and Sterile Carbopol Adjuvanted Diluent, Lot 808-002 were tested by BIVI-QC. At the start and end of the vaccination procedure, BIVI-Ames was contacted. BIVI-Ames tested pre- and post-vaccination aliquots of each IVP for virus titer in accordance with the PRRSv Titer Procedure (Section 15.1). |
| Test Results: | Test results for PRRS 94881 MLV, Serial 390-005 and for Sterile Carbopol Adjuvanted Diluent, Lot 808-002 were satisfactory IVP No. 1 had an average titer of $1 \times 10^{2.43}$ $TCID_{50}/2$ mL and IVP No. 2 had an average titer of $1 \times 10^{3.90}$ $TCID_{50}/2$ mL |
| IVP Transfer: | Two vials containing 35 mL of each IVP were transferred to the study site on D 0 just prior to vaccination. |
| IVP Retention: | A retention sample of each IVP is currently stored at $-70 \pm 10°$ C. at BIVI-Ames until the final report has been signed. |

TABLE 6.6

Control Product (CP)

| | |
|---|---|
| Generic Product Name: | Placebo |
| Formulation: | BIVI-Production produced lyophilized placebo product containing inert material comprised in the vaccine serial without PRRS 94881 MLV (Lot N240-191-062409, On D 0, BIVI-Ames reconstituted Lot N240-191-062409 with Sterile Carbopol |

TABLE 6.6-continued

Control Product (CP)

| | |
|---|---|
| | Adjuvanted Diluent, Lot 808-002 to formulate the CP, Lot No. 270-141. |
| Manufacturer: | Boehringer Ingelheim Vetmedica, Inc. 2621 North Belt Highway St. Joseph, MO 64506, USA |
| Lot Number: | N270-141 |
| Expiry Date: | An expiration date of 22 Jul. 2010 was assigned to the CP for study purposes only. |
| Storage Conditions: | Lyophilized vaccine: 2-8° C. Rehydrated CP: 2-8° C. or on ice |
| Testing: | CP was tested by BIVI-QC for EP sterility in accordance with Special Outline No. 96 |
| Test Results: | CP was determined to be sterile |
| CP Transfer: | Two vials containing 50 mL each of CP were transferred to the study site on D 0 just prior to vaccination. |
| CP Retention: | CP was formulated for this study only and was not retained. |

Challenge Material

TABLE 6.7

Challenge Material

| | |
|---|---|
| Name/number of isolate | Porcine Reproductive and Respiratory Syndrome virus |
| Location and date of isolation incl. clinical symptoms | Isolate 190136, Passage 2. Isolate #190136 was obtained from lung tissue of a new born piglet from a farm showing typical reproductive signs of PRRS (abortions in gilts and weakness in new born piglets) during an outbreak in Lower Saxony, Germany, in April 2004. The attending veterinarians submitted the samples to bioScreen (sample arrived on 21 Apr. 2004). Isolate #190136 could directly be propagated on AK-MA104 cells. |
| Formulation: | Challenge virus was thawed and diluted with MEM (Minimum Essential Medium) to a targeted titer of approximately $1 \times 10^6$ $TCID_{50}/3$ mL on D118. An adequate volume of challenge material was prepared. Two aliquots were removed from challenge material. |
| Lot Number: | N289-034 |
| Manufacture: | Boehringer Ingelheim Vetmedica, Inc. - USA |
| Storage conditions | Bulk challenge material was stored at $-70 \pm 10°$ C. Once prepared, diluted challenge material was maintained on ice until it was administered. |
| Testing: | At the start and end of the challenge procedure, BIVI-Ames was contacted. BIVI-Ames laboratory personnel tested pre- and post-challenge aliquots for virus titer in accordance with the PRRSv Titer Procedure |
| Test Results: | The challenge material had a mean titer of $1 \times 10^{6.30}$ $TCID_{50}/6$ mL dose |
| Challenge material transfer: | Three vials containing 101 mL each of challenge material were transferred to the study site on D118 just prior to administration. |
| Administration route | 2.0 mL/nostril and 2.0 mL IM in the left neck (administered to all gilts in Groups 1, 2 and 3 on D118). |
| Challenge material retention: | Challenge material was formulated for this study only and was not retained. |

Additional Treatments

MATRIX™ (6.8 mL; Alternogest; Intervet/Schering Plough Animal Health) was administered in each gilt's feed from D8 to D21 to synchronize estrus cycles.

Oxytocin (VetTek) was administered at parturition to assist gilts with farrowing, but not for initiation of farrowing. At farrowing, all live piglets received 1.0 mL iron injection (Phoenix or Durvet), IM, in the right ham for prevention of iron deficiency anemia shortly after birth. Additionally, all live piglets received gentamicin (SparHawk Laboratories Inc.) as a scour preventative shortly after birth. All treatments were recorded on the Biological & Pharmaceutical Treatment Record form.

Treatments

Dosing Justification

Each IVP was administered as a 2.0 mL dose to assigned gilts to evaluate the MID of PRRS 94881 MLV. A 2.0 mL dose of the CP was administered to gilts assigned to groups 1 and 4.

Dosing Regimen

On D0, each IVP or CP was administered to each respective gilt IM in the right neck region using a sterile 3.0 mL Luer-lock syringe and a sterile 18 g×1 inch (2.54 cm) needle by a person not collecting study data. The dosing regimen is shown below in Table 6.8.

TABLE 6.8

Dosing Regimen

| Group | Number | Treatment | Dose/Route | Study Day |
|---|---|---|---|---|
| 1 | 28 | CP | 2.0 mL IM | D0 |
| 2 | 28 | IVP No. 1 (low titer dose) | 2.0 mL IM | D0 |
| 3 | 28 | IVP No. 2 (high titer dose) | 2.0 mL IM | D0 |
| 4 | 10 | CP | 2.0 mL IM | D0 |

Methods and Precautions for Study Personnel

Personnel administering IVPs, the CP and challenge material adhered to safety precautions and wore personal protective equipment as outlined for the specific study site.

Animal Information
Details of Study Animals

TABLE 6.9

| Animal Information | |
|---|---|
| Source: | Wilson Prairie View Farms<br>N5627 Highway DD<br>Burlington, WI 53105 |
| Number of gilts: | 94 |
| Arrival date: | Gilts arrived at the Veterinary Resources, Inc. facilities in two shipments on 15 Jul 2010 (D-7) and 20 Jul 2011 (D-2). |
| Identification: | Individually ear tagged with unique number |
| Species: | Porcine |
| Breed: | Commercial crossbred |
| Gender: | Females |
| Age range: | Approximately 8 months of age on D0 |
| Ownership of test animals: | Boehringer Ingelheim Vetmedica, Inc. |
| Physiological status: | All gilts were PRRS ELISA seronegative on D0. Gilts selected for assignment to the study were observed by the Study Investigator on D-2 or D-1 and determined to be in good health and nutritional status. |
| Pregnancy results: | Gilts were checked for pregnancy on D84. |
| Group-Gilt Assignments on D0 | Group 1 (n = 28): 1, 3, 5, 6, 8, 11, 15, 18, 19, 34, 35, 39, 40, 52, 54, 68, 79, 82, 88, 90, 95, 96, 98, 101, 102, 107, 109 and 110    Group 2 (n = 28): 12, 26, 31, 32, 41, 47, 49, 56, 58, 59, 60, 64, 67, 69, 70, 72, 73, 75, 76, 77, 78, 85, 89, 93, 94, 100, 103 and 104<br>Group 3 (n = 28): 2, 7, 14, 22, 23, 25, 27, 28, 30, 33, 36, 42, 46, 48, 51, 53, 57, 61, 62, 65, 66, 80, 84, 86, 91, 92, 105 and 106    Group 4 (n = 10): 4, 10, 13, 16, 17, 20, 21, 24, 29, and 108 |
| Group-Gilt Nos. Remaining in the Study On D118 | Group 1 (n = 16): 1, 6, 11, 18, 19, 40, 54, 68, 79, 82, 88, 95, 96, 98, 102, and 107    Group 2 (n = 16): 12, 26, 31, 32, 41, 47, 49, 58, 64, 67, 72, 85, 89, 93, 100, and 104<br>Group 3 (n = 16): 7, 14, 23, 27, 33, 36, 46, 48, 57, 61, 62, 65, 66, 84, 92, and 106    Group 4 (n = 5): 4, 13, 16, 17, and 108 |

Inclusion/Exclusion Criteria

All gilts enrolled in this study were PRRS ELISA negative, non-bred and were healthy at the time of vaccination as determined by observation.

Post-Inclusion Removal of Gilts

Five (5)—Group 1 gilts (Nos. 5, 15, 34, 35 and 52), two (2)—Group 2 gilts (Nos. 77 and 94), three (3)—Group 3 gilts (Nos. 2, 25, and 30) and one (1)—Group 4 gilt (No. 20) did not display estrus and were subsequently not bred. These gilts were removed from the study by D47.

Two (2)—Group 1 gilts (Nos. 109 and 110), nine (9)—Group 2 gilts (Nos. 56, 59, 60, 69, 73, 75, 76, 78, and 103), four (4)—Group 3 gilts (Nos. 22, 28, 51 and 53) and one (1)—Group 4 gilt (No. 21) were removed from the study by D89 due to lameness, not pregnant, or late breeding.

The study protocol stated that if >16 pregnant gilts per group for Groups 1-3 were still in the study prior to challenge, extra gilts would be randomly selected for removal from the study; thus leaving 16 pregnant gilts per group for Groups 1-3. Five (5)—Group 1 gilts (Nos. 3, 8, 39, 90 and 101), one (1)—Group 2 gilt (No. 70) and five (5)—Group 3 gilts (Nos. 42, 80, 86, 91, and 105) were removed from the study by D104 based on randomizations by the statistician or selection by non-study person, reducing the group size to 16 gilts for Groups 1-3.

Due to space limitations, the Study Investigator requested that the size of Group 4 be reduced from eight (8) to five (5). The statistician randomly selected three (3) gilts (Nos. 10, 24 and 29) for removal from the study, which were removed on D109.

Animal Management and Housing
Animal Housing

Low IVP titer gilts were housed in Rooms 1 and 2, and high IVP titer gilts were housed in Rooms 3 and 4, in Building CB at VRI-Cambridge from D-1 to study completion. Gilts assigned to the challenge control and negative control groups were housed in a single room at VRI-Risdal from D-1 to D85. On D85, remaining gilts in the challenge control and negative control groups were moved to VRI-Cambridge. Sixteen (16)—challenge control gilts were housed in Building CB, Rooms 5-8 and eight (8)—negative control gilts were housed in Building CA, Room 12, for the remainder of the study. From D85 onward, each room was identical in layout with two rows of 4 farrowing crates per row. Each crate held one gilt and her progeny. Each crate was approximately 5 feet×7 feet in size, was elevated off of the floor, metal rod panels for sides and plastic-mesh for flooring. There was no nose-to-nose contact between adjacent crates. The floor of each crate was washed down at least once daily to remove excrement and waste. Each room had separate heat and ventilation, preventing cross-contamination of air between rooms. Each room was cleaned and disinfected prior to use for this study. Animal Services staff showered and donned clean clothes before entering each room.

Treatment group isolation was necessary in this study as it is well known within the scientific community that PRRSv readily spreads from pig to pig via various mechanisms including aerosolization. This includes avirulent live PRRS vaccines as these biological products include attenuated virus particles that mimic the characteristics of virulent wild-type PRRS without the capability to cause disease. Proper methods were in place to ensure that biosecurity was maintained and that vaccinated animals did not accidentally cross-contaminate non-vaccinated, PRRSv naïve negative control animals.

Each room in the facility has fans and heaters to aid in sufficient air circulation and heating. The ventilation system is separate yet identical for each room, so air is not shared between rooms. Solid feed was stored in bags, free from vermin. Water was ad libitum from a well located at the animal facility. Gilts were fed a commercially prepared, non-medicated gestation or lactation ration (Heart of Iowa Cooperative, Roland, Iowa) appropriate for their size, age, and condition.

Gilts were in good health and nutritional status before initiation of the study as determined by the Study Investigator. During the study, two gilts were observed with mild lameness and one gilt was observed with a swelling in the left neck region. The Study Investigator considered all of these to be non-specific conditions that commonly occur in groups of gilts housed in confinement. The Study Investigator determined that concomitant treatments were not required for any animals during this study.

All gilts and their pigs assigned to Groups 1-3 were disposed of by commercial incineration after euthanasia. Gilts assigned to Group 4 were disposed of by rendering after euthanasia. Group 4 piglets were not euthanized and disposed of, but were assigned to another BIVI project. No food products from animals enrolled in this study entered the human food chain.

Assessment of Efficacy

To assess the MID of PRRS 94881 MLV, low titer group (Group 2) and the high titer group (Group 3) were challenged on D118 and reproductive performance and weaned piglets post-challenge were evaluated. The primary criteria to satisfy this objective were that one or both vaccine groups must demonstrate statistically higher percentage or number of live born piglets and weaned piglets at 20 days of age (DOF+20), compared with the challenge control group (Group 1).

Other parameters analyzed to support efficacy between vaccine groups and the challenge control group included gilt clinical assessments post-vaccination, gilt PRRS serology, gilt viremia, gilt clinical observations post-challenge, piglet viremia at farrowing, total number of piglets per litter, healthy live piglets per litter, weak live piglets per litter, mummies per litter, stillborns per litter, crushed/mortalities piglets per litter, piglet clinical observations, and piglet ADWG.

Criteria for a Valid Test

The negative control group (Group 4) was not included in any analyses. The negative control group was included in the study to demonstrate that source gilts were PRRS negative at the time that the other three groups were challenged. Furthermore, the negative control group had to remain PRRS negative until study completion to exclude a possible introduction of a field PRRSv or accidental cross contamination from challenged groups.

Pre-purchase and D0 serum samples were all required to be negative for PRRS antibodies. Serum samples collected from Groups 1 and 4 up to the day of challenge and from Group 4 until study completion had to be free of PRRS antibodies for the study to be valid.

Primary Outcome Parameters

The primary efficacy variables for statistical evaluation were live piglets per gilt at birth (mean number or percentage) and live piglets per litter at DOF+20 (mean number and percentage).

9.2.1 Percentage of Live Piglets at Birth Per Gilt

Farrowing data was recorded for each gilt during the study. The day of farrowing (DOF) for each gilt was defined as the day that the first piglet was born. At the time of farrowing, each piglet was classified into one of five categories listed below in Table 6.10. A live piglet at birth was defined as any piglet that received an observation rating at birth as healthy live piglet, weak live piglet or crushed/mortality piglet (death due to crushing was confirmed at necropsy as described below). Observations were conducted by the Study Investigator or a designee and were recorded on the Farrowing/Litter Processing Record form.

TABLE 6.10

Farrowing Result Categories

| Term | Definition |
|---|---|
| Mummy | A mummified fetus that is not completely developed and is exhibiting severe autolysis or a completely developed fetus exhibiting a shiny gun metal green appearance and with no or very little hair |
| Stillborn Piglet | A completely developed dead piglet with hair |
| Weak Live Piglet | A poor-doing piglet that cannot nurse or walk |
| Healthy Live Piglet | A healthy, nursing piglet that is able to walk |
| Crushed/ Mortality | A fully developed piglet that appears to have died shortly after farrowing due to being crushed by the gilt |

Live Piglets Per Litter at DOF+20

Piglets were observed for clinical signs of disease as outlined below in Table 6.11 from DOF+1 to DOF+20. Observations were conducted by the Study Investigator or designees and were recorded on the Clinical Observations Record form.

TABLE 6.11

Clinical Observation Scoring System

| Respiration | Behavior | Cough |
|---|---|---|
| 0 = normal respiration<br>1 = panting/rapid respiration<br>2 = dyspnea<br>3 = dead | 0 = normal<br>1 = mild to moderate lethargy<br>2 = severely lethargic or recumbent<br>3 = dead | 0 = none<br>1 = soft or intermittent cough<br>2 = harsh or severe, repetitive cough<br>3 = dead |

A daily total clinical observation score was determined as a summation of respiration, behavior and cough scores by the statistician using SAS program. Any piglet receiving a clinical score of zero to eight on DOF+20 was evaluated as alive on DOF+20.

Supportive Parameters

Other parameters analyzed between vaccine groups and the challenge control group included gilt clinical assessments post-vaccination, gilt PRRS serology, gilt viremia, gilt clinical observations, piglet viremia, total piglets per litter, healthy live piglets per litter, weak live piglets per litter, mummies per litter, stillborns per litter, crushed/mortalities piglets per litter, piglet clinical observations, and piglet average daily weight gain (ADWG).

Gilt Daily Assessments All gilts were observed once daily from D-1 to D21 and from D22 to 115 at least three times a week for daily assessments post-vaccination by the Study Investigator or designees. Observations were recorded on the Daily Assessment Record form.

Gilt PRRS Serology

Venous whole blood was collected from gilts prior to purchase and on D0, D7, D14, D21, D56, D84, D118, D125, D132, DOF 0, DOF+7, DOF+13 and DOF+20. Blood collections from gilts at the time of farrowing/abortions (DOF 0) were conducted immediately after farrowing/abortions were completed or up to 8 hours post-farrowing/abortion.

Briefly, approximately 10 mL of blood was collected from each gilt into an appropriate sized Serum Separator Tube(s) (SST). Sample collections were recorded on the Sample Collection Record form. Blood in SSTs was allowed to clot at room temperature. Blood samples collected on weekdays were delivered to BIVI-Ames on the day of collection. Blood samples collected on weekends were processed by VRI personnel on the day of collection. Serum samples at VRI were held at 2-8° C. At either BIVI-Ames or VRI, blood samples were spun down and serum was harvested, split and transferred to appropriate tubes. Each tube was labeled with the gilt's ID number, the study number, the date of collection, the study day and the sample type. Serum samples at VRI were delivered to BIVI-Ames at the earliest convenient time. A completed Specimen Delivery Record form was included with each shipment. At BIVI-Ames, one set of serum samples were held at 2-8° C. and the other set of serum samples were held at −70±10° C.

The set of gilt serum samples held at 2-8° C. were tested by BIVI-Ames for PRRS antibodies. Results were reported as negative (ELISA S/P ratio of <0.4) or positive (ELISA S/P ratio of ≥0.4).

Gilt Clinical Observations Post-Challenge

Gilts were observed for clinical signs of disease from D116 to DOF+20. Observations were conducted by the Study Investigator or designees. Gilts were observed each day for respiration, behavior and cough based on the clinical observation scoring system outlined above in Table 6.11.

9 Piglet PRRS Viremia

Venous whole blood was collected from piglets on DOF 0, DOF+7, DOF+13 and DOF+20, or when a piglet was found dead. Pre-colostral blood collection was preferred from newborn piglets, but was not mandatory. If pre-colostral blood could not be collected, peri-natal blood within 12 hours of farrowing was permissible. Samples not collected before first suckling were labeled as "Peri-natal" and kept separately from pre-colostral samples.

Briefly, approximately 2.0 to 2.5 mL of blood was collected from each live piglet into an appropriate sized Serum Separator Tube(s) (SST). A minimum of 5.0 mL of blood was collected from each piglet on DOF+20 just prior to euthanasia. Blood was collected from each mummy or stillbirth or if blood could not be collected from a dead fetus, thoracic or abdominal fluid was collected. Sample collections were recorded on the Sample Collection Record form.

Piglet Average Daily Weight Gain

Individual piglets were weighed on DOF 0 and DOF+20, or on the day a piglet was found dead by the Study Investigator or designees. Individual body weights on DOF 0 were recorded on the Farrowing/Litter Processing Record form and body weights after DOF 0 were recorded on the Body Weight Record form.

PRRS Virus Quantitation in Lung Tissue

All piglets dead at delivery or dying before DOF+20 were necropsied by the Study Investigator. Necropsy results and a diagnosis were recorded on the Necropsy Report form. Two lung samples were collected from each necropsied piglet. One sample was placed into a separate WHIRLPAK® container and another sample was placed into an appropriate container filled with a sufficient volume of 10% formalin. Sample collections were recorded on the Necropsy Report form.

WHIRLPAKS® and formalin containers were appropriately labeled with animal number, study number, date of sampling, study day, sample type and whether the samples were from the left side, right side or both. Samples in WHIRLPAKS® were stored at −70±10° C. and samples in 10% formalin were stored at room temperature until delivered to BIVI-Ames. A completed Specimen Delivery Record form was included with each delivery of samples. At BIVI-Ames, samples in WHIRLPAKS® were stored at −70±10° C. until shipped from BIVI-Ames to Germany, and formalin fixed samples were stored at BIVI-Ames at room temperature.

After the study was completed, frozen tissue samples in WHIRLPAKS® were shipped and tested as described above.

Formalin fixed tissue samples were submitted to ISU VDL within one week of collection for embedding in paraffin blocks). Tissues in paraffin blocks were returned to BIVI and are currently held by BIVI-Ames at room temperature for possible future testing. A decision of whether to retain these samples or discard them will be made by the Study Sponsor and Monitor after the study report is completed.

Adverse Events

No adverse events attributed to the IVPs were reported during this study. For more information on adverse events, see Section 12.6, Gilt Assessments Post-Vaccination.

Statistical Methods

Experimental Unit

Treatment groups had to be housed in separate rooms in this study to avoid transmission of live PRRSv vaccine to non-vaccinated groups. Therefore, room was the experimental unit. However, for the purposes of this analysis, possible bias due to confounding "room" and "treatment" effects were ignored, and gilt and her corresponding litter were analyzed as the experimental unit.

Randomization

Ninety-four (94) PRRS seronegative gilts from a pool of 107 test-eligible gilts were randomly assigned to one of 4 groups prior to D0. Groups 1-3 each consisted of 28 gilts. Group 4 consisted of 10 gilts. For Group 1, Nos. 45 and 55 were excluded by the farm manager prior to shipment due to health reasons and were replaced by two extra gilts, Nos. 15 and 18, respectively. For Group 3, gilt No. 44 was excluded by the farm manager prior to shipment due to health reasons and was replaced by extra gilt No. 25.

Due to space limitations at the time of challenge, Groups 1-3 were restricted to 16 gilts per group and Group 5 was restricted to 5-8 gilts. On D85, 16 gilts per group were randomly selected to remain in the study for Groups 1-3. Since Group 4 consisted of 8 gilts on D85, this group was not further reduced by randomization. Afterwards, the Study Investigator requested that Group 4 be reduced from 8 gilts to 5 gilts. On D109, 5 gilts were randomly selected to remain in the study for Group 4.

All randomizations procedures were conducted by a biostatistician.

Analysis

The statistical analyses and data summaries were conducted by Dr. rer. hort. Martin Vanselow, Biometrie & Statistik, Zum Siemenshop 21, 30539 Hannover, Germany, +49(0) 511 606 777 650, m.vanselow@t-online.de.

The main objective of the statistical analysis was the comparison of two PRRS 94881 MLV vaccine groups (Groups 2 and 3) to an unvaccinated challenged control group (Group 1). All data were imported into SAS for management and evaluation. The data were received from the study sponsor in the form of verified SAS data sets. Cases which had been withdrawn from the study were considered for the respective parameter of analysis until date of exclusion. All data were summarized descriptively (n, minimum, maximum, mean, median, standard deviation, interquartile range, or frequency distributions, confidence interval) based on the type of the variable. The statistical analyses were performed using SAS software release 8.2 (SAS, 2001, Cary, N.C., USA: SAS Institute Inc.).

Variables for the Statistical Evaluation of the Study:
Primary Variables
Proportions of live piglets at farrowing/abortion (DOF+0)
Proportions of live piglets at 20 days of age (DOF+20)
Supportive Variables
Gilt clinical assessments post-vaccination
Gilt PRRS serology
Gilt viremia
Gilt clinical observations
Piglet viremia
Reproductive performance
Piglet clinical observations
Piglet average daily weight gain (ADWG)
Hypothesis to be Tested and Assumptions Made:

The unchallenged negative control group (Group 4) was excluded from statistical tests. The low titer and high titer groups (Groups 2 and 3, respectively) were compared to the challenge control group (Group 1). All tests between groups were designed as two-sided tests on differences. In the case of all tests, differences were considered as statistically significant only if P 0.05. Efficacy was demonstrated if the percentage or number of live born piglets and the percentage or number of weaned piglets at DOF+20 were significantly higher for one or both vaccine groups compared with the challenged control group.

Details on Data Manipulations and Evaluation:
Clinical Assessments of Gilts Post-Vaccination Frequency tables of animals with at least one positive finding between study days 1 and 21 and between study days 1 and 113 were generated. Differences between the challenge control and vaccine groups were tested by Fisher's exact test.

Clinical Observations of Gilts Post-Challenge

Frequency tables of animals with at least one positive finding between study day 116 and DOF+20 were generated. Differences between the challenge control group and vaccine groups were tested by Fisher's exact test.

Serology of Gilts

Frequency tables of "positive" ELISA results on study days 7, 14, 21, 56, 84, 118, 125, 132 (pre-farrowing) and DOF+0, DOF+7, DOF+13 and DOF+20 were generated. Differences between the challenge control and vaccine groups were tested by Fisher's exact test.

Viremia of Gilts

Viremia data were evaluated for each day of investigation separately (pre-farrowing study days 7, 14, 21, 56, 84, 118, 125, 132 and DOF+0, DOF+7, DOF+13 and DOF+20). For the qualitative evaluation of the qPCR data the analytical results 'not detected' ('n.d.') and 'negative' were classified as 'negative' and the analytical results 'positive' and a measured value were classified as 'positive'. For the quantitative evaluation 'not detected' ('n.d.') and 'negative' were replaced by a $\log_{10}$ GE/mL value of 0.0 and 'positive' was replaced by 3.0. The quantitative PCR data (PRRS viral load [$\log_{10}$ GE/mL]) were used for comparisons between challenge control (group 1) and treatment groups 2 and 3 using the Wilcoxon Mann-Whitney test. Frequency tables of 'positive' qPCR results were generated. Differences between the challenge control group and vaccine groups were tested by Fisher's exact test.

Reproductive Performance

Absolute frequencies per gilt of total number, alive, healthy, weak, stillborn, dead and alive piglets at DOF+20 were determined and used as single values for the comparisons between groups. Relative frequencies per gilt of alive, healthy, weak, stillborn and dead piglets were calculated in relation to the total number of piglets at farrowing and used as single values for the comparisons between groups. The percentage of live piglets per litter at DOF+20 was calculated in relation to the number of live piglets at farrowing minus number of mortalities and crushed piglets. Differences between the challenge control group and vaccine groups were tested by the Wilcoxon Mann-Whitney test.

Viremia of Piglets

Viremia data were evaluated for each day of investigation separately (DOF+0, DOF+7, DOF+13 and DOF+20). For the qualitative evaluation of the qPCR data the analytical results 'not detected' ('n.d.') and 'negative' were classified as 'negative' and the analytical results 'positive' and a measured value were classified as 'positive'. The percentages of 'positive' piglets per litter were calculated and used as single values for the comparisons between groups by the Wilcoxon Mann-Whitney test. For the quantitative evaluation 'not detected' ('n.d.') and 'negative' were replaced by a $\log_{10}$ GE/mL value of 0.0 and 'positive' was replaced by 3.0. The median qPCR values per litter were calculated and used as single values for the comparisons between groups by the Wilcoxon Mann-Whitney test. For the summary statistics the individual qPCR data were used. The viral loads in lung samples were evaluated descriptively only.

Body Weight and Average Daily Weight Gain of Piglets

Individual average daily weight gains (ADWG) were calculated for the time periods between DOF+0 and DOF+20. Differences between treatment groups were tested by analysis of variance (ANOVA) and subsequent t-tests. Least squares means of the groups and differences between least squares means with 95% confidence intervals were derived from the ANOVA. The analysis for DOF+20 and ADWG was repeated with weight at DOF+0 as a covariate. The weight data of piglets per gilt were summarized descriptively.

Clinical Observations of Piglets

The percentage of piglets per litter with at least one positive finding between study days DOF+1 and DOF+20 were calculated and used as single values for the comparisons between groups by the Wilcoxon Mann-Whitney test. Data were analyzed assuming a completely random design structure.

Results
Gilt Reproductive Performance

Mean percentages of live piglets per litter at farrowing (healthy+weak+crushed/mortality) were 54.4%, 75.1%, 72.3%, and 93.0% for the challenge control, low titer, high titer, and negative control groups, respectively. The low titer and high titer groups had significantly higher percentage of live piglets per litter at farrowing compared to the challenge control group (P≤0.0455). Mean number of live piglets per litter at farrowing were 6.5, 8.3, 8.6 and 10.8 for the challenge control, low titer, high titer, and negative control groups, respectively. No significant differences were detected between groups for the number of live piglets per litter at farrowing (P≤0.1039).

Mean percentages of healthy live piglets per litter were 41.4%, 65.8%, 67.9%, and 93.0% for the challenge control, low titer, high titer, and negative control groups, respectively. The low titer and high titer groups had significantly higher percentages of healthy live piglets per litter at farrowing compared to the challenge control group (P≤0.0138). Mean number of healthy live piglets per litter at farrowing were 4.9, 7.2, 8.1 and 10.8 for the challenge control, low titer, high titer, and negative control groups, respectively. The high titer group had a significantly higher number of healthy live piglets per litter at farrowing (P=0.0211), while no difference was detected for the low titer group in comparison with the challenge control group (P=0.0640).

Mean percentages of weak live piglets per litter at farrowing were 7.4%, 7.1%, 0.4%, and 0.0% for the challenge control, low titer, high titer, and negative control groups, respectively. Mean number of weak live piglets per litter at farrowing were 0.9, 0.8, 0.1 and 0.0 for the challenge control, low titer, high titer, and negative control groups, respectively. The high titer group had significantly lower percentage and number of weak live piglets per litter at farrowing compared to the challenge control group (P≤0.0090). Conversely, no differences were detected between the low titer group and the challenge control group for percentage or number of weak live piglets at farrowing (P≥0.8569).

Mean percentages of mummies per litter at farrowing were 28.1%, 14.1%, 8.7%, and 0.0% for the challenge control, low titer, high titer, and negative control groups, respectively. Mean number of mummies per litter at farrowing were 3.1, 1.6, 0.9, and 0.0 for the challenge control, low titer, high titer, and negative control groups, respectively. Both the low titer and high titer groups had significantly lower percentages and numbers of mummies per litter at farrowing compared with the challenge control group (P≤0.0190).

No significant differences were detected between the two vaccine titer groups and the challenge control group for percentage or number of stillborn or mortalities/crushed piglets per litter at farrowing (P≤0.1681).

A summary of group reproductive performance results (% piglets per litter and number of piglets per litter) on the DOF is shown below in Tables 6.12 and 6.13.

TABLE 6.12

Summary of Group Reproductive Performance Results (% piglets per litter) on the DOF

| Piglets | Group * | N | Min. | Max. | Median | Mean | 95% CI | | SD | P |
|---|---|---|---|---|---|---|---|---|---|---|
| Alive | 1 | 16 | 0 | 92 | 57.3 | 54.4 | 41.1 | 67.7 | 24.91 | |
| | 2 | 16 | 33 | 100 | 81.9 | 75.1 | 64.5 | 85.7 | 19.88 | 0.0184 |
| | 3 | 16 | 17 | 100 | 75.6 | 72.3 | 59.5 | 85.1 | 24.01 | 0.0455 |
| | 4 | 5 | 83 | 100 | 91.7 | 93.0 | 84.2 | 101.8 | 7.11 | |
| Healthy | 1 | 16 | 0 | 92 | 48.1 | 41.4 | 27.5 | 55.3 | 26.13 | |
| | 2 | 16 | 8 | 92 | 71.4 | 65.8 | 52.2 | 79.5 | 25.57 | 0.0138 |
| | 3 | 16 | 17 | 100 | 71.8 | 67.9 | 54.4 | 81.3 | 25.25 | 0.0082 |
| | 4 | 5 | 83 | 100 | 91.7 | 93.0 | 84.2 | 101.8 | 7.11 | |
| Weak | 1 | 16 | 0 | 25 | 3.6 | 7.4 | 2.6 | 12.2 | 9.04 | |
| | 2 | 16 | 0 | 25 | 0.0 | 7.1 | 2.1 | 12.2 | 9.43 | 0.9441 |
| | 3 | 16 | 0 | 7 | 0.0 | 0.4 | −0.5 | 1.3 | 1.67 | 0.0024 |
| | 4 | 5 | 0 | 0 | 0.0 | 0.0 | 0.0 | 0.0 | 0.00 | |
| Stillborn | 1 | 16 | 0 | 50 | 9.5 | 17.5 | 8.5 | 26.4 | 16.83 | |
| | 2 | 16 | 0 | 42 | 3.8 | 10.7 | 3.3 | 18.2 | 13.94 | 0.1965 |
| | 3 | 16 | 0 | 83 | 10.6 | 19.0 | 7.0 | 31.0 | 22.54 | 0.9033 |
| | 4 | 5 | 0 | 17 | 8.3 | 7.0 | −1.8 | 15.8 | 7.11 | |
| Mummies | 1 | 16 | 0 | 63 | 25.8 | 28.1 | 18.8 | 37.4 | 17.50 | |
| | 2 | 16 | 0 | 55 | 9.1 | 14.1 | 6.0 | 22.3 | 15.25 | 0.0190 |
| | 3 | 16 | 0 | 50 | 3.3 | 8.7 | 1.2 | 16.3 | 14.14 | 0.0006 |
| | 4 | 5 | 0 | 0 | 0.0 | 0.0 | 0.0 | 0.0 | 0.00 | |
| Mortalities/ Crushed | 1 | 16 | 0 | 27 | 0.0 | 5.6 | 1.1 | 10.2 | 8.55 | |
| | 2 | 16 | 0 | 18 | 0.0 | 2.1 | −0.6 | 4.8 | 5.07 | 0.2276 |
| | 3 | 16 | 0 | 25 | 0.0 | 4.0 | 0.1 | 7.8 | 7.25 | 0.6108 |
| | 4 | 5 | 0 | 0 | 0.0 | 0.0 | 0.0 | 0.0 | 0.00 | |
| Alive on DOF +20 | 1 | 15 | 0 | 100 | 33.3 | 43.6 | 23.0 | 64.3 | 37.28 | |
| | 2 | 16 | 13 | 100 | 84.5 | 73.8 | 58.5 | 89.2 | 28.80 | 0.0203 |
| | 3 | 16 | 44 | 100 | 86.6 | 83.8 | 75.1 | 92.5 | 16.37 | 0.0022 |
| | 4 | 5 | 100 | 100 | 100.0 | 100.0 | 100.0 | 100.0 | 0.00 | |

* Group 1 = Challenge control group; Group 2 = Low titer PRRS 94881 MLV group; Group 3 = High titer PRRS 94881 MLV group; Group 4 = Negative control group

TABLE 6.13

Summary of Group Reproductive Performance Results (No. of piglets per litter) on the DOF

| Piglets | Group * | N | Min. | Max. | Median | Mean | 95% CI | | SD | P |
|---|---|---|---|---|---|---|---|---|---|---|
| Total | 1 | 16 | 6 | 15 | 12.0 | 11.6 | 10.4 | 12.9 | 2.31 | |
| | 2 | 16 | 9 | 13 | 11.0 | 11.1 | 10.4 | 11.7 | 1.24 | 0.1857 |
| | 3 | 16 | 7 | 15 | 12.0 | 11.6 | 10.3 | 12.9 | 2.42 | 0.9623 |
| | 4 | 5 | 10 | 14 | 12.0 | 11.6 | 9.5 | 13.7 | 1.67 | |

TABLE 6.13-continued

Summary of Group Reproductive Performance Results
(No. of piglets per litter) on the DOF

| Piglets | Group * | N | Min. | Max. | Median | Mean | 95% CI | | SD | P |
|---|---|---|---|---|---|---|---|---|---|---|
| Alive | 1 | 16 | 0 | 11 | 6.0 | 6.5 | 4.7 | 8.3 | 3.35 | |
| | 2 | 16 | 4 | 12 | 8.0 | 8.3 | 7.0 | 9.5 | 2.27 | 0.1543 |
| | 3 | 16 | 2 | 13 | 9.0 | 8.6 | 6.6 | 10.6 | 3.77 | 0.1039 |
| | 4 | 5 | 9 | 14 | 10.0 | 10.8 | 8.4 | 13.2 | 1.92 | |
| Healthy | 1 | 16 | 0 | 11 | 5.5 | 4.9 | 3.1 | 6.7 | 3.36 | |
| | 2 | 16 | 1 | 12 | 7.0 | 7.2 | 5.7 | 8.7 | 2.83 | 0.0640 |
| | 3 | 16 | 2 | 13 | 8.5 | 8.1 | 6.1 | 10.1 | 3.76 | 0.0211 |
| | 4 | 5 | 9 | 14 | 10.0 | 10.8 | 8.4 | 13.2 | 1.92 | |
| Weak | 1 | 16 | 0 | 3 | 0.5 | 0.9 | 0.3 | 1.5 | 1.09 | |
| | 2 | 16 | 0 | 3 | 0.0 | 0.8 | 0.2 | 1.4 | 1.11 | 0.8569 |
| | 3 | 16 | 0 | 1 | 0.0 | 0.1 | −0.1 | 0.2 | 0.25 | 0.0090 |
| | 4 | 5 | 0 | 0 | 0.0 | 0.0 | 0.0 | 0.0 | 0.00 | |
| Stillborn | 1 | 16 | 0 | 6 | 1.0 | 2.0 | 0.9 | 3.1 | 2.03 | |
| | 2 | 16 | 0 | 5 | 0.5 | 1.3 | 0.4 | 2.1 | 1.65 | 0.1681 |
| | 3 | 16 | 0 | 10 | 1.0 | 2.1 | 0.8 | 3.5 | 2.58 | 0.9478 |
| | 4 | 5 | 0 | 2 | 1.0 | 0.8 | −0.2 | 1.8 | 0.84 | |
| Mummies | 1 | 16 | 0 | 7 | 3.0 | 3.1 | 2.1 | 4.1 | 1.89 | |
| | 2 | 16 | 0 | 6 | 1.0 | 1.6 | 0.7 | 2.5 | 1.67 | 0.0125 |
| | 3 | 16 | 0 | 4 | 0.5 | 0.9 | 0.2 | 1.5 | 1.20 | 0.0003 |
| | 4 | 5 | 0 | 0 | 0.0 | 0.0 | 0.0 | 0.0 | 0.00 | |
| Mortalities/ Crushed | 1 | 16 | 0 | 3 | 0.0 | 0.7 | 0.1 | 1.2 | 1.01 | |
| | 2 | 16 | 0 | 2 | 0.0 | 0.3 | −0.1 | 0.6 | 0.58 | 0.2200 |
| | 3 | 16 | 0 | 2 | 0.0 | 0.4 | 0.0 | 0.8 | 0.73 | 0.6115 |
| | 4 | 5 | 0 | 0 | 0.0 | 0.0 | 0.0 | 0.0 | 0.00 | |
| Alive on DOF +20 | 1 | 16 | 0 | 10 | 2.0 | 2.9 | 1.2 | 4.7 | 3.21 | |
| | 2 | 16 | 1 | 10 | 6.5 | 6.2 | 4.5 | 7.9 | 3.19 | 0.0063 |
| | 3 | 16 | 2 | 12 | 7.5 | 6.9 | 5.0 | 8.9 | 3.71 | 0.0026 |
| | 4 | 5 | 9 | 14 | 10.0 | 10.8 | 8.4 | 13.2 | 1.92 | |

* Group 1 = Challenge control group; Group 2 = Low titer PRRS 94881 MLV group; Group 3 = High titer PRRS 94881 MLV group; Group 4 = Negative control group Live Piglets at DOF+20

These scores highlight the number of live piglets at weaning (20 days of age). A summary of group percentage and number of live piglets per litter on DOF+20 is shown above in Tables 6.12 and 6.13.

Mean percentages of live piglets per litter at weaning (DOF+20) were 43.6%, 73.8%, 83.8%, and 100.0% for the challenge control, low titer, high titer, and negative control groups, respectively. Mean number of live piglets per litter at weaning were 2.9, 6.2, 6.9 and 10.8 for the challenge control, low titer, high titer, and negative control groups, respectively. Both the low titer and high titer groups had significantly higher percentages and numbers of alive piglets per litter at weaning (DOF+20) compared with the challenge control group (P≤0.0203).

Gilt qPCR Viremia

All gilts were qPCR negative for PRRSv RNA on D0. All challenge control and negative control gilts remained qPCR negative for PRRSv RNA up to and including the day of challenge (D118). The negative control group remained qPCR negative for the remainder of the study, with exception of gilt No. 108, which was "positive" on DOF+7. Gilt No. 108 was negative at other time points for PRRSv RNA by qPCR testing.

Post-vaccination, 50% and 36% of low titer and high titer gilts, respectively, were qPCR positive for PRRSv RNA (P≤0.0007) on D7. From D14 to D56, only 4% of low titer gilts remained qPCR positive while up to 4% of high titer gilts were qPCR positive intermittently during this observation period. No differences were detected between vaccine groups and the challenge control group from D14 to D56 for the percentage of gilts qPCR positive for PRRSv RNA (P=1.0000 or no test conducted). All vaccinated gilts were qPCR negative for PRRSv RNA on D84 and D118 (day of challenge).

Post-challenge, the low titer and higher groups had statistically lower percentages of gilts qPCR positive for PRRSv RNA compared with the challenge control group on Days 125, DOF 0, and DOF+13 (P≤0.0155). On D132, the low titer group had a significantly lower percentage of gilts qPCR positive for PRRSv RNA (P=0.0290); while no statistical difference was detected between the high titer group and the challenge control group (P=0.1556). No significant differences were detected between vaccine groups and the challenge control group on DOF+7 and DOF+20 for the percentage of gilts qPCR positive for PRRSv RNA (P≥0.1719).

A summary of group percentage of gilts qPCR positive for PRRSv RNA from D7 to DOF+20 is shown below in Tables 6.14 and 6.15.

TABLE 6.14

Summary of Group Percentage of Gilts qPCR Positive for PRRSv RNA from D 7 to D 132

| Study Day | Group* | N | % | 95% CI | | Total | P |
|---|---|---|---|---|---|---|---|
| 7 | 1 | 0 | 0 | 0.0 | 12.3 | 28 | |
| | 2 | 14 | 50 | 30.6 | 69.4 | 28 | <0.0001 |
| | 3 | 10 | 36 | 18.6 | 55.9 | 28 | 0.0007 |
| | 4 | 0 | 0 | 0.0 | 30.8 | 10 | |
| 14 | 1 | 0 | 0 | 0.0 | 12.3 | 28 | |
| | 2 | 1 | 4 | 0.1 | 18.3 | 28 | 1.0000 |
| | 3 | 0 | 0 | 0.0 | 12.3 | 28 | n.a. |
| | 4 | 0 | 0 | 0.0 | 30.8 | 10 | |
| 21 | 1 | 0 | 0 | 0.0 | 12.3 | 28 | |
| | 2 | 1 | 4 | 0.1 | 18.3 | 28 | 1.0000 |
| | 3 | 1 | 4 | 0.1 | 18.3 | 28 | 1.0000 |
| | 4 | 0 | 0 | 0.0 | 30.8 | 10 | |
| 56 | 1 | 0 | 0 | 0.0 | 14.8 | 23 | |
| | 2 | 1 | 4 | 0.1 | 19.6 | 26 | 1.0000 |
| | 3 | 1 | 4 | 0.1 | 20.4 | 25 | 1.0000 |
| | 4 | 0 | 0 | 0.0 | 33.6 | 9 | |

TABLE 6.14-continued

Summary of Group Percentage of Gilts qPCR Positive for PRRSv RNA from D 7 to D 132

| Study Day | Group* | N | % | 95% CI | | Total | P |
|---|---|---|---|---|---|---|---|
| 84 | 1 | 0 | 0 | 0.0 | 14.8 | 23 | |
| | 2 | 0 | 0 | 0.0 | 13.2 | 26 | n.a. |
| | 3 | 0 | 0 | 0.0 | 13.7 | 25 | n.a. |
| | 4 | 0 | 0 | 0.0 | 33.6 | 9 | |
| | 1 | 0 | 0 | 0.0 | 20.6 | 16 | |
| 118 (Day of challenge) | 2 | 0 | 0 | 0.0 | 20.6 | 16 | n.a. |
| | 3 | 0 | 0 | 0.0 | 20.6 | 16 | n.a. |
| | 4 | 0 | 0 | 0.0 | 52.2 | 5 | |
| 125 | 1 | 16 | 100 | 79.4 | 100.0 | 16 | |
| | 2 | 5 | 31 | 11.0 | 58.7 | 16 | 0.0001 |
| | 3 | 4 | 25 | 7.3 | 52.4 | 16 | <0.0001 |
| | 4 | 0 | 0 | 0.0 | 52.2 | 5 | |
| 132 | 1 | 10 | 63 | 35.4 | 84.8 | 16 | |
| | 2 | 3 | 19 | 4.0 | 45.6 | 16 | 0.0290 |
| | 3 | 5 | 31 | 11.0 | 58.7 | 16 | 0.1556 |
| | 4 | 0 | 0 | 0.0 | 52.2 | 5 | |

*Group 1 = Challenge control group; Group 2 = Low titer PRRS 94881 MLV group; Group 3 = High titer PRRS94881 MLV group; Group 4 = Negative control group;
n.a. = not applicable, no test conducted

TABLE 6.15

Summary of Group Percentage of Gilts qPCR Positive for PRRSv RNA from DOF 0 to DOF +20

| Study Day | Group* | N | % | 95% CI | | Total | P |
|---|---|---|---|---|---|---|---|
| DOF +0 | 1 | 15 | 94 | 69.8 | 99.8 | 16 | |
| | 2 | 4 | 25 | 7.3 | 52.4 | 16 | 0.0002 |
| | 3 | 1 | 6 | 0.2 | 30.2 | 16 | <0.0001 |
| | 4 | 0 | 0 | 0.0 | 52.2 | 5 | |
| DOF +7 | 1 | 5 | 31 | 11.0 | 58.7 | 16 | |
| | 2 | 2 | 13 | 1.6 | 38.3 | 16 | 0.3944 |
| | 3 | 1 | 6 | 0.2 | 30.2 | 16 | 0.1719 |
| | 4 | 1 | 20 | 0.5 | 71.6 | 5 | |
| DOF +13 | 1 | 7 | 47 | 21.3 | 73.4 | 15 | |
| | 2 | 0 | 0 | 0.0 | 20.6 | 16 | 0.0024 |
| | 3 | 1 | 6 | 0.2 | 30.2 | 16 | 0.0155 |
| | 4 | 0 | 0 | 0.0 | 52.2 | 5 | |
| DOF +20 | 1 | 3 | 19 | 4.0 | 45.6 | 16 | |
| | 2 | 3 | 19 | 4.0 | 45.6 | 16 | 1.0000 |
| | 3 | 0 | 0 | 0.0 | 20.6 | 16 | 0.2258 |
| | 4 | 0 | 0 | 0.0 | 52.2 | 5 | |

*Group 1 = Challenge control group; Group 2 = Low titer PRRS 94881 MLV group; Group 3 = High titer PRRS 94881 MLV group; Group 4 = Negative control group Both vaccine groups had significantly higher median viral loads compared with the challenge control group on D7 (P≤0.0007). No differences were detected between vaccine groups and the challenge control group from D14 to D56 for viral load (P=1.0000). All vaccinated gilts had zero viral load on D84 and D118 (day of challenge).

Post-challenge, the low titer and higher groups had statistically lower median viral loads compared with the challenge control group on D125, DOF 0, and DOF+13 (P≤0.0155). On D132, the low titer group had a significantly lower median viral load (P=0.0230); while no statistical difference was detected between the high titer group and the challenge control group (0.94 and 1.97 $\log_{10}$ GE/mL respectively; P=0.1144). No significant differences for viral load were detected between vaccine groups and the challenge control group on DOF+7 and DOF+20 (P≤0.1719).

A summary of group mean gilt qPCR GE/mL results from D7 to DOF+20 is shown below in Tables 6.16 and 6.17.

TABLE 6.16

Summary of Group Gilt qPCR Results ($\log_{10}$ GE/mL) From D 7 to D 132

| Study Day | Group * | N | Min. | Max. | Median | 95% CI | | QRange | Mean | P |
|---|---|---|---|---|---|---|---|---|---|---|
| 7 | 1 | 28 | 0.00 | 0.00 | 0.000 | 0.000 | 0.000 | 0.000 | 0.000 | |
| | 2 | 28 | 0.00 | 3.00 | 1.500 | 0.000 | 3.000 | 3.000 | 1.500 | <0.0001 |
| | 3 | 28 | 0.00 | 3.00 | 0.000 | 0.000 | 3.000 | 3.000 | 1.071 | 0.0007 |
| | 4 | 10 | 0.00 | 0.00 | 0.000 | 0.000 | 0.000 | 0.000 | 0.000 | |
| 14 | 1 | 28 | 0.00 | 0.00 | 0.000 | 0.000 | 0.000 | 0.000 | 0.000 | |
| | 2 | 28 | 0.00 | 3.00 | 0.000 | 0.000 | 0.000 | 0.000 | 0.107 | 1.0000 |
| | 3 | 28 | 0.00 | 0.00 | 0.000 | 0.000 | 0.000 | 0.000 | 0.000 | 1.0000 |
| | 4 | 10 | 0.00 | 0.00 | 0.000 | 0.000 | 0.000 | 0.000 | 0.000 | |
| 21 | 1 | 28 | 0.00 | 0.00 | 0.000 | 0.000 | 0.000 | 0.000 | 0.000 | |
| | 2 | 28 | 0.00 | 3.00 | 0.000 | 0.000 | 0.000 | 0.000 | 0.107 | 1.0000 |
| | 3 | 28 | 0.00 | 3.00 | 0.000 | 0.000 | 0.000 | 0.000 | 0.107 | 1.0000 |
| | 4 | 10 | 0.00 | 0.00 | 0.000 | 0.000 | 0.000 | 0.000 | 0.000 | |
| 56 | 1 | 23 | 0.00 | 0.00 | 0.000 | 0.000 | 0.000 | 0.000 | 0.000 | |
| | 2 | 26 | 0.00 | 3.00 | 0.000 | 0.000 | 0.000 | 0.000 | 0.115 | 1.0000 |
| | 3 | 25 | 0.00 | 3.00 | 0.000 | 0.000 | 0.000 | 0.000 | 0.120 | 1.0000 |
| | 4 | 9 | 0.00 | 0.00 | 0.000 | 0.000 | 0.000 | 0.000 | 0.000 | |
| 84 | 1 | 23 | 0.00 | 0.00 | 0.000 | 0.000 | 0.000 | 0.000 | 0.000 | |
| | 2 | 26 | 0.00 | 0.00 | 0.000 | 0.000 | 0.000 | 0.000 | 0.000 | 1.0000 |
| | 3 | 25 | 0.00 | 0.00 | 0.000 | 0.000 | 0.000 | 0.000 | 0.000 | 1.0000 |
| | 4 | 9 | 0.00 | 0.00 | 0.000 | 0.000 | 0.000 | 0.000 | 0.000 | |
| 118 (Day of challenge) | 1 | 16 | 0.00 | 0.00 | 0.000 | 0.000 | 0.000 | 0.000 | 0.000 | |
| | 2 | 16 | 0.00 | 0.00 | 0.000 | 0.000 | 0.000 | 0.000 | 0.000 | 1.0000 |
| | 3 | 16 | 0.00 | 0.00 | 0.000 | 0.000 | 0.000 | 0.000 | 0.000 | 1.0000 |
| | 4 | 5 | 0.00 | 0.00 | 0.000 | 0.000 | 0.000 | 0.000 | 0.000 | |
| 125 | 1 | 16 | 3.00 | 5.38 | 4.495 | 4.130 | 4.880 | 0.765 | 4.419 | |
| | 2 | 16 | 0.00 | 6.46 | 0.000 | 0.000 | 3.000 | 3.000 | 1.293 | 0.0001 |
| | 3 | 16 | 0.00 | 3.00 | 0.000 | 0.000 | 3.000 | 3.000 | 1.500 | 0.750 <0.0001 |
| | 4 | 5 | 0.00 | 0.00 | 0.000 | 0.000 | 0.000 | 0.000 | 0.000 | |

TABLE 6.16-continued

Summary of Group Gilt qPCR Results ($\log_{10}$ GE/mL) From D 7 to D 132

| Study Day | Group * | N | Min. | Max. | Median | 95% CI | | QRange | Mean | P |
|---|---|---|---|---|---|---|---|---|---|---|
| 132 | 1 | 16 | 0.00 | 4.47 | 3.000 | 0.000 | 3.000 | 3.000 | 1.967 | |
| | 2 | 16 | 0.00 | 3.00 | 0.000 | 0.000 | 0.000 | 0.000 | 0.563 | 0.0230 |
| | 3 | 16 | 0.00 | 3.00 | 0.000 | 0.000 | 3.000 | 3.000 | 0.938 | 0.1144 |
| | 4 | 5 | 0.00 | 0.00 | 0.000 | 0.000 | 0.000 | 0.000 | 0.000 | |

* Group 1 = Challenge control group; Group 2 = Low titer PRRS 94881 MLV group; Group 3 = High titer PRRS 94881 MLV group; Group 4 = Negative control group

TABLE 6.17

Summary of Group Gilt qPCR Results ($\log_{10}$ GE/mL) From DOF 0 to DOF +20

| Study Day | Group * | N | Min. | Max. | Median | 95% CI | | QRange | Mean | P |
|---|---|---|---|---|---|---|---|---|---|---|
| DOF +0 | 1 | 16 | 0.00 | 3.00 | 3.000 | 3.000 | 3.000 | 0.000 | 2.813 | |
| | 2 | 16 | 0.00 | 3.00 | 0.000 | 0.000 | 3.000 | 1.500 | 0.750 | 0.0002 |
| | 3 | 16 | 0.00 | 3.00 | 0.000 | 0.000 | 0.000 | 0.000 | 0.188 | <0.0001 |
| | 4 | 5 | 0.00 | 0.00 | 0.000 | 0.000 | 0.000 | 0.000 | 0.000 | |
| DOF +7 | 1 | 16 | 0.00 | 3.00 | 0.000 | 0.000 | 3.000 | 3.000 | 0.938 | |
| | 2 | 16 | 0.00 | 5.55 | 0.000 | 0.000 | 0.000 | 0.000 | 0.534 | 0.3944 |
| | 3 | 16 | 0.00 | 3.00 | 0.000 | 0.000 | 0.000 | 0.000 | 0.188 | 0.1719 |
| | 4 | 5 | 0.00 | 3.00 | 0.000 | 0.000 | 3.000 | 0.000 | 0.600 | |
| DOF +13 | 1 | 15 | 0.00 | 3.00 | 0.000 | 0.000 | 3.000 | 3.000 | 1.400 | |
| | 2 | 16 | 0.00 | 0.00 | 0.000 | 0.000 | 0.000 | 0.000 | 0.000 | 0.0024 |
| | 3 | 16 | 0.00 | 3.00 | 0.000 | 0.000 | 0.000 | 0.000 | 0.188 | 0.0155 |
| | 4 | 5 | 0.00 | 0.00 | 0.000 | 0.000 | 0.000 | 0.000 | 0.000 | |
| DOF +20 | 1 | 16 | 0.00 | 3.00 | 0.000 | 0.000 | 0.000 | 0.000 | 0.563 | |
| | 2 | 16 | 0.00 | 6.45 | 0.000 | 0.000 | 0.000 | 0.000 | 0.903 | 0.7924 |
| | 3 | 16 | 0.00 | 0.00 | 0.000 | 0.000 | 0.000 | 0.000 | 0.000 | 0.2258 |
| | 4 | 5 | 0.00 | 0.00 | 0.000 | 0.000 | 0.000 | 0.000 | 0.000 | |

* Group 1 = Challenge control group; Group 2 = Low titer PRRS 94881 MLV group; Group 3 = High titer PRRS 94881 MLV group; Group 4 = Negative control group Gilt Clinical Observations Scores Post-Challenge From D116 to DOF+20, 25%, 25%, 38% and 60% of challenge control, low titer, high titer and negative control gilts, respectively, exhibited clinical disease for at least one day from D116 to DOF+20. No significant differences were detected between vaccine groups and the challenge control group for the frequency of gilts positive for clinical disease from D116 to DOF+20 (P≤0.7043).

A summary of group percentage of gilts positive for clinical disease (a clinical observation score of >0) for at least one day from D116 to DOF+20 is shown below in Table 6.18.

TABLE 6.18

Summary of group percentage of gilts positive for clinical disease (a clinical observation score of >0) for at least one day from D 116 to DOF +20

| Study Days | Group* | N | % | 95% CI | | Total | P |
|---|---|---|---|---|---|---|---|
| 116- | 1 | 4 | 25 | 7.3 | 52.4 | 16 | |
| DOF +20 | 2 | 4 | 25 | 7.3 | 52.4 | 16 | 1.0000 |
| | 3 | 6 | 38 | 15.2 | 64.6 | 16 | 0.7043 |
| | 4 | 3 | 60 | 14.7 | 94.7 | 5 | |

*Group 1 = Challenge control group; Group 2 = Low titer PRRS 94881 MLV group; Group 3 = High titer PRRS 94881 MLV group; Group 4 = Negative control group Gilt PRRS ELISA Serology All gilts were PRRS seronegative on D0 and D7. All challenge control and negative control gilts remained PRRS seronegative up to and including the day of challenge (D118); while the negative control group remained PRRS seronegative for the remainder of the study (DOF+20).

On D14, 18% and 21% of low titer and high titer gilts, respectively, were PRRS seropositive. The high titer group had a significantly higher percentage of PRRS seropositive gilts on D14 (P=0.0232), while no difference was detected for the low titer group in comparison with the challenge control group (p=0.0515). These percentages reached group highs of 65% and 60% for the low titer and high titer groups, respectively on D56 (P<0.0001). On the day of the challenge (D118), 56% and 50% of low titer and high titer gilts were PRRS seropositive (P≤0.0024). On D125, 6%, 88%, and 100% of challenge control, low titer and high titer gilts, respectively, were PRRS seropositive; and the difference between the vaccine groups and the challenge control group were significant (P<0.0001). After D125, all remaining challenge control, low titer and high titer gilts were PRRS seropositive for the remainder of the study (no test conducted).

A summary of group PRRS ELISA serology results from D14 to DOF+20 is shown below in Tables 6.19 and 6.20.

TABLE 6.19

Summary of Group Gilt PRRS ELISA Serology Results from D 14 to Day 132

| Study Day | Group* | N | % | 95% CI | | Total | P |
|---|---|---|---|---|---|---|---|
| 7 | 1 | 0 | 0 | 0.0 | 12.3 | 28 | |
| | 2 | 0 | 0 | 0.0 | 12.3 | 28 | n.a. |
| | 3 | 0 | 0 | 0.0 | 12.3 | 28 | n.a. |
| | 4 | 0 | 0 | 0.0 | 30.8 | 10 | |
| 14 | 1 | 0 | 0 | 0.0 | 12.3 | 28 | |
| | 2 | 5 | 18 | 6.1 | 36.9 | 28 | 0.0515 |
| | 3 | 6 | 21 | 8.3 | 41.0 | 28 | 0.0232 |
| | 4 | 0 | 0 | 0.0 | 30.8 | 10 | |
| 21 | 1 | 0 | 0 | 0.0 | 12.3 | 28 | |
| | 2 | 13 | 46 | 27.5 | 66.1 | 28 | <0.0001 |
| | 3 | 11 | 39 | 21.5 | 59.4 | 28 | 0.0003 |
| | 4 | 0 | 0 | 0.0 | 30.8 | 10 | |

TABLE 6.19-continued

Summary of Group Gilt PRRS ELISA Serology Results from D 14 to Day 132

| Study Day | Group* | N | % | 95% CI | | Total | P |
|---|---|---|---|---|---|---|---|
| 56 | 1 | 0 | 0 | 0.0 | 14.8 | 23 | |
| | 2 | 17 | 65 | 44.3 | 82.8 | 26 | <0.0001 |
| | 3 | 15 | 60 | 38.7 | 78.9 | 25 | <0.0001 |
| | 4 | 0 | 0 | 0.0 | 33.6 | 9 | |
| 84 | 1 | 0 | 0 | 0.0 | 14.8 | 23 | |
| | 2 | 15 | 58 | 36.9 | 76.6 | 26 | <0.0001 |
| | 3 | 14 | 56 | 34.9 | 75.6 | 25 | <0.0001 |
| | 4 | 0 | 0 | 0.0 | 33.6 | 9 | |
| 118 | 1 | 0 | 0 | 0.0 | 20.6 | 16 | |
| | 2 | 9 | 56 | 29.9 | 80.2 | 16 | 0.0008 |
| | 3 | 8 | 50 | 24.7 | 75.3 | 16 | 0.0024 |
| | 4 | 0 | 0 | 0.0 | 52.2 | 5 | |
| 125 | 1 | 1 | 6 | 0.2 | 30.2 | 16 | |
| | 2 | 14 | 88 | 61.7 | 98.4 | 16 | <0.0001 |
| | 3 | 16 | 100 | 79.4 | 100.0 | 16 | <0.0001 |
| | 4 | 0 | 0 | 0.0 | 52.2 | 5 | |
| 132 | 1 | 16 | 100 | 79.4 | 100.0 | 16 | |
| | 2 | 16 | 100 | 79.4 | 100.0 | 16 | n.a. |
| | 3 | 16 | 100 | 79.4 | 100.0 | 16 | n.a. |
| | 4 | 0 | 0 | 0.0 | 52.2 | 5 | |

*Group 1 = Challenge control group; Group 2 = Low titer PRRS 94881 MLV group; Group 3 = High titer PRRS 94881 MLV group; Group 4 = Negative control group.
n.a. = not applicable, no test conducted

TABLE 6.20

Summary of Group Gilt PRRS ELISA Serology Results from DOF 0 to DOF +20

| Study Day | Group* | N | % | 95% CI | | Total | P |
|---|---|---|---|---|---|---|---|
| DOF +0 | 1 | 16 | 100 | 79.4 | 100.0 | 16 | |
| | 2 | 16 | 100 | 79.4 | 100.0 | 16 | n.a. |
| | 3 | 16 | 100 | 79.4 | 100.0 | 16 | n.a. |
| | 4 | 0 | 0 | 0.0 | 52.2 | 5 | |
| DOF +7 | 1 | 15 | 100 | 78.2 | 100.0 | 15 | |
| | 2 | 16 | 100 | 79.4 | 100.0 | 16 | n.a. |
| | 3 | 16 | 100 | 79.4 | 100.0 | 16 | n.a. |
| | 4 | 0 | 0 | 0.0 | 52.2 | 5 | |
| DOF +13 | 1 | 16 | 100 | 79.4 | 100.0 | 16 | |
| | 2 | 16 | 100 | 79.4 | 100.0 | 16 | n.a. |
| | 3 | 16 | 100 | 79.4 | 100.0 | 16 | n.a. |
| | 4 | 0 | 0 | 0.0 | 52.2 | 5 | |
| DOF +20 | 1 | 16 | 100 | 79.4 | 100.0 | 16 | |
| | 2 | 16 | 100 | 79.4 | 100.0 | 16 | n.a. |
| | 3 | 15 | 100 | 78.2 | 100.0 | 15 | n.a. |
| | 4 | 0 | 0 | 0.0 | 52.2 | 5 | |

*Group 1 = Challenge control group; Group 2 = Low titer PRRS 94881 MLV group; Group 3 = High titer PRRS 94881 MLV group; Group 4 = Negative control group.
**No test conducted on sample from Gilt No. 106.
n.a. = not applicable, no test conducted Gilt Assessments Post-Vaccination No abnormal assessments from D1 to 21 were detected in any groups and no test was conducted. From D1 to D113, 4%, 4%, 0% and 10% of challenge control, low titer, high titer and negative control gilts, respectively, exhibited an abnormal assessment for at least one day from D1 to D113. No significant differences were detected between vaccine groups and the challenge control group for abnormal assessments from D1 to D113 (P=1.0000).

Individually, No. 109 (challenge control group) exhibited lameness of the right rear leg on D85, No. 12 (low titer group) exhibited a swelling in the left neck region from D78 to D89, and No. 21 (negative control group) exhibited lameness from D81 to D83.

A summary of group percentage of gilts that exhibited an abnormal assessment for at least one day from D1 to D21 and from D1 to D113 is shown below in Table 6.21.

TABLE 6.21

Summary of Group Abnormal Assessments for At Least One Day from D 1 to D 113

| Study Days | Group* | N | % | 95% CI | | Total | P |
|---|---|---|---|---|---|---|---|
| 1-21 | 1-4 | | | no 'positive' findings | | | |
| 1-113 | 1 | 1 | 4 | 0.1 | 18.3 | 28 | |
| | 2 | 1 | 4 | 0.1 | 18.3 | 28 | 1.0000 |
| | 3 | 0 | 0 | 0.0 | 12.3 | 28 | 1.0000 |
| | 4 | 1 | 10 | 0.3 | 44.5 | 10 | |

*Group 1 = Challenge control group; Group 2 = Low titer PRRS 94881 MLV group; Group 3 = High titer PRRS 94881 MLV group; Group 4 = Negative control group Piglet Clinical Observations Scores Mean percentages of piglets per litter positive for clinical disease (a clinical observation score of >0) for at least one day from DOF+1 to DOF+20 were 91.6%, 32.5%, 33.4% and 3.2% for the challenge control, low titer, high titer, and negative control groups, respectively. Low and high titer groups had significantly lower percentages of piglets per litter positive for clinical disease for at least one day from DOF+1 to DOF+20 compared with the challenge control group (p≤0.0001).

A summary of group percentage of piglets per litter that were positive for clinical disease (a clinical observation score of >0) for at least one day from DOF+1 to DOF+20 is shown below in Table 6.22.

TABLE 6.22

Summary of group percentage of piglets per litter positive for clinical disease (a clinical observation score of >0) for at least one day from DOF +1 to DOF +20

| Study Days | Group* | N | Min. | Max. | Median | Mean | 95% CI | | SD | P |
|---|---|---|---|---|---|---|---|---|---|---|
| DOF +1 to DOF +20 | 1 | 15 | 56 | 100 | 100.0 | 91.6 | 82.9 | 100.4 | 15.78 | |
| | 2 | 16 | 0 | 100 | 25.0 | 32.5 | 15.6 | 49.4 | 31.64 | <0.0001 |
| | 3 | 16 | 0 | 100 | 25.0 | 33.4 | 19.0 | 47.9 | 27.16 | <0.0001 |
| | 4 | 5 | 0 | 9 | 0.0 | 3.2 | -2.3 | 8.8 | 4.50 | |

* Group 1 = Challenge control group; Group 2 = Low titer PRRS 94881 MLV group; Group 3 = High titer PRRS 94881 MLV group; Group 4 = Negative control group Piglet Serum/Body Fluids qPCR Results A mean of 86.3%, 58.1%, 55.0% and 0% of piglets per litter for the challenge control, low titer, high titer and negative control groups, respectively, were qPCR positive for PRRSv RNA on DOF 0. The low titer and higher groups had statistically lower percentages of piglets per litter qPCR positive for PRRSv RNA compared with the challenge control group on DOF 0 ($P \leq 0.0381$). On DOF+7, again the low titer and high titer groups had significantly lower percentages of piglets per litter qPCR positive for PRRSv RNA compared with the challenge control group ($P \leq 0.0293$). On DOF+13, only the low titer group had a significantly lower percentage of piglets per litter qPCR positive ($P=0.0216$); while no significant differences were detected for the high titer group and the challenge control for the percentage of piglets per litter qPCR positive ($P=0.0860$). No significant differences were detected between groups on DOF+20 ($P \leq 0.0614$).

A summary of group percentage of serum/body fluid qPCR PRRSv positive piglets per gilt is shown below in Table 6.23.

TABLE 6.23

A Summary of Group Percentage of Serum/Body Fluid qPCR PRRSv Positive Piglets per Gilt

| Study Day | Group* | N | Min. | Max. | Median | Mean | 95% CI | | SD | P |
|---|---|---|---|---|---|---|---|---|---|---|
| DOF +0 | 1 | 16 | 50 | 100 | 96.4 | 86.3 | 76.8 | 95.8 | 17.87 | |
| | 2 | 16 | 0 | 100 | 68.3 | 58.1 | 37.3 | 78.9 | 39.07 | 0.0381 |
| | 3 | 16 | 0 | 100 | 60.0 | 55.0 | 37.0 | 73.0 | 33.77 | 0.0018 |
| | 4 | 5 | 0 | 0 | 0.0 | 0.0 | 0.0 | 0.0 | 0.00 | |
| DOF +7 | 1 | 12 | 100 | 100 | 100.0 | 100.0 | 100.0 | 100.0 | 0.00 | |
| | 2 | 16 | 10 | 100 | 100.0 | 76.6 | 57.1 | 96.0 | 36.51 | 0.0293 |
| | 3 | 16 | 0 | 100 | 100.0 | 78.6 | 60.6 | 96.6 | 33.83 | 0.0175 |
| | 4 | 5 | 0 | 0 | 0.0 | 0.0 | 0.0 | 0.0 | 0.00 | |
| DOF +13 | 1 | 11 | 100 | 100 | 100.0 | 100.0 | 100.0 | 100.0 | 0.00 | |
| | 2 | 16 | 0 | 100 | 100.0 | 75.4 | 55.0 | 95.8 | 38.31 | 0.0216 |
| | 3 | 16 | 0 | 100 | 100.0 | 84.0 | 68.2 | 99.9 | 29.75 | 0.0860 |
| | 4 | 5 | 0 | 0 | 0.0 | 0.0 | 0.0 | 0.0 | 0.00 | |
| DOF +20 | 1 | 11 | 0 | 100 | 100.0 | 90.9 | 70.7 | 111.2 | 30.15 | |
| | 2 | 16 | 0 | 100 | 93.8 | 75.3 | 55.6 | 95.0 | 36.97 | 0.0614 |
| | 3 | 16 | 0 | 100 | 100.0 | 81.6 | 65.0 | 98.1 | 31.06 | 0.1832 |
| | 4 | 5 | 0 | 0 | 0.0 | 0.0 | 0.0 | 0.0 | 0.00 | |

*Group 1 = Challenge control group; Group 2 = Low titer PRRS 94881 MLV group; Group 3 = High titer PRRS 94881 MLV group; Group 4 = Negative control group The high titer group had a significantly lower median qPCR result compared with the challenge control group on DOF 0 ($P=0.0030$); while no difference was detected between the low titer group and the challenge control group ($P=0.0620$). On DOF+7, DOF+13 and DOF+20, both vaccine groups had significantly lower median qPCR values compared with the challenge control group ($p \leq 0.0122$).

A summary of group piglet serum/body fluid qPCR GE/mL results per gilt is shown below in Table 6.24.

TABLE 6.24

Summary of Group Piglet Serum/Body Fluid qPCR results ($\log_{10}$ GE/mL) per Gilt (P values for differences between groups based on median qPCR values)

| Study Day | Group * | N | Min. | Max. | Median | 95% CI | | QRange | Mean | P |
|---|---|---|---|---|---|---|---|---|---|---|
| DOF +0 | 1 | 180 | 0.00 | 8.69 | 6.400 | 6.080 | 6.790 | 3.195 | 5.556 | |
| | 2 | 176 | 0.00 | 8.47 | 3.000 | 3.000 | 4.420 | 6.945 | 3.560 | 0.0620 |
| | 3 | 183 | 0.00 | 8.76 | 3.000 | 0.000 | 3.000 | 6.580 | 3.049 | 0.0030 |
| | 4 | 58 | 0.00 | 0.00 | 0.000 | 0.000 | 0.000 | 0.000 | 0.000 | |
| DOF +7 | 1 | 58 | 4.47 | 8.76 | 6.950 | 6.610 | 7.370 | 1.300 | 6.914 | |
| | 2 | 103 | 0.00 | 8.12 | 3.000 | 3.000 | 4.930 | 5.640 | 3.337 | <0.0001 |
| | 3 | 115 | 0.00 | 6.91 | 4.280 | 3.000 | 4.630 | 2.120 | 3.642 | <0.0001 |
| | 4 | 54 | 0.00 | 0.00 | 0.000 | 0.000 | 0.000 | 0.000 | 0.000 | |
| DOF +13 | 1 | 52 | 4.19 | 8.62 | 6.835 | 6.430 | 6.970 | 0.995 | 6.549 | |
| | 2 | 100 | 0.00 | 8.22 | 3.000 | 3.000 | 3.000 | 4.530 | 2.678 | <0.0001 |
| | 3 | 113 | 0.00 | 6.54 | 3.000 | 3.000 | 3.000 | 1.580 | 3.413 | <0.0001 |
| | 4 | 54 | 0.00 | 0.00 | 0.000 | 0.000 | 0.000 | 0.000 | 0.000 | |
| DOF +20 | 1 | 46 | 0.00 | 6.94 | 5.595 | 5.270 | 6.520 | 1.770 | 5.554 | |
| | 2 | 98 | 0.00 | 6.59 | 3.000 | 3.000 | 3.000 | 4.000 | 2.502 | 0.0122 |
| | 3 | 111 | 0.00 | 6.28 | 3.000 | 3.000 | 3.000 | 1.160 | 3.218 | 0.0005 |
| | 4 | 54 | 0.00 | 0.00 | 0.000 | 0.000 | 0.000 | 0.000 | 0.000 | |

* Group 1 = Challenge control group; Group 2 = Low titer PRRS 94881 MLV group; Group 3 = High titer PRRS 94881 MLV group; Group 4 = Negative control group Piglet ADWG No differences were detected between groups for LS Mean body weights on DOF 0 (P≥0.2972). Both vaccine groups had higher least square mean body weights compared with the challenge control group on DOF+20 (P<0.0028), with or without DOF 0 body weights factored as a covariate in the analyses.

Mean ADWG from DOF 0 to DOF+20 were 0.1 kg/day, 0.2 kg/day, 0.2 kg/day and 0.2 kg/day for the challenge control, low titer, high titer, and negative control groups, respectively. Both vaccine groups had significantly higher ADWG compared with the challenge control group (P<0.0028), with or without DOF 0 body weights factored as a covariate in the analyses.

A summary of group DOF 0 and DOF+20 piglet body weights and DOF 0 to DOF+20 ADWG (kg/day) is shown below in Tables 6.25 and 6.26.

TABLE 6.25

Summary of Group DOF 0 and DOF +20 Piglet Body Weights and DOF 0 to DOF +20 ADWG (kg/day)

| Study Day(s) | Group* | N | Min. | Max. | Median | Mean | 95% CI | | SD |
|---|---|---|---|---|---|---|---|---|---|
| DOF +0 | 1 | 47 | 0.9 | 2.0 | 1.40 | 1.34 | 1.274 | 1.411 | 0.234 |
| Body | 2 | 99 | 0.9 | 2.1 | 1.40 | 1.43 | 1.388 | 1.479 | 0.227 |
| Weights | 3 | 111 | 0.9 | 2.0 | 1.40 | 1.40 | 1.360 | 1.448 | 0.234 |
|  | 4 | 54 | 0.9 | 1.9 | 1.40 | 1.39 | 1.335 | 1.454 | 0.218 |
| DOF +20 | 1 | 47 | 1.5 | 6.1 | 3.70 | 3.80 | 3.462 | 4.146 | 1.164 |
| Body | 2 | 99 | 2.4 | 8.3 | 5.50 | 5.42 | 5.168 | 5.673 | 1.266 |
| Weights | 3 | 111 | 2.1 | 8.2 | 5.30 | 5.19 | 5.000 | 5.388 | 1.032 |
|  | 4 | 54 | 2.4 | 6.9 | 5.20 | 5.26 | 5.008 | 5.511 | 0.922 |
| ADWG | 1 | 47 | 0.015 | 0.235 | 0.1150 | 0.1231 | 0.10649 | 0.13968 | 0.05653 |
| (DOF +0 to | 2 | 99 | 0.065 | 0.340 | 0.2000 | 0.1993 | 0.18770 | 0.21099 | 0.05837 |
| DOF +20) | 3 | 111 | 0.055 | 0.330 | 0.1950 | 0.1895 | 0.18078 | 0.19823 | 0.04638 |
|  | 4 | 54 | 0.060 | 0.260 | 0.1925 | 0.1932 | 0.18305 | 0.20343 | 0.03733 |

*Group 1 = Challenge control group; Group 2 = Low titer PRRS 94881 MLV group; Group 3 = High titer PRRS 94881 MLV group; Group 4 = Negative control group

TABLE 6.26

Summary of Group LS Mean Body Weights and DOF 0 to DOF+20 ADWG (kg/day) - Test Results (P values) on Differences between Groups

| Study Day(s) | Group* | LS Mean | 95% confidence interval | | P |
|---|---|---|---|---|---|
| DOF+0 | 1 | 1.32 | 1.169 | 1.477 |  |
| Body | 2 | 1.42 | 1.318 | 1.522 |  |
| Weights | 3 | 1.41 | 1.317 | 1.497 |  |
|  | Diff. 1-2 | −0.10 | −0.281 | 0.088 | 0.2972 |
|  | Diff. 1-3 | −0.08 | −0.262 | 0.094 | 0.3467 |
| DOF+20 | 1 | 3.82 | 3.072 | 4.567 |  |
| Body | 2 | 5.32 | 4.827 | 5.819 |  |
| Weights | 3 | 5.35 | 4.910 | 5.785 |  |
|  | Diff. 1-2 | −1.50 | −2.401 | −0.606 | 0.0016 |
|  | Diff. 1-3 | −1.53 | −2.394 | −0.662 | 0.0010 |
| DOF+20** | 1 | 4.01 | 3.341 | 4.685 |  |
| Body | 2 | 5.28 | 4.843 | 5.727 |  |
| Weights | 3 | 5.34 | 4.950 | 5.728 |  |
|  | Diff. 1-2 | −1.27 | −2.078 | −0.466 | 0.0028 |
|  | Diff. 1-3 | −1.33 | −2.103 | −0.550 | 0.0013 |
| ADWG | 1 | 0.125 | 0.0903 | 0.1594 |  |
| (DOF+0 | 2 | 0.195 | 0.1722 | 0.2181 |  |
| to | 3 | 0.197 | 0.1768 | 0.2172 |  |
| DOF+20) | Diff. 1-2 | −0.070 | −0.1118 | −0.0289 | 0.0014 |
|  | Diff. 1-3 | −0.072 | −0.1122 | −0.0322 | 0.0008 |
| ADWG | 1 | 0.130 | 0.0969 | 0.1640 |  |
| (DOF+0 | 2 | 0.194 | 0.1720 | 0.2161 |  |
| to | 3 | 0.197 | 0.1773 | 0.2162 |  |
| DOF+20**) | Diff. 1-2 | −0.064 | −0.1039 | −0.0233 | 0.0028 |
|  | Diff. 1-3 | −0.066 | −0.1052 | −0.0275 | 0.0013 |

*Group 1 = Challenge control group; Group 2 = Low titer PRRS 94881 MLV group; Group 3 = High titer PRRS 94881 MLV group; Group 4 = Negative control group.
**weight at DOF+0 was used as a covariate Piglet Necropsy Observations and Diagnoses Feti listed as stillborns, mummies or crushed at farrowing were confirmed at necropsy as correctly categorized with the exception of 8 feti. Two-challenge control feti were listed as stillborns (40-S1, 66-S1), but necropsy results revealed inflated lungs indicating they were alive at the time of birth. Two-challenge control feti were listed as crushed (1-C1, 79-C2), but necropsy results revealed non-inflated lungs for both feti, indicating they did not breath. One-low titer fetus was listed as a stillborn (85-S2), but necropsy results revealed inflated lungs indicating the piglet was alive at the time of birth. Three-high titer piglets were listed as crushed (36-C1, 36-C2, 65-C1), but necropsy results revealed non-inflated lungs for both feti, indicating they did not breath. Due to the low number of feti incorrectly listed at time of farrowing, no changes were made to gilt performance analyses.

One-challenge control piglet 102-428 died subsequently to blood collection, which was confirmed by necropsy.

Piglet Lung qPCR Results

Of the feti and dead piglets necropsied, the mean lung qPCR results were 4.68, 4.09, 3.55 and 0.0 $\log_{10}$ GE/mL for the challenge control, low titer, high titer, and negative control groups, respectively. No statistical analyses were conducted on these data.

A summary of group lung PRRSv qPCR results ($\log_{10}$ GE/mL) is shown below in Table 6.27.

TABLE 6.27

Summary of Group Piglet Lung PRRSv qPCR Results ($\log_{10}$ GE/mL)

| Group | N | Min. | Max. | Median | 95% CI | | QRange | Mean |
|---|---|---|---|---|---|---|---|---|
| 1 | 141 | 0.00 | 7.95 | 5.140 | 4.810 | 5.390 | 2.990 | 4.676 |
| 2 | 79 | 0.00 | 7.45 | 4.780 | 3.000 | 5.260 | 2.620 | 4.092 |
| 3 | 75 | 0.00 | 6.84 | 4.220 | 3.000 | 5.100 | 5.620 | 3.547 |
| 4 | 4 | 0.00 | 0.00 | 0.000 | 0.000 | 0.000 | 0.000 | 0.000 |

*Group 1 = Challenge control group; Group 2 = Low titer PRRS 94881 MLV group; Group 3 = High titer PRRS 94881 MLV group; Group 4 = Negative control group Discussion/Conclusion To achieve the study objective, four groups of PRRS susceptible gilts were included in the study design on D0: a challenge control group that received control product (Group 1); a low titer vaccine group that received $1 \times 10^{2.43}$ TCID$_{50}$ of PRRS 94881 MLV (IVP No. 1, Group 2); a high titer vaccine group that received $1 \times 10^{3.90}$ TCID$_{50}$ of PRRS 94881 MLV (IVP No. 2, Group 3); and a negative control group (Group 4) that also received control product. Each treatment was administered as a 2.0 mL dose IM at approximately 28 days prior to breeding (D0).

To determine the minimum immunizing dose of PRRS 94881 MLV, the two vaccine titer groups and the challenge control group were challenged on D118 (approximately 90 days of gestation) with a heterologous European isolate of PRRSv (isolate 190136) and evaluated post-challenge for percentage and number of live piglets per litter at birth (day of farrowing, DOF) and percentage and number of live piglets per litter at 21 days of age (DOF+21).

Validation of the Study (Negative Control Group 4)

To ensure that source gilts were free of PRRSv and that no extraneous PRRSv exposure or cross-contamination among treatment and control groups occurred during the study, a negative control group (Group 4) was included in the study design. Negative control gilts were negative for PRRS antibodies throughout the study. In addition, this group of gilts and their progeny were also negative for PRRSv viremia (qPCR) at all tested time points with exception of No. 108 on DOF+7. Gilt No. 108 was "positive" on DOF+7, while qPCR negative at all other time points and her piglets were negative for PRRSv RNA as well. This result was considered an error due to sample contamination and not due to PRRSv infection. These results support that the negative control group remained free of PRRS infection during the study and validate the results of this trial.

Validation of the PRRSv Reproductive Challenge Model (Challenge Control Group 1)

A challenge model involving a virulent EU-derived strain of PRRSv that induces sufficient and reproducible PRRS clinical disease is necessary to adequately evaluate PRRS vaccine efficacy in a laboratory setting. Following inoculation with European PRRS isolate 190136 ($1 \times 10^{6.30}$ TCID$_{50}$/6 mL), the challenge control group exhibited only 54.4% live piglets per litter at birth (93.0% for the negative control group), 17.5% and 28.1% per litter of stillborns and mummies, respectively (7.0% and 0.0%, respectively, for the negative control group), 91.6% piglets per litter exhibited clinical disease for at least one day from DOF+1 to DOF+20 (3.2% piglets per litter for the negative control group), a mean of 2.9 live piglets per litter at 20 days of age (a mean of 10.8 for the negative control group), and 86.3% of piglets per litter viremic at birth (0% for the negative control group). These results highlight that severe PRRS-specific clinical disease was induced in the unvaccinated, challenge control group of gilts and their progeny, thus validating this challenge model as an adequate clinical laboratory tool to evaluate PRRS vaccine efficacy and more specifically, the MID of PRRS 94881 MLV in gilts.

Determination of the Minimum Immunizing Dose of PRRS 94881 MLV in Gilts (Low and High Titer Vaccine Doses; Groups 2-3)

Determination of the MID of PRRS 94881 MLV in gilts was based upon the vaccine group that received the lowest titer of vaccine that resulted in higher percentages or number of live piglets per litter at birth and higher percentages of number of live piglets per litter at 20 days of age post-challenge compared with the challenge control group.

Live piglets per litter (either percent or number) at farrowing was selected as one of two key criteria for determining the MID of PRRS 94881 MLV. The first key criterion was based upon the fact that PRRSv infection in pregnant gilts and sows typically results in stillborns and mummies, with low numbers of live piglets at farrowing. Live piglets per litter at birth were defined as the summation of healthy live, weak live and crushed-mortality piglets at farrowing. Piglets listed as crushed or mortality were included in the “live” category because necropsy findings confirmed these piglets were alive at birth and died shortly thereafter due to trauma. Both the low titer and high titer groups exhibited significantly higher percentages of live piglets per litter at farrowing compared with the challenge control ($P\leq0.0455$), thus this criterion for vaccine efficacy was met. Although no significant differences were detected between the low and high titer vaccine groups and the challenge control group with respect to the mean number of live piglets per litter at farrowing ($P\geq0.1857$), the low titer and high titer groups did exhibit considerably higher mean number of live piglets per litter at farrowing (mean 8.3 and 8.6 piglets per litter, respectively) in relationship to the challenge control group (mean 6.5 piglets per litter) thus, providing further evidence and support that a beneficial vaccine treatment effect was observed in these animals post-challenge.

Live piglets per litter (either percent or number) at 20 days of age was the second criterion for determining the MID of PRRS 94881 MLV because gilt PRRS immunity will influence in utero infection of piglets and shedding of virus from gilts to live piglets. Piglets infected with PRRS in utero and born alive or infected with virulent PRRS post-farrowing via shedding from the gilt usually die before weaning secondary to PRRS. In this study, the challenge control, low titer, high titer and negative control group exhibited 43.6%, 73.8%, 83.8% and 100% live piglets per litter, respectively, at 20 days of age ($P\leq0.0203$). Likewise, the challenge control, low titer, high titer and negative control groups had a mean number of 2.9, 6.2, 6.9 and 10.8 piglets per litter, respectively, at 20 days of age ($P\leq0.0063$). Both vaccine groups had significantly higher percentage and number of live piglets at weaning ($P\leq0.0203$), thus this criterion of the study objective was met.

Further analyses of farrowing data revealed more information that supports vaccine efficacy following PRRSv challenge, especially with respect to the high titer group. The high titer group exhibited statistically a higher percentage and a higher mean number of healthy piglets at birth ($P\leq0.0211$); while exhibiting significantly lower percentages and mean numbers of weak and mummified feti ($P\leq0.0090$), in comparison with the challenge control group. These data support that the high vaccine dose induced protective immunity against a virulent and heterologous PRRSv challenge strain. The low titer group also exhibited vaccine efficacy at farrowing, as evident by a higher percentage of healthy live piglets per litter ($P=0.0138$) and significantly lower percentages and mean numbers of mummified feti ($P\leq0.0190$). Conversely, no differences were detected between groups for the percentage or number of stillborn feti or crushed/mortalities at farrowing ($P\geq0.1681$).

Seven days after challenge (D125), the low titer and high titer groups had significantly lower percentages of gilts positive for PRRSv RNA by qPCR testing, as well as significantly lower viral load for both groups, in comparison to the challenge control group ($P\leq0.0001$). These data further support that both vaccine dose levels induced adequate immunity in gilts to significantly lower viral replication following challenge. Likewise, the low and high titer groups had significantly lower percentages of gilts qPCR positive on DOF 0 and DOF+13, as well as lower viral load for both groups on these study days ($P\leq0.0155$). The low titer group had significantly lower percentage of gilts qPCR positive and lower viral load on D132 ($P\leq0.0290$); while no statistical differences were detected between the high titer and the challenge control group for the same set of parameters ($P\geq0.1144$). No statistical differences were detected between vaccine groups and challenge control group for percentage of gilts qPCR positive or viral load on DOF+7 and DOF+20 (P≥0.1719).

Typically PRRSv does not induce clinical disease in gilts and sows, other than abortion. In this study 25%, 25%, 38% and 60% of challenge control, low titer, high titer and negative control gilts, respectively, exhibited clinical disease (received a clinical observation score >0) for at least one day post-challenge. No significant differences were detected between the vaccine groups and the challenge control group with respect to percentage of gilts with clinical disease for at least one day from D116 to DOF+20 (P≥0.7043). Gilts that exhibited some form of clinical disease did so at peri-parturition and not immediately after challenge. The high percentage of negative control gilts (60%) that exhibited clinical disease and the fact that clinical disease was noted primarily around the time of farrowing for all groups in this study supports that clinical disease was not attributed to PRRS disease but rather to physiological changes associated with parturition.

All gilts in the study were PRRS ELISA seronegative on D0 thus providing confirmation of the inclusion criteria for the test animals entering the study. Likewise, all gilts were PRRS ELISA seronegative on D7. Vaccinated gilts began to exhibit PRRS ELISA seropositive results on D14 and the low and high dose groups exhibited their highest rate of seroconversion of 65% and 60%, respectively, on D56 (P<0.0001). Conversely, the challenge control group remained PRRS ELISA seronegative until 7 days post-challenge (D125). From D132 to study conclusion, all low titer, high titer and challenge control gilts were PRRS ELISA seropositive. The percentage of viremia positive gilts post-vaccination peaked on D7 for both vaccine groups as evidenced by 50% and 36% for the low and high titer groups, respectively (P≤0.0007). Viremia quickly dropped to 4% (1 of 28, No. 64) and 0% (0 of 28) for the low titer and high titer groups, respectively on D14 (P=1.0000 or no test conducted). Viremia remained at 4% for low titer (1 of 28, No. 56) and high titer (1 of 28, No. 91) groups on D21. On D56, one of 26 (4%, No. 89) low titer gilts and one of 25 (4%, No. 66) high titer gilts were positive for viremia. All gilts were negative for viremia on D84 and D118.

No significant differences were detected between both vaccine titer groups and the challenge control group with respect to percentage of gilts per group post-vaccination with an abnormal clinical assessment for at least one day from D1 to D113 (P=1.0000). Individually, only three gilts exhibited any abnormal assessments during this time frame. Two gilts exhibited lameness (one challenge control gilt and one negative control gilt) and one-low titer gilt exhibited swelling in the left neck region. Since vaccine was administered in the right neck region, no adverse events associated with this vaccine were noted.

Piglet PRRS viremia results on the DOF gave further insight to the level of protection in gilts in preventing cross-placental infection of piglets. On the DOF, a mean of 58.1% and 55.0% piglets per gilt in the low titer and high titer groups, respectively, were qPCR positive. Conversely, a mean of 86.3% piglets per gilt in the challenge control group were qPCR positive in serum/body fluids, which was significantly higher than both vaccine groups (P≤0.0381). When piglet viral load on DOF 0 was examined, high titer piglets had significantly lower viral load in comparison to challenge control piglets (P=0.0030); while no difference was detected for viral load between low titer and challenge control piglets (P=0.0620). Significant reductions (P≤0.05) in the percentage of piglets per gilt positive for viremia indicate reduced vertical transmission of virulent PRRSv from vaccinated gilt to off-spring when immunized with either dose of EU PRRS 94881 MLV. In addition, the high titer group had a median qPCR piglet value per gilt of 3.00 $\log_{10}$ GE/ml on the DOF; while the challenge control group had a median qPCR piglet value per gilt of 6.40 $\log_{10}$ GE/mL in serum/body fluids (P=0.0030). No significant difference was detected between the low dose group and the challenge control group for piglet viral load on DOF (P=0.0620). This data further supports the efficacy of the high dose of PRRS 94881 MLV when administered to gilts and sows.

The low titer and high titer groups exhibited means of 32.5% and 33.4%, respectively, for piglets per litter with clinical disease (a clinical observation score of >0) for least one day from DOF+1 to DOF+20. These results were significantly lower than for the challenge control group, which exhibited a mean of 91.6% piglets per litter for the same parameter (P≤0.0001), further supporting vaccine efficacy for both dose levels.

No significant difference was detected between groups for piglet mean body weights on DOF 0 (P≥0.2972); while both vaccine groups had significantly higher body weights on DOF+20 and ADWG from DOF 0 to DOF+20 (P≤0.0028). Once again, these results support the efficacy of both doses of PRRS 94881 MLV.

Necropsy results confirmed the correct categorization of almost all feti at farrowing. Due to the very small number of feti that were listed as crushed that were actually stillborns and stillborns that were actually crushed at farrowing, in comparison to the overall number of feti correctly categorized at farrowing, no changes were made to the gilt performance data before it was analyzed. One-challenge control piglet died subsequently to blood collection. Since this situation only involved one piglet in comparison to the large overall number of piglets in the challenge control group, this piglet was not removed from analyses.

Lung samples were collected from 141, 79, 75 and 4 dead feti/piglets from the challenge control, low titer, high titer, and negative control groups, respectively. A mean qPCR lung value of 4.68, 4.10, 3.55 and 0.00 $\log_{10}$ GE/mL was determined for the challenge control, low titer, high titer and negative control groups, respectively. No analyses were conducted on these data since piglets alive at 20 days of age were not necropsied, but these results highlight that gilts vaccinated with PRRS 94881 MLV resulted in lower viral load in the lungs of piglets when gilts were challenged with a virulent PRRSv.

In conclusion, results from this study demonstrated significantly higher percentages of live piglets per litter at farrowing (P≤0.0455) and higher percentages and numbers of piglets per litter at weaning (P≤0.0203) for both vaccine groups in comparison to the challenge control group. Thus, the study objective was met and data from this study establishes the MID of PRRS 94881 MLV in gilts as $1\times10^{2.43}$ TCID$_{50}$/2 mL. These results were achieved 118 days after vaccination, which in addition establishes duration of immunity (DOI) in gilts of approximately 4 months.

When supportive data was examined, the high dose of PRRS 94881 MLV ($1\times10^{3.90}$ TCID$_{50}$/2 mL) was associated with a higher percentage and number of healthy piglets per gilt at farrowing (P≤0.0211), a lower percentage and number of weak and mummified feti (P≤0.0090), a lower percentage of qPCR positive gilts and lower viral load in gilts post-challenge on D125, DOF 0 and DOF+13 (P≤0.0155), a lower percentage of piglets per gilt qPCR positive and lower piglet viral load on DOF 0 (P≤0.0030), a lower percentage of piglets per gilt with clinical disease (P<0.0001), and higher piglet body weights on DOF+20 and ADWG (P<0.0013).

The low dose group was associated with a higher percentage of healthy piglets per gilt at farrowing (P=0.0138), a lower percentage of number of mummified feti (P≤0.0190), a lower percentage of qPCR positive gilts and lower viral load in gilts post-challenge on D125, D132, DOF 0 and DOF+13 (P≤0.0290), a lower percentage of piglets per gilt qPCR positive on DOF 0 (P=0.0381), a lower percentage of piglets per gilt with clinical disease (P<0.0001), and higher piglet body weight on DOF+20 and ADWG (P<0.0028).

Example 7 Evaluation of the Onset of Immunity PRRS 94881 MLV in Susceptible Piglets Following Challenge with a Heterologous European Isolate of PRRS at Two Weeks Post-Vaccination The objective of this vaccination-challenge study was to assess the onset of immunity (OOI) two weeks after the administration of the vaccine candidate Porcine Reproductive and Respiratory Syndrome, European-derived Isolate 94881, Modified Live Virus (PRRS 94881 MLV) to 14±3 days of age susceptible piglets. The primary efficacy criterion to satisfy an OOI of 2 weeks post vaccination was if the vaccinate group (Group 1) demonstrated a significant difference (p≤0.05) for lung lesions post-challenge compared to the unvaccinated challenge control group (Group 2). Secondary parameters included clinical assessments after vaccination, clinical observations after challenge, rectal temperatures, average daily weight gain, assessment of PRRS antibodies and viremia in serum samples and quantitation of PRRS virus in lung samples collected at necropsy.

Piglets were randomly assigned to either Group 1 (PRRS 94881 MLV-vaccine containing $1 \times 10^{3.82}$ TCID$_{50}$/mL and challenged; n=20), Group 2 (placebo vaccine and challenged; n=20) or Group 3 (placebo vaccine and not challenged; n=10). Piglets were housed in plastic pens with raised floors (n=5/pen). Each treatment group was housed in a different room to avoid transmission of PRRSv through mechanical routes, including aerosolization.

All animals assigned to this study completed the study. No adverse events were reported during this study. The mean lung lesion scores on D24 were 27.4% and 54.8% for the PRRS 94881 MLV-vaccinated pigs and the challenge controls, respectively. The mean lung lesion score for the PRRS 94881 MLV-vaccinated pigs was significantly lower than the challenge controls (p=0.0002), and therefore the primary efficacy variable was met and the OOI was established at 2 weeks following a single vaccination. A significantly higher proportion of PRRS 94881 MLV-vaccinated pigs had positive PRRS-antibody titers on D14, D17 and D21 compared to challenge controls (p≤0.0012). The mean AUC for viremia was significantly lower for PRRS 94881 MLV-vaccinated pigs compared to challenge controls for D17-D24 (50.72 and 54.61 log$_{10}$ GE/mL, respectively; p=0.0039) post challenge. PRRS 94881 MLV-vaccinated pigs exhibited no signs of lethargy (0%) after challenge compared with 45% of the challenge control pigs (p=0.0012). PRRS 94881 MLV-vaccinated pigs had higher weight gains during the post-challenge phase (SD14-SD24) of the study compared to challenge controls (0.3 and 0.1 kg, respectively; p=0.0003).

The significant (p≤0.05) reduction of the lung lesions, clinical signs, replication of the virus in the blood and lungs post-challenge as well as the improvement of the growth performances in vaccinated animals demonstrate vaccine efficacy against virulent PRRSv when the challenge is performed 2 weeks post vaccination. It therefore supports the demonstration of an onset of immunity of at least 2 weeks post-vaccination with PRRS 94881 MLV.

Objectives/Purpose of Study

The objective of this vaccination-challenge study was to assess the onset of immunity (OOI) two weeks after the administration of the vaccine candidate Porcine Reproductive and Respiratory Syndrome, European-derived Isolate 94881, Modified Live Virus (PRRS 94881 MLV) to 14±3 days of age susceptible piglets. The primary efficacy criterion to satisfy an OOI of 2 weeks post vaccination was if the vaccinate group (Group 1) demonstrated a significant difference (p≤0.05) for decreased lung lesions post-challenge compared to the unvaccinated, challenge control group (Group 2).

The secondary efficacy parameters analyzed between the vaccine group and the challenge control group included clinical assessments post-vaccination, PRRS serology, PRRS viremia post-challenge, clinical observations post-challenge, average daily weight gain (ADWG), rectal temperatures and lung PRRSv quantitation.

A negative control group (Group 3), which was not vaccinated or challenged, was included in the study to demonstrate the source herd was free of PRRSv infection throughout the trial period and that biosecurity was not breached during this trial.

Schedule of Events

TABLE 7.1

Schedule of Events

| Study Day | Dates | Key Study Event |
|---|---|---|
| −8 | 14Dec09 | Screen for negative PRRS ELISA status |
| −1 | 21Dec09 | Arrival at VRI; Health Exam |
| −1 to 12 | 21Dec09 to 03Jan10 | Clinical Assessments |
| 0 | 22Dec09 | Collect body weights Vaccinate Group 1 with IVP, Vaccinate Groups 2 & 3 with CP |
| 7 | 29Dec09 | Blood sample |
| 13 to 24 | 04Jan10 to 15Jan10 | Clinical Observations and Rectal Temperatures |
| 14 | 05Jan10 | Collect body weights and blood sample; Challenge Groups 1 & 2 with heterologous European PRRS isolate |
| 17 and 21 | 08Jan10 and 12Jan10 | Blood sample |
| 24 | 15Jan10 | Euthanize and necropsy pigs after data and sample collection; Score lungs for pathology; collect lung tissues |

Study Design

TABLE 7.2

Study Design

| Group | Number of Piglets on D0 | Treatment on D0 (14 ± 3 days of age) | Challenge on D14 with 1 mL/nostril and 1 mL IM of PRRSv 205817 | Euthanize and Necropsy on D24 |
|---|---|---|---|---|
| 1 | 20 | 1.0 mL IM of IVP (1 × $10^{3.82}$ TCID$_{50}$/mL) | Yes | Yes |
| 2 | 20 | 1.0 mL IM of Control Product (CP; Placebo matched product without PRRS 94881 MLV) | Yes | Yes |
| 3 | 10 | 1.0 mL IM of CP | No | Yes |

Blinding Criteria

The Study Investigator and designees were blinded to the assigned treatment groups throughout the in-life phase of the study. To maintain this blinding, an individual who did not participate in assessments of the pigs (i.e., clinical assessments, clinical observations or necropsies) performed the randomization and administered the assigned IVP and CP treatments on D0. BIVI laboratory personnel were blinded to the treatment each pig received while conducting their respective tasks.

Materials

Investigational Veterinary Product (IVP) and Control Product (CP)

TABLE 7.3

| IVP | |
| --- | --- |
| Generic Product Name: | Porcine Reproductive and Respiratory Syndrome, Modified Live Virus |
| Strain: | 94881 |
| Production and Formulation: | BIVI-Production produced PRRS 94881 MLV, Lot 390-005 (Appendix 4) in accordance with Outline of Production, Code 19S1.U_ and EU Dossier Part 2b. On D0, BIVI-Ames reconstituted/diluted PRRS 94881 MLV vaccine Lot 390-005 (Appendix 4) with Phosphate buffered saline (PBS; Lot 809-003, Appendix 5) to formulate the IVP, Lot No. 257-086. Transcribed formulation records for the IVP are presented in Appendix 7 (original records available upon request). |
| Manufacturer: | Boehringer Ingelheim Vetmedica, Inc. 2621 North Belt Highway St. Joseph, MO 64506, USA |
| Lot No.: | N257-086 |
| Expiry Date: | An expiration date of 22 Dec. 2009 was assigned to the IVP for study purposes only. |
| Storage Conditions: | Lyophilized vaccine: 2-8° C. Rehydrated/diluted IVP: 2-8° C. or on ice |
| Testing: | Batch 390-005 was tested by BIVI-QC in accordance with draft Outline of Production and EU dossier Part 2F. At the start and end of the vaccination procedure, BIVI-Ames personnel were contacted. BIVI-Ames laboratory personnel tested pre- and post-vaccination aliquots for the IVP for virus titer in accordance with the PRRSv Titer Procedure (Appendix 1, Attachment 6). |
| Test Results: | Serial 390-005: Results were satisfactory (Appendix 4). IVP Lot N257-086: Mean titer of $1 \times 10^{3.82}$ $TCID_{50}$/mL (Appendix 7). |
| IVP Retention: | IVP was formulated for this study only and was not retained. |

TABLE 7.4

| CP | |
| --- | --- |
| Generic Product Name: | Placebo |
| Formulation: | BIVI-Production produced lyophilized placebo product containing inert material comprised in the vaccine serial without PRRS 94881 MLV (Lot N240-191-062409, Appendix 6). On D0, BIVI-Ames reconstituted Lot N240-191-062409 with Phosphate buffered saline (PBS; Lot 809-003, Appendix 5) to formulate the CP, Lot No. 257-085. Transcribed formulation records for the CP are presented in Appendix 7 (original records available upon request). |
| Manufacturer: | Boehringer Ingelheim Vetmedica, Inc. 2621 North Belt Highway St. Joseph, MO 64506, USA |
| Lot Number: | N257-085 |
| Expiry Date: | An expiration date of 22 Dec. 2009 was assigned to the CP for study purposes only. |
| Storage Conditions: | Lyophilized vaccine: 2-8° C. Rehydrated CP: 2-8° C. or on ice |
| Testing: | CP was tested by BIVI-QC for EP sterility in accordance with Special Outline No. 96 (Appendix 1, Attachment 5). |
| Test Results: | CP was determined to be sterile (Appendix 7). |
| CP Retention: | CP was formulated for this study only and was not retained. |

Challenge Material

TABLE 7.5

| Challenge Material | |
|---|---|
| Name/number of isolate | PRRS isolate 205817 |
| Location and date of isolation incl. clinical symptoms | The European PRRS virus isolate 205817 was derived from isolate 190136 originally obtained from lung tissue of a newborn piglet from a farm showing typical reproductive signs of PRRS (abortions in sows and weakness in newborn piglets) during an outbreak in Lower Saxony, Germany, in April 2004. The attending veterinarians submitted the lung samples to bioScreen (sample arrived on 21 Apr., 2004) for diagnostic testing. Isolate #190136 was directly propagated on MA 104 cells and a pure culture challenge stock was prepared for use in future BIVI clinical trials. A pure culture of isolate 190136 was used to inoculate pigs for evaluation of its ability to reproduce PRRS-specific respiratory disease in a controlled, laboratory trial. Challenged animals exhibited respiratory distress and revealed evidence of interstitial pneumonia upon histopathological examination. PRRS virus was successfully re-isolated from lung lesions was given the isolate designation 205817. Isolate 205817 was directly propagated on MA104 cells and a pure culture challenge stock was prepared for use in future BIVI clinical trials. |
| Formulation: | Challenge virus was thawed and diluted with MEM (Minimum Essential Medium) to a targeted titer of approximately $1 \times 10^6$ $TCID_{50}/3$ mL on D14. An adequate volume of challenge material was prepared. Two aliquots were removed from challenge material. |
| Lot Number: | N257-093 |
| Manufacture: | Boehringer Ingelheim Vetmedica, Inc. - USA |
| Storage conditions | Bulk challenge material was stored at $-70 \pm 10°$ C. Once prepared, diluted challenge material was maintained on ice until it was administered. |
| Testing: | At the start and end of the challenge procedure, BIVI-Ames was contacted. BIVI-Ames laboratory personnel tested pre- and post-challenge aliquots for virus titer in accordance with the PRRSv Titer Procedure |
| Test Results: | The challenge material had a mean titer of $1 \times 10^{4.71}$ $TCID_{50}/3$ mL dose |
| Administration route | 1.0 mL/nostril and 1.0 mL IM in the left neck (administered to all pigs in Groups 1 and 2 on D14). |
| Challenge material retention: | Challenge material was formulated for this study only and was not retained. |

Treatments

Dosing Justification

The IVP was administered as a 1.0 mL dose to assigned pigs to evaluate OOI of PRRS 94881 MLV at 2 weeks post-vaccination. The CP was administered as a 1.0 mL dose to Groups 2 and 3 as a placebo vaccine.

Dosing Regimen

IVP or CP was administered to an assigned pig in the right neck region IM on D0 using a sterile 3.0 mL Luer-lock syringe and a sterile 20 g×1 inch (2.54 cm) or 18 g×¾ inch (1.91 cm) needle by a person not collecting study data. The dosing regimen is shown below in Table 7.6.

TABLE 7.6

| Dosing Regimen | | | | |
|---|---|---|---|---|
| Group | Number | Treatment | Dose/Route | Study Day |
| 1 | 20 | IVP | 1.0 mL IM | D0 |
| 2 | 20 | CP | 1.0 mL IM | D0 |
| 3 | 10 | CP | 1.0 mL IM | D0 |

Animal Information

Details of Study Animals

TABLE 7.7

| Animal Information | |
|---|---|
| Source: | Wilson Prairie View Farm N5627 Highway DD Burlington, WI 53105 USA |
| Number of piglets: | 50 |
| Arrival date: | Pigs arrived at the Veterinary Resources, Inc. (VRI) Cambridge facility on 21 Dec. 2009 (D-1). |
| Arrival treatment: | The 50 pigs assigned to the study were administered EXCEDE ® at label dose IM in the right ham after arrival. |
| Identification: | Individually ear tagged with unique number |
| Species: | Porcine |
| Breed: | Commercial crossbred |
| Gender: | Mixed (females and castrated males) |

TABLE 7.7-continued

Animal Information

| | | |
|---|---|---|
| Age range: | 11 to 17 days of age on D0 | |
| Weight range: | 3.2 to 5.5 to kg on D0 | |
| Ownership of test animals: | Boehringer Ingelheim Vetmedica, Inc. | |
| Physiological status: | On D-1, pigs selected for assignment to the study were observed by the Study Investigator and determined to be in good health and nutritional status. Observations were recorded on the Animal Health Examination Record form. | |
| Group - Pig Assignments | Group 1 (n = 20):<br>55, 56, 60, 72, 75, 76, 77, 83, 87, 91, 99, 102, 116, 117, 124, 141, 142, 144, 156 and 162 | Group 2 (n = 20):<br>57, 61, 62, 68, 78, 81, 86, 89, 97, 110, 129, 132, 135, 150, 152, 154, 160, 165, 167 and 168 | Group 3 (n = 10):<br>51, 69, 80, 85, 104, 105, 128, 131, 133 and 155 |

Inclusion/Exclusion Criteria

All piglets enrolled in this study were PRRS ELISA negative and were healthy at the time of vaccination as determined by observation.

Post-Inclusion Removal Criteria

No pigs were removed from the study.

Animal Management and Housing

Animal Housing

Piglets were housed at Veterinary Resources, Inc. (VRI) in Cambridge, Iowa for the duration of the study. Groups 1, 2 and 3 were housed in uniform but separate rooms to ensure biosecurity. Piglets were housed in multiple pens (5 piglets/pen) within each room. Group 1 was housed in 4 pens in Room 5, Group 2 was housed in 4 pens in Room 6 and Group 3 was housed in 2 pens in Room 4. Pens consisted of plastic tubs on raised stands with plastic slatted flooring. Each pen contained a plastic 6-hole feeder and a nipple waterer. Each isolation room was constructed identical to the others and all are biohazard level 2 (BL2) compliant, hepa-filtered, mechanically ventilated with thermostat regulated temperature control.

Treatment group isolation was necessary in this study as it is well known within the scientific community that PRRSv readily spreads from pig to pig via various mechanisms including aerosolization. This includes avirulent live PRRS vaccines as these biological products include attenuated virus particles that mimic the characteristics of virulent wild-type PRRS without the capability to cause disease. Proper methods were in place to ensure that biosecurity was maintained and that vaccinated animals did not accidentally cross-contaminate non-vaccinated, PRRSv naïve negative control animals. Appropriate measures were taken by test facility staff to adequately clean and disinfect each room prior to its usage for this study.

Each room in the facility has fans and heaters to aid in sufficient air circulation and heating. The ventilation system is separate yet identical for each room, so air is not shared between rooms.

Solid feed was stored in bags, free from vermin. Water was ad libitum. Piglets were fed a commercial ration (Lean Metrics Infant, Purina Mills, St. Louis, Mo.) medicated with tiamulin (35 gm/ton) and chlortetracycline (400 gm/ton) ad libitum appropriate for their size, age, and condition; according to acceptable animal husbandry practices for the region.

The pigs were in good health and nutritional status before initiation of the study as determined by the Study Investigator.

During the study, select animals were observed with mild loss of body condition, rough haired appearance, swollen joints and varying degrees of lameness. The Study Investigator considered all of these to be non-specific conditions that commonly occur in groups of pigs housed in confinement. Coughing, sneezing, rapid respiration, dyspnea and mild to moderate lethargy were also noted in select pigs after challenge and were considered typical clinical signs associated with pneumonia, although non-specific for etiology. The Study Investigator determined that concomitant treatments were not required for any animals during this study.

All pigs assigned to this study were disposed of by commercial incineration after euthanasia and necropsy on D24. No food products from animals enrolled in this study entered the human food chain.

Assessment of Efficacy

To assess the OOI of PRRS 94881 MLV at 2 weeks post-vaccination, Groups 1 & 2 were challenged on D14 and lung lesions post-challenge were evaluated. An OOI of 2 weeks post-vaccination was achieved if Group 1 (minimum immunizing dose of PRRS 94881 MLV) demonstrated significantly decreased ($p \leq 0.05$) lung pathology post-challenge compared with the challenge control group (Group 2).

The secondary efficacy parameters analyzed between the vaccine group and the challenge control group included clinical assessments after vaccination, clinical observations after challenge, rectal temperatures, body weight and average daily weight gain (ADWG), assessment of PRRS antibodies and viremia in serum samples and quantitation of PRRS virus in lung samples collected at necropsy.

A negative control group (Group 3), which was not challenged, was included in the study to demonstrate the source herd was free of PRRS infection and that biosecurity was maintained throughout the study.

Criteria for a Valid Test

Pre-purchase and D0 serum samples were all required to be negative for PRRS antibodies.

Serum samples collected from Groups 2 and 3 up to the day of challenge and from Group 3 until study completion had to be free of PRRS antibodies for the study to be valid.

Primary Outcome Parameter

The primary efficacy variable for statistical evaluation was total lung lesion scores at D24 of the study.

Total Lung Lesion Scores

On Day 24 after data and samples were collected and recorded, all study pigs were euthanized following VRI SOP PRC1027 (Appendix 1, Attachment 8). Each pig was necropsied in accordance with VRI SOP PRC 1028 The thoracic cavity was exposed by a designee and the heart and lungs were removed. The Study Investigator examined each set of lungs, described any gross pathology noted and determined the % pathology for each lung lobe. Observations and data were recorded on the Necropsy Report Record form. A total lung lesion score was determined for each pig by using the EP formula.

Supportive Parameters

Other parameters to be analyzed between Group 1 and Group 2 included clinical assessments post-vaccination, PRRS serology, viremia post-vaccination, clinical observations post-challenge, ADWG, rectal temperatures and lung virus quantitation post challenge. These parameters were analyzed as supportive parameters and did not serve as primary parameters to satisfy the study objective.

Clinical Assessment

All pigs were observed on the days outlined in Table 7.1 for clinical assessments post-vaccination by the Study Investigator or designees. Observations were recorded on the Clinical Assessment Record form.

PRRS Serology

Venous whole blood was collected on the days outlined in Table 3. Briefly, approximately 2-5 mL of blood was collected from each piglet into an appropriate sized serum separator tube (SST). Sample collections were recorded on the Sample Collection Record form. Blood in SSTs was allowed to clot at room temperature. Blood samples were delivered to BIVI-Ames on the day of collection and Specimen Delivery Record form was completed. Blood samples were spun down by BIVI-Ames and serum was harvested, split and transferred to appropriate tubes. Each tube was labeled with the piglet's ID number, the study number, the date of collection, the study day and the sample type. At BIVI-Ames, one set of serum samples was held at 2-8° C. and the other set of serum samples was held at −70±10° C.

The serum samples collected days 0, 7, 14, 17, 21 and 24 and held at 2-8° C. were tested by BIVI-Ames for PRRS antibodies. Results were reported as negative (ELISA S/P ratio of <0.4) or positive (ELISA S/P ratio of ≥0.4).

PRRS Viremia

The other set of serum samples collected on days 0, 7, 14, 17, 21 and 24 and held at −70±10° C. at BIVI-Ames until the in-life phase of the study was completed.

A completed Specimen Delivery Record form was included with the shipment. bioScreen tested serum samples for PRRSv RNA by qPCR. Results were reported as genome equivalent/mL (log GE/mL).

Clinical Observations Post-Challenge

Piglets were observed for clinical signs of disease on the days outlined in Table 7.1. Observations were conducted by the Study Investigator or designees and were recorded on the Clinical Observation Record form. Piglets were observed each day for respiration, behavior and cough based on the clinical observation scoring system outlined below in Table 7.8.

TABLE 7.8

Clinical Observation Scoring System

| Respiration | Behavior | Cough |
| --- | --- | --- |
| 0 = normal respiration | 0 = normal | 0 = none |
| 1 = panting/rapid respiration | 1 = mild to moderate lethargy | 1 = soft or intermittent cough |
| 2 = dyspnea | 2 = severely lethargic or recumbent | 2 = harsh or severe, repetitive cough |
| 3 = dead | 3 = dead | 3 = dead |

Average Daily Weight Gain (ADWG)

Individual body weights were collected on the days outlined in Table 3. Each pig was weighed on a calibrated scale by the Study Investigator or designees. Results were reported in kg on the Body Weight Record form. Average daily weight gain was determined from the D0 to D14 and from D14 to D24.

Rectal Temperatures

Rectal temperatures were collected by the Study Investigator or designees on the days outlined in Table 6.1. Rectal temperatures were recorded in ° C. on the Clinical Observation Record form.

PRRS Virus Quantitation in Lung Tissue

For each set of lungs, two samples from the Left and Right Apical lobes, the Left and Right Cardiac lobes, the Left and Right Diaphragmatic lobes and the Intermediate lobe, were retained. Each lung sample was approximately 1 inch (2.54 cm)×1 inch (2.54 cm). For one set of lung samples, all three samples from the left side were combined into one container; while all three samples from the right side and the Intermediate lung lobe sample were combined into another container. Each container was filled with a sufficient amount of 10% formalin solution. For the other set of lung samples, all three lung samples from the left side were combined into one WHIRLPAK®; while all three samples from the right side and the Intermediate lung lobe sample were combined into another WHIRLPAK®. All containers and WHIRLPAKS® were appropriately labeled with animal number, study number, date of collection, study day, sample type and whether the samples are from the left or right side. Lung samples in WHIRLPAKS® were stored on dry ice until transported to BIVI-Ames while samples in formalin were stored at room temperature. Sample collections were recorded on the Necropsy Report Record form. Formalin fixed lung tissue samples and WHIRLPAK® lung samples were transferred to BIVI-Ames. A completed Specimen Delivery Record form was included with each shipment.

A completed Specimen Delivery Record form was included with the shipment. bioScreen tested lung samples for PRRSv RNA by qPCR (Appendix 1, Attachment 7). Left lung tissues were homogenized and tested. Right lung tissues and intermediate lung lobe samples were homogenized and tested. Results were reported as genome equivalent (log GE/mL) for left and right lung samples.

Adverse Events

No adverse events were reported during this study.

Statistical Methods

Experimental Unit

Treatment groups had to be housed in separate rooms in this study to avoid transmission of PRRSv to non-vaccinated groups. Therefore, room was the experimental unit. However, for the purposes of this analysis, possible bias due to confounding "room" and "treatment" effects were ignored, and piglet was used as the experimental unit.

Randomization

Fifty (50) piglets were blocked by weight (n=5 piglets/block). Each pig was assigned a random number using the random number function in Excel. Within each weight block, pigs were ranked in ascending numerical order of the assigned random number. The treatment groups were then assigned to pigs in this numerical order: the 2 lowest random numbers were assigned to Group 1, the next 2 numbers were assigned to Group 2 and the highest number was assigned to Group 3. Groups 1 & 2 each contained 20 pigs and Group 3 contained 10 pigs.

Analysis

The statistical analyses and data summaries were conducted by Dr. rer. hort. Martin Vanselow, Biometrie & Statistik, Zum Siemenshop 21, 30539 Hannover, Germany, +49(0) 511 606 777 650, m.vanselow@t-online.de.

Data were analyzed assuming a completely random design structure. The statistical analyses were performed using SAS software release 8.2 (SAS, Cary, USA/North Carolina, SAS Institute Inc. All tests on differences were designed as two-sided tests at α=5%.

Total Lung Lesion Scores

The total lung lesion score on the day of necropsy (D24) was measured as the percentage of lung involvement calculated according to the weighting formula recommended in the draft monograph Porcine Enzootic Pneumonia Vaccine (inactivated). This formula takes into account the relative weight of each of the seven lung lobes. The assessed percentage of lung lobe area with typical lesions was multiplied by the respective factor per lung lobe giving the total weighted lung lesions score. The factors for the respective lung lobes are presented in Table 7.9.

TABLE 7.9

Factors for Calculating Lung Lesion Scores

| Lung lobe | Factor |
|---|---|
| Left apical | 0.05 |
| Left cardiac | 0.06 |
| Left diaphragmatic | 0.29 |
| Right apical | 0.11 |
| Cardiac | 0.10 |
| Right diaphragmatic | 0.34 |
| Right accessory/intermediate | 0.05 |

The treatment groups were compared on differences using the Wilcoxon Mann-Whitney test.

Clinical Assessment Post-vaccination

Frequency tables of animals with at least one positive finding between D1 and D12 were generated. Differences between treatment groups were tested by Fisher's exact test.

PRRS Serology

Frequency tables of positive ELISA results were generated. Differences between treatment groups were tested by Fisher's exact test.

PRRS Viremia

The viremia data were evaluated separately for each day of investigation. Additionally, for viral load the areas under the individual response curves between D14 and D24 (AUC D14-D24) and between D17 and D24 (AUC D17-D24) were analyzed.

The quantitative PCR data (PRRS viral load [$\log_{10}$ GE/mL]) were used for comparisons between the treatment groups by the Wilcoxon Mann-Whitney test. Prior to the calculations the analytical result 'not detected' was replaced by a $\log_{10}$ GE/mL value of 0.0 and 'positive' was replaced by 3.0. The treatment groups were tested on differences using the Wilcoxon Mann-Whitney test.

Clinical Observations Post-Challenge

Frequency tables of animals with at least one positive finding between D15 and D24 were generated. Differences between treatment groups were tested by Fisher's exact test.

The maximum scores and the mean scores per animal from D15 to D24 for respiration, behavior, coughing and for all three added together (total) were used for the statistical evaluation. Differences between treatment groups were tested by the Wilcoxon Mann-Whitney test.

Body Weight and Average Daily Weight Gain

Individual daily weight gains were calculated for the time periods between D0 and D14 and between D14 and D24. For each day of investigation and for each time period descriptive statistics were calculated. Differences between treatment groups were tested using analysis of variance and subsequent t-tests. Least squares means of the groups and differences between least squares means with 95% confidence intervals were calculated from the analysis of variance.

Rectal Temperatures

Differences between treatment groups with respect to the original temperature data were tested using analysis of variance and subsequent t-tests. Least squares means of the groups and differences between least squares means with 95% confidence intervals were calculated from the analysis of variance.

PRRS Virus Quantitation in Lung Tissues

The quantitative PCR data (PRRS viral load [$\log_{10}$ GE/mL]) from lungs collected on D24 were used for comparisons between the treatment groups by the Wilcoxon Mann-Whitney test. The average ($\log_{10}$ GE/mL) of the left and right lung qPCR results were used for the evaluation. Prior to the calculations the analytical result 'not detected' was replaced by $\log_{10}$ GE/mL of 0.0 and 'positive' was replaced by 3.0.

Frequency tables of positive qPCR results were generated. Differences between treatment groups were tested by Fisher's exact test.

Results

Total Lung Lesion Scores

A summary of the group total lung lesion scores and the associated p-value is shown below in Table 7.10.

TABLE 7.10

| Total Lung Lesion Scores (%) | | | | | | | | | |
|---|---|---|---|---|---|---|---|---|---|
| Group[1] | N | Min. | Max. | Median | 95% CI | | QRange | Mean | p value |
| 1 | 20 | 0.06 | 59.30 | 27.550 | 12.270 | 40.600 | 29.515 | 27.368 | 0.0002 |
| 2 | 20 | 13.86 | 91.60 | 55.200 | 47.300 | 66.500 | 21.850 | 54.841 | |
| 3 | 10 | 0.00 | 0.06 | 0.000 | 0.000 | 0.000 | 0.000 | 0.006 | NI |

[1]Group 1 = PRRS 94881 MLV vaccine at MID, challenged; Group 2 = placebo-treated, challenged; Group 3 = placebo-treated, not challenged.
NI = Not included in statistical analysis.

Mean piglet D24 total lung lesion scores were 27.368% and 54.841% for the PRRS 94881 MLV-vaccinated group and challenge controls, respectively. The lesion score for the PRRS-vaccinated pigs was significantly lower than the mean lesion score for the challenge controls (p=0.0002).

PRRS Viremia

A summary of the PRRSv RNA detected in serum by qPCR data is shown below in Table 7.11.

TABLE 7.11

PRRSv RNA Detected by qPCR in Serum ($\log_{10}$ GE/mL) by Day

| Day | Group[1] | N | Min. | Max. | Median | 95% CI | | QRange | Mean | p value |
|---|---|---|---|---|---|---|---|---|---|---|
| 7 | 1 | 20 | 0.00 | 5.34 | 3.00 | 3.00 | 3.79 | 0.82 | 3.17 | <0.0001 |
|  | 2 | 20 | 0.00 | 0.00 | 0.00 | 0.00 | 0.00 | 0.00 | 0.00 |  |
|  | 3 | 10 | 0.00 | 0.00 | 0.00 | 0.00 | 0.00 | 0.00 | 0.00 | NI |
| 14 | 1 | 20 | 0.00 | 4.29 | 3.32 | 3.00 | 3.77 | 0.84 | 3.30 | <0.0001 |
|  | 2 | 20 | 0.00 | 0.00 | 0.00 | 0.00 | 0.00 | 0.00 | 0.00 |  |
|  | 3 | 10 | 0.00 | 0.00 | 0.00 | 0.00 | 0.00 | 0.00 | 0.00 | NI |
| 17 | 1 | 20 | 5.54 | 8.07 | 6.72 | 6.47 | 7.08 | 0.80 | 6.78 | <0.0001 |
|  | 2 | 20 | 6.44 | 9.02 | 8.18 | 7.47 | 8.47 | 1.09 | 8.00 |  |
|  | 3 | 10 | 0.00 | 0.00 | 0.00 | 0.00 | 0.00 | 0.00 | 0.00 | NI |
| 21 | 1 | 20 | 6.18 | 8.73 | 7.38 | 7.13 | 8.08 | 0.98 | 7.51 | 0.0565 |
|  | 2 | 20 | 7.22 | 8.86 | 7.87 | 7.62 | 8.11 | 0.57 | 7.88 |  |
|  | 3 | 10 | 0.00 | 0.00 | 0.00 | 0.00 | 0.00 | 0.00 | 0.00 | NI |
| 24 | 1 | 20 | 5.82 | 8.54 | 7.15 | 6.73 | 7.84 | 1.16 | 7.26 | 0.6251 |
|  | 2 | 20 | 6.53 | 8.29 | 7.27 | 6.97 | 7.60 | 0.67 | 7.34 |  |
|  | 3 | 10 | 0.00 | 0.00 | 0.00 | 0.00 | 0.00 | 0.00 | 0.00 | NI |
| AUC 14-24 | 1 | 20 | 56.95 | 78.02 | 65.10 | 60.39 | 70.05 | 9.76 | 65.84 | 0.4945 |
|  | 2 | 20 | 58.74 | 74.30 | 67.02 | 64.38 | 68.24 | 4.83 | 66.61 |  |
|  | 3 | 10 | 0.00 | 0.00 | 0.00 | 0.00 | 0.00 | 0.00 | 0.00 | NI |
| AUC 17-24 | 1 | 20 | 42.98 | 59.51 | 49.52 | 47.46 | 54.30 | 7.14 | 50.72 | 0.0039 |
|  | 2 | 20 | 49.08 | 60.99 | 54.35 | 52.93 | 55.38 | 3.63 | 54.61 |  |
|  | 3 | 10 | 0.00 | 0.00 | 0.00 | 0.00 | 0.00 | 0.00 | 0.00 | NI |

[1]Group 1 = PRRS 94881 MLV vaccine at MID, challenged; Group 2 = placebo-treated, challenged; Group 3 = placebo-treated, not challenged.
NI = Not included in statistical analysis.
AUC = Area under the curve; GE/ml per day PRRSv RNA was not detected in the serum of any piglets on D0. PRRS 94881 MLV-vaccinated pigs had mean values of 3.17 and 3.30 $\log_{10}$ GE/mL on D7 and D14, respectively. The values were significantly higher than challenge controls on both of these days (p<0.0001), as challenge controls did not have any PRRSv RNA detected until D17. On that day, mean values were 6.78 and 8.00 $\log_{10}$ GE/mL for PRRS 94881 MLV-vaccinated piglets and challenge controls, respectively. The D17 value for challenge controls was significantly higher than the PRRS 94881 MLV-vaccinated piglets (p<0.0001). Mean values for PRRS 94881 MLV-vaccinated pigs on D21 and D24 were 7.51 and 7.26 $\log_{10}$ GE/mL on D21 and D24 respectively, compared to 7.88 and 7.34 $\log_{10}$ GE/mL for challenge controls on the same days. There were no significant differences between PRRS 94881 MLV-vaccinated pigs on D21 or 24 (p≥0.0565). No PRRSv RNA was detected in serum from any negative control pig during this study.

There were no differences between the AUC 14-24 for PRRS 94881 MLV-vaccinated pigs and challenge controls pigs (65.84 and 66.61, respectively; p=0.4945). PRRS 94881 MLV-vaccinated pigs had a significantly lower AUC for D17-D24 compared to challenge controls (50.72 and 54.61, respectively; p=0.0039).

PRRS Virus Quantitation in Lung Tissues

Individual PRRSv qPCR results from lung tissues collected at necropsy on D24 are presented in Addendum 1, Table 30. A summary of the PRRSv RNA detected in lung tissues by qPCR data is shown below presented in Table 7.12 and a summary of the frequency of animals with positive qPCR at necropsy is shown below in Table 7.13.

TABLE 7.12

Lung Viruse Isolation, qPCR (mean log10 GE/mL) at Necropsy (D 24)

| Group[1] | N | Min. | Max. | Median | 95% CI | | QRange | Mean | p value |
|---|---|---|---|---|---|---|---|---|---|
| 1 | 20 | 6.63 | 8.26 | 7.46 | 7.07 | 7.86 | 0.84 | 7.47 | 0.0101 |
| 2 | 20 | 6.55 | 8.67 | 7.99 | 7.69 | 8.14 | 0.54 | 7.88 |  |
| 3 | 10 | 0.00 | 0.00 | 0.00 | 0.00 | 0.00 | 0.00 | 0.00 | NI |

[1]Group 1 = PRRS 94881 MLV vaccine at MID, challenged; Group 2 = placebo-treated, challenged; Group 3 = placebo-treated, not challenged.
NA = Not applicable because of lack of variability.
NI = Not included in statistical analysis.

TABLE 7.13

Frequency of Animals with Possible PRRSv RNA aPCR from Lung Tissues Collected at Necropsy (D 24)

| Day | Group | N | % | 95% CI | | Total | P |
|---|---|---|---|---|---|---|---|
| 24 | 1 | 20 | 100 | 83.2 | 100.0 | 20 | NA |
|  | 2 | 20 | 100 | 83.2 | 100.0 | 20 |  |
|  | 3 | 0 | 0 | 0.0 | 30.8 | 10 | NI |

[1] Group 1 = PRRS 94881 MLV vaccine at MID, challenged; Group 2 = placebo-treated, challenged; Group 3 = placebo-treated, not challenged.
NA = Not applicable because of lack of variability.
NI = Not included in statistical analysis.

PRRSv RNA was detected in the lung tissues of all piglets in both the PRRS 94881 MLV-vaccinated group and all piglets in the challenge control group. There was no difference between these groups. PRRSv RNA was not detected in the lung samples of any negative control piglets.

Clinical Observations Post-Challenge

The frequency of piglets with at least one positive clinical assessment score in the post-challenge period (D15-D24) is shown below in Table 7.14.

TABLE 7.14

Frequency of Piglets with a Positive Clinical Observation Post Challenge (D 15-D 24)

| Parameter | Group[1] | N positive | % positive | 95% CI | | Total | p value |
|---|---|---|---|---|---|---|---|
| Respiration | 1 | 2 | 10 | 1.2 | 31.7 | 20 | 0.2351 |
| | 2 | 6 | 30 | 11.9 | 54.3 | 20 | |
| | 3 | 0 | 0 | 0.0 | 30.8 | 10 | NI |
| Behavior | 1 | 0 | 0 | 0.0 | 16.8 | 20 | 0.0012 |
| | 2 | 9 | 45 | 23.1 | 68.5 | 20 | |
| | 3 | 0 | 0 | 0.0 | 30.8 | 10 | NI |
| Coughing | 1 | 6 | 30 | 11.9 | 54.3 | 20 | 0.2003 |
| | 2 | 11 | 55 | 31.5 | 76.9 | 20 | |
| | 3 | 0 | 0 | 0.0 | 30.8 | 10 | NI |
| Total | 1 | 6 | 30 | 11.9 | 54.3 | 20 | 0.0562 |
| | 2 | 13 | 65 | 40.8 | 84.6 | 20 | |
| | 3 | 0 | 0 | 0.0 | 30.8 | 10 | NI |

[1]Group 1 = PRRS 94881 MLV vaccine at MID, challenged; Group 2 = placebo-treated, challenged; Group 3 = placebo-treated, not challenged.
NI = Not included in statistical analysis.

Abnormal respiration was observed in both the PRRS 94881 MLV-vaccinated group (10%) and in the challenge control group (30%), however, these values were not significantly different (p=0.2351).

Abnormal behavior was only observed in the challenge control group (45%), and not in the PRRS 94881 MLV-vaccinated group (0%). The PRRS 94881 MLV-vaccinated group had a significantly lower incidence of abnormal behavior than the challenge controls (p=0.0012).

Coughing was observed in both the PRRS 94881 MLV-vaccinated group (30%) and in the challenge control group (55%). These values were not significantly different (p=0.2003).

The percentages of piglets with total clinical scores >0 were 30% and 65% for the PRRS 94881 MLV-vaccinated group and the challenge control group, respectively. These values were not significantly different (p=0.0562).

No clinical signs were observed in the negative control group at any time after challenge.

A summary of the group maximum clinical observation scores for the post-challenge period (D15 through D24) is shown below in Table 7.15.

Abnormal respiration was observed in both the PRRS 94881 MLV-vaccinated group and the challenge controls after challenge administration, with maximum scores of 1 (panting/rapid respiration) and 2 (dyspnea), respectively. There was no significant difference between these respiration scores (p=0.1872). The median maximum respiration score was 0 for both groups.

No abnormal behavior was observed in the PRRS 94881 MLV-vaccinated group in the post-challenge period (maximum score=0). In contrast, the challenge control group had a maximum behavior score of 1 (mild to moderate lethargy; p=0.0012) although the median score for this group was 0. The maximum score for the PRRS 94881 MLV-vaccinated group was significantly lower than the score for the challenge control group (p=0.0012). Median maximum behavior scores were 0 for both groups.

Coughing was observed in both the PRRS 94881 MLV-vaccinated group and in the challenge control group after challenge. Maximum scores were 1 (soft or intermittent cough) and 2 (harsh or severe, repetitive cough), and median scores were 0 and 1, for PRRS 94881 MLV-vaccinated and challenge controls, respectively. There were no significant differences between these groups (p=0.1129). Median maximum coughing scores were 0 and 1 for the PRRS 94881 MLV-vaccinated group and challenge control group, respectively.

Maximum total scores were 1 and 4 and median total scores were 0 and 1 for the PRRS 94881 MLV-vaccinated group and the challenge control group, respectively. The maximum score for the PRRS 94881 MLV-vaccinated group was significantly lower than the score for the challenge control group (p=0.0072). Median total scores were 0 and 1 for the PRRS 94881 MLV-vaccinated group and challenge control group, respectively.

No clinical signs were observed from D15 through D24 in the non-challenged negative control group during this study. This group had a maximum score of 0 for each parameter.

A summary of the group mean clinical observation scores for the post-challenge period (D15 through D24) is shown below in Table 7.16.

TABLE 7.15

Post-Challenge Maximum Clinical Scores, D 15 through D 24

| Parameter | Group[1] | N | Min. | Max. | Median | 95% CI | | QRange | Mean | p value |
|---|---|---|---|---|---|---|---|---|---|---|
| Respiration | 1 | 20 | 0 | 1 | 0 | 0 | 0 | 0 | 0.1 | 0.1872 |
| | 2 | 20 | 0 | 2 | 0 | 0 | 1 | 1 | 0.4 | |
| | 3 | 10 | 0 | 0 | 0 | 0 | 0 | 0 | 0.0 | NI |
| Behavior | 1 | 20 | 0 | 0 | 0 | 0 | 0 | 0 | 0.0 | 0.0012 |
| | 2 | 20 | 0 | 1 | 0 | 0 | 1 | 1 | 0.5 | |
| | 3 | 10 | 0 | 0 | 0 | 0 | 0 | 0 | 0.0 | NI |
| Coughing | 1 | 20 | 0 | 1 | 0 | 0 | 1 | 1 | 0.3 | 0.1129 |
| | 2 | 20 | 0 | 2 | 1 | 0 | 1 | 1 | 0.7 | |
| | 3 | 10 | 0 | 0 | 0 | 0 | 0 | 0 | 0.0 | NI |
| Total | 1 | 20 | 0 | 1 | 0 | 0 | 1 | 1 | 0.3 | 0.0072 |
| | 2 | 20 | 0 | 4 | 1 | 0 | 2 | 2 | 1.2 | |
| | 3 | 10 | 0 | 0 | 0 | 0 | 0 | 0 | 0.0 | NI |

[1]Group 1 = PRRS 94881 MLV vaccine at MID, challenged; Group 2 = placebo-treated, challenged; Group 3 = placebo-treated, not challenged.
NI = Not included in statistical analysis.

TABLE 7.16

Post-Challenge Mean Clinical Scores, D 15 through D 24

| Parameter | Group[1] | N | Min. | Max. | Median | 95% CI | | QRange | Mean | p value |
|---|---|---|---|---|---|---|---|---|---|---|
| Respiration | 1 | 20 | 0.0 | 0.2 | 0.00 | 0.00 | 0.00 | 0.00 | 0.02 | 0.1394 |
|  | 2 | 20 | 0.0 | 0.6 | 0.00 | 0.00 | 0.10 | 0.10 | 0.07 |  |
|  | 3 | 10 | 0.0 | 0.0 | 0.00 | 0.00 | 0.00 | 0.00 | 0.00 | NI |
| Behavior | 1 | 20 | 0.0 | 0.0 | 0.00 | 0.00 | 0.00 | 0.00 | 0.00 | 0.0012 |
|  | 2 | 20 | 0.0 | 0.8 | 0.00 | 0.00 | 0.10 | 0.10 | 0.12 |  |
|  | 3 | 10 | 0.0 | 0.0 | 0.00 | 0.00 | 0.00 | 0.00 | 0.00 | NI |
| Coughing | 1 | 20 | 0.0 | 0.4 | 0.00 | 0.00 | 0.10 | 0.10 | 0.07 | 0.0835 |
|  | 2 | 20 | 0.0 | 0.7 | 0.10 | 0.00 | 0.30 | 0.35 | 0.17 |  |
|  | 3 | 10 | 0.0 | 0.0 | 0.00 | 0.00 | 0.00 | 0.00 | 0.00 | NI |
| Total | 1 | 20 | 0.0 | 0.4 | 0.00 | 0.00 | 0.10 | 0.15 | 0.08 | 0.0103 |
|  | 2 | 20 | 0.0 | 1.4 | 0.25 | 0.00 | 0.40 | 0.50 | 0.35 |  |
|  | 3 | 10 | 0.0 | 0.0 | 0.00 | 0.00 | 0.00 | 0.00 | 0.00 | NI |

[1]Group 1 = PRRS 94881 MLV vaccine at MID, challenged; Group 2 = placebo-treated, challenged; Group 3 = placebo-treated, not challenged.
NI = Not included in statistical analysis Mean clinical observation scores followed a pattern similar to maximum clinical scores with significant differences only observed between the PRRS 94881 MLV-vaccinated group and the challenge control group for mean behavior score (p=0.0012) and mean total score (p=0.0103).

Mean respiration scores were 0.02 and 0.07 for the PRRS 94881 MLV-vaccinated group and the challenge control group, respectively. Mean behavior scores were 0.00 and 0.12 for the PRRS 94881 MLV-vaccinated group and the challenge control group, respectively. Mean coughing scores were 0.07 and 0.17 for the PRRS 94881 MLV-vaccinated group and the challenge control group, respectively. Mean total scores were 0.08 and 0.35 for the PRRS 94881 MLV-vaccinated group and challenge control group, respectively.

No clinical signs were observed from D15 through D24 in the non-challenged negative controls during this study. This group had a mean score of 0 for each parameter.

Body Weight and Average Daily Weight Gain

A summary of the body weights on D0, D14 and D24 and ADWG for D0 to D14 and D14 to D24 are shown below in Table 7.17.

TABLE 7.17

Body Weight and Average Daily Weight Gain (kg and kg/d)

| Day(s) | Group[1] | N | Min. | Max. | Median | Mean | SD |
|---|---|---|---|---|---|---|---|
| 0 | 1 | 20 | 3.3 | 5.5 | 3.95 | 4.14 | 0.589 |
|  | 2 | 20 | 3.2 | 5.2 | 4.05 | 4.17 | 0.603 |
|  | 3 | 10 | 3.4 | 5.1 | 4.00 | 4.07 | 0.556 |
| 14 | 1 | 20 | 5.6 | 9.4 | 7.60 | 7.64 | 1.029 |
|  | 2 | 20 | 6.0 | 8.9 | 7.30 | 7.39 | 0.909 |
|  | 3 | 10 | 5.5 | 9.3 | 6.95 | 7.22 | 1.187 |
| 24 | 1 | 20 | 7.0 | 13.9 | 10.40 | 10.26 | 1.693 |
|  | 2 | 20 | 6.4 | 10.9 | 8.80 | 8.87 | 1.328 |
|  | 3 | 10 | 6.8 | 12.9 | 10.90 | 10.64 | 1.807 |
| ADWG 0-14 | 1 | 20 | 0.164 | 0.343 | 0.2571 | 0.2500 | 0.05254 |
|  | 2 | 20 | 0.179 | 0.307 | 0.2357 | 0.2304 | 0.03939 |
|  | 3 | 10 | 0.150 | 0.307 | 0.2071 | 0.2250 | 0.04906 |
| ADWG 14-24 | 1 | 20 | 0.090 | 0.460 | 0.2600 | 0.2620 | 0.08907 |
|  | 2 | 20 | −0.060 | 0.290 | 0.1600 | 0.1475 | 0.09060 |
|  | 3 | 10 | 0.130 | 0.440 | 0.3700 | 0.3420 | 0.10130 |

[1]Group 1 = PRRS 94881 MLV vaccine at MID, challenged; Group 2 = placebo-treated, challenged; Group 3 = placebo-treated, not challenged.

Mean body weights on D0 were 4.1 and 4.2 kg for the PRRS 94881 MLV-vaccinated group and the challenge control group, respectively. By D14, mean body weights were 7.6 and 7.4 kg for the PRRS 94881 MLV-vaccinated group and the challenge control group, respectively. On D24, mean body weights were 10.3 and 8.9 kg for the PRRS 94881 MLV-vaccinated group and the challenge control group, respectively. Average daily weight gains (ADWG) for the vaccination period (D0 to D14) were 0.25 and 0.23 kg/d for the PRRS 94881 MLV-vaccinated group and the challenge control group, respectively. ADWGs for the challenge period (D14 to D24) were 0.26 and 0.15 kg/d for the PRRS 94881 MLV-vaccinated group and challenge control group, respectively. ADWGs for the negative controls were 0.23 and 0.34 kg/d for D0-D14 and D14-D24, respectively.

Negative control piglets had mean body weights of 4.1, 7.2 and 10.6 kg on D0, D14 and D28, respectively.

A summary of the LS Mean and statistical analysis of body weights and ADWG for the PRRS 94881 MLV-vaccinated group and the challenge control group is shown below in Table 7.18.

TABLE 7.18

LS Mean Body Weight and Daily Gain (kg)

| Day(s) | Group[1] | LS Mean | 95% confidence interval | | p value |
|---|---|---|---|---|---|
| 0 | 1 | 4.14 | 3.865 | 4.405 | 0.8743 |
|  | 2 | 4.17 | 3.895 | 4.435 |  |
|  | Diff. 1-2 | −0.03 | −0.411 | 0.351 |  |
| 14 | 1 | 7.64 | 7.196 | 8.074 | 0.4297 |
|  | 2 | 7.39 | 6.951 | 7.829 |  |
|  | Diff. 1-2 | 0.25 | −0.376 | 0.866 |  |
| 24 | 1 | 10.26 | 9.566 | 10.944 | 0.0063 |
|  | 2 | 8.87 | 8.176 | 9.554 |  |
|  | Diff. 1-2 | 1.39 | 0.416 | 2.364 |  |
| ADWG 0-14 | 1 | 0.2500 | 0.22898 | 0.27102 | 0.1889 |
|  | 2 | 0.2304 | 0.20934 | 0.25138 |  |
|  | Diff. 1-2 | 0.0196 | −0.01008 | 0.04937 |  |
| ADWG 14-24 | 1 | 0.2620 | 0.22133 | 0.30267 | 0.0003 |
|  | 2 | 0.1475 | 0.10683 | 0.18817 |  |
|  | Diff. 1-2 | 0.1145 | 0.05699 | 0.17201 |  |

[1]Group 1 = PRRS 94881 MLV vaccine at MID, challenged; Group 2 = placebo-treated, challenged.

Day 0 LS Mean body weights were 4.14 and 4.17 kg for the PRRS 94881 MLV-vaccinated piglets and the challenge control group, respectively. The difference was −0.03 kg, which was not significantly different (p=0.8743). On D14, LS Mean body weights were 7.64 and 7.39 kg for the PRRS 94881 MLV-vaccinated group and the challenge control group, respectively. The difference was 0.25 kg, which was also not significantly different (p=0.4297). On D24, the LS Mean body weights were 10.26 and 8.87 for the PRRS 94881 MLV-vaccinated group and the challenge control group, respectively. The difference on this day was 1.39 kg, and the vaccinated group weight was significantly higher than the challenge control group (p=0.0063).

LS Mean ADWGs for the vaccination period (D0-D14) were 0.25 and 0.23 kg/d for the PRRS 94881 MLV-vaccinated group and the challenge control group, respectively. These values were not significantly different (p=0.1889). LS Mean ADWGs during the post-challenge period (D14-D24) were 0.26 and 0.15 for the PRRS 94881 MLV-vaccinated group and the challenge control group, respectively. The ADWG for the PRRS 94881 MLV-vaccinated group was significantly higher than the ADWG for the challenge control group (p=0.0003).

Rectal Temperatures

A summary of rectal temperatures is shown below in Tables 7.19 and 7.20. A summary of the LS Mean and statistical analysis of rectal temperature for the PRRS 94881 MLV-vaccinated group and the challenge control group is shown below in Tables 7.21 and 7.22.

TABLE 7.19

Rectal Temperature (° C.) Day 13-22

| Day | Group[1] | N | Min. | Max. | Median | Mean | SD |
|---|---|---|---|---|---|---|---|
| 13 | 1 | 20 | 39.3 | 40.3 | 39.80 | 39.77 | 0.247 |
|  | 2 | 20 | 38.9 | 40.0 | 39.35 | 39.39 | 0.292 |
|  | 3 | 10 | 39.0 | 39.7 | 39.15 | 39.26 | 0.267 |
| 14 | 1 | 20 | 39.4 | 40.2 | 39.75 | 39.76 | 0.226 |
|  | 2 | 20 | 39.0 | 39.8 | 39.40 | 39.37 | 0.220 |
|  | 3 | 10 | 39.1 | 40.3 | 39.40 | 39.51 | 0.375 |
| 15 | 1 | 20 | 39.3 | 40.4 | 39.65 | 39.69 | 0.258 |
|  | 2 | 20 | 39.4 | 41.1 | 39.70 | 39.90 | 0.538 |
|  | 3 | 10 | 39.1 | 40.3 | 39.40 | 39.52 | 0.371 |
| 16 | 1 | 20 | 39.9 | 41.3 | 40.80 | 40.68 | 0.417 |
|  | 2 | 20 | 39.3 | 40.3 | 39.75 | 39.77 | 0.279 |
|  | 3 | 10 | 39.1 | 39.9 | 39.45 | 39.46 | 0.263 |
| 17 | 1 | 20 | 39.2 | 40.6 | 39.80 | 39.89 | 0.363 |
|  | 2 | 20 | 39.4 | 40.6 | 39.85 | 39.90 | 0.285 |
|  | 3 | 10 | 39.2 | 40.0 | 39.50 | 39.53 | 0.226 |
| 18 | 1 | 20 | 39.3 | 41.0 | 39.95 | 39.99 | 0.492 |
|  | 2 | 20 | 39.5 | 41.2 | 40.20 | 40.29 | 0.472 |
|  | 3 | 10 | 38.9 | 39.7 | 39.30 | 39.30 | 0.211 |
| 19 | 1 | 20 | 39.7 | 41.6 | 40.35 | 40.40 | 0.464 |
|  | 2 | 20 | 39.5 | 41.1 | 40.65 | 40.55 | 0.451 |
|  | 3 | 10 | 39.0 | 39.6 | 39.20 | 39.22 | 0.199 |
| 20 | 1 | 20 | 39.7 | 41.5 | 40.50 | 40.52 | 0.449 |
|  | 2 | 20 | 39.5 | 41.5 | 40.65 | 40.61 | 0.531 |
|  | 3 | 10 | 39.1 | 40.1 | 39.40 | 39.49 | 0.281 |
| 21 | 1 | 20 | 39.6 | 41.1 | 40.30 | 40.22 | 0.413 |
|  | 2 | 20 | 39.4 | 41.0 | 40.10 | 40.12 | 0.371 |
|  | 3 | 10 | 39.2 | 40.2 | 39.45 | 39.59 | 0.351 |
| 22 | 1 | 20 | 39.8 | 41.0 | 40.20 | 40.34 | 0.391 |
|  | 2 | 20 | 39.6 | 41.2 | 40.30 | 40.41 | 0.437 |
|  | 3 | 10 | 39.0 | 40.0 | 39.40 | 39.45 | 0.276 |

[1]Group 1 = PRRS 94881 MLV vaccine at MID, challenged; Group 2 = placebo-treated, challenged; Group 3 = placebo-treated, not challenged.

TABLE 7.20

Rectal Temperature (° C.) Day 23-24

| Day | Group[1] | N | Min. | Max. | Median | Mean | SD |
|---|---|---|---|---|---|---|---|
| 23 | 1 | 20 | 39.6 | 41.2 | 40.25 | 40.36 | 0.454 |
|  | 2 | 20 | 39.5 | 41.6 | 40.60 | 40.60 | 0.482 |
|  | 3 | 10 | 39.3 | 40.1 | 39.70 | 39.68 | 0.290 |
| 24 | 1 | 20 | 39.8 | 41.3 | 40.30 | 40.39 | 0.421 |
|  | 2 | 20 | 39.7 | 41.6 | 40.30 | 40.50 | 0.531 |
|  | 3 | 10 | 39.1 | 40.2 | 39.60 | 39.66 | 0.389 |

[1]Group 1 = PRRS 94881 MLV vaccine at MID, challenged; Group 2 = placebo-treated, challenged; Group 3 = placebo-treated, not challenged

TABLE 7.21

LS Mean Rectal Temperature (° C.) Day 13-20

| Day | Group[1] | LSMean | 95% confidence interval | | p value |
|---|---|---|---|---|---|
| 13 | 1 | 39.77 | 39.648 | 39.892 | <0.0001 |
|  | 2 | 39.39 | 39.268 | 39.512 |  |
|  | Diff. 1-2 | 0.38 | 0.207 | 0.553 |  |
| 14 | 1 | 39.76 | 39.654 | 39.856 | <0.0001 |
|  | 2 | 39.37 | 39.269 | 39.471 |  |
|  | Diff. 1-2 | 0.39 | 0.242 | 0.528 |  |
| 15 | 1 | 39.69 | 39.494 | 39.876 | 0.1241 |
|  | 2 | 39.90 | 39.704 | 40.086 |  |
|  | Diff. 1-2 | −0.21 | −0.480 | 0.060 |  |
| 16 | 1 | 40.68 | 40.514 | 40.836 | <0.0001 |
|  | 2 | 39.77 | 39.609 | 39.931 |  |
|  | Diff. 1-2 | 0.91 | 0.678 | 1.132 |  |
| 17 | 1 | 39.89 | 39.737 | 40.033 | 0.8852 |
|  | 2 | 39.90 | 39.752 | 40.048 |  |
|  | Diff. 1-2 | −0.02 | −0.224 | 0.194 |  |
| 18 | 1 | 39.99 | 39.767 | 40.203 | 0.0528 |
|  | 2 | 40.29 | 40.072 | 40.508 |  |
|  | Diff. 1-2 | −0.31 | −0.614 | 0.004 |  |
| 19 | 1 | 40.40 | 40.188 | 40.602 | 0.3065 |
|  | 2 | 40.55 | 40.338 | 40.752 |  |
|  | Diff. 1-2 | −0.15 | −0.443 | 0.143 |  |
| 20 | 1 | 40.52 | 40.293 | 40.737 | 0.5659 |
|  | 2 | 40.61 | 40.383 | 40.827 |  |
|  | Diff. 1-2 | −0.09 | −0.405 | 0.225 |  |

[1]Group 1 = PRRS 94881 MLV vaccine at MID, challenged; Group 2 = placebo-treated, challenged; Group 3 = placebo-treated, not challenged

TABLE 7.22

LS Mean Rectal Temperature (° C.) Day 21-24

| Day | Group[1] | LSMean | 95% confidence interval | | p value |
|---|---|---|---|---|---|
| 21 | 1 | 40.22 | 40.037 | 40.393 | 0.4489 |
|  | 2 | 40.12 | 39.942 | 40.298 |  |
|  | Diff. 1-2 | 0.10 | −0.156 | 0.346 |  |
| 22 | 1 | 40.34 | 40.152 | 40.528 | 0.6231 |
|  | 2 | 40.41 | 40.217 | 40.593 |  |
|  | Diff. 1-2 | −0.07 | −0.331 | 0.201 |  |
| 23 | 1 | 40.36 | 40.143 | 40.567 | 0.1062 |
|  | 2 | 40.60 | 40.388 | 40.812 |  |
|  | Diff. 1-2 | −0.25 | −0.545 | 0.055 |  |
| 24 | 1 | 40.39 | 40.168 | 40.602 | 0.4526 |
|  | 2 | 40.50 | 40.283 | 40.717 |  |
|  | Diff. 1-2 | −0.12 | −0.422 | 0.192 |  |

[1]Group 1 = PRRS 94881 MLV vaccine at MID, challenged; Group 2 = placebo-treated, challenged; Group 3 = placebo-treated, not challenged Mean and LS Mean rectal temperature for the PRRS 94881 MLV-vaccinated piglets were 39.77° C. on the day before challenge, and ranged from 39.69° C. (D15) to 40.68° C. (D16) after challenge. Mean and LS Mean rectal temperature for the challenge controls were 39.39° C. on the day before challenge and ranged from 39.77° C. (D16) to 40.61° C. (D20) after challenge. Least square Means rectal temperatures were significantly lower for challenge controls compared to PPRS 94881 MLV-vaccinated piglets before challenge administration (D13 and D14) and on D16 after challenge (p<0.0001). There were no other significant differences in rectal temperatures between PRRS 94881 MLV-vaccinated pigs and challenge controls in this study (p≥0.0528). Mean and LS Mean rectal temperatures for the negative controls remained 39.68° C. throughout the study.

Clinical Assessment Post-Vaccination

A summary of the percentage of piglet with at least one positive assessment from D1 through D12 is shown below in Table 7.23.

TABLE 7.23

Percentage of Piglets With at Least One Positive Clinical Assessments from D 1-D 12

| Group[1] | N positive | % positive | 95% CI | | Total | p value |
|---|---|---|---|---|---|---|
| 1 | 0 | 0 | 0.0 | 16.8 | 20 | 1.0000 |
| 2 | 1 | 5 | 0.1 | 24.9 | 20 | |
| 3 | 0 | 0 | 0.0 | 30.8 | 10 | NI |

[1]Group 1 = PRRS 94881 MLV vaccine at MID, challenged; Group 2 = placebo-treated, challenged; Group 3 = placebo-treated, not challenged.
NI = Not included in statistical analysis.

No piglets in either the PRRS 94881 MLV-vaccinated group or the negative controls had any clinical assessment findings during the vaccination period D-1 through D12. Piglet 110 in challenge control group was observed with a sore behind the right front leg beginning on D9. There was no significant difference between PRRS 94881 MLV-vaccinated piglets and challenge controls for this parameter (p=1.0000).

PRRS Serology

A summary of the frequency of piglets with positive PRRS-antibody titers is shown below in Table 7.24.

TABLE 7.24

Frequency of Piglets with Positive PRRS-Antibody Titer by Day

| Day | Group[1] | N positive | % positive | 95% CI | | Total | p value |
|---|---|---|---|---|---|---|---|
| 7 | 1 | 0 | 0 | 0.0 | 16.8 | 20 | NA |
| | 2 | 0 | 0 | 0.0 | 16.8 | 20 | |
| | 3 | 0 | 0 | 0.0 | 30.8 | 10 | NI |
| 14 | 1 | 17 | 85 | 62.1 | 96.8 | 20 | <0.0001 |
| | 2 | 0 | 0 | 0.0 | 16.8 | 20 | |
| | 3 | 0 | 0 | 0.0 | 30.8 | 10 | NI |
| 17 | 1 | 19 | 95 | 75.1 | 99.9 | 20 | <0.0001 |
| | 2 | 0 | 0 | 0.0 | 16.8 | 20 | |
| | 3 | 0 | 0 | 0.0 | 30.8 | 10 | NI |
| 21 | 1 | 20 | 100 | 83.2 | 100.0 | 20 | 0.0012 |
| | 2 | 11 | 55 | 31.5 | 76.9 | 20 | |
| | 3 | 0 | 0 | 0.0 | 30.8 | 10 | NI |
| 24 | 1 | 20 | 100 | 83.2 | 100.0 | 20 | 1.0000 |
| | 2 | 19 | 95 | 75.1 | 99.9 | 20 | |
| | 3 | 0 | 0 | 0.0 | 30.8 | 10 | NI |

[1]Group 1 = PRRS 94881 MLV vaccine at MID, challenged; Group 2 = placebo-treated, challenged; Group 3 = placebo-treated, not challenged.
NA = Not applicable, no analysis conducted.
NI = Not included in statistical analysis.

All piglets in all treatment groups were PRRS-antibody negative on D0 and D7. By D14, 85% of the PRRS 94881 MLV-vaccinated pigs had positive PRRS antibody titers. This number increased to 95% on D17 and was 100% on both D21 and D24. No pigs in the challenge control group developed positive PRRS-antibody titers until D21 (7 days after challenge administration) when 55% of the pigs had positive titers. This value increased to 95% by D24. On D14, D17 and D21, the PRRS 94881 MLV-vaccinated pigs had a significantly higher proportion of pigs with positive PRRS antibody titers compared to the challenge control group (p≤0.0012). No pigs in the negative control group developed PRRS antibody titers during this study.

Discussion/Conclusion

To achieve the study objective, three groups were included in the study design on D0: a vaccine group that received $1 \times 10^{3.82}$ TCID$_{50}$ of PRRS 94881 MLV (Group 1); a challenge control group that received control product (Group 2) and a negative control group (Group 3) that also received control product.

Twenty (20) healthy, PRRS susceptible and seronegative piglets were inoculated IM with 1 ml of PRRS 94881 MLV at approximately 14 days of age. Thirty (20 piglets—challenge control group and 10 piglets—negative control group) PRRS susceptible and seronegative piglets were inoculated IM with 1 ml of control product at approximately 14 days of age.

To determine if an onset of immunity of 2 weeks for PRRS 94881 MLV was achieved, the vaccine group and the challenge control group were challenged 14 days post-vaccination with a heterologous European isolate of PRRSv (isolate 205817) and evaluated post-challenge for relevant reduction in lung lesions.

Validation of the Study (Negative Control Group 3)

To ensure that source piglets were free of PRRSv and that no extraneous PRRSv exposure or cross-contamination among treatment and control groups occurred during the study, a negative control group (Group 3) was included in the study design. Piglets in the negative control group were negative for PRRSv (viremia; qPCR) as well as for PRRS antibodies throughout the study, thus validating this trial.

Validation of the Challenge Model (Challenge Control Group 2)

A challenge model that induces sufficient PRRS clinical disease is necessary to adequately evaluate PRRS vaccine onset of immunity in a laboratory setting. Following inoculation with European PRRS isolate 205817 by the method described earlier, the challenge control group exhibited a mean rectal temperature of ≥40.50° C. on D19, D20 D23 and D24 (≤39.68° C. on same days, negative control group), a mean ADWG of 0.15 kg/day compared with a mean ADWG of 0.34 kg/day for the negative control group from D14 to D24, abnormal behavior, coughing, and a median lung lesion score of 55.2% (0.00%; negative control group). These results highlight that severe PRRS-specific clinical disease was induced in the challenge control group even though the challenge virus titer was slightly lower than the targeted dose, thus validating this challenge model as an adequate clinical laboratory tool to evaluate PRRS vaccine efficacy and more specifically, the OOI of PRRS 94881 MLV.

Determination of Two Week Onset of Immunity of PRRS 94881 MLV (Group 1)

Determination of an onset of immunity (OOI) for PRRS 94881 MLV of 2 weeks post-vaccination was based upon the vaccine group exhibiting a significant (p≤0.05) reduction in post-challenge lung lesions compared with the challenge control group.

Lung lesions were selected as the primary parameter for determination of 2 week OOI because this parameter provides the most clinically relevant and convincing evidence of efficacy when evaluating a new vaccine within the PRRS respiratory challenge model in pigs. Lung lesion development is one of the hallmarks of PRRS respiratory disease in pigs. Lung lesions are often accompanied by subsequent manifestations of secondary PRRSv disease characteristics such as clinical signs, pyrexia, decreased ADWG, etc.

The PRRS 94881 MLV-vaccinated group exhibited a significant reduction in gross lung pathology post-challenge, as evidenced by median total lung lesion score of 27.6% in comparison to the challenge control group, which exhibited a median total lung lesion score of 55.2% (p=0.0002). Thus, an OOI of 2 weeks for PRRS 94881 MLV at dosage of $1 \times 10^{3.82}$ TCID$_{50}$ was established based upon the primary parameter of a significant reduction for lung lesions post-challenge. This result was achieved with a vaccine dose slightly lower than the minimum immunizing dose of $1\times10^{4.5}$ TCID$_{50}$/dose.

Viremia post-challenge was selected as the most important secondary parameter because it represents the level of viral replication and persistence occurring within the host animal upon exposure. A significant ($p\leq0.05$) reduction in viremia would correspond with a PRRS vaccine that induces adequate immunity to limit PRRS pathogenesis within the host. At 3 days post-challenge (D17), PRRS 94881 MLV-vaccinated group was associated with a significant reduction in median viremia (qPCR) compared with the challenge control group (6.72 GE/mL vs. 8.18 GE/mL; $p\leq0.0001$). To further evaluate viremia post-challenge between groups, the quantity of the viral load over a specific duration of time post challenge was calculated, as represented as "area under curve" or AUC. The PRRS 94881 MLV-vaccinated group had a median AUC value from D17 to D24 of 49.52 GE/mL/day; while the challenge control group had a median AUC value of 54.35 GE/ml/day. The median AUC value was significantly lower for the vaccine group compared with the challenge control group from D17 to D24 ($p=0.0039$). Whether viremia was examined 3 days post-challenge or over the course of the post-challenge period, PRRS 94881 MLV administered 2 weeks prior to challenge with a virulent heterologous European strain of PRRS significantly ($p\leq0.05$) reduced viremia after challenge inoculation.

In association with a reduction of PRRS viremia post-challenge, a significant ($p\leq0.05$) reduction in the viral load in lung tissue would also be of great importance from the standpoint of PRRS vaccine immunity. A reduction of viral load in the lung tissue may be associated with reduced viral stability, replication and persistence within the host and may secondarily lead to reduced shedding of PRRSv to other pigs. In this study, lung tissues from PRRS 94881 MLV-vaccinated group had a median lung qPCR result of 7.46 log$_{10}$ GE/mL 10 days post challenge (D24) while the challenge control group had a median lung qPCR result of 7.88 log$_{10}$ GE/mL. The difference between the vaccine group and the challenge control group was significant ($p=0.0101$), thus further supporting an OOI of 2 weeks.

A marked reduction in severity and frequency of clinical signs post-challenge in piglets would also be supportive of PRRS vaccine efficacy and establishment of an OOI of 2 weeks for PRRS 94881 MLV. Abnormal respiration of sufficient severity and frequency was not noted in either group post-challenge and no differences were detected ($p\leq0.1394$). Conversely, the severity and frequency of coughing was about equal between groups and no differences were detected ($p\geq0.0835$). Differences were detected between groups for severity and frequency of abnormal behavior (lethargy) post-challenge. Zero of 20 (0%) and 9 of 20 (45%), PRRS 94881 MLV-vaccinated and challenge control piglets, respectively, exhibited abnormal behavior for at least one day post-challenge ($p=0.0012$). Likewise, the PRRS 94881 MLV-vaccinated group exhibited lower maximum abnormal clinical scores and mean abnormal clinical post-challenge compared with the challenge control group ($p=0.0012$). Total clinical scores (summation of respiration, behavior and coughing scores) were significantly different between groups when maximum scores and mean scores from D15 to D24 were analyzed. Due to the influence of abnormal behavior scores on total scores, the PRRS 94881 MLV-vaccinated group had a significantly lower maximum total score and lower mean total score compared with the challenge control group ($p\leq0.0103$). The differences between groups for severity and frequency of abnormal behavior further support an OOI of 2 weeks post-vaccination.

Pre-challenge, the PRRS 94881 MLV-vaccinated group had slightly higher mean rectal temperatures compared with the challenge control group on D13 (39.77° C. vs. 39.39° C., respectively; $p<0.0001$) and on D14 (39.76° C. vs. 39.37° C., respectively; $p<0.0001$). Although significant ($p\leq0.05$) differences were detected between groups pre-challenge, these differences were not biologically relevant. Post-challenge, the only day in which a significant ($p\leq0.05$) difference was detected between groups for mean rectal temperature was on D16 (2 days post-challenge). On D16, vaccinated and challenge control groups had mean rectal temperatures of 40.68° C. and 39.77° C., respectively, and difference between groups was significant ($p<0.0001$). The mean rectal temperature 4-5 days post challenge elevated above 40° C. and remained above 40° C. until the end of the study for both groups.

The presence of significant abnormal behavior, viremia, lung pathology and viral load in lung tissues due to PRRS in the challenge control group resulted in significant ($p\leq0.05$) differences between groups for ADWG post-challenge. In this study, the vaccinated and challenge control groups had mean ADWG from D14 to D24 of 0.3 kg/day and 0.1 kg/day, respectively, and the difference between groups was significant ($p=0.0003$). A significant ($p\leq0.05$) difference between groups for ADWG post-challenge further supports the establishment of an OOI of 2 weeks post-vaccination.

Post-Vaccination Parameters Examined in this Study

No abnormal clinical assessments related to PRRS 94881 MLV vaccination or control product were observed in piglets following inoculation on D0. One-challenge control piglet exhibited a sore behind the right front leg beginning on D9 which appeared not to be associated with administration of the control product.

All piglets were PRRS ELISA serology negative on D0, thus confirming that all piglets met the inclusion criterion of being PRRS negative upon entry into the study. The majority of piglets receiving PRRS 94881 MLV PRRS sero-converted by D14 and all PRRS-vaccinated piglets were seropositive by 7 days post-challenge (D21). Conversely, the challenge control remained seronegative until 7 days post-challenge, when this group began to demonstrate PRRS seroconversion. The negative control group remained PRRS seronegative throughout the entire study.

At 7 and 14 days post-vaccination, the PRRS 94881 MLV-vaccinated group exhibited mean qPCR results of 3.17 and 3.30, log$_{10}$ GE/mL, respectively. These results highlight that within 2 weeks post-vaccination, a dosage of $1\times10^{3.82}$ TCID$_{50}$ of PRRS 94881 MLV induced sufficient replication of the MLV that is often required to build protective immunity already at 2 weeks after vaccination. Conversely, the challenge control group and the negative control group were negative for PRRSv viremia from D0 to D14.

Conclusion

The significant ($p\leq0.05$) reduction of the lung lesions, clinical signs, replication of the virus in the blood and lungs post-challenge as well as the improvement of the growth performances support the establishment of a 2 week OOI following vaccination with a single dose of PRRS 94881 MLV at $1\times10^{3.82}$ TCID$_{50}$/mL in piglets at approximately 14 days of age.

Example 8 Evaluation of Duration of Immunity of PRRS 94881 MLV in Susceptible Two Week Old Pigs Following Challenge with a Heterologous European Isolate of PRRS at 26 Weeks Post-Vaccination The objective of this vaccination-challenge study was to evaluate the duration of immunity (DOI) 26 weeks after the administration of the vaccine candidate Porcine Reproductive and Respiratory Syndrome, European-derived Isolate 94881, Modified Live Virus (PRRS 94881 MLV) to 14±3 days of age PRRS seronegative pigs. The primary efficacy criterion to satisfy a DOI of 26 weeks post-vaccination was a significant reduction in ($p \leq 0.05$) lung lesions scores (gross or histological) post-challenge in the PRRS 94881 MLV vaccinate group (Group 1) compared to the challenge control group (Group 2).

On Day 0 (D0), 22 pigs assigned to the vaccinate group received 1.0 mL IM of PRRS 94881 MLV ($1 \times 10^{4.27}$ $TCID_{50}$) IM (Group 1), 22 pigs assigned to the challenge control group received 1.0 mL IM of control product (product-matched placebo without PRRS 94881 MLV, Group 2) and 12 pigs assigned to the negative control group also received 1.0 mL IM of control product (Group 3). Groups 1 and 2 were challenged on D179 (Day post-challenge {DPC} 0) with a virulent strain of European PRRSv and pigs were monitored 10 days post-challenge for clinical signs, average daily weight gain, and viremia. Pigs were necropsied on D189 (DPC 10) and gross and histological lung lesions, and lung viral load were determined.

Median gross lung lesion scores on D189 (DPC 10) were 0.1% and 13.8% for PRRS 94881 MLV-vaccinated pigs and challenge controls, respectively ($p<0.0001$). Median histological lung lesion scores on DPC 10 were 6.0 and 19.5 for PRRS 94881 MLV-vaccinated pigs and challenge controls, respectively ($p<0.0001$). PRRS 94881 MLV-vaccinated pigs had significantly less serum viral load at 3, 7 and 10 days post-challenge compared to challenge controls ($p \leq 0.0001$). The post-challenge area under the curve (AUC) analysis for viremia from DPC 0 to DPC 10 and DPC 3 to DPC 10 were also significantly lower for PRRS 94881 MLV-vaccinated pigs (15.54 and 8.88 $\log_{10}$ GE/mL per day, respectively) compared with the challenge control group (44.77 and 36.43 $\log_{10}$ GE/mL per day, respectively, $p<0.0001$). The median qPCR values for lung tissues collected at necropsy were 3.69 and 6.25 $\log_{10}$ GE/mL for PRRS 94881 MLV-vaccinated pigs and challenge controls, respectively ($p<0.0001$). There were no significant differences in clinical signs post-challenge ($p \leq 0.4878$).

A significant reduction ($p \leq 0.05$) of gross and histological lung lesions, viral load in lung tissues collected at necropsy and post-challenge viremia for PRRS 94881 MLV-vaccinated pigs compared to challenge controls supported vaccine efficacy against virulent PRRSv when challenged 26 weeks post-vaccination. The results of this study establish a 26 week duration of immunity post-vaccination in pigs vaccinated with PRRS 94881 MLV at 2 weeks of age. These results were achieved with a vaccine dose of $1 \times 10^{4.27}$ $TCID_{50}$/mL, which was slightly below the minimum immunizing dose ($1 \times 10^{4.5}$ $TCID_{50}$/mL) for this investigational veterinary product.

Objective(s)/Purpose of the Study

The objective of this vaccination-challenge study was to evaluate the duration of immunity (DOI) of Porcine Reproductive and Respiratory Syndrome, European-derived Isolate 94881, Modified Live Virus, Code 19S1.U (PRRS 94881 MLV) administered to PRRS seronegative pigs, 14±3 days of age against a virulent challenge with a heterologous European isolate of PRRS at 26 weeks post-vaccination. The primary efficacy criterion to satisfy a DOI of 26 weeks post-vaccination was a significant reduction ($p \leq 0.05$) in lung lesions scores (gross or histological) post-challenge in the PRRS 94881 MLV vaccinate group (Group 1) compared to the challenge control group (Group 2)

Secondary efficacy parameters included post-vaccination and post-challenge viremia, clinical assessments after vaccination, PRRS serology, post-challenge clinical observations, average daily weight gain (ADWG), rectal temperatures and lung PRRSv quantitation. Viremia post-challenge was considered to be the most important secondary parameter since it is an objective and quantifiable parameter. Rectal temperature and clinical observations were then considered supportive in the DOI definition process. Lastly, growth performance, serology and virus detection in lungs were used as supportive parameters towards the primary parameters in satisfying the study objective.

Schedule of Events

TABLE 8.1

Schedule of Events

| Study Day | Dates | Key Study Event |
|---|---|---|
| −7 | 4 Feb. 2010 | Blood samples collected to screen for negative PRRS ELISA status |
| −2 | 9 Feb. 2010 | Health Exam performed |
| −1 to 21 | 10 Feb. 2010- 4 Mar. 2010 | Clinical Assessments performed daily |
| 0 | 11 Feb. 2010 | Body weights recorded; Blood samples collected for serology and viremia; Group 1 vaccinated with IVP, Groups 2 & 3 vaccinated with CP |
| 7 | 18 Feb. 2010 | Blood samples collected for serology and viremia |
| 13 | 24 Feb. 2010 | Pigs vaccinated with 1.0 mL CIRCOFLEX ® vaccine Microchip inserted SC in the left neck of each study pig |
| 14 | 25 Feb. 2010 | Blood samples collected for serology and viremia |
| 21 | 4 Mar. 2010 | Blood samples collected for serology and viremia |
| 22 to 177 | 5 Mar. 2010- 7 Aug. 2010 | Clinical Assessments at least 3 times/week |
| 28 | 11 Mar. 2010 | Blood samples collected for serology and viremia |
| 56 | 8 Apr. 2010 | Blood samples collected for serology and viremia |
| 84 | 6 May. 2010 | Blood samples collected for serology and viremia |
| 112 | 3 Jun. 2010 | Blood samples collected for serology and viremia |
| 140 | 1 Jul. 2010 | Blood samples collected for serology and viremia |
| 168 | 29 Jul. 2010 | Blood samples collected for serology and viremia |

TABLE 8.1-continued

Schedule of Events

| Study Day | Dates | Key Study Event |
|---|---|---|
| D 178 (DPC −1) to D 189 (DPC 10) | 8 Aug. 2010- 19 Aug. 2010 | Daily Clinical Observations and Rectal Temperatures |
| D 179 (DPC 0) | 9 Aug. 2010 | Body weights collected; Blood samples collected for serology and viremia; Groups 1 and 2 challenged with heterologous European PRRS isolate |
| D 182 (DPC 3) | 12 Aug. 2010 | Blood samples collected for serology and viremia |
| D 186 (DPC 7) | 16 Aug. 2010 | Blood samples collected for serology and viremia |
| D 188 (DPC 9) | 18 Aug. 2010 | Body weights collected |
| D 189 (DPC 10) | 19 Aug. 2010 | Blood samples collected for serology and viremia Pigs euthanized and necropsied Lung lesions scored for pathology Lung tissues collected for virus isolation and histopathology |

Study Design

This was a blinded vaccination-challenge efficacy study conducted in 56 weaned, PRRS seronegative pigs, 14±3 days of age on Day 0 (D0). A summary of the study is provided in Table 8.2.

TABLE 8.2

Study Design

| Group | Number of Pigs on D 0 | Treatment on D 0 (14 ± 3 days of age) | Challenged on D 179 (DPC 0) with 1.0 mL/nostril and 1.0 mL IM of PRRSv 205817 (mean 1 × $10^{6.27}$ $TCID_{50}$/3 mL) | Euthanized and Necropsied on D 189 (DPC 10) |
|---|---|---|---|---|
| 1 | 22 | 1.0 mL IM of IVP (PRRS 94881 MLV) | Yes | Yes |
| 2 | 22 | 1.0 mL IM of Control Product (CP; Placebo matched product without PRRS 94881 MLV) | Yes | Yes |
| 3 | 12 | 1.0 mL IM of CP | No | Yes |

Blinding Criteria

The Study Investigator and designees were blinded to the assigned treatment groups throughout the in-life phase of the study. To maintain this blinding, the BIVI monitor performed the randomization and an individual who did not participate in assessments of the pigs (i.e., clinical assessments, clinical observations or necropsies) administered the assigned IVP and CP treatments on D0. BIVI laboratory personnel were blinded to the treatment each pig received while conducting their respective tasks.

Materials

Investigational Veterinary Product (IVP) and Control Product

TABLE 8.3

IVP

| | |
|---|---|
| Generic Product Name: | Porcine Reproductive and Respiratory Syndrome, Modified Live Virus |
| Strain: | 94881 |
| Production and Formulation: | BIVI-St. Joseph Production produced PRRS 94881 MLV, Lot 390-005 (Section 15.4) in accordance with Outline of Production, Code 19S1.U_ and EU Dossier Part 2b. On D 0, BIVI-Ames reconstituted/diluted PRRS 94881 MLV vaccine Lot 390-005 with Phosphate buffered saline (PBS; Lot 809-002, Section 15.5) to formulate the IVP, Lot No. N257-137 at a target dosage of approximately 1 × $10^{4.5}$ $TCID_{50}$/mL |
| Manufacturer: | Boehringer Ingelheim Vetmedica, Inc. 2621 North Belt Highway St. Joseph, MO 64506, USA |
| Lot No.: | 390-005, reconstituted to Lot N257-137 |
| Expiry Date: | An expiration date of 11 Feb. 2010 was assigned to the IVP for study purposes only. |
| Storage Conditions: | Lyophilized vaccine: 2-8° C. Rehydrated/diluted IVP: on ice |

TABLE 8.3-continued

| | IVP |
|---|---|
| Testing: | PRRS 94881 MLV, Lot 390-005 and PBS, Lot 809-002 were tested by BIVI-QC in accordance with draft Outline of Production (Section 15.1) and as further specified in the EU dossier Part 2.F. BIVI-Ames laboratory personnel tested pre- and post-vaccination aliquots of the IVP for virus titer in accordance with the PRRSv Titer Procedure (Section 15.1). |
| Test Results: | Lot 390-005: Results were satisfactory (Section 15.4). Lot 809-002: Results were satisfactory (Section 15.5). IVP Lot N257-137: Mean titer of $1 \times 10^{4.27}$ TCID$_{50}$/mL (Section 15.7). |
| IVP Retention: | IVP was reconstituted/diluted for immediate use in this study only and was not retained beyond the vaccination event. |

TABLE 8.4

| | CP |
|---|---|
| Generic Product Name: | Placebo |
| Formulation: | BIVI-Production produced lyophilized placebo product containing inert material comprised in the vaccine serial without PRRS 94881 MLV (Lot N240-191-062409, Section 15.6). On D 0, BIVI-Ames reconstituted Lot N240-191-062409 with Phosphate buffered saline (PBS; Lot 809-002, Section 15.5) to formulate the CP, Lot No. N257-134 |
| Manufacturer: | Boehringer Ingelheim Vetmedica, Inc. 2621 North Belt Highway St. Joseph, MO 64506, USA |
| Lot Number: | Lot N240-191-062409, reconstituted to Lot N257-134 |
| Expiry Date: | An expiration date of 11 Feb. 2010 was assigned to the CP for study purposes only. |
| Storage Conditions: | Lyophilized vaccine: 2-8° C. Rehydrated CP: 2-8° C. or on ice |
| Testing: | Lot N240-191-062409 and Lot N257-134 were tested by BIVI-QC for EP sterility |
| Test Results: | Lot N240-191-062409: Results were satisfactory for sterility (Section 15.6). Lot 809-002: Results were satisfactory for sterility CP was determined to be sterile (Section 15.7). |
| CP Retention: | CP was reconstituted for use in this study only and was not retained beyond the vaccination event. |

Challenge Material

TABLE 8.5

| | Challenge Material |
|---|---|
| Name/number of isolate | PRRS isolate 205817 |
| Location and date of isolation incl. clinical symptoms | The European PRRS virus isolate 205817 was derived from isolate 190136 originally obtained from lung tissue of a newborn pig from a farm with typical reproductive signs of PRRS (abortions in sows and weakness in newborn pigs) during an outbreak in Lower Saxony, Germany, in April 2004. The attending veterinarians submitted the lung samples to bioScreen (sample arrived on 21 Apr. 2004) for diagnostic testing. Isolate 190136 was directly propagated on MA 104 cells and a pure culture challenge stock was prepared. A pure culture of isolate 190136 was used to inoculate pigs for evaluation of its ability to reproduce PRRS-specific respiratory disease in a controlled, laboratory trial. Challenged animals exhibited respiratory distress and revealed evidence of interstitial pneumonia upon histopathological examination. PRRS virus successfully re-isolated from lung lesions was given the isolate designation of 205817. Isolate 205817 was directly propagated on MA104 cells and a pure culture challenge stock was prepared for use in future BIVI clinical trials. |
| Formulation: | Challenge virus was propagated in AK-MA104 cells and formulated to a targeted titer of approximately $1 \times 10^6$ TCID$_{50}$/3 mL dose on D 179. An adequate volume of challenge material was prepared. Two x 5 mL aliquots were removed from challenge material for assay purposes before the challenge material was transported to VRI. |

TABLE 8.5-continued

| Challenge Material | |
|---|---|
| Lot Number: | N270-179 |
| Manufacture: | Boehringer Ingelheim Vetmed Inclusion/Exclusion Criteria All pigs enrolled in this study were PRRS ELISA negative (ELISA S/P ratio of <0.4) and were healthy at the time of vaccination (D0) as determined by observation.

Post-Inclusion Removal Criteria

No pigs were removed from the study. Three pigs were found dead before challenge administration. Further results on these three pigs are presented in Section 12.8.

Animal Management and Housing

Pigs were housed at Veterinary Resources, Inc. (VRI) in Cambridge, Iowa for the duration of the study. Pigs were housed in multiple pens (11 or 12 pigs/pen) within each room, with vaccinated (Group 1) and control animals (Groups 2 and 3) housed in uniform but separate rooms to ensure biosecurity. PRRS 94881 MLV pigs were housed in Room CB8 until D78, then in CC1 until D105, and then CC3 for the remainder of the study. Challenge control pigs were housed in Room CC2 throughout the study. Negative control pigs were housed in Room CB6 until D73 and then in CB7 for the remainder of the study. Animal pens were elevated with plastic slatted flooring, with age appropriate feeders and nipple cup drinkers. Each isolation room was constructed identical to the others and all were biohazard level 2 (BL2) compliant, hepafiltered, mechanically ventilated with thermostat regulated temperature control.

Treatment group isolation was necessary in this study as it is well known within the scientific community that PRRSv readily spreads from pig to pig via various mechanisms including aerosolization. This includes avirulent live PRRS vaccines as these biological products include attenuated virus particles that mimic the characteristics of virulent wild-type PRRS without the capability to cause disease. Proper methods were in place to ensure that biosecurity was maintained and that vaccinated animals did not accidentally cross-contaminate non-vaccinated, PRRSv naïve negative control animals.

Appropriate measures were taken by test facility staff to adequately clean and disinfect each room prior to its usage for this study.

Each room in the facility had fans and heaters to aid in sufficient air circulation and heating. The ventilation system was separate yet identical for each room, so air was not shared between rooms.

Feed was stored in bags, free from vermin. Feed and water were available ad libitum. Pigs were fed Lean Metrics Infant Medicated feed (Purina Mills LLC, St. Louis, Mo.) from arrival to D5, when they were switched to Lean Metrics Senior Medicated feed (Purina Mills LLC, St. Louis, Mo.). On D64 the pigs were switched to Lean Metrics Complete 85 feed (Purina Mills LLC, St. Louis, Mo.), and on D82 they were switched to Lean Metrics Complete CE85, T40 (Purina Mills LLC, St. Louis, Mo.), which they were fed for the remainder of the study. Throughout the study, the feeds provided were appropriate for the size, age, and condition of the pigs according to acceptable animal husbandry practices for the region.

The pigs were in good health and nutritional status before initiation of the study as determined by the Study Investigator. During the study, select animals were observed with other conditions, including thinness, coughing, swellings, rough hair coat, depression, abscesses, and poor body condition. The Study Investigator considered all of these conditions to be typical of group housed growing/maturing pigs. These conditions were considered transient or inconsequential and were not treated.

Assessment of Effectiveness

To assess the DOI of PRRS 94881 MLV at 26 weeks post-vaccination, the PRRS 94881 MLV and challenge control groups were challenged on D179 (DPC 0) and lung lesions post-challenge were evaluated 10 days later (DPC 10). A DOI of 26 weeks post-vaccination was achieved if PRRS 94881 MLV group had significantly decreased ($p \leq 0.05$) lung pathology (gross or histological) post-challenge compared with the challenge control group.

The secondary efficacy parameters analyzed between the vaccine group and the challenge control group included post-vaccination and post-challenge viremia, post-challenge clinical observations, post-challenge rectal temperatures, post-vaccination clinical assessments, average daily weight gain (ADWG) and PRRS serology. Viremia post-challenge was considered to be the most important secondary parameter since it is an objective and quantifiable parameter. Rectal temperature and clinical observations were then considered supportive in the DOI definition process. Lastly, growth performance, serology and virus detection in lungs were used as supportive parameters towards the primary parameters in satisfying the study objective.

Criteria for a Valid Test

All pigs were required to be PRRS ELISA negative (ELISA S/P ratio of <0.4) at pre-purchase screening and on D0. Challenge control pigs were required to be negative for PRRS antibodies up to challenge and the negative control group was required to be negative for PRRS antibodies throughout the study.

Primary Outcome Parameter

The primary efficacy outcome variable was lung pathology (gross and histological lesions) at D189 (DPC 10) of the study.

Gross Lung Lesion Scores

On D189, after samples and data were collected and recorded, all remaining study pigs were euthanized following VRI SOP PRC1027 (Section 15.1). Each pig was necropsied in accordance with VRI SOP PRC 1028 (Section 15.1). The thoracic cavity of each pig was exposed by a designee and the heart and lungs were removed. The Study Investigator examined each set of lungs, described any gross pathology and determined the percentage of pathology for each lung lobe. Observations and data were recorded on the Necropsy Report Record form.

Histological Lung Lesion Scores

For each set of lungs, two samples from the Left and Right Apical lobes, the Left and Right Cardiac lobes, the Left and Right Diaphragmatic lobes and the Intermediate lobe were retained. Each lung sample was approximately 1 inch (2.54 cm)×1 inch (2.54 cm). For one set of lung samples, all three samples from the left side were combined into one container; while all three samples from the right side and the Intermediate lung lobe sample were combined into another container. Each container was filled with a sufficient amount of 10% formalin solution. For the other set of lung samples, all three lung samples from the left side were combined into one WHIRLPAK®; while all three samples from the right side and the Intermediate lung lobe sample were combined into another WHIRLPAK®. All containers and WHIRLPAKS® were appropriately labeled with animal number, study number, date of collection, study day, sample type and whether the samples were from the left or right side. Lung samples in formalin were stored at room temperature while lung samples in WHIRLPAKS® were stored on dry ice until transported to BIVI-Ames. Sample collections were recorded on the Necropsy Report Record form. Formalin fixed lung tissue samples and WHIRLPAK® lung samples were transferred to BIVI-Ames. A completed Specimen Delivery Record form was included with each shipment.

Formalin fixed lung tissue samples were held by BIVI-Ames at room temperature until submitted to Iowa State University Veterinary Diagnostic Laboratory (ISU VDL) by BIVI-Ames. Lung samples were handled and processed by ISU VDL personnel according to ISU VDL procedures within one week of necropsy. A single slide was generated for each pig containing seven sections (one each of all seven lung lobes). Each H & E slide was identified with a unique identifier code. ISU VDL provided a computer record containing the study number, identifier codes and associated pig tissues.

Once daily, on the days in which the study slides were read for histopathology, an ISU VDL pathologist (K. Schwartz) first read the EU PRRS positive and negative control slides. Afterwards, the pathologist read the H & E stained lung slides for pneumocytic hypertrophy and hyperplasia, septal infiltration with mononuclear cells, necrotic debris, intra-alveolar accumulation of inflammatory cells and perivascular accumulation of inflammatory cells. Results were recorded in an Excel spreadsheet. The lung histopathology scoring system is shown below in Table 8.8.

TABLE 8.8

Lung Histopathology Scoring System

| Pneumocytic hypertrophy and hyperplasia | Intra-alveolar accumulation of inflammatory cells |
| --- | --- |
| 0 = Not present<br>1 = Mild<br>2 = Moderate<br>3 = Severe | 0 = Not present<br>1 = Mild<br>2 = Moderate<br>3 = Severe |
| Septal infiltration with mononuclear cells | Perivascular accumulation of inflammatory cells |
| 0 = Not present<br>1 = Mild<br>2 = Moderate<br>3 = Severe | 0 = Not present<br>1 = Mild<br>2 = Moderate<br>3 = Severe |
| Necrotic debris | Definitions of scoring system applied to histological parameters (except necrotic debris): |
| 0 = Not present<br>3 = Yes present | 0 = not present: no detectable lesions present within an area of view<br>1 = Mild lesions: few positive cells (1-5 cells/area) present within an area of view<br>2 = Moderate lesions: multiple positive cells (>5 cells/area) at single location or few cells (1-5 cells/area) at multiple locations within an area of view.<br>3 = Severe lesions: multiple positive cells (>5 cells/area) at multiple locations within an area of view. |

Upon completion of the reading of all slides, slides were returned to the Sponsor Representative and will be archived at Boehringer Ingelheim Vetmedica, Inc., St. Joseph, Mo. upon completion of the final report.

Secondary Parameters

Secondary variables included post-vaccination and post-challenge viremia, post-challenge clinical observations, post-challenge rectal temperatures, average daily weight gain (ADWG), lung PRRSv quantitation, post-vaccination clinical assessments, and PRRS serology.

Serum PRRS qPCR

Venous whole blood was collected at pre-purchase and on Days 0, 7, 14, 21, 28, 56, 84, 112, 140, 168, 179 (DPC 0), 182 (DPC 3), 186 (DPC 7), and 189 (DPC 10). Briefly, approximately 2-5 mL of blood was collected from each pig into an appropriate sized serum separator tube (SST). Sample collections were recorded on the Sample Collection Record form. Blood in SSTs was allowed to clot at room temperature. Blood samples were delivered to BIVI-Ames on the day of collection and Specimen Delivery Record form was completed. Blood samples were spun down by BIVI-Ames and serum was harvested, split and transferred to appropriate tubes. Each tube was labeled with the pig's ID number, the study number, the date of collection, the study day and the sample type. At BIVI-Ames, one set of serum samples was held at 2-8° C. and the other set of serum samples was held at −70±10° C.

Clinical Observations Post-Challenge

Pigs were observed for clinical signs of disease from D178 (DPC −1) to D189 (DPC 10). Observations were conducted by the Study Investigator or designees and were recorded on the Clinical Observation Record form. Pigs were observed each day for respiration, behavior and cough based on the clinical observation scoring system outlined below in Table 8.9.

TABLE 8.9

Clinical Observation Scoring System

| Respiration | Behavior | Cough |
| --- | --- | --- |
| 0 = normal respiration | 0 = normal | 0 = no coughing |
| 1 = panting/rapid respiration | 1 = mild to moderate lethargy | 1 = soft or intermittent cough |
| 2 = dyspnea | 2 = severely lethargic or recumbent | 2 = harsh or severe, repetitive cough |
| 3 = dead | 3 = dead | 3 = dead |

Rectal Temperatures

Rectal temperatures were collected by the Study Investigator or designees from D178 (DPC −1) to D189 (DPC 10). Rectal temperatures were recorded in ° C. units on the Clinical Observation Record form.

Body Weight and Average Daily Weight Gain

Individual body weights were collected on D0, D179 (DPC 0) and D188 (DPC 9). Each pig was weighed on a calibrated scale by the Study Investigator or designees. Results were recorded in kg units on the Body Weight Record form. Average daily weight gain was determined from the D179 (DPC 0) to D188 (DPC 9).

Lung PRRS qPCR

Lung tissue samples in WHIRLPAKS® were held at −70±10° C. at BIVI-Ames until shipped to address listed in Section 9.3.1. A completed Specimen Delivery Record form was included with the shipment. bioScreen tested lung samples for PRRSv RNA by qPCR (Section 15.1). Left lung tissues were homogenized and tested. Right lung tissues and intermediate lung lobe samples were homogenized and tested. Results were reported as genome equivalent ($\log_{10}$ GE/mL) for left and right lung samples. A geometric mean titer of right and left GE/mL values will be calculated for each pig by the statistician using SAS program.

Clinical Assessment Post-Vaccination

All pigs were observed for clinical assessments post-vaccination by the Study Investigator or designees. Observations were conducted daily from D-1 to D21 and then at least three times a week from D22 to D177. Observations were recorded on the Clinical Assessment Record form.

PRRS Serology

The serum samples collected at pre-purchase and on Days 0, 7, 14, 21, 28, 56, 84, 112, 140, 168, 179 (DPC 0), 182 (DPC 3), 186 (DPC 7), and 189 (DPC 10) and held at 2-8° C. were tested by BIVI-Ames for PRRS antibodies (Section 15.1). Results were reported as negative (ELISA S/P ratio of <0.4) or positive (ELISA S/P ratio of ≥0.4).

Adverse Events

No adverse events attributed to PRRS 94881 MLV were noted in this study.

Statistical Methods

Experimental Unit

Treatment groups were housed in separate rooms in this study to avoid transmission of PRRSv to non-vaccinated groups. Therefore, room was the experimental unit. However, for the purposes of analyses, possible bias due to confounding "room" and "treatment" effects were ignored, and pig was used as the statistical unit.

Randomization

Fifty-six (56) pigs were randomly assigned to one of three groups. Randomization was performed by the BIVI. At the time of shipment Nos. 140 and 143 (challenge control group), as well as No. 168 (PRRS 94881 MLV group), were culled. Number 178 was randomly selected to replace No. 140, No. 177 was randomly selected to replace 143, and No. 179 was randomly selected to replace No. 168 from a pool of five extra pigs that met the inclusion criteria.

Analysis

Statistical analyses and data summaries were conducted by Dr. rer. hort. Martin Vanselow, Biometrie & Statistik, Zum Siemenshop 21, 30539 Hannover, Germany, +49(0) 511 606 777 650, m.vanselow@t-online.de. Data were analyzed assuming a completely random design structure. The statistical analyses were performed using SAS software release 8.2 or higher (SAS, 2001, Cary, USA/North Carolina, SAS Institute Inc.). PRRS 94881 MLV pig 179 and challenge control pigs 124 and 161 died before challenge and were excluded from post-challenge analyses. All tests on differences were designed as two-sided tests at $\alpha=5\%$. The statistician's report is presented in Section 15.9.

Gross Lung Lesion Scores

The gross lung lesion score for each pig was calculated using the factors shown below in Table 8.10 multiplied by the % pathology for a specific lung lobe. Calculations were conducted using SAS program.

TABLE 8.10

Factors for Calculating Gross Lung Lesion Scores

| Lung lobe | Factor |
|---|---|
| Left apical | 0.05 |
| Left cardiac | 0.06 |
| Left diaphragmatic | 0.29 |
| Right apical | 0.11 |
| Cardiac | 0.10 |
| Right diaphragmatic | 0.34 |
| Right accessory/intermediate | 0.05 |

Treatment groups were compared on differences using the Wilcoxon Mann-Whitney test.

Histological Lung Lesion Scores

Individual histological scores of the lung samples were accumulated per lobe and animal. This sum score was divided by the number of lobes examined per animal. The results were used as single values for the comparison between treatment groups. Treatment groups were tested on differences using the Wilcoxon Mann-Whitney test.

Lung PRRS qPCR

The quantitative PCR data (PRRS viral load [$\log_{10}$ GE/mL]) from lungs collected on D189 were used for comparisons between the treatment groups by the Wilcoxon Mann-Whitney test. The average ($\log_{10}$ GE/mL) of the left and right lung qPCR results were used for the evaluation. Prior to the calculations the analytical result 'not detected' was replaced by $\log_{10}$ GE/mL of 0.0 and 'positive' was replaced by 3.0.

Frequency tables of positive qPCR results were generated. Differences between treatment groups were tested by Fisher's exact test.

Serum PRRS qPCR

The viremia data were evaluated separately for each day of investigation. Additionally, for viral load the areas under the individual response curves between D179 and D189 (AUC 0-10) and between D182 and D189 (AUC 3-10) were analyzed.

The quantitative PCR data (PRRS viral load [$\log_{10}$ GE/mL]) were used for comparisons between the treatment groups by the Wilcoxon Mann-Whitney test. Prior to the calculations the analytical result 'not detected' was replaced by a $\log_{10}$ GE/mL value of 0.0 and 'positive' was replaced by 3.0. The treatment groups were tested on differences using the Wilcoxon Mann-Whitney test.

Frequency tables of positive qPCR results were generated. Differences between treatment groups were tested by Fisher's exact test.

Clinical Observations Post-Challenge

Frequency tables of animals with at least one positive finding between D180 and D189 were generated. Total scores were the summation of respiration score+behavior score+cough score. Calculations were conducted using SAS program. Differences between treatment groups were tested by Fisher's exact test.

The maximum scores and the mean scores per animal from D180 to D189 for respiration, behavior, coughing and for all three added together (total) were used for the statistical evaluation. Differences between treatment groups were tested by the Wilcoxon Mann-Whitney test.

Body Weight and Average Daily Weight Gain

Individual daily weight gains were calculated for the time period between D179 to D188. For each day of investigation and for the time period descriptive statistics were calculated. Differences between treatment groups were tested using analysis of variance and subsequent t-tests. Least squares means of the groups and differences between least squares means with 95% confidence intervals were calculated from the analysis of variance.

Rectal Temperatures

Differences between treatment groups with respect to the original temperature data were tested using analysis of variance and subsequent t-tests. Least squares means of the groups and differences between least squares means with 95% confidence intervals were calculated from the analysis of variance.

Clinical Assessment Post-Vaccination

Frequency tables of animals with at least one positive finding between D1 and D21 were generated. Differences between treatment groups were tested by Fisher's exact test.

PRRS Serology

Frequency tables of positive ELISA results were generated for each time point. Differences between treatment groups were tested by Fisher's exact test.

Results

Gross Lung Lesion Scores

Median gross lung lesion scores on D189 (DPC 10) were 0.1% and 13.8% for the PRRS 94881 MLV-vaccinated group and challenge controls, respectively. The median gross lung lesion score for PRRS-vaccinated pigs was significantly lower than the median gross lung lesion score for the challenge controls ($p<0.0001$). The median gross lung lesion score for the negative control group was 0.0%.

Number 123 (challenge control group) could not be scored for lung lesions on D189 due to diffuse pleuritis and adhesions. Moraxella osloensis, *Staphylococcus wameri*, *Staphyloccous hyicus* and *Pseudomonas* species were isolated from this pig's lung tissues post necropsy.

A summary of group gross lung lesion scores and the associated p-value is shown below in Table 8.11.

TABLE 8.11

Summary of Group Gross Lung Lesion Scores (%) on D 189

| Group[1] | N[3] | Min. | Max. | Median | 95% CI | | Q Range | Mean | p value |
|---|---|---|---|---|---|---|---|---|---|
| 1 | 21 | 0.00 | 12.40 | 0.060 | 0.050 | 0.550 | 0.400 | 1.099 | <0.0001 |
| 2 | 19[2] | 0.06 | 69.20 | 13.800 | 2.690 | 22.650 | 20.850 | 15.842 | |
| 3 | 12 | 0.00 | 0.59 | 0.000 | 0.000 | 0.110 | 0.085 | 0.093 | NI |

[1]Group 1 = PRRS 94881 MLV vaccine; Group 2 = Challenge control group; Group 3 = Negative control group.
[2]No. 123 was not scored due to diffuse pleuritis and adhesions due to bacterial infections.
[3]One PRRS 94881 MLV pig and two challenge control pigs died pre-challenge and were not included in analysis.
NI = Not included in statistical analysis Histological Lung Lesion Scores Median histological lung lesion scores were 6.0 and 19.5 for the PRRS 94881 MLV-vaccinated group and challenge controls, respectively. The median histological lung lesion score for the PRRS-vaccinated group was significantly lower than the median histological lung lesion score for challenge controls ($p<0.0001$). The median histological lung lesion score for the negative control group was 9.0.

A summary of the group histological lung lesion scores and the associated p-value is shown below in Table 8.12.

TABLE 8.12

Summary of Group Histological Lung Lesion Scores

| Group[1] | N[2] | Min. | Max. | Median | 95% CI | | Q Range | Mean | p value |
|---|---|---|---|---|---|---|---|---|---|
| 1 | 21 | 2 | 20 | 6.0 | 3.0 | 8.0 | 5.0 | 6.6 | <0.0001 |
| 2 | 20 | 8 | 47 | 19.5 | 15.0 | 23.0 | 10.0 | 20.2 | |
| 3 | 12 | 0 | 15 | 9.0 | 7.0 | 14.0 | 6.5 | 9.1 | NI |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis
NI = Not included in statistical analysis Lung PRRS qPCR Median qPCR lung values from lung tissues were 3.69 and 6.25 $\log_{10}$ GE/mL for PRRS 94881 MLV-vaccinated pigs and challenge controls, respectively. The median qPCR value for PRRS 94881 MLV-vaccinated pigs was significantly lower than the median qPCR value for challenge controls (p<0.0001). No PRRSv RNA was detected in lung samples of any negative control pigs.

A summary of group lung qPCR values and test result (p value) is below in Table 8.13.

TABLE 8.13

Summary of Group Lung qPCR (mean $\log_{10}$ GE/mL) Values

| Group[1] | N[2] | Min. | Max. | Median | 95% CI | | Q Range | Mean | p value |
|---|---|---|---|---|---|---|---|---|---|
| 1 | 21 | 0.00 | 6.83 | 3.69 | 1.50 | 5.21 | 3.18 | 3.36 | <0.0001 |
| 2 | 20 | 4.80 | 7.40 | 6.25 | 5.62 | 6.68 | 1.26 | 6.22 | |
| 3 | 12 | 0.00 | 0.00 | 0.00 | 0.00 | 0.00 | 0.00 | 0.00 | NI |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis.
NI = Not included in statistical analysis PRRSv RNA was detected in lung tissues of 90% and 100% of PRRS 94881 MLV-vaccinated pigs and challenge control pigs, respectively. There was no statistical difference between the vaccinated group and challenge controls (p=0.4878).

A summary of group frequency of PRRS qPCR positive lung tissues from pigs at necropsy is shown below in Table 8.14.

TABLE 8.14

Group Frequency of PRRSv qPCR Positive Lung Tissues

| Group[1] | N Positive | % Positive | 95% CI | | Total Number[2] | p value |
|---|---|---|---|---|---|---|
| 1 | 19 | 90 | 69.6 | 98.8 | 21 | 0.4878 |
| 2 | 20 | 100 | 83.2 | 100.0 | 20 | |
| 3 | 0 | 0 | 0.0 | 26.5 | 12 | NI |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis.
NI = Not included in statistical analysis Serum PRRS qPCR PRRSv RNA was not detected in the serum of any pigs on D0. Post-vaccination, PRRS 94881 MLV-vaccinated pigs had median values of 3.00, 0, 0, 3.00, 0, 0, 0, 0 and 0 $\log_{10}$ GE/mL on D7, D14, D21, D28, D56, D84, D112, D140 and D168 respectively. The values were significantly higher than challenge controls on D7, D14, D21 and D28 (p≤0.0013), as challenge controls did not have any PRRSv RNA detected until D182 (DPC 3).

PRRSv RNA was not detected in the serum of any pigs on D179 (DPC 0). Post-challenge, PRRS 94881 MLV-vaccinated pigs had median values of 4.44, 0 and 0 $\log_{10}$ GE/mL on D182 (DPC 3), D186 (DPC 7), and D189 (DPC 10), respectively, compared with 5.88, 5.30 and 4.24 $\log_{10}$ GE/mL for challenge controls on the same days. Median values for the challenge controls were higher than the PRRS 94881 MLV group on all post-challenge days (p≤0.0001).

No PRRSv RNA was detected in serum from any negative control pig during this study.

The median AUC values for PRRS 94881 MLV-vaccinated pigs were 15.54 and 8.88 $\log_{10}$ GE/mL per day from DPC 0 to DPC 10 and from DPC 3 to DPC 10, respectively. In contrast, the median AUC values for challenge controls were 44.77 and 36.43 $\log_{10}$ GE/mL per day from DPC 0 to DPC 10 and from DPC 3 to DPC 10, respectively. Median values for the PRRS MLV group were significantly lower than median values for the challenge controls for both periods (p<0.0001).

Summaries of serum PRRS qPCR data are shown below in Tables 8.15 and 8.16.

TABLE 8.15

Summary of Serum PRRS qPCR Results ($\log_{10}$ GE/mL) from D 0 to D 168

| Day | Group[1] | N | Min. | Max. | Median | 95% CI | | QRange | Mean | p value |
|---|---|---|---|---|---|---|---|---|---|---|
| 0 | 1 | 22 | 0.00 | 0.00 | 0.00 | 0.00 | 0.00 | 0.00 | 0.00 | 1.0000 |
| | 2 | 22 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 7 | 1 | 21 | 3.00 | 4.63 | 3.00 | 3.00 | 3.00 | 0.00 | 3.23 | <0.0001 |
| | 2 | 22 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 14 | 1 | 21 | 0.00 | 3.00 | 0.00 | 0.00 | 3.00 | 3.00 | 1.43 | 0.0005 |
| | 2 | 21 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 21 | 1 | 21 | 0.00 | 3.00 | 0.00 | 0.00 | 3.00 | 3.00 | 1.29 | 0.0013 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 28 | 1 | 21 | 0.00 | 3.88 | 3.00 | 0.00 | 3.00 | 3.00 | 1.93 | <0.0001 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 56 | 1 | 21 | 0.00 | 3.00 | 0.00 | 0.00 | 0.00 | 0.00 | 0.57 | 0.1069 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |

TABLE 8.15-continued

Summary of Serum PRRS qPCR Results (log₁₀ GE/mL) from D 0 to D 168

| Day | Group[1] | N | Min. | Max. | Median | 95% CI | | QRange | Mean | p value |
|---|---|---|---|---|---|---|---|---|---|---|
| 84 | 1 | 21 | 0.00 | 0.00 | 0.00 | 0.00 | 0.00 | 0.00 | 0.00 | 1.0000 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 112 | 1 | 21 | 0.00 | 0.00 | 0.00 | 0.00 | 0.00 | 0.00 | 0.00 | 1.0000 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 140 | 1 | 21 | 0.00 | 0.00 | 0.00 | 0.00 | 0.00 | 0.00 | 0.00 | 1.0000 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |
| 168 | 1 | 21 | 0.00 | 0.00 | 0.00 | 0.00 | 0.00 | 0.00 | 0.00 | 1.0000 |
| | 2 | 20 | 0.00 | 0.00 | 0.00 | 0.00 | 0.00 | 0.00 | 0.00 | |
| | 3 | 12 | 0.00 | 0.00 | 0.00 | 0.00 | 0.00 | 0.00 | 0.00 | NI |

[1]Group 1 = PRRS 94881 MLV vaccine; Group 2 = Challenge control group; Group 3 = Negative control group.
NI = Not included in statistical analysis

TABLE 8.16

Summary of Serum PRRS qPCR Results (log₁₀ GE/mL) from D 179 to D 189

| Day | Group[1] | N | Min. | Max. | Median | 95% CI | | QRange | Mean | p value |
|---|---|---|---|---|---|---|---|---|---|---|
| 179 | 1 | 21 | 0.00 | 0.00 | 0.00 | 0.00 | 0.00 | 0.00 | 0.00 | 1.0000 |
| (DPC | 2 | 20 | 0.00 | 0.00 | 0.00 | 0.00 | 0.00 | 0.00 | 0.00 | |
| 0) | 3 | 12 | 0.00 | 0.00 | 0.00 | 0.00 | 0.00 | 0.00 | 0.00 | NI |
| 182 | 1 | 21 | 3.00 | 5.58 | 4.44 | 3.93 | 5.28 | 1.51 | 4.42 | <0.0001 |
| (DPC | 2 | 20 | 5.09 | 6.33 | 5.88 | 5.75 | 6.00 | 0.32 | 5.81 | |
| 3) | 3 | 12 | 0.00 | 0.00 | 0.00 | 0.00 | 0.00 | 0.00 | 0.00 | NI |
| 186 | 1 | 21 | 0.00 | 3.74 | 0.00 | 0.00 | 0.00 | 0.00 | 0.61 | <0.0001 |
| (DPC | 2 | 20 | 3.66 | 6.57 | 5.30 | 4.86 | 5.69 | 1.08 | 5.30 | |
| 7) | 3 | 12 | 0.00 | 0.00 | 0.00 | 0.00 | 0.00 | 0.00 | 0.00 | NI |
| 189 | 1 | 21 | 0.00 | 0.00 | 0.00 | 0.00 | 0.00 | 0.00 | 0.00 | <0.0001 |
| (DPC | 2 | 20 | 0.00 | 5.88 | 4.24 | 3.71 | 4.42 | 1.18 | 3.97 | |
| 10) | 3 | 12 | 0.00 | 0.00 | 0.00 | 0.00 | 0.00 | 0.00 | 0.00 | NI |
| AUC | 1 | 21 | 10.50 | 31.22 | 15.54 | 13.76 | 19.53 | 5.95 | 17.61 | <0.0001 |
| DPC | 2 | 20 | 36.86 | 52.16 | 44.77 | 43.23 | 48.03 | 6.24 | 44.84 | |
| 0-10 | 3 | 12 | 0.00 | 0.00 | 0.00 | 0.00 | 0.00 | 0.00 | 0.00 | NI |
| AUC | 1 | 21 | 6.00 | 23.45 | 8.88 | 7.86 | 11.16 | 3.40 | 10.97 | <0.0001 |
| DPC 3- | 2 | 20 | 27.77 | 43.02 | 36.43 | 34.60 | 38.53 | 5.23 | 36.12 | |
| DPC 10 | 3 | 12 | 0.00 | 0.00 | 0.00 | 0.00 | 0.00 | 0.00 | 0.00 | NI |

[1]Group 1 = PRRS 94881 MLV vaccine; Group 2 = Challenge control group; Group 3 = Negative control group.
NI = Not included in statistical analysis.
AUC = Area under the curve; log₁₀ GE/mL per day Post-vaccination, the PRRS 94881 MLV group had significantly higher proportions of qPCR positive pigs on D7, D14, D21 and D28 compared with the challenge control group. (p≤0.0013). No significant difference was detected between groups on D56 for the proportion of qPCR positive pigs (p=0.1069).

On D182 (DPC 3), 100% of pigs in the PRRS 94881 MLV and challenge control groups were qPCR positive (no test conducted). On D186 (DPC 7) and D189 (DPC 10), the PRRS MLV group had significantly lower proportion of qPCR positive pigs compared with the challenge control group (<0.0001).

Summaries of group proportions of qPCR positive data are shown below in Tables 8.17 and 8.18.

TABLE 8.17

Summary of Group Proportion of Serum qPCR Positive Results Post-Vaccination

| Day | Group[1] | N Positive | % Positive | 95% CI | | Total Number | p value |
|---|---|---|---|---|---|---|---|
| 0 | 1 | 0 | 0 | 0.0 | 15.4 | 22 | n.a. |
| | 2 | 0 | 0 | 0.0 | 15.4 | 22 | |
| | 3 | 0 | 0 | 0.0 | 26.5 | 12 | NI |

TABLE 8.17-continued

Summary of Group Proportion of Serum qPCR Positive Results Post-Vaccination

| Day | Group[1] | N Positive | % Positive | 95% CI | | Total Number | p value |
|---|---|---|---|---|---|---|---|
| 7 | 1 | 21 | 100 | 83.9 | 100.0 | 21 | <0.0001 |
| | 2 | 0 | 0 | 0.0 | 15.4 | 22 | |
| | 3 | 0 | 0 | 0.0 | 26.5 | 12 | NI |
| 14 | 1 | 10 | 48 | 25.7 | 70.2 | 21 | 0.0005 |
| | 2 | 0 | 0 | 0.0 | 16.1 | 21 | |
| | 3 | 0 | 0 | 0.0 | 26.5 | 12 | NI |
| 21 | 1 | 9 | 43 | 21.8 | 66.0 | 21 | 0.0013 |
| | 2 | 0 | 0 | 0.0 | 16.8 | 20 | |
| | 3 | 0 | 0 | 0.0 | 26.5 | 12 | NI |
| 28 | 1 | 13 | 62 | 38.4 | 81.9 | 21 | <0.0001 |
| | 2 | 0 | 0 | 0.0 | 16.8 | 20 | |
| | 3 | 0 | 0 | 0.0 | 26.5 | 12 | NI |
| 56 | 1 | 4 | 19 | 5.4 | 41.9 | 21 | 0.1069 |
| | 2 | 0 | 0 | 0.0 | 16.8 | 20 | |
| | 3 | 0 | 0 | 0.0 | 26.5 | 12 | NI |
| 84 | 1 | 0 | 0 | 0.0 | 16.1 | 21 | n.a. |
| | 2 | 0 | 0 | 0.0 | 16.8 | 20 | |
| | 3 | 0 | 0 | 0.0 | 26.5 | 12 | NI |
| 112 | 1 | 0 | 0 | 0.0 | 16.1 | 21 | n.a. |
| | 2 | 0 | 0 | 0.0 | 16.8 | 20 | |
| | 3 | 0 | 0 | 0.0 | 26.5 | 12 | NI |

TABLE 8.17-continued

Summary of Group Proportion of Serum qPCR Positive Results Post-Vaccination

| Day | Group[1] | N Positive | % Positive | 95% CI | | Total Number | p value |
|---|---|---|---|---|---|---|---|
| 140 | 1 | 0 | 0 | 0.0 | 16.1 | 21 | n.a. |
|  | 2 | 0 | 0 | 0.0 | 16.8 | 20 |  |
|  | 3 | 0 | 0 | 0.0 | 26.5 | 12 | NI |
| 168 | 1 | 0 | 0 | 0.0 | 16.1 | 21 | n.a. |
|  | 2 | 0 | 0 | 0.0 | 16.8 | 20 |  |
|  | 3 | 0 | 0 | 0.0 | 26.5 | 12 | NI |

[1] Group 1 = PRRS 94881 MLV vaccine; Group 2 = Challenge control group; Group 3 = Negative control group.
n.a. = no test conducted;
NI = Not included in statistical analysis

TABLE 8.18

Summary of Group Proportion of Serum qPCR Positive Results Post-Challenge

| Day | Group[1] | N Positive | % Positive | 95% CI | | Total Number | p value |
|---|---|---|---|---|---|---|---|
| 179 (DPC 0) | 1 | 0 | 0 | 0.0 | 16.1 | 21 | n.a. |
|  | 2 | 0 | 0 | 0.0 | 16.8 | 20 |  |
|  | 3 | 0 | 0 | 0.0 | 26.5 | 12 | NI |
| 182 (DPC 3) | 1 | 21 | 100 | 83.9 | 100.0 | 21 | n.a. |
|  | 2 | 20 | 100 | 83.2 | 100.0 | 20 |  |
|  | 3 | 0 | 0 | 0.0 | 26.5 | 12 | NI |
| 186 (DPC 7) | 1 | 4 | 19 | 5.4 | 41.9 | 21 | <0.0001 |
|  | 2 | 20 | 100 | 83.2 | 100.0 | 20 |  |
|  | 3 | 0 | 0 | 0.0 | 26.5 | 12 | NI |
| 189 (DPC 10) | 1 | 0 | 0 | 0.0 | 16.1 | 21 | <0.0001 |
|  | 2 | 19 | 95 | 75.1 | 99.9 | 20 |  |
|  | 3 | 0 | 0 | 0.0 | 26.5 | 12 | NI |

[1] Group 1 = PRRS 94881 MLV vaccine; Group 2 = Challenge control group; Group 3 = Negative control group.
n.a. = no test conducted;
NI = Not included in statistical analysis

Clinical Observations Post-Challenge

Abnormal respiration was not observed in any PRRS 94881 MLV-vaccinated pigs after challenge, compared with one—challenge control pig (No. 149) which demonstrated a score of "1" on D185 (DPC 6). No difference was detected between groups for the percentage of pigs that demonstrated abnormal respiration for at least one day post-challenge (p=0.4878).

Abnormal behavior and coughing were not observed post-challenge in any PRRS 94881 MLV-vaccinated pigs or in challenge control pigs.

The percentages of pigs with total clinical scores >0 for at least one day post-challenge were 0% and 5% for the PRRS 94881 MLV-vaccinated group and the challenge control group, respectively. These values were not significantly different (p=0.4878).

No clinical signs were observed in the negative control group from D179 to D189.

A summary of group frequencies of pigs with at least one positive clinical observation score during the post-challenge period is shown below in Table 8.19.

TABLE 8.19

Summary of Group Frequencies of Pigs with at least One Positive Clinical Observation Score Post-challenge

| Parameter | Group[1] | N Positive | % Positive | 95% CI | | Total Number[2] | p value |
|---|---|---|---|---|---|---|---|
| Respiration | 1 | 0 | 0 | 0.0 | 16.1 | 21 | 0.4878 |
|  | 2 | 1 | 5 | 0.1 | 24.9 | 20 |  |
|  | 3 | 0 | 0 | 0.0 | 26.5 | 12 | NI |
| Behavior | 1 | 0 | 0 | 0.0 | 16.1 | 21 | NA |
|  | 2 | 0 | 0 | 0.0 | 16.8 | 20 |  |
|  | 3 | 0 | 0 | 0.0 | 26.5 | 12 | NI |
| Coughing | 1 | 0 | 0 | 0.0 | 16.1 | 21 | NA |
|  | 2 | 0 | 0 | 0.0 | 16.8 | 20 |  |
|  | 3 | 0 | 0 | 0.0 | 26.5 | 12 | NI |
| Total | 1 | 0 | 0 | 0.0 | 16.1 | 21 | 0.4878 |
|  | 2 | 1 | 5 | 0.1 | 24.9 | 20 |  |
|  | 3 | 0 | 0 | 0.0 | 26.5 | 12 | NI |

[1] Group 1 = PRRS 94881 MLV vaccine; Group 2 = Challenge control group; Group 3 = Negative control group.
[2] One PRRS 94881 MLV pig and two challenge control pigs died pre-challenge and were not included in analysis.
NI = Not included in statistical analysis;
NA = test not applicable due to lack of variability There was no difference between groups for maximum respiration scores or maximum total scores post-challenge (p=0.4878).

A summary of the group maximum clinical observation scores for the post-challenge period (DPC 1 through DPC 10) is shown below in Table 8.20.

TABLE 8.20

Summary of Group Post-Challenge Maximum Clinical Scores

| Parameter | Group[1] | N[2] | Min. | Max. | Median | 95% CI | | QRange | Mean | p value |
|---|---|---|---|---|---|---|---|---|---|---|
| Respiration | 1 | 21 | 0 | 0 | 0 | 0 | 0 | 0 | 0.0 | 0.4878 |
|  | 2 | 20 | 0 | 1 | 0 | 0 | 0 | 0 | 0.1 |  |
|  | 3 | 12 | 0 | 0 | 0 | 0 | 0 | 0 | 0.0 | NI |
| Behavior | 1 | 21 | 0 | 0 | 0 | 0 | 0 | 0 | 0.0 | 1.0000 |
|  | 2 | 20 | 0 | 0 | 0 | 0 | 0 | 0 | 0.0 |  |
|  | 3 | 12 | 0 | 0 | 0 | 0 | 0 | 0 | 0.0 | NI |
| Coughing | 1 | 21 | 0 | 0 | 0 | 0 | 0 | 0 | 0.0 | 1.0000 |
|  | 2 | 20 | 0 | 0 | 0 | 0 | 0 | 0 | 0.0 |  |
|  | 3 | 12 | 0 | 0 | 0 | 0 | 0 | 0 | 0.0 | NI |
| Total | 1 | 21 | 0 | 0 | 0 | 0 | 0 | 0 | 0.0 | 0.4878 |
|  | 2 | 20 | 0 | 1 | 0 | 0 | 0 | 0 | 0.1 |  |
|  | 3 | 12 | 0 | 0 | 0 | 0 | 0 | 0 | 0.0 | NI |

[1] Group 1 = PRRS 94881 MLV vaccine; Group 2 = Challenge control group; Group 3 = Negative control group.
[2] One PRRS 94881 MLV pig and two challenge control pigs died pre-challenge and were not included in analysis.
NI = Not included in statistical analysis Mean clinical observation scores followed a pattern similar to the percentage of pigs with positive clinical scores. There were no significant differences between the PRRS 94881 MLV-vaccinated group and the challenge control group (p≤0.4878).

A summary of the group mean clinical observation scores for the post-challenge period (DPC 1 through DPC 10) is shown below in Table 8.21.

TABLE 8.21

Summary of Group Post-Challenge Mean Clinical Scores

| Parameter | Group[1] | N[2] | Min. | Max. | Median | 95% CI | | QRange | Mean | p value |
|---|---|---|---|---|---|---|---|---|---|---|
| Respiration | 1 | 21 | 0.0 | 0.0 | 0.00 | 0.00 | 0.00 | 0.00 | 0.00 | 0.4878 |
| | 2 | 20 | 0.0 | 0.1 | 0.00 | 0.00 | 0.00 | 0.00 | 0.01 | |
| | 3 | 12 | 0.0 | 0.0 | 0.00 | 0.00 | 0.00 | 0.00 | 0.00 | NI |
| Behavior | 1 | 21 | 0.0 | 0.0 | 0.00 | 0.00 | 0.00 | 0.00 | 0.00 | 1.0000 |
| | 2 | 20 | 0.0 | 0.0 | 0.00 | 0.00 | 0.00 | 0.00 | 0.00 | |
| | 3 | 12 | 0.0 | 0.0 | 0.00 | 0.00 | 0.00 | 0.00 | 0.00 | NI |
| Coughing | 1 | 21 | 0.0 | 0.0 | 0.00 | 0.00 | 0.00 | 0.00 | 0.00 | 1.0000 |
| | 2 | 20 | 0.0 | 0.0 | 0.00 | 0.00 | 0.00 | 0.00 | 0.00 | |
| | 3 | 12 | 0.0 | 0.0 | 0.00 | 0.00 | 0.00 | 0.00 | 0.00 | NI |
| Total | 1 | 21 | 0.0 | 0.0 | 0.00 | 0.00 | 0.00 | 0.00 | 0.00 | 0.4878 |
| | 2 | 20 | 0.0 | 0.1 | 0.00 | 0.00 | 0.00 | 0.00 | 0.01 | |
| | 3 | 12 | 0.0 | 0.0 | 0.00 | 0.00 | 0.00 | 0.00 | 0.00 | NI |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis.
NI = Not included in statistical analysis Body Weight and Average Daily Weight Gain The difference between groups was not significant (p=0.2389). On D179 (DPC 0), mean and LS Mean body weights were 134.6 and 128.2 kg for the PRRS 94881 MLV group and the challenge control group, respectively. The difference was not significantly different (p=0.1090). On D188 (DPC 9), the mean and LS Mean body weights were 138.3 and 130.3 kg for the PRRS 94881 MLV group and the challenge control group, respectively. The body weight for the vaccinated group was significantly higher than the challenge control group on D188 (p=0.0455).

LS Mean ADWGs for the challenge period (DPC 0 through DPC 9) were 0.4 and 0.2 kg/d for the PRRS 94881 MLV group and the challenge control group, respectively. These values were not significantly different (p=0.1041).

Negative control pigs had mean body weights of 2.7, 117.2 and 120.0 kg on D0, D179 and D188, respectively. The ADWG for the negative control group from D179 to D188 was 0.5 kg/d.

A summary of the group mean body weights on D0, D179 (DPC 0) and D188 (DPC 9) and ADWG from DPC 0 to DPC 9 are shown below in Table 8.22. A summary of LS Mean and statistical analysis of body weights and ADWG for the PRRS 94881 MLV group and the challenge control group is shown below in Table 8.23.

TABLE 8.22

Summary of Group Body Weight and Average Daily Weight Gain (kg and kg/d)

| Day(s) | Group[1] | N | Min. | Max. | Median | Mean | SD |
|---|---|---|---|---|---|---|---|
| 0 Body Weights | 1 | 22 | 2.8 | 5.4 | 4.00 | 3.96 | 0.730 |
| | 2 | 22 | 2.4 | 4.8 | 3.75 | 3.72 | 0.547 |
| | 3 | 12 | 2.7 | 4.5 | 3.60 | 3.71 | 0.552 |
| D 179 Body Weights (DPC 0) | 1 | 21 | 108.5 | 155.0 | 136.60 | 134.57 | 12.737 |
| | 2 | 20 | 103.3 | 152.6 | 130.10 | 128.15 | 12.288 |
| | 3 | 12 | 117.2 | 156.5 | 133.05 | 134.61 | 10.900 |
| D 188 Body Weights (DPC 9) | 1 | 21 | 112.2 | 157.8 | 141.50 | 138.28 | 12.879 |
| | 2 | 20 | 109.4 | 150.9 | 131.90 | 130.27 | 11.896 |
| | 3 | 12 | 120.0 | 162.5 | 136.60 | 139.11 | 11.922 |
| ADWG DPC 0 to DPC 9 | 1 | 21 | −0.422 | 0.956 | 0.4111 | 0.4124 | 0.31653 |
| | 2 | 20 | −0.589 | 0.844 | 0.2889 | 0.2350 | 0.36530 |
| | 3 | 12 | −1.600 | 2.656 | 0.5111 | 0.5000 | 0.92391 |

[1]Group 1 = PRRS 94881 MLV vaccine; Group 2 = Challenge control group; Group 3 = Negative control group

TABLE 8.23

Summary of Group LS Mean Body Weight and Daily Gain (kg and kg/d)

| Day(s) | Group[1] | LS Mean | 95% confidence interval | | p value |
|---|---|---|---|---|---|
| 0 Body Weights | 1 | 3.96 | 3.674 | 4.241 | 0.2389 |
| | 2 | 3.72 | 3.446 | 4.000 | |
| | Diff. 1-2 | 0.23 | −0.162 | 0.631 | |

TABLE 8.23-continued

Summary of Group LS Mean Body Weight
and Daily Gain (kg and kg/d)

| Day(s) | Group[1] | LS Mean | 95% confidence interval | | p value |
|---|---|---|---|---|---|
| D 179 Body | 1 | 134.57 | 129.040 | 140.093 | 0.1090 |
| Weights | 2 | 128.15 | 122.487 | 133.813 | |
| (DPC 0) | Diff. 1-2 | 6.42 | −1.496 | 14.329 | |
| D 188 Body | 1 | 138.28 | 132.800 | 143.756 | 0.0455 |
| Weights | 2 | 130.27 | 124.652 | 135.878 | |
| (DPC 9) | Diff. 1-2 | 8.01 | 0.170 | 15.856 | |
| ADWG | 1 | 0.4124 | 0.26180 | 0.56297 | 0.1041 |
| DPC 0 to | 2 | 0.2350 | 0.08070 | 0.38930 | |
| DPC 9 | Diff. 1-2 | 0.1774 | −0.03822 | 0.39299 | |

[1]Group 1 = PRRS 94881 MLV vaccine; Group 2 = Challenge control group; Group 3 = Negative control group Rectal Temperatures Mean rectal temperature for the PRRS 94881 MLV group was 39.3° C. on the day of challenge (D179), and means ranged from 39.1° C. (D189, DPC 10) to 39.8° C. (D181, DPC 2) after challenge. Mean rectal temperature for the challenge control group was 39.1° C. on the day of challenge, and means ranged from 39.1° C. (D183, DPC 4) to 39.9° C. (D182, DPC 3) after challenge. Mean rectal temperatures for negative control group remained 39.3° C. throughout the same time period.

A summary of group rectal temperatures is shown below in Table 8.24.

TABLE 8.24

Summary of Group Rectal Temperature (°
C.) Days D 179 (DPC 0) through D 189 (DPC 10)

| Day | Group[1] | N[2] | Min. | Max. | Median | Mean | SD |
|---|---|---|---|---|---|---|---|
| D 179 | 1 | 21 | 38.5 | 40.0 | 39.40 | 39.33 | 0.360 |
| (DPC | 2 | 20 | 38.6 | 40.0 | 39.00 | 39.07 | 0.380 |
| 0) | 3 | 12 | 38.8 | 39.7 | 39.30 | 39.27 | 0.257 |
| D 180 | 1 | 21 | 38.7 | 40.4 | 39.40 | 39.46 | 0.370 |
| (DPC | 2 | 20 | 38.9 | 40.9 | 39.60 | 39.61 | 0.527 |
| 1) | 3 | 12 | 38.8 | 39.5 | 39.00 | 39.09 | 0.227 |
| D 181 | 1 | 21 | 39.0 | 41.0 | 39.80 | 39.82 | 0.473 |
| (DPC | 2 | 20 | 38.6 | 40.5 | 39.35 | 39.42 | 0.487 |
| 2) | 3 | 12 | 38.8 | 39.2 | 38.80 | 38.90 | 0.141 |
| D 182 | 1 | 21 | 38.5 | 40.6 | 39.50 | 39.52 | 0.542 |
| (DPC | 2 | 20 | 39.0 | 41.1 | 40.05 | 39.86 | 0.588 |
| 3) | 3 | 12 | 38.7 | 39.4 | 39.00 | 39.05 | 0.254 |
| D 183 | 1 | 21 | 38.9 | 40.8 | 39.50 | 39.52 | 0.411 |
| (DPC | 2 | 20 | 38.4 | 40.3 | 39.00 | 39.08 | 0.508 |
| 4) | 3 | 11 | 38.8 | 39.4 | 39.10 | 39.08 | 0.209 |
| D 184 | 1 | 21 | 39.0 | 40.3 | 39.70 | 39.72 | 0.360 |
| (DPC | 2 | 20 | 38.7 | 39.7 | 39.10 | 39.15 | 0.302 |
| 5) | 3 | 12 | 38.8 | 39.5 | 39.10 | 39.10 | 0.191 |
| D 185 | 1 | 21 | 39.1 | 40.5 | 39.60 | 39.66 | 0.376 |
| (DPC | 2 | 20 | 38.9 | 40.9 | 39.25 | 39.48 | 0.546 |
| 6) | 3 | 12 | 38.4 | 39.4 | 38.85 | 38.88 | 0.313 |
| D 186 | 1 | 21 | 38.1 | 40.4 | 39.20 | 39.22 | 0.413 |
| (DPC | 2 | 20 | 38.6 | 40.4 | 39.35 | 39.39 | 0.479 |
| 7) | 3 | 12 | 38.5 | 39.6 | 38.90 | 38.98 | 0.328 |
| D 187 | 1 | 21 | 38.8 | 39.9 | 39.20 | 39.23 | 0.290 |
| (DPC | 2 | 20 | 38.8 | 40.8 | 39.45 | 39.58 | 0.573 |
| 8) | 3 | 12 | 38.5 | 39.5 | 38.85 | 38.93 | 0.296 |
| D 188 | 1 | 21 | 38.8 | 39.9 | 39.10 | 39.17 | 0.288 |
| (DPC | 2 | 20 | 38.3 | 40.5 | 39.00 | 39.20 | 0.598 |
| 9) | 3 | 12 | 38.4 | 39.1 | 38.85 | 38.85 | 0.173 |
| D 189 | 1 | 21 | 38.7 | 39.7 | 39.00 | 39.06 | 0.256 |
| (DPC | 2 | 20 | 39.0 | 40.8 | 39.50 | 39.51 | 0.408 |
| 10) | 3 | 12 | 38.6 | 39.3 | 39.05 | 39.00 | 0.226 |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis Least square Mean rectal temperatures were significantly higher for PRRS 94881 MLV-vaccinated pigs compared to challenge controls on DPC 0 (p=0.0281), DPC 2 (p=0.0095), DPC 4 (p=0.0034) and DPC 5 (p<0.0001). Least square Mean rectal temperatures were significantly lower for PRRS 94881 MLV-vaccinated pigs compared to challenge controls on DPC 8 (p=0.0183) and on DPC 10 (p=0.0001). No significant differences were detected between groups for the remaining days post-challenge (p≤0.0642). A summary of group LS Mean and statistical analysis of rectal temperature is shown below in Table 8.25.

TABLE 8.25

Summary of Group LS Mean Rectal Temperature
(° C.) D 179 (DPC 0) through D 189 (DPC 10)

| Day | Group[1] | LSMean | 95% confidence interval | | p value |
|---|---|---|---|---|---|
| D 179 | 1 | 39.33 | 39.170 | 39.496 | 0.0281 |
| (DPC 0) | 2 | 39.07 | 38.903 | 39.237 | |
| | Diff. 1-2 | 0.26 | 0.030 | 0.497 | |
| D 180 | 1 | 39.46 | 39.257 | 39.657 | 0.3025 |
| (DPC 1) | 2 | 39.61 | 39.400 | 39.810 | |
| | Diff. 1-2 | −0.15 | −0.434 | 0.138 | |
| D 181 | 1 | 39.82 | 39.612 | 40.036 | 0.0095 |
| (DPC 2) | 2 | 39.42 | 39.198 | 39.632 | |
| | Diff. 1-2 | 0.41 | 0.105 | 0.712 | |
| D 182 | 1 | 39.52 | 39.274 | 39.773 | 0.0642 |
| (DPC 3) | 2 | 39.86 | 39.604 | 40.116 | |
| | Diff. 1-2 | −0.34 | −0.693 | 0.021 | |
| D 183 | 1 | 39.52 | 39.320 | 39.727 | 0.0034 |
| (DPC 4) | 2 | 39.08 | 38.867 | 39.283 | |
| | Diff. 1-2 | 0.45 | 0.158 | 0.740 | |
| D 184 | 1 | 39.72 | 39.572 | 39.866 | <0.0001 |
| (DPC 5) | 2 | 39.15 | 38.999 | 39.301 | |
| | Diff. 1-2 | 0.57 | 0.359 | 0.779 | |
| D 185 | 1 | 39.66 | 39.457 | 39.869 | 0.2164 |
| (DPC 6) | 2 | 39.48 | 39.269 | 39.691 | |
| | Diff. 1-2 | 0.18 | −0.112 | 0.478 | |
| D 186 | 1 | 39.22 | 39.027 | 39.421 | 0.2408 |
| (DPC 7) | 2 | 39.39 | 39.188 | 39.592 | |
| | Diff. 1-2 | −0.17 | −0.448 | 0.116 | |
| D 187 | 1 | 39.23 | 39.034 | 39.432 | 0.0183 |
| (DPC 8) | 2 | 39.58 | 39.376 | 39.784 | |
| | Diff. 1-2 | −0.35 | −0.631 | −0.062 | |
| D 188 | 1 | 39.17 | 38.966 | 39.377 | 0.8454 |
| (DPC 9) | 2 | 39.20 | 38.989 | 39.411 | |
| | Diff. 1-2 | −0.03 | −0.323 | 0.266 | |
| D 189 | 1 | 39.06 | 38.908 | 39.207 | 0.0001 |
| (DPC 10) | 2 | 39.51 | 39.352 | 39.658 | |
| | Diff. 1-2 | −0.45 | −0.662 | −0.234 | |

[1]Group 1 = PRRS 94881 MLV vaccine; Group 2 = Challenge control group; Group 3 = Negative control group Three of 21 (14%) PRRS 94881 MLV vaccinated pigs and 5 of 20 (25%) challenge controls had a rectal temperature ≥40.5° C. for at least one day post-challenge. No difference was detected between groups for the proportion of pigs that exhibited a rectal temperature ≥40.5° C. for at least one day post-challenge (p=0.4537). A summary of group proportion of pigs with pyrexia (≥40.5° C.) for at least one day post-challenge is shown below in Table 8.26.

TABLE 8.26

Summary of Group Proportion of Pyrexia (≥40.5°
C.) for at Least One Day Post-Challenge

| Day | Group[1] | N Positive | % Positive | 95% CI | | Total Number[2] | p value |
|---|---|---|---|---|---|---|---|
| D 180 | 1 | 3 | 14 | 3.0 | 36.3 | 21 | 0.4537 |
| (DPC 1) | 2 | 5 | 25 | 8.7 | 49.1 | 20 | |
| to D 189 | 3 | 0 | 0 | 0.0 | 26.5 | 12 | NI |
| (DPC 10) | | | | | | | |

[1]Group 1 = PRRS 94881 MLV vaccine; Group 2 = Challenge control group; Group 3 = Negative control group.
[2]One PRRS 94881 MLV pig and two challenge control pigs died pre-challenge and were not included in analysis.
NI = Not included in statistical analysis Clinical Assessment Post-Vaccination Four of 22 (18%) PRRS 94881 MLV pigs, 8 of 22 (36%) challenge control pigs and 2 of 12 (17%) negative control pigs exhibited an abnormal clinical assessment for at least one day from D1 to D21. There was no significant difference between groups for this parameter (p=0.3102).

A summary of group percentage of pigs with at least one abnormal clinical assessment from D1 through D21 is shown below in Table 8.27.

TABLE 8.27

Summary of Group Percentage of Pigs with At Least One Abnormal Clinical Assessments from D 1-D 21

| Group[1] | N Positive | % Positive | 95% CI | | Total Number | p value |
|---|---|---|---|---|---|---|
| 1 | 4 | 18 | 5.2 | 40.3 | 22 | 0.3102 |
| 2 | 8 | 36 | 17.2 | 59.3 | 22 | |
| 3 | 2 | 17 | 2.1 | 48.4 | 12 | NI |

[1]Group 1 = PRRS 94881 MLV vaccine; Group 2 = Challenge control group; Group 3 = Negative control group.
NI = Not included in statistical analysis Overall, 7 PRRS 94881 MLV pigs exhibited an abnormal clinical assessment for at least one day between D1 to D177: Pig 121 exhibited belly swelling from D61 to D146, a swollen sheath from D147 to D167, belly swelling on D168, a swollen sheath from D169-172 and belly swelling from 173 to 177. Pig 141 was thin from D4-D10, was depressed from D4-D6 and rough hair coat on D5. Pig 144 exhibited coughing on D26. Pig 146 exhibited swelling on the sternum on D82. Pig 147 was weak on legs from D84-D86 and was shaking on D84. Pig 154 was thin from D4-D6. Pig 179 was thin from D2-D5, exhibited rough hair coat on D5 and was found dead on D6. Thirteen pigs in the challenge control group exhibited an abnormal clinical assessment for at least one day from D1 to D177: Pig 124 exhibited shaking and tremors on D20 and was found dead on D21. Pig 134 exhibited a swollen sheath from D46-D68, belly swelling from D69-D143, an umbilical hernia on D144, and belly swelling from D145 to D177. Pig 137 exhibited a swollen sheath from D108-D143. Pig 138 exhibited a swollen sheath from D115-D143. Pig 148 exhibited lameness or a swollen leg from D16-20 and coughing on D35. Pig 149 was thin from D5-D9 and on D12, and exhibited rough hair coat from D12-D15. Pig 150 was thin from D4-D9 and on D13, exhibited poor body condition from D10-D12, and was depressed on D11. Pig 161 was thin from D4-D9, exhibited rough hair coat and central nervous system signs on D9 and was found dead on D10. Pig 167 exhibited a swollen sheath from D117-D143. Pig 170 was thin from D4-D7 and exhibited depression on D7. Pig 172 exhibited a sore or a swollen dew claw from D120-D143. Pig 177 exhibited depression on D19 and swelling on the neck from D156-D159. Pig 178 exhibited depression on D5, from D17-20, and from D28-D36, was lame and/or swollen leg from D15-D47, was thin from D16-D18, and was stiff on legs from D39-D47. Six pigs in the negative control exhibited an abnormal clinical assessment for at least one day from D1 to D177: Pig 120 exhibited coughing from D5-7 and on D12. Pig 126 was thin from D2-18, exhibited depression from D4-D5, on D10, and from D17-D19, rough hair coat on D5, and labored respiration from D18-D22. Pig 132 exhibited an abscess from D49-D56. Pig 145 exhibited a swollen sheath from D37-D43 and from D46 to D74, and a sore on the sheath from D75-D83 and from D85 to D87. Pig 151 exhibited lameness and/or a swollen leg from D78-D83 and on D85. Pig 155 exhibited an abscess on D69-D77.

Three mortalities occurred prior to challenge. Pig 179 (PRRS 94881 MLV, D6): Necropsy revealed minimal lesions (thin, poor body condition). Laboratory testing showed mild macrophagic interstitial pneumonia. Immunohistochemistry was negative for PRRS. Intestinal samples were autolyzed but did not show evidence of severe necrosis or severe inflammation. Smooth *Escherichia coli* and *Enterococcus* spp were isolated (Section 15.9). Pig 124 (Challenge control, D21): No gross lesions were identified at necropsy. Laboratory testing revealed severe suppurative to pyogranulomatous meningoencephalitis with suppurative perivasculitis. Marked pulmonary and hepatic congestion were also evident. The diagnosis was *Streptococcus suis* associated meningoencephalitis. Pig 161 (Challenge control, D10): Necropsy revealed minimal lesions (thin, poor body condition). *Bordetella bronchiseptica*, *Streptococcus* alpha hemolytic and *Staphylococcus auricularis* were isolated from lung tissues.

PRRS Serology

All pigs were PRRS ELISA negative on D0 and D7. By D14, 90% of PRRS 94881 MLV-vaccinated pigs had positive PRRS ELISA titers. This number increased to 95% on D21 and was 100%, 100%, 100%, 90%, 100% and 95% on D28, D56, D84, D112, D140 and D168, respectively. None of the challenge control pigs developed PRRS antibody titers during the vaccination phase of this study, and from D14 through D168, a significantly higher percentage of PRRS 94881 MLV-vaccinated pigs had positive PRRS antibody titers compared to challenge controls (p<0.0001).

During the challenge phase of the study, the percentages of PRRS 94881 MLV-vaccinated pigs with positive PRRS ELISA titers were 95%, 95%, 100% and 100% on DPC 0, DPC 3, DPC 7 and DPC10, respectively. In contrast, challenge control pigs did not develop PRRS antibody titers until DPC 7, when 30% had titers. This increased to 80% on DPC 10. The PRRS 94881 MLV-vaccinated pigs had higher percentages of animals with positive PRRS antibody titers throughout the challenge phase of the study (350.0478).

Pigs in the negative control group were PRRS ELISA seronegative throughout the study with the exception of two pigs on D112. Numbers 116 and 120 were PRRS ELISA seropositive on D112.

A summary of group percentages of pigs with positive PRRS-antibody titers before challenge is shown below in Table 8.28. Data from the challenge portion of the study are shown below in Table 8.29.

TABLE 8.27

Summary of Group Frequency of Pigs with Positive PRRS-Antibody Titer by Day, Days 0-168

| Day | Group[1] | N Positive | % Positive | 95% CI | | Total Number | p value |
|---|---|---|---|---|---|---|---|
| 0 | 1 | 0 | 0 | 0.0 | 15.4 | 22 | NA |
| | 2 | 0 | 0 | 0.0 | 15.4 | 22 | |
| | 3 | 0 | 0 | 0.0 | 26.5 | 12 | NI |
| 7 | 1 | 0 | 0 | 0.0 | 16.1 | 21 | NA |
| | 2 | 0 | 0 | 0.0 | 15.4 | 22 | |
| | 3 | 0 | 0 | 0.0 | 26.5 | 12 | NI |
| 14 | 1 | 19 | 90 | 69.6 | 98.8 | 21 | <0.0001 |
| | 2 | 0 | 0 | 0.0 | 16.1 | 21 | |
| | 3 | 0 | 0 | 0.0 | 26.5 | 12 | NI |
| 21 | 1 | 20 | 95 | 76.2 | 99.9 | 21 | <0.0001 |
| | 2 | 0 | 0 | 0.0 | 16.8 | 20 | |
| | 3 | 0 | 0 | 0.0 | 26.5 | 12 | NI |

TABLE 8.27-continued

Summary of Group Frequency of Pigs with Positive
PRRS-Antibody Titer by Day, Days 0-168

| Day | Group[1] | N Positive | % Positive | 95% CI | | Total Number | p value |
|---|---|---|---|---|---|---|---|
| 28  | 1 | 21 | 100 | 83.9 | 100.0 | 21 | <0.0001 |
|     | 2 | 0  | 0   | 0.0  | 16.8  | 20 |  |
|     | 3 | 0  | 0   | 0.0  | 26.5  | 12 | NI |
| 56  | 1 | 21 | 100 | 83.9 | 100.0 | 21 | <0.0001 |
|     | 2 | 0  | 0   | 0.0  | 16.8  | 20 |  |
|     | 3 | 0  | 0   | 0.0  | 26.5  | 12 | NI |
| 84  | 1 | 21 | 100 | 83.9 | 100.0 | 21 | <0.0001 |
|     | 2 | 0  | 0   | 0.0  | 16.8  | 20 |  |
|     | 3 | 0  | 0   | 0.0  | 26.5  | 12 | NI |
| 112 | 1 | 19 | 90  | 69.6 | 98.8  | 21 | <0.0001 |
|     | 2 | 0  | 0   | 0.0  | 16.8  | 20 |  |
|     | 3 | 2  | 17  | 2.1  | 48.4  | 12 | NI |
| 140 | 1 | 21 | 100 | 83.9 | 100.0 | 21 | <0.0001 |
|     | 2 | 0  | 0   | 0.0  | 16.8  | 20 |  |
|     | 3 | 0  | 0   | 0.0  | 26.5  | 12 | NI |
| 168 | 1 | 20 | 95  | 76.2 | 99.9  | 21 | <0.0001 |
|     | 2 | 0  | 0   | 0.0  | 16.8  | 20 |  |
|     | 3 | 0  | 0   | 0.0  | 26.5  | 12 | NI |

[1]Group 1 = PRRS 94881 MLV vaccine; Group 2 = Challenge control group; Group 3 = Negative control group.
NI = Not included in statistical analysis.
NA = Not applicable, no analysis conducted

TABLE 8.29

Summary of Group Frequency of Pigs with Positive
PRRS-Antibody Titer by Day, DPC 0 through DPC 10

| Day | Group[1] | N Positive | % Positive | 95% CI | | Total Number | p value |
|---|---|---|---|---|---|---|---|
| D 179 (DPC 0)  | 1 | 20 | 95  | 76.2 | 99.9  | 21 | <0.0001 |
|                | 2 | 0  | 0   | 0.0  | 16.8  | 20 |  |
|                | 3 | 0  | 0   | 0.0  | 26.5  | 12 | NI |
| D 182 (DPC 3)  | 1 | 20 | 95  | 76.2 | 99.9  | 21 | <0.0001 |
|                | 2 | 0  | 0   | 0.0  | 16.8  | 20 |  |
|                | 3 | 0  | 0   | 0.0  | 26.5  | 12 | NI |
| D 186 (DPC 7)  | 1 | 21 | 100 | 83.9 | 100.0 | 21 | <0.0001 |
|                | 2 | 6  | 30  | 11.9 | 54.3  | 20 |  |
|                | 3 | 0  | 0   | 0.0  | 26.5  | 12 | NI |
| D 189 (DPC 10) | 1 | 21 | 100 | 83.9 | 100.0 | 21 | 0.0478 |
|                | 2 | 16 | 80  | 56.3 | 94.3  | 20 |  |
|                | 3 | 0  | 0   | 0.0  | 26.5  | 12 | NI |

[1]Group 1 = PRRS 94881 MLV vaccine; Group 2 = Challenge control group; Group 3 = Negative control group.
NI = Not included in statistical analysis.

Discussion/Conclusion

To achieve the study objective, twenty-two (22) healthy, PRRS susceptible and seronegative pigs were inoculated IM with 1 mL of PRRS 94881 MLV at approximately 14 days of age. Thirty-four (22 pigs—challenge control group and 12 pigs—negative control group) PRRS susceptible and seronegative pigs were inoculated IM with 1 mL of control product at approximately 14 days of age.

Validation of the Study and Challenge Model

Pigs in the negative control group remained negative for PRRSv (viremia; qPCR) throughout the study. Two pigs (Nos. 116 and 120) in the negative control group had positive ELISA titers on D112, while all other ELISA results for this group were negative. Considering that no viremia was detected in these pigs or in the group as whole; likewise, all other serum samples were ELISA negative, the results for these two pigs on D112 were considered false positives possibly due to an unassignable lab error. Thus, this was a valid study. Unrelated to the establishment of a valid study, the negative control group had a median histological lung lesion score of 9.0 on D189 in contrast to a median gross lesion score of 0.0%. These data highlight that pigs housed under normal swine husbandry conditions for an extended period of time develop minor lung lesions that are inconsequential and not related to specific pathogens.

Following inoculation with European PRRS isolate 205817 by the method described earlier, the challenge control group exhibited a mean ADWG from DPC 0 to DPC 9 of 0.2 kg/day (a mean ADWG of 0.5 kg/day for the negative control group), a median gross lung lesion score of 13.8% (0.0% for the negative control group), a median histological lung lesion score of 19.5 (9.0 for the negative control group) and a median value of 6.25 $\log_{10}$ GE/mL for the detection of PRRSv RNA in lung tissue (median of 0.0 $\log_{10}$ GE/mL for negative control group). These results highlight that PRRS-specific clinical disease was induced in the challenge control group, thus validating this challenge model as an adequate clinical laboratory tool to evaluate PRRS vaccine efficacy and more specifically, 26 week duration of immunity of PRRS 94881 MLV.

Determination of 26 Week Duration of Immunity of PRRS 94881 MLV

Determination of DOI for PRRS 94881 MLV of 26 weeks post-vaccination was based upon the vaccine group exhibiting a significant reduction ($p \leq 0.05$) in post-challenge lung lesions (gross or histological) compared with the challenge control group.

Gross and histological lung lesions were selected as the primary parameter for determination of 26 week DOI because this parameter provides the most clinically relevant and convincing evidence of efficacy when evaluating a new vaccine within the PRRS respiratory challenge model in pigs. Lung lesion development is one of the hallmarks of PRRS respiratory disease in pigs and can be considered the source for all subsequent manifestations of secondary PRRSv disease characteristics such as clinical signs, pyrexia, decreased ADWG, etc.

The PRRS 94881 MLV group exhibited a significant reduction in gross lung pathology post-challenge, as evidenced by a median gross lung lesion score of 0.1% in comparison to the challenge control group, which exhibited a median gross lung lesion score of 13.8% ($p < 0.0001$). In addition, the PRRS 94881 MLV group exhibited a significant reduction in histological lung lesion scores, as evidenced by a median histology lung lesion score of 6.0 for the PRRS 94881 MLV group compared with a median histology lung lesion score of 19.5 for the challenge control group ($p < 0.0001$).

Thus, DOI of 26 weeks for PRRS 94881 MLV at dosage of $1 \times 10^{4.27}$ TCID$_{50}$ was established based upon the primary parameter of a significant reduction for lung lesions post-challenge. This result was achieved with a vaccine dose slightly lower than the targeted minimum immunizing dose of $1 \times 10^{4.5}$ TCID$_{50}$/mL. One challenge control pig (No. 123) could not be scored for gross lung lesions because of pleuritis and adhesions due to bacterial infections, but was scored for histological lung lesions. The omission of this pig from the challenge control group's gross lung lesion score analysis did not affect the outcome of this study.

Viremia post-challenge was selected as the most important secondary parameter because it represents the level of viral replication and persistence occurring within the host animal upon exposure. A significant reduction ($p \leq 0.05$) in viremia would correspond with a PRRS vaccine that induces adequate immunity to limit PRRS pathogenesis within the host. At 3, 7 and 10 days post-challenge, the PRRS 94881 MLV-vaccinated group demonstrated a significant reduction in viremia (qPCR) compared with the challenge control group ($p < 0.0001$). To further evaluate post-challenge viremia between groups, the quantity of the viral load over a specific duration of time post-challenge was calculated, as represented as "area under curve" or AUC. The PRRS 94881

MLV-vaccinated group had a median AUC value from DPC 0 to DPC 10 of 15.54 $\log_{10}$ GE/mL/day; while the challenge control group had a median AUC value of 44.77 $\log_{10}$ GE/mL/day (p<0.0001). In addition, the PRRS 94881 MLV-vaccinated group had a median AUC value from DPC 3 to DPC 10 of 8.88 $\log_{10}$ GE/mL/day; while the challenge control group had a median AUC value for this period of 36.43 $\log_{10}$ GE/mL/day (p<0.0001). Whether viremia was examined at specific time points post-challenge or over the course of the post-challenge period, PRRS 94881 MLV administered 26 weeks prior to challenge with a virulent heterologous European strain of PRRS significantly (p≤0.05) reduced viremia after challenge inoculation.

In association with a reduction of PRRS viremia post-challenge, a significant (p≤0.05) reduction in the viral load in lung tissue would also be of great importance from the standpoint of PRRS vaccine immunity. A reduction of viral load in the lung tissue may be associated with reduced viral stability, replication and persistence within the host and may secondarily lead to reduced shedding of PRRSv to other pigs. In this study, lung tissues from the PRRS 94881 MLV group had a median lung qPCR result of 3.69 $\log_{10}$ GE/mL 10 days post challenge (DPC 10) while the challenge control group had a median lung qPCR result of 6.25 $\log_{10}$ GE/mL. The difference between the vaccine group and the challenge control group was significant (p<0.0001), thus further supporting duration of immunity of 26 weeks.

A marked reduction in severity and frequency of clinical signs post-challenge in pigs would also be supportive of PRRS vaccine efficacy and establishment of DOI of 26 weeks for PRRS 94881 MLV. Only one pig exhibited clinical signs following challenge: pig 149 (challenge control) had a respiratory score of "1" (panting/rapid respiration) on D185. No pigs in the PRRS 94881 MLV-vaccinated group exhibited clinical signs during the post-challenge phase of this study and there were no statistical differences between the vaccinated and challenge control groups (p=0.4878 or no test conducted). Clinical signs post-challenge were not strong enough in this study to assess the DOI.

Pyrexia between groups varied post-challenge. PRRS 94881 MLV-vaccinated pigs exhibited significantly lower LS Mean rectal temperatures on two days (DPC 8 and DPC 10; (p≤0.183) and higher LS Mean rectal temperatures on four days (DPC 0, DPC 2, DPC 4 and DPC 5; (p≤0.0281) compared with challenge control pigs. Otherwise, no significant differences were detected between groups post-challenge (p≤0.0642). Although statistical differences between groups were detected post-challenge, these differences were not biologically meaningful, considering that mean rectal temperatures remained ≤39.9° C. (challenge control group, D182) for all groups. No difference was detected between groups with respect to the proportion of pigs with pyrexia for at least one day post-challenge (p=0.4537).

The presence of significant viremia, lung pathology and viral load in lung tissues due to PRRS in the challenge control group resulted in a significant (p≤0.05) difference between groups for body weight on DPC 9. In this study, the vaccinated and challenge control groups had LS mean body weights on DPC 9 of 138.3 kg and 130.3 kg, respectively (p=0.0455). The LS mean ADWG from DPC 0 to DPC 9 were 0.4 kg/day and 0.2 kg/day, for vaccinated and challenge groups, respectively. This difference was not statistically significant (p=0.1041).

Post-Vaccination Parameters Examined in this Study

Three pigs were found dead during the vaccination phase of this study. Pig 179 (PRRS 94881 MLV-vaccinated) was found dead on D6 associated with smooth *Escherichia coli* and *Enterococcus* spp. infections. Pig 161 (challenge control group) was found dead on D10 associated with *Bordetella bronchiseptica, Streptococcus* alpha hemolytic and *Staphylococcus aruricularis* infections. Pig 124 (challenge control group) was found dead on D21 associated with a *Streptococcus suis* infection that lead to meningoencephalitis. To control and prevent any more deaths, pigs were mass treated with injectable vitamins and antibiotics. Following treatments, no more deaths occurred. Since deaths occurred in both treatment groups it can be assumed that the IVP itself was not associated with infections. More likely, pigs arrived at the research facility harboring these infections. Data for these pigs were included when available. Gross and histological lung lesion scores from these pigs were omitted from lung lesion analyses since these pigs died before challenge administration. The loss of one—PRRS 94881 MLV pig and two—challenge control pig during the extended time period from vaccination to challenge did not affect the outcome of the study.

No abnormal clinical assessments related to PRRS 94881 MLV vaccination or control product were observed in pigs following inoculation on D0. Seven pigs in the PRRS 94881 MLV-vaccinated group had abnormal assessments post-vaccination; while thirteen challenge control pigs had abnormal assessments. Excluding the three pigs that died due to bacterial infections, these abnormal assessments included thinness, coughing, swellings, rough hair coat, depression, abscesses and poor body condition at various time points, none of which lasted an extended period of time. In the author's opinion, these findings were not related to the administration of either experimental product, but rather are typical findings in growing/maturing pigs, under group housing situations, over an extended period of time.

All pigs were PRRS ELISA serology negative on D0, thus confirming that all pigs met the inclusion criterion of being PRRS sero-negative upon entry into the study. The majority of pigs (90%) receiving PRRS 94881 MLV sero-converted to PRRS by D14 and all PRRS-vaccinated pigs were sero-positive by D28. Conversely, the challenge control pigs remained seronegative until 7 days post-challenge, when this group began to demonstrate PRRS seroconversion. As covered earlier, two—negative control pigs were PRRS ELISA seropositive on D112, which was considered an incidental finding, possible due to an unassignable lab error.

At 7, 14, 21 and 28 days post-vaccination, the PRRS 94881 MLV-vaccinated group exhibited median qPCR results of 3.00, 0, 0 and 3.00 $\log_{10}$ GE/mL, respectively. These results highlight that within 4 weeks post-vaccination, a dosage of $1\times10^{4.27}$ TCID$_{50}$ of PRRS 94881 MLV induced sufficient replication of the MLV that is often required to build protective immunity already at 4 weeks after vaccination. Conversely, the challenge control group was negative for PRRS viremia until three days post-challenge.

Conclusion

A significant reduction (p≤30.05) of gross and histological lung lesions at necropsy, viral load in lung tissues at necropsy and viremia post-challenge for the PRRS 94881 MLV group compared to challenge control group demonstrated vaccine efficacy against virulent PRRSv when vaccinated at 2 weeks of age and challenged 26 weeks post-vaccination. The results of this study therefore support the demonstration of duration of immunity of 26 weeks post-vaccination with PRRS 94881 MLV. These results were achieved with a vaccine dose of $1\times10^{4.27}$ TCID$_{50}$/mL, which was slightly lower than the minimum immunizing dose ($1\times10^{4.5}$ TCID$_{50}$/mL).

The sequences of the PRRSV 94881 attenuated strain and the parental strain are as follow:

```
SEQ ID NO: 1: FULL LENGTH NUCLEOTIDE SEQUENCE OF PRRS Master Seed
Virus of 94881
    1   TTTGTGTACC TTGGAGGCGT GGGTACAGCC CTGCCCCACC CTTTGGTCCC TGTTCTAGCC

61   CGACAAGTAC CCTTCTCTCT CGGGGCGAGC GCGCCGCCTG CTGCTCCCTT GCGGCGGGAA

121   GGACCTCCCG AGTATTTCCG GAGAGCACCT GCTTTACGGG ATCTCCGCCC TTTAACCATG

181   TCTGGGATGT TCTCCCGGTG CATGTGCACC CCGGCTGCCC GGGTATTTTG GAACGCCGGC

241   CAAGTCTATT GCACACGGTG TCTCAGTGCA CGGTCTCTTC TCTCTCCAGA ACTTCAGGAC

301   ACGGACCTCG GTGCAGTTGG CTTGTTTCAC AAGCCTAAAG ACAAGCTCCA TTGGAAAGTT

361   CCCATTGGTA TCCCCCAGGT GGAATGTTCT CCATCTGGGT GTTGCTGGCT GTCAACCATT

421   TTTCCTTTAG CGCGCATGAC CTCCGGCAAT CACAACTTCC TTCAACGACT CGTGAAGGTT

481   GCTGATGTAT TGTACCGTGA CGGTTGCTTA ACCCCTAGAC ACCTCGTGA ACTCCAAGTT

541   TACGAGCGTG GTTGCAATTG GTATCCGATT ACGGGGCCTG TGCCTGGGAT GGCTGTGTAC

601   GCGAACTCCA TGCACGTGTC CGACCAACCG TTCCCTGGTG CCACTCATGT GTTAACAAAT

661   TCCCCTTTGC CTCAACGGGC TTGTCGGCAG CCGTTCTGTC CGTTCGAAGA GGCCCATTCT

721   AGCATATACA GGTGGGAAAA ATTTGTAATT TTTATGGATT CCTCCTCCGA CGGTCGATCT

781   CGCATGATGT GGACTCCGGA ATCCGATGAC TCCACGGCTT GGAAGTTCT GCCGCCCGAG

841   CTAGAACACC AGGTCAAGGT CCTTGTTCGG AGCTTTCCCG CCCATCACCT TGTCGACCTT

901   GCCGATTGGG AGCTCACTGA GTCCCCTGAT AACGGTTTTT CCTTCAGCAC GTCACATCCT

961   TGCGGCTACC TTGTTCGGGA CCCGGCTGTA TCCGAAGGCA AGTGTTGGCT TTCCTGCTTT

1021   TTGAGCCAGT CAGCCGAAGT GCTCAGTCGC GAGGCGCATC TGGCTACCGC CTATGGTTAC

1081   CAAACCAAGT GGGGTGTGCC TGGCAAGTAC ATCCAGCGCA GACTTCAAGT TCACGGTCTC

1141   CGTGCTGTGG TCGACCCTGA TGGTCCCATT CACGTTGAAG CATTGTCTTG CCCCCAGTCT

1201   TGGATCAGGC ACTTGACCCT GAATGATGAT GTCACCCCGG GATTCGTTCG CCTAATGTCT

1261   CTTCGCATTG TGCCGAACAC AGAGCCTACC ACACACCGGA TCTTTCGTTT TGGAGTGCAC

1321   AAGTGGTATG GTGCCGCCGG CAAACGGGCC CGTGGCAAGC GTGCCGCCAA AAGTGAGAAA

1381   GACTCGGCTT CCACCCTCAA GGTTGCCCGA CCGACTTCCA CCAGTGGAAT CGTCACCTAC

1441   TCCCCACCTG CGGACGGGTC TTGTGGTTGG CATGCCCTTG CCGCCATACT GAACCGGATG

1501   ATTAATAATG ACTTCACGTC CCCTCTGCCT CGGTACAACA GGCCGGAGGA CGATTGGGCT

1561   TCTGATGGTG ACCTTGCTCA GGCCATTCAA TGTTTGCAAC TACCTGCCGC CATAGCTCGG

1621   AACCGCGCCT GCCCTAACGC CAAATACCTC ATAAAACTCA ACGGAGTTCA TTGGGAGGTA

1681   GAGGTGAGGC CTGGAATGGC TCCTCGCTCC CTCTCTCGTG AGTGCGTTGT TGGCGTCTGC

1741   TCTGAAGGCT GTGTCGCGTC GCCTTACCCG GAGGACGGGT TGCCTAAACG TGCACTTGAG

1801   GCCCTGGCGT CTGCTTATAG ACTGCCTTCA GACTGTGTTT GTGATGGTAT TATTGACTTC

1861   CTTGCCAATC CACCTCCCCA GGAGTTCTGG ACTCTTGACA AAATGTTGAC TTCCCCGTCA

1921   CCGGAGCAGT CCGGCTTCTC TAGTCTGTAT AAATTGTTGT TAGAGATCTT GCCGCAGAAA

1981   TGCGGATCCA CAGAAGGGGA ATTCATCTAT ACTGTTGAGA GGATGTTGAA GGATTGTCCG

2041   AGCTCCAAAC AGGCCATGGC CCTCCTTGCA AAAATTAAGG TCCCATCCTC AAAGGCCCCA

2101   TCCGTGACTC TGAACGAGTG CTTCCCCACG GATGTTCCAG TCAACTCTGA GTTAATATCT

2161   TGGGAAGAGC CCAAAGACCC TGGCGCTGCT GTTGTCCTAT GTCCATCGGA TGCAAAGAA

2221   TCTAAGGAAA CAGCCCCTGA AGAAGCTCAA GCGAGAAACC GTAAGGTCCT TCACCCTGTG
```

-continued

```
2281  GTCCTTACCG AGGAACTTAG CGAGCAACAG GTGCAGGTGG TTGAGGGTGA TCAGGATATG

2341  CCACTGGATT TGACTTGGCC AACCTTAACC GCTACGGCGA CCCCTGTTAG AGGGCCGGTA

2401  CCGGACAATT TGAGCTCTGG CATTGGTGCC CAGCCCGCTA CCGTTCAAGA ACTCATTCTG

2461  GCGAGGCCTG CACCCCGTCT TGTTGAGCGC TGTGGCACGG AGTCGAACGG CAGCAGTTCA

2521  TTTCTGGATT TGCCTGACGT GCAGACCTCG GACCAGCCTT TAGACCTGTC CCTGGCCGCG

2581  TGGCCTGTAA GGGCTACCGC GTCTGACCCC GGTTGGATCC ACGGTAGGCG TGAGCCTGTC

2641  TTTGTGAAGC CTCGAGGTGT TTTCTCTGAT GGCGAGTCGG CCCTTCAGTT CGGAGAGCTT

2701  TCCGAAGCCA GTTCTGTCGT CGATGACCGG ACAAAAGAAG CTCCGGTGGT TGACGCCCCC

2761  ATCGATTTGA CAACTTCGAA CGAGACGCTC TCTGGGTCTG ACCCCTTTGA ATTCGCCAAA

2821  TTCAGGCGCC CGCGTTTCTC CGCGCAAGCT TAATCGACC GAGGTGGTCC GCTTGCCGAT

2881  GTTCATGCAA AGATAAAGAG TCGGGTATAT GAACAATGCC TTCAAGCTTG TGAACCTGGT

2941  AGTCGTGCGA CCCCAGCCAC CAAGAAGTGG CTCGACAAAA TGTGGGACAG GGTGGACATG

3001  AAAACTTGGC GCTGCACCTC GCAGTTCCAA GCTGGTCACA TTCTTGAGTC CCTCAAATTC

3061  CTCCCTGACA TGATTCAAGA CACACCGCCT CCTGTTCCCA GGAAGAACCG AGCTGGTGAC

3121  AGTGCCGGCC TGAAGCAACT GGTGGCGCAG TGGGATAGGA ATCGAGTGT GACACCCCCC

3181  ACAAAACCGG TTGGACCGGT GCTTGACCAG GCCGTCCCTC TGCCTATGGA CATCCAGCAA

3241  GGAGATGCCA CTCCGCTGA CAAGCCACCC CATTCGCAAA ACCCTTCTAG TCAAGTAGAT

3301  GTGGGTGGAG GTTGGAAAAG TTTTATGCTC TCCGGCACCC GTTTCGCGGG GTCCGTTAGT

3361  CAGCGCCTTA CGACATGGGT TTTTGAGGTT CTCTCCCATC TCCCAGCTTT TATGCTCACA

3421  CTTTTCTCGC CACGGGCTC TATGGCTCCA GGTGATTGGC TGTTTGCAGG TGCTGTTCTA

3481  CTTGCTCTCC TGCTCTGCCG TTCTTACCCA ATACTCGGAT GCCTTCCCTT ATTGGGTGTC

3541  TTTTCTGGTT CTGTGCGGTG TGTTCGTTTG GGTGTTTTTG GTTCTTGGAT GGCTTTTGCT

3601  GTATTTTTAT TCTCGACTCC ACCCGACCCA GTCGGTTCTT CTTGTGACCA CGATTCGCCG

3661  GAGTGTCATG CTGAGCTTTT GGCTCTTGAG CAGCGCCAAC TTTGGGAACC TGTGCGCAGC

3721  CTTGTGGTCG GGCCATCGGG CCTCTTATGC GTCATTCTTG GCAAGTTACT CGGTGGGTCA

3781  CGTTGTCTCT GGTTTGTTCT CCTACGTATA TGCATGCTCG CAGATTTGGC AATTTCTCTT

3841  ATTTATGTGG TGTCCCAAGG GCGTTGTCAC AAGTGTTGGG GAAAGTGTAT AAGGACGGCT

3901  CCTGCAGAAG TGGCCCTTAA TGTGTTTCCT TTTTCGCGCG CCACCCGCTC ATCTCTTGTG

3961  TCCTTGTGTG ATCGGTTCCA AGCGCCAAAA GGAGTTGACC CCGTGCACTT GGCGACAGGC

4021  TGGCGCGGGT GCTGGTGTGG TGAGAGCCCT ATTCATCAAT CACACCAAAA ACCGATAGCT

4081  TATGCCAACT TGGATGAAAA GAAGATATCC GCCCAGACGG TGATTGCTGT CCCGTATGAT

4141  CCTAGTCAGG CCATTAAATG CCTGAAAGTT TTGCAGGCAG GAGGGGCTAT TGTGGACCAG

4201  CCTACGCCCG AGGTCGTCCG TGTGTCTGAG ATTCCCTTCT CGGCCCCATT TTTTCCGAAG

4261  GTCCCAGTCA ACCCAGACTG CAGGGTTGTG GTAGATTCGG ACACTTTTGT GGCTGCGGTC

4321  CGCTGCGGTT ATTCGACAGC ACAACTGGTC CTTGGTCGGG CAACTTTGC CAAGCTAAAT

4381  CAGACCCCCC TCAGGAACTC TGTCCCCACC AAAACAACTG GTGGGGCCTC ATACACCCTT

4441  GCCGTGGCCC AGGTATCTGT GTGGACTCTT GTTCATTTCA TCCTCGGCCT TTGGTTAACG

4501  TCACCTCAAG TGTGTGGTCG AGGGACCTCT GACCCGTGGT GTTCGAACCC TTTTTCGTAT

4561  CCTACTTATG GCCCCGGAGT TGTGTGTTCC TCTCGACTCT GCGTGTCTGC CGACGGAGTT

4621  ACCCTGCCAT TGTTCTCAGC CGTTGCCCAT CTTTCCGGTA GAGAGGTGGG GATTTTTATT

4681  TTGGTGCTTG CCTCCTTGGG CGCTTTAGCC CACCGCTTGG CTCTTAAGGC AGACATGTCA
```

-continued

```
4741 ATGGTCTTTT TGGCGTTTTG TGCTTACGCC TGGCCCATGA GCTCCTGGTT AATTTGCTTC

4801 TTTCCTATGC TCTTGAGGTG GGTAACCCTT CATCCTCTCA CTATGCTTTG GGTGCACTCA

4861 TTTTTGGTGT TTTGCCTACC AGCTGCCGGC GTTCTCTCGC TGGGAATAAC CGGTCTTCTT

4921 TGGGCAGTTG GCCGTTTCAC CCAGGTTGCC GGAATTATCA CACCTTATGA CATCCACCAG

4981 TATACCTCCG GACCACGTGG TGCAGCTGCT GTAGCAACGG CTCCAGAAGG TACTTACATG

5041 GCGGCCGTTC GGAGAGCCGC TTTGACTGGA CGGACTTTGA TCTTCACACC ATCTGCAGTC

5101 GGATCCCTTC TTGAAGGTGC TTTCAGAACT CAAAAGCCCT GCCTTAACAC CGTGAATGTC

5161 GTAGGCTCTT CCCTTGGTTC TGGAGGAGTT TTCACCATTG ATGGCAGAAG AGTCATCGTC

5221 ACTGCCACCC ATGTGTTGAA TGGTAACACA GCCAGGGTCA CTGGTGATTC CTACAACCGC

5281 ATGCACACGT TCAATACTAA TGGTGATTAT GCCTGGTCCC ATGCTGATGA CTGGCAAGGC

5341 GTTGCCCCTA TGGTTAAGAT CGCTAAGGGG TATCGCGGTC GTGCCTACTG GCAAACGTCA

5401 ACCGGAGTCG AACCTGGCAT CATGGGGGAA GGATTCGCCT TCTGTTTCAC TAACTGTGGC

5461 GACTCAGGGT CACCTGTCAT TTCAGAAGCT GGTGACCTTA TTGGAGTCCA TACCGGTTCA

5521 AACAAACTCG GTTCTGGTCT TGTGACAACC CCTGAAGGGG AGACCTGCTC CATCAAGGAA

5581 ACTAGGCTCT CTGACCTTTC TAGACATTTT GCAGGTCCAA GCGTCCCTCT TGGGGACATT

5641 AAGTTGAGCC CAGCCATCAT CCCTGATGTG ACAACTATTC CGAGTGACTT GGCATCGCTC

5701 CTTGCTTCTG TCCCCGTGAT GGAAGGTGGC CTCTCAACTG TCCAGCTTTT GTGCGTCTTT

5761 TTCCTTCTCT GGCGCATGAT GGGCCATGCC TGGACACCCA TTGTTGCCGT AGGCTTCTTT

5821 TTGCTGAATG AAATTCTCCC AGCAGTCTTG GTCCGAGCTG TGTTCTCTTT TGCACTCTTT

5881 GTACTTGCAT GGGCCACCCC CTGGTCGGCA CAAGTGTTGA TGATTAGACT CCTCACGGCG

5941 GCTCTCAACC GCAACAGGTT GTCCCTGGCG TTCTACGCAT TCGGAGGTGT CGTTGGCCTG

6001 GCCACAGAAA TCGGGACTTT TGCTGGTGGA TGGCCTGAAC TGTCCCAAGC CCTCTCGACA

6061 TACTGCTTCC TGCCCAGGTT CCTTGCTGTG ACTAGTTATG TCCCCACCAT CATCATCGGT

6121 GGGCTCCATG CCCTCGGCGT AATTTTGTGG TTATTCAAAT ACCGATGCCT CCACAACATG

6181 CTGGTTGGTG ATGGGAGTTT CTCAAGCGCT TTCTTCCTAC GGTATTTTGC TGAGGGTAAT

6241 CTTAGGAAAG GCGTGTCGCA GTCCTGTGGC ATGAATAACG AATCCCTGAC AGCTGCTTTG

6301 GCTTGCAAGT TGTCGCAAGC TGACCTTGAT TTTTTGTCCA GTTAACGAA CTTCAAGTGC

6361 TTTGTGTCCG CTTCAAACAT GAAAAATGCA GCTGGCCAAT ACATCGAGGC GGCGTATGCT

6421 AGAGCTCTGC GTCAGGAGCT GGCCTCCTTG GTTCAGGTTA CAAGATGAA AGGAGTATTG

6481 GCCAAGCTCG AGGCTTTCGC TGAGACGGCC ACTCCGTCAC TTGACACAGG GGACGTGATT

6541 GTTCTGCTTG GGCAACACCC CCATGGATCC ATCCTCGACA TTAATGTGGG GGGTGAAAGG

6601 AAAACTGTGT CTGTGCAAGA AACACGATGC CTGGGTGGTT CCAAATTCAG TGTCTGCACT

6661 GTCGTGTCCA ACACGCCCGT GGATACCTTG ACCGGTATCC CACTTCAGAC GCCAACCCCA

6721 CTTTTTGAAA ATGGCCCGCG CCATCGCAGC GAGGACGACG ACCTCAAAGT TGAGAGAATG

6781 AAAAAACACT GTGTATCCCT CGGCTTCCAC AAAATCAATG GTAAAGTTTA CTGCAAAATT

6841 TGGGACAAGT CTAACGGCGA CACCTTTTAC ACGGATGATT CCCGATACAC TCAAGACCAT

6901 GCTTTTCAGG ACAGGTCAAC CGACTATAGA GACAGGGATT ATGAAGGTGT ACAGACCGCC

6961 CCCCAACAGG GATTCGATCC AAAGTCCGAA GCCCCTGTTG CACTGTTGT AATCGGTGGC

7021 ATTACGTATA ACAGGCATCT GGTCAAAGGT AAGGAGGTCC TAGTTCCCAA ACCTGACAAC

7081 TGCCTTGAAG CTGCCAGACT GTCCCTTGAG CAAGCTCTTG CTGGGATGGG CCAAACTTGT

7141 GACCTTACAG CTACCGAAGT GGAGAAACTA AAGCGCATCA TTAGTCAACT CCAAGGTCTG
```

-continued

```
7201  ACCACTGAAC AGGCTTTAAA CTGCTAGCCG CCAGCGGCTT GACCCGCTGT GGCCGCGGCG

7261  GCCTAGTTGT AACTGAAACG GCGGTAAAAA TCGTAAAATA CCACAGCAGA ACTTTCACCT

7321  TAGGCTCTTT AGACCTAAAA GTCACCTCCG AGGTGGAGGT GAAGAAATCA ACTGAGCAGG

7381  GGCACGCTGT CGTGGCGAAC TTATGTTCCG GTGTCGTCTT GATGAGGCCT CACCCACCGT

7441  CCCTTGTTGA CGTTCTCCTC AAACCCGGAC TTGACACAAC ACCCGGCATT CAACCAGGGC

7501  ATGGGGCCGG GAATATGGGC GTGAACGGTT CTATTTGGGA TTTTGAAACT GCACCCACAA

7561  AGGTAGAACT AGAGTTGTCC AAGCAAATAA TCCAAGCATG TGAAGTCAGG CGCGGGGACG

7621  CCCCTAACCT CCAACTCCCC TACAAGCTTT ATCCTGTCAG GGGGGACCCC GAGCGGCGTA

7681  AAGGTCGCCT TGTCAACACT AGGTTTGGAG ATTTACCTTA CAAAACTCCC CAAGACACCA

7741  AGTCCGCAAT TCATGCGGCT TGTTGCCTGC ATCCCAATGG GGTCCTCGTG TCTGATGGCA

7801  AATCCACGCT GGGTACCACT CTTCAACATG GTTTCGAGCT TTATGTCCCC ACTGTACCTT

7861  ATAGTGTCAT GGAATACCTT GATTCACGCC CTGACACCCC TTTTATGTGT ACTAAACATG

7921  GCACTTCCAA GGCTGCTGCA GAGGACCTCC AAAAATATGA CCTATCCACT CAAGGGTTTG

7981  TCTTGCCTGG GGTCCTACGC CTAGTGCGCA GGTTCATCTT TAGCCATGTT GGTAAGGCGC

8041  CACCACTGTT CCTTCCATCA ACCTACCCTG CCAAGAACTC CATGGCAGGG GTCAATGGCC

8101  AGAGGTTCCC AACAAAGGAT GTCCAGAGCA TACCTGAAAT TGATGAAATG TGCGCCCGTG

8161  CCGTCAAGGA AAATTGGCAG ACTGTGACAC CTTGCACCCT CAAAAACAG TACTGTTCCA

8221  AACCTAAAAC TAGAACCATC CTAGGTACCA ACAACTTCAT AGCCTTGGCT CACAGGTCAG

8281  CACTCAGTGG TGTCACCCAG GCGTTCATGA AGAAGGCCTG GAAGTCCCCA ATTGCCTTGG

8341  GGAAAAACAA GTTTAAGGAA TTGCATTGCA CTGTCGCCGG CAGATGCCTT GAGGCTGACC

8401  TGGCTTCCTG CGATCGCAGC ACCCCCGCCA TTGTGAGGTG GTTTGTTGCC AACCTCCTGT

8461  ATGAACTTGC AGGATGTGAA GAGTACTTGC CTAGCTACGT GCTCAACTGT TGCCATGACC

8521  TTGTGGCAAC GCAGGATGGC GCTTTCACAA AACGCGGTGG CCTGTCGTCC GGGGACCCCG

8581  TCACCAGTGT GTCCAACACC GTCTACTCAC TGATAATTTA CGCCCAGCAC ATGGTGCTTT

8641  CGGCCTTGAA GATGGGTCAT GAAATTGGTC TCAAGTTCCT TGAGGAACAG CTCAAATTTG

8701  AGGACCTTCT TGAAATCCAG CCCATGTTAG TGTATTCTGA TGACCTCGTC TTGTATGCGG

8761  AAAGACCCAC TTTTCCCAAC TACCATTGGT GGGTCGAGCA TCTTGACCTG ATGTTGGGCT

8821  TTAAAACGGA CCCAAAGAAA ACTGTCATAA CTGATAAACC CAGTTTTCTC GGCTGCAGAA

8881  TTGAAGCAGG ACGGCAGTTA GTCCCCAATC GCGACCGTAT TCTGGCTGCT CTTGCATATC

8941  ATATGAAGGC GCAGAACGCC TCAGAGTATT ATGCGTCCGC TGCCGCAATT CTGATGGATT

9001  CGTGTGCTTG CATTGACCAT GACCCCGAGT GGTATGAGGA TCTTATCTGC GGCATCGCCC

9061  GGTGTGCTCG CCAGGACGGT TACCGTTTTC CAGGCCCGGC ATTTTTCATG TCCATGTGGG

9121  AGAAGCTGAA AAGTCATAAT GAAGGGAAGA AATGCCGTCA CTGCGGCATC TGCGACGCCA

9181  AAGCCGACTA TGCGTCCGCC TGTGGACTTG ATTTGTGTTT GTTCCATTCA CACTTTCATC

9241  AACACTGCCC AGTCACTCTG AGCTGTGGCC ACCATGCCGG TTCAAAGGAA TGTTCGCAGT

9301  GTCAGTCACC TGTCGGGGCT GGCAAATCCC CCCTTGACGC TGTGCTGAAA CAAATCCCGT

9361  ACAAACCTCC TCGTACCATT ATCATGAAGG TGGACAACAA AACAACGACC CTTGACCCGG

9421  GAAGATATCA GTCCCGTCGA GGTCTTGTTG CAGTCAAAAG AGGTATTGCA GGTAATGAGG

9481  TTGATCTTTC TGATGGAGAC TACCAAGTGG TGCCTCTTTT GCCGACTTGC AAAGACATAA

9541  ACATGGTGAA GGTGGCTTGC AACGTACTAC TCAGCAAGTT TATAGTAGGG CCGCCAGGTT

9601  CCGGAAAAAC CACCTGGCTA CTGAACCAAG TCCAGGACGA TGATGTCATT TACACACCTA
```

```
                       -continued
 9661   CTCATCAGAC AATGTTTGAC ATAGTCAGTG CTCTTAAAGT TTGCAGGTAT TCCATCCCAG

9721   GAGCCTCAGG ACTCCCTTTT CCACCACCTG CCAGGTCCGG GCCGTGGGTT AGGCTCATCG

9781   CCAGCGGACA TGTCCCTGGC CGAGTGTCAT ATCTCGATGA GGCAGGATAT TGCAATCATC

9841   TAGACATTCT AAGGCTGCTT TCCAAAACAC CCCTTGTGTG TTTGGGTGAC CTTCAGCAAC

9901   TTCACCCGGT CGGCTTTGAT TCCTATTGTT ATGTGTTCGA TCAGATGCCT CAGAAGCAGC

9961   TGACCACCAT TTATAGATTT GGCCCTAACA TCTGTGCAGC CATCCAGCCT TGTTACAGGG

10021   AGAAACTTGA ATCCAAGGCC AGGAACACCA GAGTGGTTTT CACCACCCGG CCTGTGGCCT

10081   TTGGTCAGGT CCTGACACCG TACCACAAAG ATCGTACCGG CTCTGCAATA ACTATAGATT

10141   CATCCCAGGG GGCGACCTTC GACATTGTGA CATTGCATCT ACCATCGCCA AAGTCCCTAA

10201   ACAAATCCCG AGCACTTGTA GCCATCACTC GGGCAAGACA TGGGTTGTTC ATTTATGACC

10261   CTCATGACCA ACTCCAGGAG TTTTTCAACT TAACCCCCGA GCGCACTGAT TGTAACCTTG

10321   CGTTCAGCCG TGGGGATGAG CTGGTTGTTT TGAATGTGGA TAATGCGGTC ACAACTGTAG

10381   CGAAGGCCCT AGAGACAGGT TCACCCCGAT TTCGAGTATC GGACCCGAGG TGCAAGTCTC

10441   TCTTAGCCGC TTGTTCGGCC AGTCTAGAAG GGAGCTGCAT GCCACTACCA CAAGTAGCAC

10501   ATAACCTGGG GTTTTACTTT TCCCCGGACA GCCCAGCTTT TGCACCCCTG CCAAAAGAGC

10561   TGGCGCCACA TTGGCCAGTG GTCACCCACC AGAATAATCG AGCGTGGCCT GATCGACTTG

10621   TCGCTAGTAT GCGCCCAATT GATGCCCGCT ACAGCAAGCC AATGGTCGGT GCAGGGTATG

10681   TGGTCGGGCC ATCCATTTTT CTTGGCACTC CTGGTGTGGT GTCATACTAT CTCACATTAT

10741   ACATCGGGGG CGAGCCTCAG GCCCTGCCAG AAACACTCGT TCAACAGGA CGTATAGCCA

10801   CAGATTGTCG GGAATATCTC GACGCGGCTG AGGAAGAGGC AGCGAGAGAA CTTCCCCACG

10861   CATTTATTGG CGATGTCAAA GGCACTACGA TCGGGGGTG TCACCACATT ACATCGAAAT

10921   ACCTACCTAG GTCCCTGCCT AAAGACTCTG TTGCTGTGGT TGGGGTGAGT TCGCCCGGTA

10981   GGGCTGCTAA AGCCGTGTGC ACTCTCACCG ATGTGTACCT CCCCGAACTC CGACCATATT

11041   TGCAACCGGA GACGGCATCA AAATGCTGGA AACTTAAACT GGATTTCAGG GATGTTCGAC

11101   TGATGGTCTG GAAAGGCGCC ACAGCCTATT TCCAGTTGGA AGGGCTGACA TGGTCAGCGC

11161   TGCCCGATTA TGCTAGGTTC ATTCAGCTAC CCAAGGATGC CGTTGTGTAC ATCGATCCGT

11221   GTATAGGGCC GGCAACAGCC AATCGCAAGG TTGTGCGAAC CACAGACTGG CGGGCCGACC

11281   TGGCAGTGAC ACCGTATGAT TACGGTGCTC AGGTCATTTT GACAACAGCC TGGTTCGAGG

11341   ACCTTGGGCC GCAGTGGAAG ATTTTGGGGT TGCAGCCTTT CAGACGAACA TTTGGCTTTG

11401   AGAACACTGA AGATTGGGCA ATTCTCGCAC GCCGTATGAA TGACGGCAAA GATTACACTG

11461   ACTATAATTG GCATTGTGTA CGAGAACGCC CACACGCAAT TTACGGGCGC GCCCGTGACC

11521   ATACGTATCA TTTTGCCCTT GGCACTGAAC TGCAAGTAGA GCTGGGCAGA CCCCGGCTGC

11581   CTCCTGAGCA AGTGCCGTGA ACGCGGAGTG ATGCAATGGG TTTACTGTGG AGTAAAATCA

11641   GTCAGTTGTT CGTGGATGCC TTCACTGAGT TCCTTGTTAG TGTGGTTGAC ATTGTCATCT

11701   TTCTCGCCAT ATTGTTGGG TTCACTGTTG CAGGCTGGTT ATTGGTCTTC CTTCTCAGAG

11761   TGGTTTGCTC CGCGTTTCTC CGTTCGCGCT CTGCCATTCA CTCTTCCGAA CTATCGAAGG

11821   TCCTATGAGG GCTTGCTACC CAACTGCAGA CCGGATGTCC CACAATTCGC AGTTAAGCAC

11881   CCGTTGGGTA TACTTTGGCA TATGCGAGTC TCCCACCTAA TTGACGAAAT GGTCTCTCGC

11941   CGCATTTACC GGACCATGGA ACATTCGGGT CAAGCGGCCT GGAAGCAGGT TGTTAGTGAA

12001   GCCACTCTCA CAAAACTGTC AAGGCTTGAC GTAGTCACTC ATTTCCAACA CCTGGCCGCA

12061   GTGGAGGCTG ATTCTTGCCG CTTCCTTAGC TCACGACTCG CGATGCTGAA AAACCTTGCC
```

```
                                  -continued
12121  GTTGGCAATG TGAGCCTGGA GTACAACACT ACTTTGGACC GCGTTGAGCT CATCTTTCCC

12181  ACACCAGGTA CGAGGCCCAA GTTGACCGAT TTTAGGCAAT GGCTTATCAG CGTGCACGCT

12241  TCCATCTTCT CCTCTGTGGC TTCGTCTGTT ACCTTGTTCA CAGTGCTTTG GCTTCGAATT

12301  CCAGCTCTAC GCTATGTTTT TGGTTTCCAT TGGCCCACGG CAACACATCA TTCGAACTAA

12361  CTATCAATTA CACTATATGT AAGCCATGCC CTACCAGTCA AGCTGCCCAA CAAAGACTCG

12421  AGCCTGGCCG TAACGTGTGG TGCAAAATAG GGCACGACAG GTGTGAGGAA CGTGACCATG

12481  ATGAGTTGTC AATGTCCATT CCGTCCGGGT ACGACAACCT CAAACTTGAG GGTTATTATG

12541  CTTGGCTGGC TTTTTTGTCC TTTTCCTACG CGGCCCAATT CCATCCGGAG CTGTTCGGAA

12601  TAGGAAACGT GTCGCGCGTC TTTGTGGATA AGCGACACCA GTTCATTTGC GCCGAGCATG

12661  ATGGACAAAA TTCAACCATA TCTGCCAGAC ACAACATCTC CGCGTCGTAT GCGGTGTATT

12721  ACCATCATCA AATAGACGGG GGCAATTGGT TTCATTTGGA ATGGCTGCGA CCATTCTTTT

12781  CCTCCTGGCT GGTGCTCAAC ATCTCATGGT TTCTGAGGCG TTCGCCTGCA AGCCCTGCTT

12841  CTCGACGCAT CTATCAGATA TTAAGACCAA CACGACCGCG GCTGCCGGTT TCATGGTCCT

12901  TCAGAACATC AATTGTTTCC AATCTCACAG GGCCTCAACA GCGCAAGGTA CCACTCCCCT

12961  CAGGAGGTCG TCCCAATGTC GTGAAGCCGT CGGCATTCCC CAGTACATCA CGATAACGGC

13021  TAATGTGACC GATGAATCGT ATTTGTACAA CGCGGACTTG CTGATGCTTT CCGCGTGCCT

13081  TTTCTACGCC TCGGAAATGA GCGAGAAAGG CTTCAAAGTC ATCTTTGGGA ATATTTCTGG

13141  CGTTGTTTCC GCTTGTGTTA ATTTCACAGA TTATGTGGCC CATGTGACCC AACACACTCA

13201  GCAGCACCAT TTGGTAATTG ATCACATTCG GTTACTACAC TTCTTGACAC CGTCTACGAT

13261  GAGGTGGGCT ACAACCATTG CTTGTTTGCT TGCCATTCTT TTGGCGGTAT GAAATGTTCT

13321  TGCAAGTTGG GGCATTTCTT GACTCCTCAC TCTTGCTTCT GGTGGCTTTT TTTGCTGTGT

13381  ACCGGCTTGT CTTGGTCCTT TGTCGATGGC AACGACGACA GCTCGACATC CCAATACATA

13441  TATAATTTGA CGATATGCGA GCTGAATGGG ACCGAATGGT TGTCCGGTCA TTTTGATTGG

13501  GCAGTCGAAA CCTTTGTGCT TTACCCAGTT GCCACTCATA TCATTTCACT GGGTTTTCTC

13561  ACAACAAGCC ATTTCCTTGA TGCGCTCGGT CTCGGCGCTG TGTCCGCCAC AGGATTCATT

13621  GGCGAGCGGT ATGTACTTAG CAGCATGTAC GGCGTTTGCG CCTTCGCGGC GTTCGTATGT

13681  TTTGTCATCC GTGCTGCTAA AAATTGCATG GCTTGCCGCT ATGCCCGCAC CCGGTTTACC

13741  AACTTCATCG TGGACGACCG GGGAAGAATC CATCGATGGA AGTCTTCAAT AGTGGTGGAG

13801  AAATTGGGCA AGCTGAAGT CGGTGGTGAC CTTGTCAACA TTAAGCATGT TGTCCTCGAA

13861  GGGGTTAAAG CTCAACCTTT GACGAGGACT TCGGCTGAGC AATGGGAAGC CTAGACGACT

13921  TTTGCAACGA TCCCACCGCC GCACAAAAAC TCGTGCTGGC CTTTAGCATC ACATATACAC

13981  CCATAATGAT ATACGCCCTT AAGGTGTCAC GCGGCCGACT CCTGGGGCTG TTGCACATCT

14041  TGATATTTCT GAATTGTTCC TTTACTTTTG GGTACATGAC ATATGTGCAT TTTCAATCCA

14101  CCAACCGTGT CGCATTCACT CTGGGGGCTG TAGTCGCCCT TTTGTGGGGT GTTTACAGCC

14161  TCACAGAGTC ATGGAAGTTC ATCACTTCCA GATGCAGATT GTGTTGCCTA GGCCGGCGAT

14221  ACATTCTGGC CCCTGCCCAT CACGTAGAAA GTGCTGCAGG CCTCCATTCA ATCCCAGCGT

14281  CTGGTAACCG AGCATACGCT GTGAGAAAGC CCGGACTAAC ATCAGTGAAC GGCACTCTAG

14341  TACCTGGGCT TCGGAGCCTC GTGCTGGGCG GCAAACGAGC TGTTAAACGA GGAGTGGTTA

14401  ACCTCGTCAA GTATGGCCGG TAAGAACCAG AGCCAGAAGA AAGAAGAAA TGCAGCTCCG

14461  ATGGGGAAAG GCCAGCCAGT CAATCAACTG TGCCAGTTGC TGGGTACAAT GATAAAGTCC

14521  CAGCGCCAGC AATCTAGGGG AGGACAGGCC AAAAAGAAGA AGCCTGAGAA GCCACATTTT
```

-continued

```
14581  CCCCTAGCTG CTGAAGATGA CATTCGGCAC CATCTCACCC AGGCCGAACG TTCCCTCTGC

14641  TTGCAATCGA TCCAGACGGC TTTCAATCAA GGCGCAGGAA CTGCGTCGCT TTCATCCAGC

14701  GGGAAGGTCA GTTTCCAGGT TGAGTTCATG CTGCCGGTTG CTCATACAGT GCGCCTGATT

14761  CGCGTGACTT CTACATCCGC CAGTCAGGGT GCAAATTAAT TTGACAGTCA GGTGAATGGC

14821  CGCGATTGAC GTGTGGCCTC TAA
```

SEQ ID NO: 2: ORF 1a OF 94881 MSV ENCODED BY SEQUENCE OF SEQ ID NO: 1
BETWEEN NUCLEOTIDES 178..7227

MSGMFSRCMCTPAARVFWNAGQVYCTRCLSARSLLSPELQDTDLGAVGLFHKPKDK

LHWKVPIGIPQVECSPSGCCWLSTIFPLARMTSGNHNFLQRLVKVADVLYRDGCLTPR

HLRELQVYERGCNWYPITGPVPGMAVYANSMHVSDQPFPGATHVLTNSPLPQRACR

QPFCPFEEAHSSIYRWEKFVIFMDSSSDGRSRMMWTPESDDSTALEVLPPELEHQVK

VLVRSFPAHHLVDLADWELTESPDNGFSFSTSHPCGYLVRDPAVSEGKCWLSCFLSQ

SAEVLSREAHLATAYGYQTKWGVPGKYIQRRLQVHGLRAVVDPDGPIHVEALSCPQS

WIRHLTLNDDVTPGFVRLMSLRIVPNTEPTTHRIFRFGVHKWYGAAGKRARGKRAAKS

EKDSASTLKVARPTSTSGIVTYSPPADGSCGWHALAAILNRMINNDFTSPLPRYNRPED

DWASDGDLAQAIQCLQLPAAIARNRACPNAKYLIKLNGVHWEVEVRPGMAPRSLSRE

CVVGVCSEGCVASPYPEDGLPKRALEALASAYRLPSDCVCDGIIDFLANPPPQEFWTL

DKMLTSPSPEQSGFSSLYKLLLEILPQKCGSTEGEFIYTVERMLKDCPSSKQAMALLAK

IKVPSSKAPSVTLNECFPTDVPVNSELISWEEPKDPGAAVVLCPSDAKESKETAPEEAQ

ARNRKVLHPVVLTEELSEQQVQVVEGDQDMPLDLTWPTLTATATPVRGPVPDNLSSGI

GAQPATVQELILARPAPRLVERCGTESNGSSSFLDLPDVQTSDQPLDLSLAAWPVRAT

ASDPGWIHGRREPVFVKPRGVFSDGESALQFGELSEASSVVDDRTKEAPVVDAPIDLT

TSNETLSGSDPFEFAKFRRPRFSAQALIDRGGPLADVHAKIKSRVYEQCLQACEPGSR

ATPATKKWLDKMWDRVDMKTWRCTSQFQAGHILESLKFLPDMIQDTPPPVPRKNRAG

DSAGLKQLVAQWDRKSSVTPPTKPVGPVLDQAVPLPMDIQQGDAISADKPPHSQNPS

SQVDVGGGWKSFMLSGTRFAGSVSQRLTTWVFEVLSHLPAFMLTLFSPRGSMAPGD

WLFAGAVLLALLLCRSYPILGCLPLLGVFSGSVRCVRLGVFGSWMAFAVFLFSTPPDP

VGSSCDHDSPECHAELLALEQRQLWEPVRSLVVGPSGLLCVILGKLLGGSRCLWFVLL

RICMLADLAISLIYVVSQGRCHKCWGKCIRTAPAEVALNVFPFSRATRSSLVSLCDRFQ

APKGVDPVHLATGWRGCWCGESPIHQSHQKPIAYANLDEKKISAQTVIAVPYDPSQAI

KCLKVLQAGGAIVDQPTPEVVRVSEIPFSAPFFPKVPVNPDCRVVVDSDTFVAAVRCG

YSTAQLVLGRGNFAKLNQTPLRNSVPTKTTGGASYTLAVAQVSVWTLVHFILGLWLTS

PQVCGRGTSDPWCSNPFSYPTYGPGVVCSSRLCVSADGVTLPLFSAVAHLSGREVGI

FILVLASLGALAHRLALKADMSMVFLAFCAYAWPMSSWLICFFPMLLRWVTLHPLTML

WVHSFLVFCLPAAGVLSLGITGLLWAVGRFTQVAGIITPYDIHQYTSGPRGAAAVATAP

EGTYMAAVRRAALTGRTLIFTPSAVGSLLEGAFRTQKPCLNTVNVVGSSLGSGGVFTID

GRRVIVTATHVLNGNTARVTGDSYNRMHTFNTNGDYAWSHADDWQGVAPMVKIAKG

YRGRAYWQTSTGVEPGIMGEGFAFCFTNCGDSGSPVISEAGDLIGVHTGSNKLGSGL

VTTPEGETCSIKETRLSDLSRHFAGPSVPLGDIKLSPAIIPDVTTIPSDLASLLASVPVME

GGLSTVQLLCVFFLLWRMMGHAWTPIVAVGFFLLNEILPAVLVRAVFSFALFVLAWATP

WSAQVLMIRLLTAALNRNRLSLAFYAFGGVVGLATEIGTFAGGWPELSQALSTYCFLP

RFLAVTSYVPTIIIGGLHALGVILWLFKYRCLHNMLVGDGSFSSAFFLRYFAEGNLRKGV

-continued

SQSCGMNNESLTAALACKLSQADLDFLSSLTNFKCFVSASNMKNAAGQYIEAAYARAL

RQELASLVQVDKMKGVLAKLEAFAETATPSLDTGDVIVLLGQHPHGSILDINVGGERKT

VSVQETRCLGGSKFSVCTVVSNTPVDTLTGIPLQTPTPLFENGPRHRSEDDDLKVERM

KKHCVSLGFHKINGKVYCKIWDKSNGDTFYTDDSRYTQDHAFQDRSTDYRDRDYEGV

QTAPQQGFDPKSEAPVGTVVIGGITYNRHLVKGKEVLVPKPDNCLEAARLSLEQALAG

MGQTCDLTATEVEKLKRIISQLQGLTTEQALNC

SEQ ID NO: 3 ORF 1B OF 94881 MSV ENCODED BY SEQUENCE OF SEQ ID NO: 1
BETWEEN NUCLEOTIDES 7209...11600
TGFKLLAASGLTRCGRGGLVVTETAVKIVKYHSRTFTLGSLDLKVTSEVEVKKSTEQGH

AVVANLCSGVVLMRPHPPSLVDVLLKPGLDTTPGIQPGHGAGNMGVNGSIWDFETAP

TKVELELSKQIIQACEVRRGDAPNLQLPYKLYPVRGDPERRKGRLVNTRFGDLPYKTP

QDTKSAIHAACCLHPNGVLVSDGKSTLGTTLQHGFELYVPTVPYSVMEYLDSRPDTPF

MCTKHGTSKAAAEDLQKYDLSTQGFVLPGVLRLVRRFIFSHVGKAPPLFLPSTYPAKN

SMAGVNGQRFPTKDVQSIPEIDEMCARAVKENWQTVTPCTLKKQYCSKPKTRTILGTN

NFIALAHRSALSGVTQAFMKKAWKSPIALGKNKFKELHCTVAGRCLEADLASCDRSTP

AIVRWFVANLLYELAGCEEYLPSYVLNCCHDLVATQDGAFTKRGGLSSGDPVTSVSNT

VYSLIIYAQHMVLSALKMGHEIGLKFLEEQLKFEDLLEIQPMLVYSDDLVLYAERPTFPN

YHWWVEHLDLMLGFKTDPKKTVITDKPSFLGCRIEAGRQLVPNRDRILAALAYHMKAQ

NASEYYASAAAILMDSCACIDHDPEWYEDLICGIARCARQDGYRFPGPAFFMSMWEKL

KSHNEGKKCRHCGICDAKADYASACGLDLCLFHSHFHQHCPVTLSCGHHAGSKECSQ

CQSPVGAG KSPLDAVLKQIPYKPPRTIIMKVDNKTTTLDPGRYQSRRGLVAVKRGIAGN

EVDLSDGDYQVVPLLPTCKDINMVKVACNVLLSKFIVGPPGSGKTTWLLNQVQDDDVI

YTPTHQTMFDIVSALKVCRYSIPGASGLPFPPPARSGPWVRLIASGHVPGRVSYLDEA

GYCNHLDILRLLSKTPLVCLGDLQQLHPVGFDSYCYVFDQMPQKQLTTIYRFGPNICAA

IQPCYREKLESKARNTRVVFTTRPVAFGQVLTPYHKDRTGSAITIDSSQGATFDIVTLHL

PSPKSLNKSRALVAITRARHGLFIYDPHDQLQEFFNLTPERTDCNLAFSRGDELVVLNV

DNAVTTVAKALETGSPRFRVSDPRCKSLLAACSASLEGSCMPLPQVAHNLGFYFSPDS

PAFAPLPKELAPHWPVVTHQNNRAWPDRLVASMRPIDARYSKPMVGAGYVVGPSIFL

GTPGVVSYYLTLYIGGEPQALPETLVSTGRIATDCREYLDAAEEEAARELPHAFIGDVK

GTTIGGCHHITSKYLPRSLPKDSVAVVGVSSPGRAAKAVCTLTDVYLPELRPYLQPETA

SKCWKLKLDFRDVRLMVWKGATAYFQLEGLTWSALPDYARFIQLPKDAVVYIDPCIGP

ATANRKVVRTTDWRADLAVTPYDYGAQVILTTAWFEDLGPQWKILGLQPFRRTFGFEN

TEDWAILARRMNDGKDYTDYNWHCVRERPHAIYGRARDHTYHFALGTELQVELGRPR

LPPEQVP

SEQ ID NO: 4 ORF 2 OF 94881 MSV ENCODED BY SEQUENCE OF SEQ ID NO: 1
BETWEEN NUCLEOTIDES 11611..12360
MQWVYCGVKSVSCSWMPSLSSLLVWLTLSSFSPYCLGSLLQAGYWSSFSEWFAPRF

SVRALPFTLPNYRRSYEGLLPNCRPDVPQFAVKHPLGILWHMRVSHLIDEMVSRRIYR

TMEHSGQAAWKQVVSEATLTKLSRLDVVTHFQHLAAVEADSCRFLSSRLAMLKNLAV

GNVSLEYNTTLDRVELIFPPTPGTRPKLTDFRQWLISVHASIFSSVASSVTLFTVLWLRIP

ALRYVFGFHWPTATHHSN

-continued

SEQ ID NO: 5 ORF 3 OF 94881 MSV ENCODED BY SEQUENCE OF SEQ ID NO: 1
BETWEEN NUCLEOTIDES 12219..13016
MAYQRARFHLLLCGFVCYLVHSALASNSSSTLCFWFPLAHGNTSFELTINYTICKPCPT

SQAAQQRLEPGRNVWCKIGHDRCEERDHDELSMSIPSGYDNLKLEGYYAWLAFLSFS

YAAQFHPELFGIGNVSRVFVDKRHQFICAEHDGQNSTISARHNISASYAVYYHHQIDGG

NWFHLEWLRPFFSSWLVLNISWFLRRSPASPASRRIYQILRPTRPRLPVSWSFRTSIVS

NLTGPQQRKVPLPSGGRPNVVKPSAFPSTSR

SEQ ID NO: 6 ORF 4 OF 94881 MSV ENCODED BY SEQUENCE OF SEQ ID NO: 1
BETWEEN NUCLEOTIDES 12761..13312
MAATILFLLAGAQHLMVSEAFACKPCFSTHLSDIKTNTTAAAGFMVLQNINCFQSHRAS

TAQGTTPLRRSSQCREAVGIPQYITITANVTDESYLYNADLLMLSACLFYASEMSEKGF

KVIFGNISGVVSACVNFTDYVAHVTQHTQQHHLVIDHIRLLHFLTPSTMRWATTIACLLAI

LLAV

SEQ ID NO: 7 ORF 5 OF 94881 MSV ENCODED BY SEQUENCE OF SEQ ID NO: 1
BETWEEN NUCLEOTIDES 13309..13914
MKCSCKLGHFLTPHSCFWWLFLLCTGLSWSFVDGNDDSSTSQYIYNLTICELNGTEWL

SGHFDWAVETFVLYPVATHIISLGFLTTSHFLDALGLGAVSATGFIGE RYVLSSMYGVC

AFAAFVCFVIRAAKNCMACRYARTRFTNFIVDDRGIHRWKSSIVVEKLGKAEVGGDLV

NIKHVVLEGVKAQPLTRTSAEQWEA

SEQ ID NO: 8 ORF 6 OF 94881 MSV ENCODED BY SEQUENCE OF SEQ ID NO: 1
BETWEEN NUCLEOTIDES 13902..14423
MGSLDDFCNDPTAAQKLVLAFSITYTPIMIYALKVSRGRLLGLLHILIFLNCSFTFGYMTY
VHFQSTNRVAFTLGAVVALLWGVYSLTESWKFITSRCRLCCLGRRYILAPAHHVESAA
GLHSIPASGNRAYAVRKPGLTSVNGTLVPGLRSLVLGGKRAVKRGVVNLVKYGR

SEQ ID NO: 9 ORF 7 OF 94881 MSV ENCODED BY SEQUENCE OF SEQ ID NO: 1
BETWEEN NUCLEOTIDES 14413..14799
MAGKNQSQKKRRNAAPMGKGQPVNQLCQLLGTMIKSQRQQSRGGQAKKKKPEKPH
FPLAAEDDIRHHLTQAERSLCLQSIQTAFNQGAGTASLSSSGKVSFQVEFMLPVAHTV
RLIRVTSTSASQGAN

SEQ ID NO: 10 FULL LENGTH NUCLEOTIDE SEQUENCE OF PARENT PRRS
STRAIN 94881
       1  TTTGTGTACC TTGGAGGCGT GGGTACAGCC CTGCCCCACC CCTTGGCCCC TGTTCTAGCC

61  CGACAGGTAC CCTTCTCTCT CGGGGCGAGC GCGCCGCCTG CTGCTCCCTT GCGGCGGGAA

121  GGACCTCCCG AGTATTTCCG GAGAGCACCT GCTTTACGGG ATCTCCGCCC TTTAACCATG

181  TCTGGGATGT TCTCCCGGTG CATGTGCACC CCGGCTGCCC GGGTATTTTG GAACGCCGGC

241  CAAGTCTATT GCACACGGTG TCTCAGTGCA CGGTCTCTTC TCTCTCCAGA ACTTCAGGAC

301  ACGGACCTCG GTGCAGTTGG CTTGTTTCAC AAGCCTAAAG ACAAGCTCCA TTGGAAAGTT

361  CCCATTGGTA TCCCCCAGGT GGAATGTTCT CCATCTGGGT GTTGCTGGCT GTCAACCATT

421  TTTCCTTTAG CGCGCATGAC CTCCGGCAAT CACAACTTCC TTCAACGACT CGTGAAGGTT

481  GCTGACGTAT TGTACCGTGA CGGTTGCTTA ACCCCTAGAC ACCTCCGTGA ACTCCAAGTT

541  TACGAGCGTG GTTGCAATTG GTATCCGATT ACGGGGCCTG TGCCTGGGAT GGCTGTGTAC

601  GCGAACTCCA TGCACGTGTC CGACCAACCG TTCCCTGGTG CCACTCATGT GTTAACAAAT

661  TCCCCTTTGC CTCAACGGGC TTGTCGGCAG CCGTTCTGTC CGTTCGAAGA GGCCCATTCT

721  AGCATATACA GGTGGGAAAA ATTTGTAATT TTTATGGATT CCTCCTCCGA CGGTCGATCT

781  CGCATGATGT GGACTCCGGA ATCCGATGAC TCCACGGCTT TGGAAGTTCT GCCGCCCGAG

841  CTAGAACACC AGGTCAAGGT CCTTGTTCGG AGCTTTCCCG CCCATCACCT TGTCGACCTT

901  GCCGATTGGG AGCTCACTGA GTCCCCTGAG AACGGTTTTT CCTTCAGCAC GTCACATCCT

961  TGCGGCTACC TTGTTCGGGA CCCGGCTGTA TCCGAAGGCA AGTGTTGGCT TTCCTGCTTT

1021  TTGAGCCAGT CAGCCGAAGT GCTCAGTCGC GAGGCGCATC TGGCTACCGC CTATGGTTAC

-continued

```
1081  CAAACCAAGT GGGGTGTGCC TGGCAAGTAC ATCCAGCGCA GACTTCAAGT TCACGGTCTC
1141  CGTGCTGTGG TCGACCCTGA TGGTCCCATT CACGTTGAAG CATTGTCTTG CCCCCAGTCT
1201  TGGATCAGGC ACTTGACCCT GAATGATGAT GTCACCCCGG GATTCGTTCG CCTAATGTCT
1261  CTTCGCATTG TGCCGAACAC AGAGCCTACC ACACACCGGA TCTTTCGTTT TGGAGTGCAC
1321  AAGTGGTATG GTGCCGCCGG CAAACGGGCC CGTGGCAAGC GTGCCGCCAA AAGTGAGAAA
1381  GACTCGGCTT CCACCCTCAA GGTTGCCCGA CCGACTTCCA CCAGTGGAAT CGTCACCTAC
1441  TCCCCACCTG CGGACGGGTC TTGTGGTTGG CATGCCCTTG CCGCCATACT GAACCGGATG
1501  ATTAATAATG ACTTCACGTC CCCTCTGCCT CGGTACAACA GGCCGGAGGA CGATTGGGCT
1561  TCTGATGGTG ACCTTGCTCA GGCCATTCAA TGTTTGCAAC TACCTGCCGC CATAGCTCGG
1621  AACCGCGCCT GCCCTAACGC CAAATACCTC GTAAAACTCA ACGGAGTTCA TTGGGAGGTA
1681  GAGGTGAGGC CTGGAATGGC TCCTCGCTCC CTCTCTCGTG AGTGCGTTGT TGGCGTCTGC
1741  TCTGAAGGCT GTGTCGCGTC GCCTTACCCG GAGGACGGGT TGCCTAAACG TGCACTTGAG
1801  GCCCTGGCGT CTGCTTATAG ACTGCCTTCA GACTGTGTTT GTGATGGTAT TATTGACTTC
1861  CTTGCCAATC CACCTCCCCA GGAGTTCTGG ACTCTTGACA AATGTTGAC TTCCCCGTCA
1921  CCGGAGCAGT CCGGCTTCTC TAGTCTGTAT AAATTGTTGT TAGAGGTCTT GCCGCAGAAA
1981  TGCGGATCCA CAGAAGGGGA ATTCATCTAT ACTGTTGAGA GGATGTTGAA GGATTGTCCG
2041  AGCTCCAAAC AGGCCATGGC CCTCCTTGCA AAAATTAAGG TCCCATCCTC AAAGGCCCCA
2101  TCCGTGACTC TGAACGAGTG CTTCCCCACG GATGTTCCAG TCAACTCTGA GTTAATATCT
2161  TGGGAAGAGC CCAAAGACCC TGGCGCTGCT GTTGTCCTAT GTCCATCGGA TGCAAAAGAA
2221  TCTAAGGAAA CAGCCCCTGA AGAAGCTCAA GCGAGAAACC GTAAGGTCCT CCACCCTGTG
2281  GTCCTTACCG AGGAACTTAG CGAGCAACAG GTGCAGGTGG TTGAGGGTGA TCAGGATATG
2341  CCACTGGATT TGACTTGGCC AACCTTAACC GCTACGGCGA CCCCTGTTAG AGGGCCGGTA
2401  CCGGACAATT TGAGCTCTGG CATTGGTGCC CAGCCCGCTA CCGTTCAAGA ACTCATTCTG
2461  GCGAGGCCTG CACCCCGTCT TGTTGAGCGC TGTGGCACGG AGTCGAACGG CAGCAGTTCA
2521  TTTCTGGATT TGCCTGACGT GCAGACCTCG GACCAGCCTT TAGACCTGTC CCTGGCCGCG
2581  TGGCCTGTAA GGGCTACCGC GTCTGACCCC GGTTGGATCC ACGGTAGGCG TGAGCCTGTC
2641  TTTGTGAAGC CTCGAGGTGT TTTCTCTGAT GGCGAGTCGG CCCTTCAGTT CGGAGAGCTT
2701  TCCGAAGCCA GTTCTGTCGT CGATGACCGG ACAAAAGAAG CTCCGGTGGT TGACGCCCCC
2761  ATCGATTTGA CAACTTCGAA CGGACGCTC TCTGGGTCTG ACCCCTTTGA ATTCGCCAAA
2821  TTCAGGCGCC CGCGTTTCTC CGCGCAAGCT TTAATCGACC GAGGTGGTCC GCTTGCCGAT
2881  GTTCATGCAA AGATAAAGAG TCGGGTATAT GAACAATGCC TTCAAGCTTG TGAACCTGGT
2941  AGTCGTGCGA CCCCAGCCAC CAAGAAGTGG CTCGACAAAA TGTGGGACAG GGTGGACATG
3001  AAAACTTGGC GCTGCACCTC GCAGTTCCAA GCTGGTCACA TTCTTGAGTC CCTCAAATTC
3061  CTCCCTGACA TGATTCAAGA CACACCGCCT CCTGTTCCCA GGAAGAACCG AGCTGGTGAC
3121  AGTGCCGGCC TGAAGCAACT GGTGGCGCAG TGGGATAGGA AATTGAGTGT GACACCCCCC
3181  ACAAACCGG TTGGACCGGT GCTTGACCAG ACCGTCCCTC TGCCTATGGA CATCCAGCAA
3241  GAAGATGCCA TCTCCGCTGA CAAGCCACCC CATTCGCAAA ACCCTTCTAG TCAAGTAGAT
3301  GTGGGTGGAG GTTGGAAAAG TTTTATGCTC TCCGGCACCC GTTTCGCGGG GTCCGTTAGT
3361  CAGCGCCTTA CGACATGGGT TTTTGAGGTT CTCTCCCATC TCCCAGCTTT TATGCTCACA
3421  CTTTTCTCGC CACGGGGCTC TATGGCTCCA GGTGATTGGC TGTTTGCAGG TGCTGTTCTA
3481  CTTGCTCTCC TGCTCTGCCG TTCTTACCCA ATACTCGGAT GCCTTCCCTT ATTGGGTGTC
```

```
3541  TTTTCTGGTT CTGTGCGGTG TGTTCGTTTG GGTGTTTTTG GTTCTTGGAT GGCTTTTGCT
3601  GTATTTTTAT TCTCGACTCC ACCCGACCCA GTCGGTTCTT CTTGTGACCA CGATTCGCCG
3661  GAGTGTCATG CTGAGCTTTT GGCTCTTGAG CAGCGCCAAC TTTGGGAACC TGTGCGCAGC
3721  CTTGTGGTCG GGCCATCGGG CCTCTTATGC GTCATTCTTG GCAAGTTACT CGGTGGGTCA
3781  CGTTGTCTCT GGTTTGTTCT CCTACGTATA TGCATGCTCG CAGATTTGGC AATTTCTCTT
3841  ATTTATGTGG TGTCCCAAGG GCGTTGTCAC AAGTGTTGGG GAAAGTGTAT AAGGACGGCT
3901  CCTGCAGAAG TGACCCTTAA TGTGTTTCCT TTTTCGCGCG CCACCCGCTC ATCTCTTGTG
3961  TCCTTGTGTG ATCGGTTCCA AGCGCCAAAA GGAGTTGACC CCGTGCACTT GGCGACAGGC
4021  TGGCGCGGGT GCTGGTGTGG TGAGAGCCCT ATTCATCAAT CACACCAAAA ACCGATAGCT
4081  TATGCCAACT TGGATGAAAA GAAGATATCC GCCCAGACGG TGATTGCTGT CCCGTATGAT
4141  CCCAGTCAGG CCATTAAATG CCTGAAAGTT TTGCAGGCAG GAGGGGCTAT TGTGGACCAG
4201  CCTACGCCCG AGGTCGTCCG TGTGTCTGAG ATTCCCTTCT CGGCCCCATT TTTTCCGAAG
4261  GTCCCAGTCA ACCCAGATTG CAGGGTTGTG GTAGATTCGG ACACTTTTGT GGCTGCGGTC
4321  CGCTGCGGTT ATTCGACAGC ACAACTGGTC CTTGGTCGGG GCAACTTTGC CAAGCTAAAT
4381  CAGACCCCCC TCAGGAACTC TGTCCCCACC AAAACAACTG GTGGGGCCTC ATACACCCTT
4441  GCCGTGGCCC AGGTATCTGT GTGGACTCTT GTTCATTTCA TCCTCGGCCT TTGGTTAACG
4501  TCACCTCAAG TGTGTGGTCG AGGGACCTCT GACCCGTGGT GTTCGAACCC TTTTTCGTAT
4561  CCTACTTATG GCCCCGGAGT TGTGTGTTCC TCTCGACTCT GCGTGTCTGC CGACGGAGTT
4621  ACCCTGCCAT TGTTCTCAGC CGTTGCCCAT CTTTCCGGTA GAGAGGTGGG GATTTTTATT
4681  TTGGTGCTTG CCTCCTTGGG CGCTTTAGCC CACCGCTTGG CTCTTAAGGC AGACATGTCA
4741  ATGGTCTTTT TGGCGTTTTG TGCTTACGCC TGGCCCATGA GCTCCTGGTT AATTTGCTTC
4801  TTTCCTATGC TCTTGAGGTG GGTAACCCTT CATCCTCTCA CTATGCTTTG GGTGCACTCA
4861  TTTTTGGTGT TTTGCCTACC AGCTGCCGGC GTTCTCTCGC TGGGAATAAC CGGTCTTCTT
4921  TGGGCAGTTG GCCGTTTCAC CCAGGTTGCC GGAATTATCA CACCTTATGA CATCCACCAG
4981  TATACCTCCG GACCACGTGG TGCAGCTGCT GTAGCAACGG CTCCAGAAGG TACTTACATG
5041  GCGGCCGTTC GGAGAGCCGC TTTGACTGGA CGGACTTTGA TCTTCACACC ATCTGCAGTC
5101  GGATCCCTTC TTGAAGGTGC TTTCAGAACT CAAAAGCCCT GCCTTAACAC CGTGAATGTC
5161  GTAGGCTCTT CCCTTGGTTC TGGAGGAGTT TTCACCATTG ATGGCAGAAG AGTCATCGTC
5221  ACTGCCACCC ATGTGTTGAA TGGTAACACA GCCAGGGTCA CTGGTGATTC CTACAACCGC
5281  ATGCACACGT TCAATACTAA TGGTGATTAT GCCTGGTCCC ATGCTGATGA CTGGCAAGGC
5341  GTTGCCCCTA TGGTTAAGAT CGCTAAGGGG TATCGCGGTC GTGCCTACTG GCAAACGTCA
5401  ACCGGAGTCG AACCTGGCAT CATGGGGGAA GGATTCGCCT TCTGTTTCAC TAACTGTGGC
5461  GACTCAGGGT CACCTGTCAT TTCAGAAGCT GGTGACCTTA TTGGAGTCCA TACCGGTTCA
5521  AACAAACTCG GTTCTGGTCT TGTGACAACC CCTGAAGGGG AGACCTGCTC CATCAAGGAA
5581  ACTAGGCTCT CTGACCTTTC TAGACATTTT GCAGGTCCAA GCGTCCCTCT TGGGGACATT
5641  AAGTTGAGCC CAGCCATCAT CCCTGATGTG ACAACTATTC CGAGTGACTT GGCATCGCTC
5701  CTTGCTTCTG TCCCCGTGAT GGAAGGTGGC CTCTCAACTG TCCAGCTTTT GTGCGTCTTT
5761  TTCCTTCTCT GGCGCATGAT GGGCCATGCC TGGACACCCA TTGTTGCCGT AGGCTTCTTT
5821  TTGCTGAATG AAATTCTCCC AGCAGTCTTG GTCCGAGCTG TGTTCTCTTT TGCACTCTTT
5881  GTACTTGCAT GGGCCACCCC CTGGTCGGCA CAAGTGTTGA TGATTAGACT CCTCACGGCG
5941  GCTCTCAACC GCAACAGGTT GTCCCTGGCG TTCTACGCAC TCGGAGGTGT CGTTGGCCTG
```

```
                                      -continued
6001  GCCACAGAAA TCGGGACTTT TGCTGGTGGA TGGCCTGAAC TGTCCCAAGC CCTCTCGACA

6061  TACTGCTTCC TGCCCAGGTT CCTTGCTGTG ACTAGTTATG TCCCCACCAT CATCATCGGT

6121  GGGCTCCATG CCCTCGGCGT AATTTTGTGG TTATTCAAAT ACCGATGCCT CCACAACATG

6181  CTGGTTGGTG ATGGGAGTTT CTCAAGCGCT TTCTTCCTAC GGTATTTTGC TGAGGGTAAT

6241  CTTAGGAAAG GCGTGTCGCA GTCCTGTGGC ATGAATAACG AATCCCTGAC AGCTGCTTTG

6301  GCTTGCAAGT TGTCGCAAGC TGACCTTGAT TTTTTGTCCA GTTAACGAA CTTCAAGTGC

6361  TTTGTGTCCG CTTCAAACAT GAAAAATGCA GCTGGCCAAT ACATCGAGGC GGCGTATGCT

6421  AGAGCTCTGC GTCAGGAGCT GGCCTCCTTG GTTCAGGTTG ACAAGATGAA AGGAGTATTG

6481  GCCAAGCTCG AGGCTTTCGC TGAGACGGCC ACTCCGTCAC TTGACACAGG TGACGTGATT

6541  GTTCTGCTTG GCAACACCC CCATGGATCC ATCCTCGACA TTAATGTGGG GGGTGAAAGG

6601  AAAACTGTGT CTGTGCAAGA AACACGATGC CTGGGTGGTT CCAAATTCAG TGTCTGCACT

6661  GTCGTGTCCA ACACGCCCGT GGATACCTTG ACCGGCATCC CACTTCAGAC GCCAACCCCA

6721  CTTTTTGAAA ATGGCCCGCG CCATCGCAGC GAGGACGACG ACCTTAAAGT TGAGAGAATG

6781  AAAAAACACT GTGTATCCCT CGGCTTCCAC AAAATCAATG GTAAAGTTTA CTGCAAAATT

6841  TGGGACAAGT CTAACGGCGA CACCTTTTAC ACGGATGATT CCCGATACAC TCAAGACCAT

6901  GCTTTTCAGG ACAGGTCAAC CGACTATAGA GACAGGGATT ATGAAGGTGT ACAGACCGCC

6961  CCCCAACAGG GATTCGATCC AAAGTCCGAA GCCCCTGTTG GCACTGTTGT AATCGGTGGC

7021  ATTACGTATA ACAGGCATCT GGTCAAAGGT AAGGAGGTCC TAGTTCCCAA ACCTGACAAC

7081  TGCCTTGAAG CTGCCAGACT GTCCCTTGAG CAAGCTCTTG CTGGGATGGG CCAAACTTGT

7141  GACCTTACAG CTACCGAAGT GGAGAAACTA AAGCGCATCA TTAGTCAACT CCAAGGTCTG

7201  ACCACTGAAC AGGCTTTAAA CTGCTAGCCG CCAGCGGCTT GACCCGCTGT GGCCGCGGCG

7261  GCCTAGTTGT AACTGAAACG GCGGTAAAAA TCGTAAAATA CCACAGCAGA ACTTTCACCT

7321  TAGGCTCTTT AGACCTAAAA GTCACCTCCG AGGTGGAGGT GAAGAAATCA ACTGAGCAGG

7381  GGCACGCTGT CGTGGCGAAC TTATGTTCCG GTGTCGTCTT GATGAGGCCT CACCCACCGT

7441  CCCTTGTTGA CGTTCTCCTC AAACCCGGAC TTGACACAAC ACCCGGCATT CAACCAGGGC

7501  ATGGGGCCGG AATATGGGC GTGAACGGTT CTATTTGGGA TTTTGAAACT GCACCCACAA

7561  AGGTAGAACT AGAGTTGTCC AAGCAAATAA TCCAAGCATG TGAAGTCAGG CGCGGGGACG

7621  CCCCTAACCT CCAACTCCCC TACAAGCTTT ATCCTGTCAG GGGGGACCCC GAGCGGCGTA

7681  AAGGTCGCCT TGTCAACACT AGGTTTGGAG ATTTACCTTA CAAAACTCCC CAAGACACCA

7741  AGTCCGCAAT TCATGCGGCT TGTTGCCTGC ATCCCAATGG GGTCCTCGTG TCTGATGGTA

7801  AATCCACGCT GGGTACCACT CTTCAACATG GTTTCGAGCT TTATGTCCCC ACTGTACCTT

7861  ATAGTGTCAT GGAATACCTT GATTCACGCC CTGACACCCC TTTTATGTGT ACTAAACATG

7921  GCACTTCCAA GGCTGCTGCA GAGGACCTCC AAAAATATGA CCTATCCACT CAAGGGTTTG

7981  TCTTGCCTGG GGTCCTACGC CTAGTGCGCA GGTTCATCTT TAGCCATGTT GGTAAGGCGC

8041  CACCACTGTT CCTTCCATCA ACCTACCCTG CCAAGAACTC CATGGCAGGG GTCAATGGCC

8101  AGAGGTTCCC AACAAAGGAT GTCCAGAGCA TACCTGAAAT TGATGAAATG TGCGCCCGTG

8161  CCGTCAAGGA AAATTGGCAG ACTGTGACAC CTTGCACCCT CAAAAAACAG TACTGTTCCA

8221  AACCTAAAAC TAGAACCATC CTAGGTACCA CAACTTCAT AGCCTTGGCT CACAGGTCAG

8281  CACTCAGTGG TGTCACCCAG GCGTTCATGA AGAAGGCCTG GAAGTCCCCA ATTGCCTTGG

8341  GGAAAACAA GTTTAAGGAA TTGCATTGCA CTGTCGCCGG CAGATGCCTT GAGGCTGACC

8401  TGGCTTCCTG CGATCGCAGC ACCCCCGCCA TTGTGAGGTG GTTTGTTGCC AACCTCCTGT
```

```
8461  ATGAACTTGC AGGATGTGAA GAGTACTTGC CTAGCTACGT GCTCAACTGT TGCCATGACC
8521  TTGTGGCAAC GCAGGATGGC GCTTTCACAA AACGCGGTGG CCTGTCGTCC GGGGACCCCG
8581  TCACCAGTGT GTCCAACACC GTCTACTCAC TGATAATTTA CGCCCAGCAC ATGGTGCTTT
8641  CGGCCTTGAA GATGGGTCAT GAAATTGGTC TCAAGTTCCT TGAGGAACAG CTCAAATTTG
8701  AGGACCTTCT TGAAATCCAG CCCATGTTAG TGTATTCTGA TGACCTCGTC TTGTATGCGG
8761  AAAGACCCAC TTTTCCCAAC TACCATTGGT GGGTCGAGCA TCTTGACCTG ATGTTGGGCT
8821  TTAAAACGGA CCCAAAGAAA ACTGTCATAA CTGATAAACC CAGTTTTCTC GGCTGCAGAA
8881  TTGAAGCAGG ACGGCAGTTA GTCCCCAATC GCGACCGTAT TCTGGCTGCT CTTGCATATC
8941  ATATGAAGGC GCAGAACGCC TCAGAGTATT ATGCGTCCGC TGCCGCAATT CTGATGGATT
9001  CGTGTGCTTG CATTGACCAT GACCCCGAGT GGTATGAGGA CCTTATCTGC GGCATCGCCC
9061  GGTGTGCTCG CCAGGACGGT TACCGTTTTC CAGGCCCGGC ATTTTTCATG TCCATGTGGG
9121  AGAAGCTGAA AAGTCATAAC GAAGGGAAGA AATGCCGTCA CTGCGGCATC TGCGACGCCA
9181  AAGCCGACTA TGCGTCCGCC TGTGGACTTG ATTTGTGTTT GTTCCATTCA CACTTTCATC
9241  AACACTGCCC AGTCACTCTG AGCTGTGGCC ACCATGCCGG TTCAAAGGAA TGTTCGCAGT
9301  GTCAGTCACC TGTCGGGGCT GGCAAATCCC CCCTTGACGC TGTGCTGAAA CAAATCCCGT
9361  ACAAACCTCC TCGTACCATT ATCATGAAGG TGGACAACAA AACAACGACC CTTGACCCGG
9421  GAAGATATCA GTCCCGTCGA GGTCTTGTTG CAGTCAAAAG AGGTATTGCA GGTAATGAGG
9481  TTGATCTTTC TGATGGAGAC TACCAAGTGG TGCCTCTTTT GCCGACTTGC AAAGACATAA
9541  ACATGGTGAA GGTGGCTTGC AACGTACTAC TCAGCAAGTT TATAGTAGGG CCGCCAGGTT
9601  CCGGAAAAAC CACCTGGCTA CTGAACCAAG TCCAGGACGA TGATGTCATT TACACACCTA
9661  CTCATCAGAC AATGTTTGAC ATAGTCAGTG CTCTTAAAGT TTGCAGGTAT TCCATCCCAG
9721  GAGCCTCAGG ACTCCCTTTT CCACCACCTG CCAGGTCCGG GCCGTGGGTT AGGCTCATCG
9781  CCAGCGGACA TGTCCCTGGC CGAGTGTCAT ATCTCGATGA GGCAGGATAT TGCAATCATC
9841  TAGACATTCT AAGGCTGCTT TCCAAAACAC CCCTTGTGTG TTTGGGTGAC CTTCAGCAAC
9901  TTCACCCGGT CGGCTTTGAT TCCTATTGTT ATGTGTTCGA TCAGATGCCT CAGAAGCAGC
9961  TGACCACCAT TTATAGATTT GGCCCTAACA TCTGTGCAGC CATCCAGCCT TGTTACAGGG
10021 AGAAACTTGA ATCCAAGGCC AGGAACACCA GAGTGGTTTT CACCACCCGG CCTGTGGCCT
10081 TTGGTCAGGT CCTGACACCG TACCACAAAG ATCGTACCGG CTCTGCAATA ACTATAGATT
10141 CATCCCAGGG GGCGACCTTC GACATTGTGA CATTGCATCT ACCATCGCCA AAGTCCCTAA
10201 ACAAATCCCG AGCACTTGTA GCCATCACTC GGGCAAGACA TGGGTTGTTC ATTTATGACC
10261 CTCATGACCA ACTCCAGGAG TTTTTCAACT TAACCCCCGA GCGCACTGAT TGTAACCTTG
10321 CGTTCAGCCG TGGGGATGAG CTGGTTGTTT TGAATGTGGA TAATGCGGTC ACAACTGTAG
10381 CGAAGGCCCT AGAGACAGGT TCACCCCGAT TTCGAGTATC GGACCCGAGG TGCAAGTCTC
10441 TCTTAGCCGC TTGTTCGGCC AGTCTAGAAG GGAGCTGCAT GCCACTACCA CAAGTAGCAC
10501 ATAACCTGGG GTTTTACTTT TCCCCGGACA GCCCAGCTTT TGCACCCCTG CCAAAAGAGC
10561 TGGCGCCACA TTGGCCAGTG GTCACCCACC AGAATAATCG AGCGTGGCCT GATCGACTTG
10621 TCGCTAGTAT GCGCCCAATT GATGCCCGCT ACAGCAAGCC AATGGTCGGT GCAGGGTATG
10681 TGGTCGGGCC ATCCATTTTT CTTGGCACTC CTGGTGTGGT GTCATACTAT CTCACATTAT
10741 ACATCGGGGG CGAGCCTCAG GCCCTGCCAG AAACACTCGT TTCAACAGGA CGTATAGCCA
10801 CAGATTGTCG GGAATATCTC GACGCGGCTG AGGAAGAGGC AGCGAGAGAA CTTCCCCACG
10861 CATTTATTGG CGATGTCAAA GGCACTACGG TCGGGGGGTG TCACCACATT ACATCGAAAT
```

-continued

```
10921  ACCTACCTAG GTCCCTGCCT AAAGACTCTG TTGCTGTGGT TGGGGTGAGT TCGCCCGGTA
10981  GGGCTGCTAA AGCCGTGTGC ACTCTCACCG ATGTGTACCT CCCCGAACTC CGACCATATT
11041  TGCAACCGGA GACGGCATCA AAATGCTGGA AACTTAAACT GGATTTCAGG GATGTTCGAC
11101  TGATGGTCTG GAAAGGCGCC ACAGCCTATT TCCAGTTGGA AGGGCTGACA TGGTCAGCGC
11161  TGCCCGATTA TGCTAGGTTC ATTCAGCTAC CCAAGGATGC CGTTGTGTAC ATCGATCCGT
11221  GTATAGGGCC GGCAACAGCC AATCGCAAGG TTGTGCGAAC CACAGACTGG CGGGCCGACC
11281  TGGCAGTGAC ACCGTATGAT TACGGTGCTC AGGTCATTTT GACAACAGCC TGGTTCGAGG
11341  ACCTTGGGCC GCAGTGGAAG ATTTTGGGGT TGCAGCCTTT CAGACGAACA TTTGGCTTTG
11401  AGAACACTGA AGATTGGGCA ATTCTCGCAC GCCGTATGAA TGACGGCAAA GATTACACTG
11461  ACTATAATTG GCATTGTGTA CGAGAACGCC CACACGCAAT TTACGGGCGC GCCCGTGACC
11521  ATACGTATCA TTTTGCCCTT GGCACTGAAC TGCAAGTAGA GCTGGGCAGA CCCCGGCTGC
11581  CTCCTGAGCA AGTGCCGTGA ACGCGGAGTG ATGCAATGGG TTCACTGTGG AGTAAAATCA
11641  GTCAGTTGTT CGTGGATGCC TTCACTGAGT TCCTTGTTAG TGTGGTTGAC ATTGTCATCT
11701  TTCTCGCCAT ATTGTTTGGG TTCACTGTTG CAGGCTGGTT ATTGGTCTTC CTTCTCAGAG
11761  TGGTTTGCTC CGCGTTTCTC CGTTCGCGCT CTGCCATTCA CTCTCCCGAA CTATCGAAGG
11821  TCCTATGAGG GCTTGCTACC CAACTGCAGA CCGGATGTCC CACAATTCGC AGTTAAGCAC
11881  CCGTTGGGTA TACTTTGGCA TATGCGAGTC TCCCACCTAA TTGACGAAAT GGTCTCTCGC
11941  CGCATTTACC GGACCATGGA ACATTCGGGT CAAGCGGCCT GGAAGCAGGT TGTTAGTGAA
12001  GCCACTCTCA CAAAACTGTC AAGGCTTGAC GTAGTCACTC ATTTCCAACA CCTGGCCGCA
12061  GTGGAGGCTG ATTCTTGCCG CTTCCTTAGC TCACGACTCG CGATGCTGAA AAACCTTGCC
12121  GTTGGCAATG TGAGCCTGGA GTACAACACT ACTTTGGACC GCGTTGAGCT CATCTTTCCC
12181  ACACCAGGTA CGAGGCCCAA GTTGACCGAT TTTAGGCAAT GGCTTATCAG CGTGCACGCT
12241  TCCATCTTCT CCTCTGTGGC TTCGTCTGTT ACCTTGTTCA CAGTGCTTTG GCTTCGAATT
12301  CCAGCTCTAC GCTATGTTTT TGGTTTCCAT TGGCCCACGG CAACACATCA TTCGAACTAA
12361  CTATCAATTA CACTATATGT AAGCCATGCC CTACCAGTCA AGCTGCCCAA CAAAGACTCG
12421  AGCCTGGCCG TAACGTGTGG TGCAAAATAG GGCACGACAG GTGTGAGGAA CGTGACCATG
12481  ATGAGTTGTC AATGTCCATT CCGTCCGGGT ACGACAACCT CAAACTTGAG GGTTATTATG
12541  CTTGGCTGGC TTTTTTGTCC TTTTCCTACG CGGCCCAATT CCATCCGGAG CTGTTCGGAA
12601  TAGGAAACGT GTCGCGCGTC TTTGTGGATA AGCGACACCA GTTCATTTGC GCCGAGCATG
12661  ATGGACAAAA TTCAACCATA TCTGCCAGAC ACAACATCTC CGCGTCGTAT GCGGTGTATT
12721  ACCATCATCA AATAGACGGG GGCAATTGGT TCATTTGGA ATGGCTGCGA CCATTCTTTT
12781  CCTCCTGGCT GGTGCTCAAC ATCTCATGGT TTCTGAGGCG TTCGCCTGCA AGCCCTGCTT
12841  CTCGACGCAT CTATCAGATA TTAAGACCAA CACGACCGCG GCTGCCGGTT TCATGGTCCT
12901  TCAGAACATC AATTGTTTCC AATCTCACAG GGCCTCAACA GCGCAAGGTA CCACTCCCCT
12961  CAGGAGGTCG TCCCAATGTC GTGAAGCCGT CGGCATTCCC CAGTACATCA CGATAACGGC
13021  TAATGTGACC GATGAATCGT ATTTGTACAA CGCGGACTTG CTGATGCTTT CCGCGTGCCT
13081  TTTCTACGCC TCGGAAATGA GCGAGAAAGG CTTCAAAGTC ATCTTTGGGA ATATTTCTGG
13141  CGTTGTTTCC GCTTGTGTTA ATTTCACAGA TTATGTGGCC CATGTGACCC AACACACTCA
13201  GCAGCACCAT TTGGTAATTG ATCACATTCG GTTACTACAC TTCTTGACAC CGTCTACGAT
13261  GAGGTGGGCT ACAACCATTG CTTGTTTGTT TGCCATTCTT TTGGCGGTAT GAAATGTTCT
13321  TGCAAGTTGG GGCATTTCTT GACTCCTCAC TCTTGCTTCT GGTGGCTTTT TTTGCTGTGT
```

```
                                        -continued
13381  ACCGGCTTGT CTTGGTCCTT TGTCGATGGC AACGACAACA GCTCGACATC CCAATACATA

13441  TATAATTTGA CGATATGCGA GCTGAATGGG ACCGAATGGT TGTCCGGTCA TTTTGATTGG

13501  GCAGTCGAAA CCTTTGTGCT TTACCCAGTT GCCACTCATA TCATTTCACT GGGTTTTCTC

13561  ACAACAAGCC ATTTCCTTGA TGCGCTCGGT CTCGGCGCTG TGTCCGCCAC AGGATTCATT

13621  GGCGAGCGGT ATGTACTTAG CAGCATGTAC GGCGTTTGCG CCTTCGCGGC GCTCGTATGT

13681  TTTGTCATCC GTGCTGCTAA AAATTGCATG GCTTGCCGCT ATGCCCGCAC CCGGTTTACC

13741  AACTTCATCG TGGACGACCG GGGAAGAATC CATCGATGGA AGTCTTCAAT AGTGGTGGAG

13801  AAATTGGGCA AGCTGAAGT CGGTGGTGAC CTTGTCAACA TTAAGCATGT TGTCCTCGAA

13861  GGGGTTAAAG CTCAACCCTT GACGAGGACT TCGGCTGAGC AATGGGAAGC CTAGACGACT

13921  TTTGCAACGA TCCCACCGCC GCACAAAAAC TCGTGCTGGC CTTTAGCATC ACATATACAC

13981  CCATAATGAT ATACGCCCTT AAGGTGTCAC GCGGCCGACT CCTGGGGCTG TTGCACATCT

14041  TGATATTTCT GAATTGTTCC TTTACTTTTG GGTACATGAC ATATGTGCAT TTTCAATCCA

14101  CCAACCGTGT CGCACTCACT CTGGGGGCTG TAGTCGCCCT TTTGTGGGGT GTTTACAGCC

14161  TCACAGAGTC ATGGAAGTTC ATCACTTCCA GATGCAGATT GTGTTGCCTA GGCCGGCGAT

14221  ACATTCTGGC CCCTGCCCAT CACGTAGAAA GTGCTGCAGG CCTCCATTCA ATCCCAGCGT

14281  CTGGTAACCG AGCATACGCT GTGAGAAAGC CCGGACTAAC ATCAGTGAAC GGCACTCTAG

14341  TACCTGGGCT TCGGAGCCTC GTGCTGGGCG GCAAACGAGC TGTTAAACGA GGAGTGGTTA

14401  ACCTCGTCAA GTATGGCCGG TAAGAACCAG AGCCAGAAGA AAGAAGAAA TGCAGCTCCG

14461  ATGGGGAAAG GCCAGCCAGT CAATCAACTG TGCCAGTTGC TGGGTACAAT GATAAAGTCC

14521  CAGCGCCAGC AATCTAGGGG AGGACAGGCC AAAAAGAAGA AGCCTGAGAA GCCACATTTT

14581  CCCCTAGCTG CTGAAGATGA CATTCGGCAC CATCTCACCC AGGCCGAACG TTCCCTCTGC

14641  TTGCAATCGA TCCAGACGGC TTTCAATCAA GGCGCAGGAA CTGCGTCGCT TTCATCCAGC

14701  GGGAAGGTCA GTTTCCAGGT TGAGTTCATG CTGCCGGTTG CTCATACAGT GCGCCTGATT

14761  CGCGTGACTT CTACATCCGC CAGTCAGGGT GCAAATTAAT TGACAGTCA GGTGAATGGC

14821  CGCGATTGAC GTGTGGCCTC TAA
```

SEQ ID NO: 11 ORF 1a OF PARENTAL PRRSV STRAIN 94881 ENCODED BY
SEQUENCE OF SEQ ID NO: 10 BETWEEN NUCLEOTIDES 178..7227
MSGMFSRCMCTPAARVFWNAGQVYCTRCLSARSLLSPELQDTDLGAVGLFHKPKDKLHWKVPIGIPQVECSPSOCCW

LSTIFPLARMTSGNHNFLQRLVKVADVLYRDGCLTPRHLRELQVYERGCNWYPITGPVPGMAVYANSMHVSDQPFPG

ATHVLTNSPLPQRACRQPFCPFEEAHSSIYRWEKFVIFMDSSSDORSRMMWTPESDDSTALEVLPPELEHQVKVLVR

SFPAHHLVDLADWELTESPENGFSFSTSHPCGYLVRDPAVSEGKCWLSCFLSQSAEVLSREAHLATAYGYQTKWGVP

GKYIQRRLQVHGLRAVVDPDGPIHVEALSCPQSWIRHLTLNDDVTPGFVRLMSLRIVPNTEPTTHRIFRFGVHKWYG

AAGKRARGKRAAKSEKDSASTLKVARPTSTSGIVTYSPPADOSCOWHALAAILNRMINNDFTSPLPRYNRPEDDWAS

DODLAQAIQCLQLPAAIARNRACPNAKYLVKLNGVHWEVEVRPGMAPRSLSRECVVGVCSEGCVASPYPEDGLPKRA

LEALASAYRLPSDCVCDGIIDFLANPPPQEFWTLDKMLTSPSPEQSGFSSLYKLLLEVLPQKCGSTEGEFIYTVERM

LKDCPSSKQAMALLAKIKVPSSKAPSVTLNECFPTDVPVNSELISWEEPKDPGAAVVLCPSDAKESKETAPEEAQAR

NRKVLHPVVLTEELSEQQVQVVEGDQDMPLDLTWPTLTATATPVRGPVPDNLSSGIGAQPATVQELILARPAPRLVE

RCGTESNGSSSFLDLPDVQTSDQPLDLSLAAWPVRATASDPGWIHGRREPVFVKPROVFSDGESALQFGELSEASSV

VDDRTKEAPVVDAPIDLTTSNETLSGSDPFEFAKFRRPRFSAQALIDROGPLADVHAKIKSRVYEQCLQACEPGSRA

TPATKKWLDKMWDRVDMKTWRCTSQFQAGHILESLKFLPDMIQDTPPPVPRKNRAGDSAGLKQLVAQWDRKLSVTPP

TKPVGPVLDQTVPLPMDIQQEDAISADKPPHSQNPSSQVDVGGGWKSFMLSGTRFAGSVSQRLTTWVFEVLSHLPAF

MLTLFSPRGSMAPGDWLFAGAVLLALLLCRSYPILGCLPLLGVFSGSVRCVRLGVFGSWMAFAVFLFSTPPDPVGSS

-continued

CDHDSPECHAELLALEQRQLWEPVRSLVVGPSGLLCVILGKLLGGSRCLWFVLLRICMLADLAISLIYVVSQGRCHK

CWGKCIRTAPAEVTLNVFPFSRATRSSLVSLCDRFQAPKGVDPVHLATGWRGCWCGESPIHQSHQKPIAYANLDEKK

ISAQTVIAVPYDPSQAIKCLKVLQAGGAIVDQPTPEVVRVSEIPFSAPFFPKVPVNPDCRVVVDSDTFVAAVRCGYS

TAQLVLGRGNFAKLNQTPLRNSVPTKTTGGASYTLAVAQVSVWTLVHFILGLWLTSPQVCGRGTSDPWCSNPFSYPT

YGPGVVCSSRLCVSADGVTLPLFSAVAHLSGREVGIFILVLASLGALAHRLALKADMSMVFLAFCAYAWPMSSWLIC

FFPMLLRWVTLHPLTMLWVHSFLVFCLPAAGVLSLGITGLLWAVGRFTQVAGIITPYDIHQYTSGPRGAAAVATAPE

GTYMAAVRRAALTGRTLIFTPSAVGSLLEGAFRTQKPCLNTVNVVGSSLGSGGVFTIDGRRVIVTATHVLNGNTARV

TGDSYNRMHTFNTNGDYAWSHADDWQGVAPMVKIAKGYRGRAYWQTSTGVEPGIMGEGFAFCFTNCGDSGSPVISEA

GDLIGVHTGSNKLGSGLVTTPEGETCSIKETRLSDLSRHFAGPSVPLGDIKLSPAIIPDVTTIPSDLASLLASVPVM

EGGLSTVQLLCVFFLLWRMMGHAWTPIVAVGFFLLNEILPAVLVRAVFSFALFVLAWATPWSAQVLMIRLLTAALNR

NRLSLAFYALGGVVGLATEIGTFAGGWPELSQALSTYCFLPRFLAVTSYVPTIIIGGLHALGVILWLFKYRCLHNML

VGDGSFSSAFFLRYFAEGNLRKGVSQSCGMNNESLTAALACKLSQADLDFLSSLTNFKCFVSASNMKNAAGQYIEAA

YARALRQELASLVQVDKMKGVLAKLEAFAETATPSLDTGDVIVLLGQHPHGSILDINVGGERKTVSVQETRCLGGSK

FSVCTVVSNTPVDTLTGIPLQTPTPLFENGPRHRSEDDDLKVERMKKHCVSLGFHKINGKVYCKIWDKSNGDTFYTD

DSRYTQDHAFQDRSTDYRDRDYEGVQTAPQQGFDPKSEAPVGTVVIGGITYNRHLVKGKEVLVPKPDNCLEAARLSL

EQALAGMGQTCDLTATEVEKLKRIISQLQGLTTEQALNC

SEQ ID NO: 12 ORF 1B OF PARENTAL PRRSV STRAIN 94881 ENCODED BY
SEQUENCE OF SEQ ID NO: 10 BETWEEN NUCLEOTIDES 7209..11600

TGFKLLAASGLTRCGRGGLVVTETAVKIVKYHSRTFTLGSLDLKVTSEVEVKKSTEQGHAVVANLCSGVVLMRPHPP

SLVDVLLKPGLDTTPGIQPGHGAGNMGVNGSIWDFETAPTKVELELSKQIIQACEVRRGDAPNLQLPYKLYPVRGDP

ERRKGRLVNTRFGDLPYKTPQDTKSAIHAACCLHPNGVLVSDGKSTLGTTLQHGFELYVPTVPYSVMEYLDSRPDTP

FMCTKHGTSKAAAEDLQKYDLSTQGFVLPGVLRLVRRFIFSHVGKAPPLFLPSTYPAKNSMAGVNGQRFPTKDVQSI

PEIDEMCARAVKENWQTVTPCTLKKQYCSKPKTRTILGTNNFIALAHRSALSGVTQAFMKKAWKSPIALGKNKFKEL

HCTVAGRCLEADLASCDRSTPAIVRWFVANLLYELAGCEEYLPSYVLNCCHDLVATQDGAFTKRGGLSSGDPVTSVS

NTVYSLIIYAQHMVLSALKMGHEIGLKFLEEQLKFEDLLEIQPMLVYSDDLVLYAERPTFPNYHWWVEHLDLMLGFK

TDPKKTVITDKPSFLGCRIEAGRQLVPNRDRILAALAYHMKAQNASEYYASAAAILMDSCACIDHDPEWYEDLICGI

ARCARQDGYRFPGPAFFMSMWEKLKSHNEGKKCRHCGICDAKADYASACGLDLCLFHSHFHQHCPVTLSCGHHAGSK

ECSQCQSPVGAGKSPLDAVLKQIPYKPPRTIIMKVDNKTTTLDPGRYQSRRGLVAVKRGIAGNEVDLSDGDYQVVPL

LPTCKDINMVKVACNVLLSKFIVGPPGSGKTTWLLNQVQDDDVIYTPTHQTMFDIVSALKVCRYSIPGASGLPFPPP

ARSGPWVRLIASGHVPGRVSYLDEAGYCNHLDILRLLSKTPLVCLGDLQQLHPVGFDSYCYVFDQMPQKQLTTIYRF

GPNICAAIQPCYREKLESKARNTRVVFTTRPVAFGQVLTPYHKDRTGSAITIDSSQGATFDIVTLHLPSPKSLNKSR

ALVAITRARHGLFIYDPHDQLQEFFNLTPERTDCNLAFSRGDELVVLNVDNAVTTVAKALETGSPRFRVSDPRCKSL

LAACSASLEGSCMPLPQVAHNLGFYFSPDSPAFAPLPKELAPHWPVVTHQNNRAWPDRLVASMRPIDARYSKPMVGA

GYVVGPSIFLGTPGVVSYYLTLYIGGEPQALPETLVSTGRIATDCREYLDAAEEEAARELPHAFIGDVKGTTVGGCH

HITSKYLPRSLPKDSVAVVGVSSPGRAAKAVCTLTDVYLPELRPYLQPETASKCWKLKLDFRDVRLMVWKGATAYFQ

LEGLTWSALPDYARFIQLPKDAVVYIDPCIGPATANRKVVRTTDWRADLAVTPYDYGAQVILTTAWFEDLGPQWKIL

GLQPFRRTFGFENTEDWAILARRMNDGKDYTDYNWHCVRERPHAIYGRARDHTYHFALGTELQVELGRPRLPPEQVP

SEQ ID NO: 13 ORF 2 OF PARENTAL PRRSV STRAIN 94881 ENCODED BY
SEQUENCE OF SEQ ID NO: 10 BETWEEN NUCLEOTIDES 11611..12360

MQWVHCGVKSVSCSWMPSLSSLLVWLTLSSFSPYCLGSLLQAGYWSSFSEWFAPRFSVRALPFTLPNYRRSYEGLLP

NCRPDVPQFAVKHPLGILWHMRVSHLIDEMVSRRIYRTMEHSGQAAWKQVVSEATLTKLSRLDVVTHFQHLAAVEAD

SCRFLSSRLAMLKNLAVGNVSLEYNTTLDRVELIFPTPGTRPKLTDFRQWLISVHASIFSSVASSVTLFTVLWLRIP

ALRYVFGFHWPTATHHSN

-continued

SEQ ID NO: 14 ORF 3 OF PARENTAL PRRSV STRAIN 94881 ENCODED BY
SEQUENCE OF SEQ ID NO: 10 BETWEEN NUCLEOTIDES 12219..13016
MAYQRARFHLLLCGFVCYLVHSALASNSSSTLCFWFPLAHGNTSFELTINYTICKPCPTSQAAQQRLEPGRNVWCKI

GHDRCEERDHDELSMSIPSGYDNLKLEGYYAWLAFLSFSYAAQFHPELFGIGNVSRVFVDKRHQFICAEHDGQNSTI

SARHNISASYAVYYHHQIDGGNWFHLEWLRPFFSSWLVLNISWFLRRSPASPASRRIYQILRPTRPRLPVSWSFRTS

IVSNLTGPQQRKVPLPSGGRPNVVKPSAFPSTSR

SEQ ID NO: 15 ORF 4 OF PARENTAL PRRSV STRAIN 94881 ENCODED BY
SEQUENCE OF SEQ ID NO: 10 BETWEEN NUCLEOTIDES 12761..13312
MAATILFLLAGAQHLMVSEAFACKPCFSTHLSDIKTNTTAAAGFMVLQNINCFQSHRASTAQGTTPLRRSSQCREAV
GIPQYITITANVTDESYLYNADLLMLSACLFYASEMSEKGFKVIFGNISGVVSACVNFTDYVAHVTQHTQQHHLVID
HIRLLHFLTPSTMRWATTIACLFAILLAV

SEQ ID NO: 16 ORF 5 OF PARENTAL PRRSV STRAIN 94881 ENCODED BY
SEQUENCE OF SEQ ID NO: 10 BETWEEN NUCLEOTIDES 13309..13914
MKCSCKLGHFLTPHSCFWWLFLLCTGLSWSFVDGNDNSSTSQYIYNLTICELNGTEWLSGHFDWAVETFVLYPVATH
IISLGFLTTSHFLDALGLGAVSATGFIGERYVLSSMYGVCAFAALVCFVIRAAKNCMACRYARTRFTNFIVDDRGRI
HRWKSSIVVEKLGKAEVGGDLVNIKHVVLEGVKAQPLTRTSAEQWEA

SEQ ID NO: 17 ORF 6 OF PARENTAL PRRSV STRAIN 94881 ENCODED BY
SEQUENCE OF SEQ ID NO: 10 BETWEEN NUCLEOTIDES 13902..14423
MGSLDDFCNDPTAAQKLVLAFSITYTPIMIYALKVSRGRLLGLLHILIFLNCSFTFGYMTYVHFQSTNRVALTLGAV
VALLWGVYSLTESWKFITSRCRLCCLGRRYILAPAHHVESAAGLHSIPASGNRAYAVRKPGLTSVNGTLVPGLRSLV
LGGKRAVKRGVVNLVKYGR

SEQ ID NO: 18 ORF 7 OF PARENTAL PRRSV STRAIN 94881 ENCODED BY
SEQUENCE OF SEQ ID NO: 10 BETWEEN NUCLEOTIDES 14413..14799
MAGKNQSQKKRRNAAPMGKGQPVNQLCQLLGTMIKSQRQQSROGQAKKKKPEKPHFPLAAEDDIRHHLTQAERSLCL
QSIQTAFNQGAGTASLSSSOKVSFQVEFMLPVAHTVRLIRVTSTSASQGAN

SEQ ID NO: 19 Nucleotide encoding attenuated PRRSV 94881 ORF1A
 178    ATG

181    TCTGGGATGT TCTCCCGGTG CATGTGCACC CCGGCTGCCC GGGTATTTTG GAACGCCGGC

241    CAAGTCTATT GCACACGGTG TCTCAGTGCA CGGTCTCTTC TCTCTCCAGA ACTTCAGGAC

301    ACGGACCTCG GTGCAGTTGG CTTGTTTCAC AAGCCTAAAG ACAAGCTCCA TTGGAAAGTT

361    CCCATTGGTA TCCCCCAGGT GGAATGTTCT CCATCTGGGT GTTGCTGGCT GTCAACCATT

421    TTTCCTTTAG CGCGCATGAC CTCCGGCAAT CACAACTTCC TTCAACGACT CGTGAAGGTT

481    GCTGATGTAT TGTACCGTGA CGGTTGCTTA ACCCCTAGAC ACCTCCGTGA ACTCCAAGTT

541    TACGAGCGTG GTTGCAATTG GTATCCGATT ACGGGGCCTG TGCCTGGGAT GGCTGTGTAC

601    GCGAACTCCA TGCACGTGTC CGACCAACCG TTCCCTGGTG CCACTCATGT GTTAACAAAT

661    TCCCCTTTGC CTCAACGGGC TTGTCGGCAG CCGTTCTGTC CGTTCGAAGA GGCCCATTCT

721    AGCATATACA GGTGGGAAAA ATTTGTAATT TTTATGGATT CCTCCTCCGA CGGTCGATCT

781    CGCATGATGT GGACTCCGGA ATCCGATGAC TCCACGGCTT TGGAAGTTCT GCCGCCCGAG

841    CTAGAACACC AGGTCAAGGT CCTTGTTCGG AGCTTTCCCG CCCATCACCT TGTCGACCTT

901    GCCGATTGGG AGCTCACTGA GTCCCCTGAT AACGGTTTTT CCTTCAGCAC GTCACATCCT

961    TGCGGCTACC TTGTTCGGGA CCCGGCTGTA TCCGAAGGCA AGTGTTGGCT TTCCTGCTTT

1021    TTGAGCCAGT CAGCCGAAGT GCTCAGTCGC GAGGCGCATC TGGCTACCGC CTATGGTTAC

1081    CAAACCAAGT GGGGTGTGCC TGGCAAGTAC ATCCAGCGCA GACTTCAAGT TCACGGTCTC

1141    CGTGCTGTGG TCGACCCTGA TGGTCCCATT CACGTTGAAG CATTGTCTTG CCCCCAGTCT

1201    TGGATCAGGC ACTTGACCCT GAATGATGAT GTCACCCCGG GATTCGTTCG CCTAATGTCT

1261    CTTCGCATTG TGCCGAACAC AGAGCCTACC ACACACCGGA TCTTTCGTTT TGGAGTGCAC

1321    AAGTGGTATG GTGCCGCCGG CAAACGGGCC CGTGGCAAGC GTGCCGCCAA AAGTGAGAAA

1381    GACTCGGCTT CCACCCTCAA GGTTGCCCGA CCGACTTCCA CCAGTGGAAT CGTCACCTAC

1441    TCCCCACCTG CGGACGGGTC TTGTGGTTGG CATGCCCTTG CCGCCATACT GAACCGGATG

1501    ATTAATAATG ACTTCACGTC CCCTCTGCCT CGGTACAACA GGCCGGAGGA CGATTGGGCT

-continued

```
1561  TCTGATGGTG ACCTTGCTCA GGCCATTCAA TGTTTGCAAC TACCTGCCGC CATAGCTCGG

1621  AACCGCGCCT GCCCTAACGC CAAATACCTC ATAAAACTCA ACGGAGTTCA TTGGGAGGTA

1681  GAGGTGAGGC CTGGAATGGC TCCTCGCTCC CTCTCTCGTG AGTGCGTTGT TGGCGTCTGC

1741  TCTGAAGGCT GTGTCGCGTC GCCTTACCCG GAGGACGGGT TGCCTAAACG TGCACTTGAG

1801  GCCCTGGCGT CTGCTTATAG ACTGCCTTCA GACTGTGTTT GTGATGGTAT TATTGACTTC

1861  CTTGCCAATC CACCTCCCCA GGAGTTCTGG ACTCTTGACA AAATGTTGAC TTCCCCGTCA

1921  CCGGAGCAGT CCGGCTTCTC TAGTCTGTAT AAATTGTTGT TAGAGATCTT GCCGCAGAAA

1981  TGCGGATCCA CAGAAGGGGA ATTCATCTAT ACTGTTGAGA GGATGTTGAA GGATTGTCCG

2041  AGCTCCAAAC AGGCCATGGC CCTCCTTGCA AAAATTAAGG TCCCATCCTC AAAGGCCCCA

2101  TCCGTGACTC TGAACGAGTG CTTCCCCACG GATGTTCCAG TCAACTCTGA GTTAATATCT

2161  TGGGAAGAGC CCAAAGACCC TGGCGCTGCT GTTGTCCTAT GTCCATCGGA TGCAAAAGAA

2221  TCTAAGGAAA CAGCCCCTGA AGAAGCTCAA GCAGAAACC GTAAGGTCCT TCACCCTGTG

2281  GTCCTTACCG AGGAACTTAG CGAGCAACAG GTGCAGGTGG TTGAGGGTGA TCAGGATATG

2341  CCACTGGATT TGACTTGGCC AACCTTAACC GCTACGGCGA CCCCTGTTAG AGGGCCGGTA

2401  CCGGACAATT TGAGCTCTGG CATTGGTGCC CAGCCCGCTA CCGTTCAAGA ACTCATTCTG

2461  GCGAGGCCTG CACCCCGTCT TGTTGAGCGC TGTGGCACGG AGTCGAACGG CAGCAGTTCA

2521  TTTCTGGATT TGCCTGACGT GCAGACCTCG GACCAGCCTT TAGACCTGTC CCTGGCCGCG

2581  TGGCCTGTAA GGGCTACCGC GTCTGACCCC GGTTGGATCC ACGGTAGGCG TGAGCCTGTC

2641  TTTGTGAAGC CTCGAGGTGT TTTCTCTGAT GGCGAGTCGG CCCTTCAGTT CGGAGAGCTT

2701  TCCGAAGCCA GTTCTGTCGT CGATGACCGG ACAAAAGAAG CTCCGGTGGT TGACGCCCCC

2761  ATCGATTTGA CAACTTCGAA CGAGACGCTC TCTGGGTCTG ACCCCTTTGA ATTCGCCAAA

2821  TTCAGGCGCC CGCGTTTCTC CGCGCAAGCT TTAATCGACC GAGGTGGTCC GCTTGCCGAT

2881  GTTCATGCAA AGATAAAGAG TCGGGTATAT GAACAATGCC TTCAAGCTTG TGAACCTGGT

2941  AGTCGTGCGA CCCCAGCCAC CAAGAAGTGG CTCGACAAAA TGTGGGACAG GGTGGACATG

3001  AAAACTTGGC GCTGCACCTC GCAGTTCCAA GCTGGTCACA TTCTTGAGTC CCTCAAATTC

3061  CTCCCTGACA TGATTCAAGA CACACCGCCT CCTGTTCCCA GGAAGAACCG AGCTGGTGAC

3121  AGTGCCGGCC TGAAGCAACT GGTGGCGCAG TGGGATAGGA AATCGAGTGT GACACCCCCC

3181  ACAAAACCGG TTGGACCGGT GCTTGACCAG GCCGTCCCTC TGCCTATGGA CATCCAGCAA

3241  GGAGATGCCA TCTCCGCTGA CAAGCCACCC CATTCGCAAA ACCCTTCTAG TCAAGTAGAT

3301  GTGGGTGGAG GTTGGAAAAG TTTTATGCTC TCCGGCACCC GTTTCGCGGG GTCCGTTAGT

3361  CAGCGCCTTA CGACATGGGT TTTTGAGGTT CTCTCCCATC TCCCAGCTTT TATGCTCACA

3421  CTTTTCTCGC CACGGGCTC TATGGCTCCA GGTGATTGGC TGTTTGCAGG TGCTGTTCTA

3481  CTTGCTCTCC TGCTCTGCCG TTCTTACCCA ATACTCGGAT GCCTTCCCTT ATTGGGTGTC

3541  TTTTCTGGTT CTGTGCGGTG TGTTCGTTTG GGTGTTTTTG GTTCTTGGAT GGCTTTTGCT

3601  GTATTTTTAT TCTCGACTCC ACCCGACCCA GTCGGTTCTT CTTGTGACCA CGATTCGCCG

3661  GAGTGTCATG CTGAGCTTTT GGCTCTTGAG CAGCGCCAAC TTTGGGAACC TGTGCGCAGC

3721  CTTGTGGTCG GCCCATCGGG CCTCTTATGC GTCATTCTTG CAAGTTACT CGGTGGGTCA

3781  CGTTGTCTCT GGTTTGTTCT CCTACGTATA TGCATGCTCG CAGATTTGGC AATTTCTCTT

3841  ATTTATGTGG TGTCCCAAGG GCGTTGTCAC AAGTGTTGGG AAAGTGTAT AAGGACGGCT

3901  CCTGCAGAAG TGGCCCTTAA TGTGTTTCCT TTTTCGCGCG CCACCCGCTC ATCTCTTGTG

3961  TCCTTGTGTG ATCGGTTCCA AGCGCCAAAA GGAGTTGACC CCGTGCACTT GGCGACAGGC
```

-continued

```
4021  TGGCGCGGGT GCTGGTGTGG TGAGAGCCCT ATTCATCAAT CACACCAAAA ACCGATAGCT
4081  TATGCCAACT TGGATGAAAA GAAGATATCC GCCCAGACGG TGATTGCTGT CCCGTATGAT
4141  CCTAGTCAGG CCATTAAATG CCTGAAAGTT TTGCAGGCAG GAGGGGCTAT TGTGGACCAG
4201  CCTACGCCCG AGGTCGTCCG TGTGTCTGAG ATTCCCTTCT CGGCCCCATT TTTTCCGAAG
4261  GTCCCAGTCA ACCCAGACTG CAGGGTTGTG GTAGATTCGG ACACTTTTGT GGCTGCGGTC
4321  CGCTGCGGTT ATTCGACAGC ACAACTGGTC CTTGGTCGGG CAACTTTGC CAAGCTAAAT
4381  CAGACCCCCC TCAGGAACTC TGTCCCCACC AAAACAACTG GTGGGGCCTC ATACACCCTT
4441  GCCGTGGCCC AGGTATCTGT GTGGACTCTT GTTCATTTCA TCCTCGGCCT TTGGTTAACG
4501  TCACCTCAAG TGTGTGGTCG AGGGACCTCT GACCCGTGGT GTTCGAACCC TTTTTCGTAT
4561  CCTACTTATG CCCCGGAGT TGTGTGTTCC TCTCGACTCT GCGTGTCTGC CGACGGAGTT
4621  ACCCTGCCAT TGTTCTCAGC CGTTGCCCAT CTTTCCGGTA GAGAGGTGGG GATTTTTATT
4681  TTGGTGCTTG CCTCCTTGGG CGCTTTAGCC CACCGCTTGG CTCTTAAGGC AGACATGTCA
4741  ATGGTCTTTT TGGCGTTTTG TGCTTACGCC TGGCCCATGA GCTCCTGGTT AATTTGCTTC
4801  TTTCCTATGC TCTTGAGGTG GGTAACCCTT CATCCTCTCA CTATGCTTTG GGTGCACTCA
4861  TTTTTGGTGT TTTGCCTACC AGCTGCCGGC GTTCTCTCGC TGGGAATAAC CGGTCTTCTT
4921  TGGGCAGTTG GCCGTTTCAC CCAGGTTGCC GGAATTATCA CACCTTATGA CATCCACCAG
4981  TATACCTCCG GACCACGTGG TGCAGCTGCT GTAGCAACGG CTCCAGAAGG TACTTACATG
5041  GCGGCCGTTC GGAGAGCCGC TTTGACTGGA CGGACTTTGA TCTTCACACC ATCTGCAGTC
5101  GGATCCCTTC TTGAAGGTGC TTTCAGAACT CAAAAGCCCT GCCTTAACAC CGTGAATGTC
5161  GTAGGCTCTT CCCTTGGTTC TGGAGGAGTT TTCACCATTG ATGGCAGAAG AGTCATCGTC
5221  ACTGCCACCC ATGTGTTGAA TGGTAACACA GCCAGGGTCA CTGGTGATTC CTACAACCGC
5281  ATGCACACGT TCAATACTAA TGGTGATTAT GCCTGGTCCC ATGCTGATGA CTGGCAAGGC
5341  GTTGCCCCTA TGGTTAAGAT CGCTAAGGGG TATCGCGGTC GTGCCTACTG GCAAACGTCA
5401  ACCGGAGTCG AACCTGGCAT CATGGGGGAA GGATTCGCCT TCTGTTTCAC TAACTGTGGC
5461  GACTCAGGGT CACCTGTCAT TTCAGAAGCT GGTGACCTTA TTGGAGTCCA TACCGGTTCA
5521  AACAAACTCG GTTCTGGTCT TGTGACAACC CCTGAAGGGG AGACCTGCTC CATCAAGGAA
5581  ACTAGGCTCT CTGACCTTTC TAGACATTTT GCAGGTCCAA GCGTCCCTCT TGGGGACATT
5641  AAGTTGAGCC CAGCCATCAT CCCTGATGTG ACAACTATTC CGAGTGACTT GGCATCGCTC
5701  CTTGCTTCTG TCCCCGTGAT GGAAGGTGGC CTCTCAACTG TCCAGCTTTT GTGCGTCTTT
5761  TTCCTTCTCT GGCGCATGAT GGGCCATGCC TGGACACCCA TTGTTGCCGT AGGCTTCTTT
5821  TTGCTGAATG AAATTCTCCC AGCAGTCTTG GTCCGAGCTG TGTTCTCTTT TGCACTCTTT
5881  GTACTTGCAT GGGCCACCCC CTGGTCGGCA CAAGTGTTGA TGATTAGACT CCTCACGGCG
5941  GCTCTCAACC GCAACAGGTT GTCCCTGGCG TTCTACGCAT TCGGAGGTGT CGTTGGCCTG
6001  GCCACAGAAA TCGGGACTTT TGCTGGTGGA TGGCCTGAAC TGTCCCAAGC CCTCTCGACA
6061  TACTGCTTCC TGCCCAGGTT CCTTGCTGTG ACTAGTTATG TCCCCACCAT CATCATCGGT
6121  GGGCTCCATG CCCTCGGCGT AATTTTGTGG TTATTCAAAT ACCGATGCCT CCACAACATG
6181  CTGGTTGGTG ATGGGAGTTT CTCAAGCGCT TCTTCCTAC GGTATTTTGC TGAGGGTAAT
6241  CTTAGGAAAG GCGTGTCGCA GTCCTGTGGC ATGAATAACG AATCCCTGAC AGCTGCTTTG
6301  GCTTGCAAGT TGTCGCAAGC TGACCTTGAT TTTTTGTCCA GTTAACGAA CTTCAAGTGC
6361  TTTGTGTCCG CTTCAAACAT GAAAAATGCA GCTGGCCAAT ACATCGAGGC GGCGTATGCT
6421  AGAGCTCTGC GTCAGGAGCT GGCCTCCTTG GTTCAGGTTG ACAAGATGAA AGGAGTATTG
```

-continued

```
6481 GCCAAGCTCG AGGCTTTCGC TGAGACGGCC ACTCCGTCAC TTGACACAGG GGACGTGATT

6541 GTTCTGCTTG GCAACACCC CCATGGATCC ATCCTCGACA TTAATGTGGG GGGTGAAAGG

6601 AAAACTGTGT CTGTGCAAGA ACACGATGC CTGGGTGGTT CCAAATTCAG TGTCTGCACT

6661 GTCGTGTCCA ACACGCCCGT GGATACCTTG ACCGGTATCC CACTTCAGAC GCCAACCCCA

6721 CTTTTTGAAA ATGGCCCGCG CCATCGCAGC GAGGACGACG ACCTCAAAGT TGAGAGAATG

6781 AAAAAACACT GTGTATCCCT CGGCTTCCAC AAAATCAATG GTAAAGTTTA CTGCAAAATT

6841 TGGGACAAGT CTAACGGCGA CACCTTTTAC ACGGATGATT CCCGATACAC TCAAGACCAT

6901 GCTTTTCAGG ACAGGTCAAC CGACTATAGA GACGGGATT ATGAAGGTGT ACAGACCGCC

6961 CCCCAACAGG GATTCGATCC AAAGTCCGAA GCCCCTGTTG GCACTGTTGT AATCGGTGGC

7021 ATTACGTATA ACAGGCATCT GGTCAAAGGT AAGGAGGTCC TAGTTCCCAA ACCTGACAAC

7081 TGCCTTGAAG CTGCCAGACT GTCCCTTGAG CAAGCTCTTG CTGGGATGGG CCAAACTTGT

7141 GACCTTACAG CTACCGAAGT GGAGAAACTA AAGCGCATCA TTAGTCAACT CCAAGGTCTG

7201 ACCACTGAAC AGGCTTTAAA CTGCTAG
```

SEQ ID NO: 20 Nucleotide encoding attenuated PRRSV 94881 ORF1B

```
7209 AC AGGCTTTAAA CTGCTAGCCG CCAGCGGCTT GACCCGCTGT GGCCGCGGCG

7261 GCCTAGTTGT AACTGAAACG GCGGTAAAAA TCGTAAAATA CCACAGCAGA ACTTTCACCT

7321 TAGGCTCTTT AGACCTAAAA GTCACCTCCG AGGTGGAGGT GAAGAAATCA ACTGAGCAGG

7381 GGCACGCTGT CGTGGCGAAC TTATGTTCCG GTGTCGTCTT GATGAGGCCT CACCCACCGT

7441 CCCTTGTTGA CGTTCTCCTC AAACCCGGAC TTGACACAAC ACCCGGCATT CAACCAGGGC

7501 ATGGGGCCGG GAATATGGGC GTGAACGGTT CTATTTGGGA TTTTGAAACT GCACCCACAA

7561 AGGTAGAACT AGAGTTGTCC AAGCAAATAA TCCAAGCATG TGAAGTCAGG CGCGGGGACG

7621 CCCCTAACCT CCAACTCCCC TACAAGCTTT ATCCTGTCAG GGGGGACCCC GAGCGGCGTA

7681 AAGGTCGCCT TGTCAACACT AGGTTTGGAG ATTTACCTTA CAAAACTCCC CAAGACACCA

7741 AGTCCGCAAT TCATGCGGCT TGTTGCCTGC ATCCCAATGG GGTCCTCGTG TCTGATGGCA

7801 AATCCACGCT GGGTACCACT CTTCAACATG GTTTCGAGCT TTATGTCCCC ACTGTACCTT

7861 ATAGTGTCAT GGAATACCTT GATTCACGCC CTGACACCCC TTTTATGTGT ACTAAACATG

7921 GCACTTCCAA GGCTGCTGCA GAGGACCTCC AAAAATATGA CCTATCCACT CAAGGGTTTG

7981 TCTTGCCTGG GGTCCTACGC CTAGTGCGCA GGTTCATCTT TAGCCATGTT GGTAAGGCGC

8041 CACCACTGTT CCTTCCATCA ACCTACCCTG CCAAGAACTC CATGGCAGGG TCAATGGCC

8101 AGAGGTTCCC AACAAAGGAT GTCCAGAGCA TACCTGAAAT TGATGAAATG TGCGCCCGTG

8161 CCGTCAAGGA AAATTGGCAG ACTGTGACAC CTTGCACCCT CAAAAAACAG TACTGTTCCA

8221 AACCTAAAAC TAGAACCATC CTAGGTACCA ACAACTTCAT AGCCTTGGCT CACAGGTCAG

8281 CACTCAGTGG TGTCACCCAG GCGTTCATGA AGAAGGCCTG GAAGTCCCCA ATTGCCTTGG

8341 GGAAAACAA GTTTAAGGAA TTGCATTGCA CTGTCGCCGG CAGATGCCTT GAGGCTGACC

8401 TGGCTTCCTG CGATCGCAGC ACCCCCGCCA TTGTGAGGTG GTTTGTTGCC AACCTCCTGT

8461 ATGAACTTGC AGGATGTGAA GAGTACTTGC CTAGCTACGT GCTCAACTGT TGCCATGACC

8521 TTGTGGCAAC GCAGGATGGC GCTTTCACAA AACGCGGTGG CCTGTCGTCC GGGGACCCCG

8581 TCACCAGTGT GTCCAACACC GTCTACTCAC TGATAATTTA CGCCCAGCAC ATGGTGCTTT

8641 CGGCCTTGAA GATGGGTCAT GAAATTGGTC TCAAGTTCCT TGAGGAACAG CTCAAATTTG

8701 AGGACCTTCT TGAAATCCAG CCCATGTTAG TGTATTCTGA TGACCTCGTC TTGTATGCGG

8761 AAAGACCCAC TTTTCCCAAC TACCATTGGT GGGTCGAGCA TCTTGACCTG ATGTTGGGCT
```

```
                                              -continued
 8821   TTAAAACGGA CCCAAAGAAA ACTGTCATAA CTGATAAACC CAGTTTTCTC GGCTGCAGAA

8881   TTGAAGCAGG ACGGCAGTTA GTCCCCAATC GCGACCGTAT TCTGGCTGCT CTTGCATATC

8941   ATATGAAGGC GCAGAACGCC TCAGAGTATT ATGCGTCCGC TGCCGCAATT CTGATGGATT

9001   CGTGTGCTTG CATTGACCAT GACCCCGAGT GGTATGAGGA TCTTATCTGC GGCATCGCCC

9061   GGTGTGCTCG CCAGGACGGT TACCGTTTTC CAGGCCCGGC ATTTTTCATG TCCATGTGGG

9121   AGAAGCTGAA AAGTCATAAT GAAGGGAAGA AATGCCGTCA CTGCGGCATC TGCGACGCCA

9181   AAGCCGACTA TGCGTCCGCC TGTGGACTTG ATTTGTGTTT GTTCCATTCA CACTTTCATC

9241   AACACTGCCC AGTCACTCTG AGCTGTGGCC ACCATGCCGG TTCAAAGGAA TGTTCGCAGT

9301   GTCAGTCACC TGTCGGGGCT GGCAAATCCC CCCTTGACGC TGTGCTGAAA CAAATCCCGT

9361   ACAAACCTCC TCGTACCATT ATCATGAAGG TGGACAACAA AACAACGACC CTTGACCCGG

9421   GAAGATATCA GTCCCGTCGA GGTCTTGTTG CAGTCAAAAG AGGTATTGCA GGTAATGAGG

9481   TTGATCTTTC TGATGGAGAC TACCAAGTGG TGCCTCTTTT GCCGACTTGC AAAGACATAA

9541   ACATGGTGAA GGTGGCTTGC AACGTACTAC TCAGCAAGTT TATAGTAGGG CCGCCAGGTT

9601   CCGGAAAAAC CACCTGGCTA CTGAACCAAG TCCAGGACGA TGATGTCATT TACACACCTA

9661   CTCATCAGAC AATGTTTGAC ATAGTCAGTG CTCTTAAAGT TTGCAGGTAT TCCATCCCAG

9721   GAGCCTCAGG ACTCCCTTTT CCACCACCTG CCAGGTCCGG GCCGTGGGTT AGGCTCATCG

9781   CCAGCGGACA TGTCCCTGGC CGAGTGTCAT ATCTCGATGA GGCAGGATAT TGCAATCATC

9841   TAGACATTCT AAGGCTGCTT TCCAAAACAC CCCTTGTGTG TTTGGGTGAC CTTCAGCAAC

9901   TTCACCCGGT CGGCTTTGAT TCCTATTGTT ATGTGTTCGA TCAGATGCCT CAGAAGCAGC

9961   TGACCACCAT TTATAGATTT GGCCCTAACA TCTGTGCAGC CATCCAGCCT TGTTACAGGG

10021   AGAAACTTGA ATCCAAGGCC AGGAACACCA GAGTGGTTTT CACCACCCGG CCTGTGGCCT

10081   TTGGTCAGGT CCTGACACCG TACCACAAAG ATCGTACCGG CTCTGCAATA ACTATAGATT

10141   CATCCCAGGG GGCGACCTTC GACATTGTGA CATTGCATCT ACCATCGCCA AAGTCCCTAA

10201   ACAAATCCCG AGCACTTGTA GCCATCACTC GGGCAAGACA TGGGTTGTTC ATTTATGACC

10261   CTCATGACCA ACTCCAGGAG TTTTTCAACT TAACCCCCGA GCGCACTGAT TGTAACCTTG

10321   CGTTCAGCCG TGGGGATGAG CTGGTTGTTT TGAATGTGGA TAATGCGGTC ACAACTGTAG

10381   CGAAGGCCCT AGAGACAGGT TCACCCCGAT TTCGAGTATC GGACCCGAGG TGCAAGTCTC

10441   TCTTAGCCGC TTGTTCGGCC AGTCTAGAAG GGAGCTGCAT GCCACTACCA CAAGTAGCAC

10501   ATAACCTGGG GTTTTACTTT TCCCCGGACA GCCCAGCTTT TGCACCCCTG CCAAAAGAGC

10561   TGGCGCCACA TTGGCCAGTG GTCACCCACC AGAATAATCG AGCGTGGCCT GATCGACTTG

10621   TCGCTAGTAT GCGCCCAATT GATGCCCGCT ACAGCAAGCC AATGGTCGGT GCAGGGTATG

10681   TGGTCGGGCC ATCCATTTTT CTTGGCACTC CTGGTGTGGT GTCATACTAT CTCACATTAT

10741   ACATCGGGGG CGAGCCTCAG GCCCTGCCAG AAACACTCGT TTCAACAGGA CGTATAGCCA

10801   CAGATTGTCG GGAATATCTC GACGCGGCTG AGGAAGAGGC AGCGAGAGAA CTTCCCCACG

10861   CATTTATTGG CGATGTCAAA GGCACTACGA TCGGGGGTG TCACCACATT ACATCGAAAT

10921   ACCTACCTAG GTCCCTGCCT AAAGACTCTG TTGCTGTGGT TGGGGTGAGT TCGCCCGGTA

10981   GGGCTGCTAA AGCCGTGTGC ACTCTCACCG ATGTGTACCT CCCCGAACTC CGACCATATT

11041   TGCAACCGGA GACGGCATCA AAATGCTGGA AACTTAAACT GGATTTCAGG GATGTTCGAC

11101   TGATGGTCTG GAAAGGCGCC ACAGCCTATT CCAGTTGGA AGGGCTGACA TGGTCAGCGC

11161   TGCCCGATTA TGCTAGGTTC ATTCAGCTAC CCAAGGATGC CGTTGTGTAC ATCGATCGT

11221   GTATAGGGCC GGCAACAGCC AATCGCAAGG TTGTGCGAAC CACAGACTGG CGGGCCGACC
```

-continued

```
11281 TGGCAGTGAC ACCGTATGAT TACGGTGCTC AGGTCATTTT GACAACAGCC TGGTTCGAGG

11341 ACCTTGGGCC GCAGTGGAAG ATTTTGGGGT TGCAGCCTTT CAGACGAACA TTTGGCTTTG

11401 AGAACACTGA AGATTGGGCA ATTCTCGCAC GCCGTATGAA TGACGGCAAA GATTACACTG

11461 ACTATAATTG GCATTGTGTA CGAGAACGCC CACACGCAAT TTACGGCGC GCCCGTGACC

11521 ATACGTATCA TTTTGCCCTT GGCACTGAAC TGCAAGTAGA GCTGGGCAGA CCCCGGCTGC

11581 CTCCTGAGCA AGTGCCGTGA
SEQ ID NO: 21 Nucleotide encoding attenuated PRRSV 94881 ORF2
11611 ATGCAATGGG TTTACTGTGG AGTAAAATCA

11641 GTCAGTTGTT CGTGGATGCC TTCACTGAGT TCCTTGTTAG TGTGGTTGAC ATTGTCATCT

11701 TTCTCGCCAT ATTGTTTGGG TTCACTGTTG CAGGCTGGTT ATTGGTCTTC CTTCTCAGAG

11761 TGGTTTGCTC CGCGTTTCTC CGTTCGCGCT CTGCCATTCA CTCTTCCGAA CTATCGAAGG

11821 TCCTATGAGG GCTTGCTACC CAACTGCAGA CCGGATGTCC CACAATTCGC AGTTAAGCAC

11881 CCGTTGGGTA TACTTTGGCA TATGCGAGTC TCCCACCTAA TTGACGAAAT GGTCTCTCGC

11941 CGCATTTACC GGACCATGGA ACATTCGGGT CAAGCGGCCT GGAAGCAGGT TGTTAGTGAA

12001 GCCACTCTCA CAAAACTGTC AAGGCTTGAC GTAGTCACTC ATTTCCAACA CCTGGCCGCA

12061 GTGGAGGCTG ATTCTTGCCG CTTCCTTAGC TCACGACTCG CGATGCTGAA AAACCTTGCC

12121 GTTGGCAATG TGAGCCTGGA GTACAACACT ACTTTGGACC GCGTTGAGCT CATCTTTCCC

12181 ACACCAGGTA CGAGGCCCAA GTTGACCGAT TTAGGCAAT GGCTTATCAG CGTGCACGCT

12241 TCCATCTTCT CCTCTGTGGC TTCGTCTGTT ACCTTGTTCA CAGTGCTTTG GCTTCGAATT

12301 CCAGCTCTAC GCTATGTTTT TGGTTTCCAT GGCCCACGG CAACACATCA TTCGAACTAA
SEQ ID NO: 22 Nucleotide encoding attenuated PRRSV 94881 ORF3
12219 AT GGCTTATCAG CGTGCACGCT

12241 TCCATCTTCT CCTCTGTGGC TTCGTCTGTT ACCTTGTTCA CAGTGCTTTG GCTTCGAATT

12301 CCAGCTCTAC GCTATGTTTT TGGTTTCCAT GGCCCACGG CAACACATCA TTCGAACTAA

12361 CTATCAATTA CACTATATGT AAGCCATGCC CTACCAGTCA AGCTGCCCAA CAAAGACTCG

12421 AGCCTGGCCG TAACGTGTGG TGCAAAATAG GGCACGACAG GTGTGAGGAA CGTGACCATG

12481 ATGAGTTGTC AATGTCCATT CCGTCCGGGT ACGACAACCT CAAACTTGAG GGTTATTATG

12541 CTTGGCTGGC TTTTTTGTCC TTTTCCTACG CGGCCCAATT CCATCCGGAG CTGTTCGGAA

12601 TAGGAAACGT GTCGCGCGTC TTTGTGGATA AGCGACACCA GTTCATTTGC GCCGAGCATG

12661 ATGGACAAAA TTCAACCATA TCTGCCAGAC ACAACATCTC CGCGTCGTAT GCGGTGTATT

12721 ACCATCATCA AATAGACGGG GCAATTGGT TCATTTGA ATGGCTGCGA CCATTCTTTT

12781 CCTCCTGGCT GGTGCTCAAC ATCTCATGGT TTCTGAGGCG TTCGCCTGCA AGCCCTGCTT

12841 CTCGACGCAT CTATCAGATA TTAAGACCAA CACGACCGCG CTGCCGGTT TCATGGTCCT

12901 TCAGAACATC AATTGTTTCC AATCTCACAG GGCCTCAACA GCGCAAGGTA CCACTCCCCT

12961 CAGGAGGTCG TCCCAATGTC GTGAAGCCGT CGGCATTCCC CAGTACATCA CGATAA
SEQ ID NO: 23 Nucleotide encoding attenuated PRRSV 94881 ORF4
12761 ATGGCTGCGA CCATTCTTTT

12781 CCTCCTGGCT GGTGCTCAAC ATCTCATGGT TTCTGAGGCG TTCGCCTGCA AGCCCTGCTT

12841 CTCGACGCAT CTATCAGATA TTAAGACCAA CACGACCGCG CTGCCGGTT TCATGGTCCT

12901 TCAGAACATC AATTGTTTCC AATCTCACAG GGCCTCAACA GCGCAAGGTA CCACTCCCCT

12961 CAGGAGGTCG TCCCAATGTC GTGAAGCCGT CGGCATTCCC CAGTACATCA CGATAACGGC

13021 TAATGTGACC GATGAATCGT ATTTGTACAA CGCGGACTTG CTGATGCTTT CCGCGTGCCT

13081 TTTCTACGCC TCGGAAATGA GCGAGAAAGG CTTCAAAGTC ATCTTTGGGA ATATTCTGG
```

-continued

```
13141 CGTTGTTTCC GCTTGTGTTA ATTTCACAGA TTATGTGGCC CATGTGACCC AACACACTCA

13201 GCAGCACCAT TTGGTAATTG ATCACATTCG GTTACTACAC TTCTTGACAC CGTCTACGAT

13261 GAGGTGGGCT ACAACCATTG CTTGTTTGCT TGCCATTCTT TTGGCGGTAT GA
```

SEQ ID NO: 24 Nucleotide encoding attenuated PRRSV 94881 ORF5
```
13309   AT GAAATGTTCT

13321 TGCAAGTTGG GGCATTTCTT GACTCCTCAC TCTTGCTTCT GGTGGCTTTT TTTGCTGTGT

13381 ACCGGCTTGT CTTGGTCCTT TGTCGATGGC AACGACGACA GCTCGACATC CCAATACATA

13441 TATAATTTGA CGATATGCGA GCTGAATGGG ACCGAATGGT TGTCCGGTCA TTTTGATTGG

13501 GCAGTCGAAA CCTTTGTGCT TTACCCAGTT GCCACTCATA TCATTTCACT GGGTTTTCTC

13561 ACAACAAGCC ATTTCCTTGA TGCGCTCGGT CTCGGCGCTG TGTCCGCCAC AGGATTCATT

13621 GGCGAGCGGT ATGTACTTAG CAGCATGTAC GGCGTTTGCG CCTTCGCGGC GTTCGTATGT

13681 TTTGTCATCC GTGCTGCTAA AAATTGCATG GCTTGCCGCT ATGCCCGCAC CCGGTTTACC

13741 AACTTCATCG TGGACGACCG GGGAAGAATC CATCGATGGA AGTCTTCAAT AGTGGTGGAG

13801 AAATTGGGCA AAGCTGAAGT CGGTGGTGAC CTTGTCAACA TTAAGCATGT TGTCCTCGAA

13861 GGGGTTAAAG CTCAACCTTT GACGAGGACT TCGGCTGAGC AATGGGAAGC CTAG
```

SEQ ID NO: 25 Nucleotide encoding attenuated PRRSV 94881 ORF6
```
13902   ATGGGAAGC CTAGACGACT

13921 TTTGCAACGA TCCCACCGCC GCACAAAAAC TCGTGCTGGC CTTTAGCATC ACATATACAC

13981 CCATAATGAT ATACGCCCTT AAGGTGTCAC GCGGCCGACT CCTGGGGCTG TTGCACATCT

14041 TGATATTTCT GAATTGTTCC TTTACTTTTG GGTACATGAC ATATGTGCAT TTTCAATCCA

14101 CCAACCGTGT CGCATTCACT CTGGGGGCTG TAGTCGCCCT TTTGTGGGGT GTTTACAGCC

14161 TCACAGAGTC ATGGAAGTTC ATCACTTCCA GATGCAGATT GTGTTGCCTA GGCCGGCGAT

14221 ACATTCTGGC CCCTGCCCAT CACGTAGAAA GTGCTGCAGG CCTCCATTCA ATCCCAGCGT

14281 CTGGTAACCG AGCATACGCG GTGAGAAAGC CCGGACTAAC ATCAGTGAAC GGCACTCTAG

14341 TACCTGGGCT TCGGAGCCTC GTGCTGGGCG GCAAACGAGC TGTTAAACGA GGAGTGGTTA

14401 ACCTCGTCAA GTATGGCCGG TAA
```

SEQ ID NO: 26 Nucleotide encoding attenuated PRRSV 94881 ORF7
```
14413    ATGGCCGG TAAGAACCAG AGCCAGAAGA AAGAAGAAA TGCAGCTCCG

14461 ATGGGGAAAG GCCAGCCAGT CAATCAACTG TGCCAGTTGC TGGGTACAAT GATAAAGTCC

14521 CAGCGCCAGC AATCTAGGGG AGGACAGGCC AAAAAGAAGA AGCCTGAGAA GCCACATTTT

14581 CCCCTAGCTG CTGAAGATGA CATTCGGCAC CATCTCACCC AGGCCGAACG TTCCCTCTGC

14641 TTGCAATCGA TCCAGACGGC TTTCAATCAA GGCGCAGGAA CTGCGTCGCT TTCATCCAGC

14701 GGGAAGGTCA GTTTCCAGGT TGAGTTCATG CTGCCGGTTG CTCATACAGT GCGCCTGATT

14761 CGCGTGACTT CTACATCCGC CAGTCAGGGT GCAAATTAAT TGACAGTCA GGTGAATGGC

14821 CGCGATTGAC GTGTGGCCTC TAA
```

SEQ ID NO: 27 Nucleotide encoding parental PRRSV 94881 ORF1a
```
 178         ATG

181 TCTGGGATGT CTCCCGGTG CATGTGCACC CCGGCTGCCC GGGTATTTTG GAACGCCGGC

241 CAAGTCTATT GCACACGGTG TCTCAGTGCA CGGTCTCTTC TCTCTCCAGA ACTTCAGGAC

301 ACGGACCTCG GTGCAGTTGG CTTGTTCAC AAGCCTAAAG ACAAGCTCCA TTGGAAAGTT

361 CCCATTGGTA TCCCCCAGGT GGAATGTTCT CCATCTGGGT GTTGCTGGCT GTCAACCATT

421 TTTCCTTTAG CGCGCATGAC CTCCGGCAAT CACAACTTCC TTCAACGACT CGTGAAGGTT

481 GCTGACGTAT TGTACCGTGA CGGTTGCTTA ACCCCTAGAC ACCTCCGTGA ACTCCAAGTT
```

-continued

```
 541 TACGAGCGTG GTTGCAATTG GTATCCGATT ACGGGGCCTG TGCCTGGGAT GGCTGTGTAC
 601 GCGAACTCCA TGCACGTGTC CGACCAACCG TTCCCTGGTG CCACTCATGT GTTAACAAAT
 661 TCCCCTTTGC CTCAACGGGC TTGTCGGCAG CCGTTCTGTC CGTTCGAAGA GGCCCATTCT
 721 AGCATATACA GGTGGGAAAA ATTTGTAATT TTTATGGATT CCTCCTCCGA CGGTCGATCT
 781 CGCATGATGT GGACTCCGGA ATCCGATGAC TCCACGGCTT TGGAAGTTCT GCCGCCCGAG
 841 CTAGAACACC AGGTCAAGGT CCTTGTTCGG AGCTTTCCCG CCCATCACCT TGTCGACCTT
 901 GCCGATTGGG AGCTCACTGA GTCCCTGAG AACGGTTTTT CCTTCAGCAC GTCACATCCT
 961 TGCGGCTACC TTGTTCGGGA CCCGGCTGTA TCCGAAGGCA AGTGTTGGCT TTCCTGCTTT
1021 TTGAGCCAGT CAGCCGAAGT GCTCAGTCGC GAGGCGCATC TGGCTACCGC CTATGGTTAC
1081 CAAACCAAGT GGGGTGTGCC TGGCAAGTAC ATCCAGCGCA GACTTCAAGT TCACGGTCTC
1141 CGTGCTGTGG TCGACCCTGA TGGTCCCATT CACGTTGAAG CATTGTCTTG CCCCCAGTCT
1201 TGGATCAGGC ACTTGACCCT GAATGATGAT GTCACCCCGG GATTCGTTCG CCTAATGTCT
1261 CTTCGCATTG TGCCGAACAC AGAGCCTACC ACACACCGGA TCTTTCGTTT TGGAGTGCAC
1321 AAGTGGTATG GTGCCGCCGG CAAACGGGCC CGTGGCAAGC GTGCCGCCAA AAGTGAGAAA
1381 GACTCGGCTT CCACCCTCAA GGTTGCCCGA CCGACTTCCA CCAGTGGAAT CGTCACCTAC
1441 TCCCCACCTG CGGACGGGTC TTGTGGTTGG CATGCCCTTG CCGCCATACT GAACCGGATG
1501 ATTAATAATG ACTTCACGTC CCCTCTGCCT CGGTACAACA GGCCGGAGGA CGATTGGGCT
1561 TCTGATGGTG ACCTTGCTCA GGCCATTCAA TGTTTGCAAC TACCTGCCGC CATAGCTCGG
1621 AACCGCGCCT GCCCTAACGC CAAATACCTC GTAAAACTCA ACGGAGTTCA TTGGGAGGTA
1681 GAGGTGAGGC CTGGAATGGC TCCTCGCTCC CTCTCTCGTG AGTGCGTTGT TGGCGTCTGC
1741 TCTGAAGGCT GTGTCGCGTC GCCTTACCCG GAGGACGGGT TGCCTAAACG TGCACTTGAG
1801 GCCCTGGCGT CTGCTTATAG ACTGCCTTCA GACTGTGTTT GTGATGGTAT TATTGACTTC
1861 CTTGCCAATC CACCTCCCCA GGAGTTCTGG ACTCTTGACA AAATGTTGAC TTCCCCGTCA
1921 CCGGAGCAGT CCGGCTTCTC TAGTCTGTAT AAATTGTTGT TAGAGGTCTT GCCGCAGAAA
1981 TGCGGATCCA CAGAAGGGGA ATTCATCTAT ACTGTTGAGA GGATGTTGAA GGATTGTCCG
2041 AGCTCCAAAC AGGCCATGGC CCTCCTTGCA AAAATTAAGG TCCCATCCTC AAAGGCCCCA
2101 TCCGTGACTC TGAACGAGTG CTTCCCCACG GATGTTCCAG TCAACTCTGA GTTAATATCT
2161 TGGGAAGAGC CCAAAGACCC TGGCGCTGCT GTTGTCCTAT GTCCATCGGA TGCAAAAGAA
2221 TCTAAGGAAA CAGCCCCTGA AGAAGCTCAA GCGAGAAACC GTAAGGTCCT CCACCCTGTG
2281 GTCCTTACCG AGGAACTTAG CGAGCAACAG GTGCAGGTGG TTGAGGGTGA TCAGGATATG
2341 CCACTGGATT TGACTTGGCC AACCTTAACC GCTACGGCGA CCCCTGTTAG AGGGCCGGTA
2401 CCGGACAATT TGAGCTCTGG CATTGGTGCC CAGCCCGCTA CCGTTCAAGA ACTCATTCTG
2461 GCGAGGCCTG CACCCCGTCT TGTTGAGCGC TGTGGCACGG AGTCGAACGG CAGCAGTTCA
2521 TTTCTGGATT TGCCTGACGT GCAGACCTCG GACCAGCCTT TAGACCTGTC CCTGGCCGCG
2581 TGGCCTGTAA GGGCTACCGC GTCTGACCCC GGTTGGATCC ACGGTAGGCG TGAGCCTGTC
2641 TTTGTGAAGC CTCGAGGTGT TTTCTCTGAT GGCGAGTCGG CCCTTCAGTT CGGAGAGCTT
2701 TCCGAAGCCA GTTCTGTCGT CGATGACCGG ACAAAAGAAG CTCCGGTGGT TGACGCCCCC
2761 ATCGATTTGA CAACTTCGAA CGAGACGCTC TCTGGGTCTG ACCCCTTTGA ATTCGCCAAA
2821 TTCAGGCGCC CGCGTTTCTC CGCGCAAGCT TTAATCGACC GAGGTGGTCC GCTTGCCGAT
2881 GTTCATGCAA AGATAAAGAG TCGGGTATAT GAACAATGCC TTCAAGCTTG TGAACCTGGT
2941 AGTCGTGCGA CCCCAGCCAC CAAGAAGTGG CTCGACAAAA TGTGGGACAG GGTGGACATG
```

```
-continued
3001 AAAACTTGGC GCTGCACCTC GCAGTTCCAA GCTGGTCACA TTCTTGAGTC CCTCAAATTC
3061 CTCCCTGACA TGATTCAAGA CACACCGCCT CCTGTTCCCA GGAAGAACCG AGCTGGTGAC
3121 AGTGCCGGCC TGAAGCAACT GGTGGCGCAG TGGGATAGGA AATTGAGTGT GACACCCCCC
3181 ACAAAACCGG TTGGACCGGT GCTTGACCAG ACCGTCCCTC TGCCTATGGA CATCCAGCAA
3241 GAAGATGCCA TCTCCGCTGA CAAGCCACCC CATTCGCAAA ACCCTTCTAG TCAAGTAGAT
3301 GTGGGTGGAG GTTGGAAAAG TTTTATGCTC TCCGGCACCC GTTTCGCGGG GTCCGTTAGT
3361 CAGCGCCTTA CGACATGGGT TTTTGAGGTT CTCTCCCATC TCCCAGCTTT TATGCTCACA
3421 CTTTTCTCGC CACGGGGCTC TATGGCTCCA GGTGATTGGC TGTTTGCAGG TGCTGTTCTA
3481 CTTGCTCTCC TGCTCTGCCG TTCTTACCCA ATACTCGGAT GCCTTCCCTT ATTGGGTGTC
3541 TTTTCTGGTT CTGTGCGGTG TGTTCGTTTG GGTGTTTTTG GTTCTTGGAT GGCTTTTGCT
3601 GTATTTTTAT TCTCGACTCC ACCCGACCCA GTCGGTTCTT CTTGTGACCA CGATTCGCCG
3661 GAGTGTCATG CTGAGCTTTT GGCTCTTGAG CAGCGCCAAC TTTGGGAACC TGTGCGCAGC
3721 CTTGTGGTCG GGCCATCGGG CCTCTTATGC GTCATTCTTG GCAAGTTACT CGGTGGGTCA
3781 CGTTGTCTCT GGTTTGTTCT CCTACGTATA TGCATGCTCG CAGATTTGGC AATTTCTCTT
3841 ATTTATGTGG TGTCCCAAGG GCGTTGTCAC AAGTGTTGGG AAAGTGTAT AAGGACGGCT
3901 CCTGCAGAAG TGACCCTTAA TGTGTTTCCT TTTTCGCGCG CCACCCGCTC ATCTCTTGTG
3961 TCCTTGTGTG ATCGGTTCCA AGCGCCAAAA GGAGTTGACC CCGTGCACTT GGCGACAGGC
4021 TGGCGCGGGT GCTGGTGTGG TGAGAGCCCT ATTCATCAAT CACACCAAAA ACCGATAGCT
4081 TATGCCAACT TGGATGAAAA GAAGATATCC GCCCAGACGG TGATTGCTGT CCCGTATGAT
4141 CCCAGTCAGG CCATTAAATG CCTGAAAGTT TTGCAGGCAG GAGGGGCTAT TGTGGACCAG
4201 CCTACGCCCG AGGTCGTCCG TGTGTCTGAG ATTCCCTTCT CGGCCCCATT TTTTCCGAAG
4261 GTCCCAGTCA ACCCAGATTG CAGGGTTGTG GTAGATTCGG ACACTTTTGT GGCTGCGGTC
4321 CGCTGCGGTT ATTGACAGC ACAACTGGTC CTTGGTCGGG CAACTTTGC CAAGCTAAAT
4381 CAGACCCCCC TCAGGAACTC TGTCCCCACC AAAACAACTG GTGGGGCCTC ATACACCCTT
4441 GCCGTGGCCC AGGTATCTGT GTGGACTCTT GTTCATTTCA TCCTCGGCCT TTGGTTAACG
4501 TCACCTCAAG TGTGTGGTCG AGGGACCTCT GACCCGTGGT GTTCGAACCC TTTTTCGTAT
4561 CCTACTTATG GCCCCGGAGT TGTGTGTTCC TCTCGACTCT GCGTGTCTGC CGACGGAGTT
4621 ACCCTGCCAT TGTTCTCAGC CGTTGCCCAT CTTTCCGGTA GAGAGGTGGG GATTTTTATT
4681 TTGGTGCTTG CCTCCTTGGG CGCTTTAGCC CACCGCTTGG CTCTTAAGGC AGACATGTCA
4741 ATGGTCTTTT TGGCGTTTTG TGCTTACGCC TGGCCCATGA GCTCCTGGTT AATTTGCTTC
4801 TTTCCTATGC TCTTGAGGTG GGTAACCCTT CATCCTCTCA CTATGCTTTG GGTGCACTCA
4861 TTTTTGGTGT TTTGCCTACC AGCTGCCGGC GTTCTCTCGC TGGGAATAAC CGGTCTTCTT
4921 TGGGCAGTTG GCCGTTTCAC CCAGGTTGCC GGAATTATCA CACCTTATGA CATCCACCAG
4981 TATACCTCCG GACCACGTGG TGCAGCTGCT GTAGCAACGG CTCCAGAAGG TACTTACATG
5041 GCGGCCGTTC GGAGAGCCGC TTTGACTGGA CGGACTTTGA TCTTCACACC ATCTGCAGTC
5101 GGATCCCTTC TTGAAGGTGC TTTCAGAACT CAAAAGCCCT GCCTAACAC CGTGAATGTC
5161 GTAGGCTCTT CCCTTGGTTC TGGAGGAGTT TTCACCATTG ATGGCAGAAG AGTCATCGTC
5221 ACTGCCACCC ATGTGTTGAA TGGTAACACA GCCAGGGTCA CTGGTGATTC CTACAACCGC
5281 ATGCACACGT TCAATACTAA TGGTGATTAT GCCTGGTCCC ATGCTGATGA CTGGCAAGGC
5341 GTTGCCCCTA TGGTTAAGAT CGCTAAGGGG TATCGCGGTC GTGCCTACTG GCAAACGTCA
5401 ACCGGAGTCG AACCTGGCAT CATGGGGGAA GGATTCGCCT TCTGTTTCAC TAACTGTGGC
```

```
5461 GACTCAGGGT CACCTGTCAT TTCAGAAGCT GGTGACCTTA TTGGAGTCCA TACCGGTTCA

5521 AACAAACTCG GTTCTGGTCT TGTGACAACC CCTGAAGGGG AGACCTGCTC CATCAAGGAA

5581 ACTAGGCTCT CTGACCTTTC TAGACATTTT GCAGGTCCAA GCGTCCCTCT TGGGGACATT

5641 AAGTTGAGCC CAGCCATCAT CCCTGATGTG ACAACTATTC CGAGTGACTT GGCATCGCTC

5701 CTTGCTTCTG TCCCCGTGAT GGAAGGTGGC CTCTCAACTG TCCAGCTTTT GTGCGTCTTT

5761 TTCCTTCTCT GGCGCATGAT GGGCCATGCC TGGACACCCA TTGTTGCCGT AGGCTTCTTT

5821 TTGCTGAATG AAATTCTCCC AGCAGTCTTG GTCCGAGCTG TGTTCTCTTT TGCACTCTTT

5881 GTACTTGCAT GGGCCACCCC CTGGTCGGCA CAAGTGTTGA TGATTAGACT CCTCACGGCG

5941 GCTCTCAACC GCAACAGGTT GTCCCTGGCG TTCTACGCAC TCGGAGGTGT CGTTGGCCTG

6001 GCCACAGAAA TCGGGACTTT TGCTGGTGGA TGGCCTGAAC TGTCCCAAGC CCTCTCGACA

6061 TACTGCTTCC TGCCCAGGTT CCTTGCTGTG ACTAGTTATG TCCCCACCAT CATCATCGGT

6121 GGGCTCCATG CCCTCGGCGT AATTTTGTGG TTATTCAAAT ACCGATGCCT CCACAACATG

6181 CTGGTTGGTG ATGGGAGTTT CTCAAGCGCT TTCTTCCTAC GGTATTTTGC TGAGGGTAAT

6241 CTTAGGAAAG GCGTGTCGCA GTCCTGTGGC ATGAATAACG AATCCCTGAC AGCTGCTTTG

6301 GCTTGCAAGT TGTCGCAAGC TGACCTTGAT TTTTTGTCCA GTTAACGAA CTTCAAGTGC

6361 TTTGTGTCCG CTTCAAACAT GAAAAATGCA GCTGGCCAAT ACATCGAGGC GGCGTATGCT

6421 AGAGCTCTGC GTCAGGAGCT GGCCTCCTTG GTTCAGGTTG ACAAGATGAA AGGAGTATTG

6481 GCCAAGCTCG AGGCTTTCGC TGAGACGGCC ACTCCGTCAC TTGACACAGG TGACGTGATT

6541 GTTCTGCTTG GCAACACCCC CCATGGATCC ATCCTCGACA TTAATGTGGG GGGTGAAAGG

6601 AAAACTGTGT CTGTGCAAGA ACACGATGC CTGGGTGGTT CCAAATTCAG TGTCTGCACT

6661 GTCGTGTCCA ACACGCCCGT GGATACCTTG ACCGGCATCC CACTTCAGAC GCCAACCCCA

6721 CTTTTTGAAA ATGGCCCGCG CCATCGCAGC GAGGACGACG ACCTTAAAGT TGAGAGAATG

6781 AAAAAACACT GTGTATCCCT CGGCTTCCAC AAAATCAATG GTAAAGTTTA CTGCAAAATT

6841 TGGGACAAGT CTAACGGCGA CACCTTTTAC ACGGATGATT CCCGATACAC TCAAGACCAT

6901 GCTTTTCAGG ACAGGTCAAC CGACTATAGA GACAGGGATT ATGAAGGTGT ACAGACCGCC

6961 CCCCAACAGG GATTCGATCC AAAGTCCGAA GCCCCTGTTG GCACTGTTGT AATCGGTGGC

7021 ATTACGTATA ACAGGCATCT GGTCAAAGGT AAGGAGGTCC TAGTTCCCAA ACCTGACAAC

7081 TGCCTTGAAG CTGCCAGACT GTCCCTTGAG CAAGCTCTTG CTGGGATGGG CCAAACTTGT

7141 GACCTTACAG CTACCGAAGT GGAGAAACTA AAGCGCATCA TTAGTCAACT CCAAGGTCTG

7201 ACCACTGAAC AGGCTTTAAA CTGCTAGCCG CCAGCGGCTT GACCCGCTGT GGCCGCGGCG

SEQ ID NO: 28 Nucleotide encoding parental PRRSV 94881 ORF1b
7209         AC AGGCTTTAAA CTGCTAGCCG CCAGCGGCTT GACCCGCTGT GGCCGCGGCG

7261 GCCTAGTTGT AACTGAAACG GCGGTAAAAA TCGTAAAATA CCACAGCAGA ACTTTCACCT

7321 TAGGCTCTTT AGACCTAAAA GTCACCTCCG AGGTGGAGGT GAAGAAATCA ACTGAGCAGG

7381 GGCACGCTGT CGTGGCGAAC TTATGTTCCG GTGTCGTCTT GATGAGGCCT CACCCACCGT

7441 CCCTTGTTGA CGTTCTCCTC AAACCCGGAC TTGACACAAC ACCCGGCATT CAACCAGGGC

7501 ATGGGGCCGG GAATATGGGC GTGAACGGTT CTATTTGGGA TTTTGAAACT GCACCCACAA

7561 AGGTAGAACT AGAGTTGTCC AAGCAAATAA TCCAAGCATG TGAAGTCAGG CGCGGGGACG

7621 CCCCTAACCT CCAACTCCCC TACAAGCTTT ATCCTGTCAG GGGGGACCCC GAGCGGCGTA

7681 AAGGTCGCCT TGTCAACACT AGGTTTGGAG ATTTACCTTA CAAAACTCCC CAAGACACCA

7741 AGTCCGCAAT TCATGCGGCT TGTTGCCTGC ATCCCAATGG GGTCCTCGTG TCTGATGGTA
```

-continued

```
7801  AATCCACGCT GGGTACCACT CTTCAACATG GTTTCGAGCT TTATGTCCCC ACTGTACCTT

7861  ATAGTGTCAT GGAATACCTT GATTCACGCC CTGACACCCC TTTTATGTGT ACTAAACATG

7921  GCACTTCCAA GGCTGCTGCA GAGGACCTCC AAAAATATGA CCTATCCACT CAAGGGTTTG

7981  TCTTGCCTGG GGTCCTACGC CTAGTGCGCA GGTTCATCTT TAGCCATGTT GGTAAGGCGC

8041  CACCACTGTT CCTTCCATCA ACCTACCCTG CCAAGAACTC CATGGCAGGG GTCAATGGCC

8101  AGAGGTTCCC AACAAAGGAT GTCCAGAGCA TACCTGAAAT TGATGAAATG TGCGCCCGTG

8161  CCGTCAAGGA AAATTGGCAG ACTGTGACAC CTTGCACCCT CAAAAACAG TACTGTTCCA

8221  AACCTAAAAC TAGAACCATC CTAGGTACCA ACAACTTCAT AGCCTTGGCT CACAGGTCAG

8281  CACTCAGTGG TGTCACCCAG GCGTTCATGA AGAAGGCCTG GAAGTCCCCA ATTGCCTTGG

8341  GGAAAAACAA GTTTAAGGAA TTGCATTGCA CTGTCGCCGG CAGATGCCTT GAGGCTGACC

8401  TGGCTTCCTG CGATCGCAGC ACCCCCGCCA TTGTGAGGTG GTTTGTTGCC AACCTCCTGT

8461  ATGAACTTGC AGGATGTGAA GAGTACTTGC CTAGCTACGT GCTCAACTGT TGCCATGACC

8521  TTGTGGCAAC GCAGGATGGC GCTTTCACAA AACGCGGTGG CCTGTCGTCC GGGGACCCCG

8581  TCACCAGTGT GTCCAACACC GTCTACTCAC TGATAATTTA CGCCCAGCAC ATGGTGCTTT

8641  CGGCCTTGAA GATGGGTCAT GAAATTGGTC TCAAGTTCCT TGAGGAACAG CTCAAATTTG

8701  AGGACCTTCT TGAAATCCAG CCCATGTTAG TGTATTCTGA TGACCTCGTC TTGTATGCGG

8761  AAAGACCCAC TTTTCCCAAC TACCATTGGT GGGTCGAGCA TCTTGACCTG ATGTTGGGCT

8821  TTAAAACGGA CCCAAAGAAA ACTGTCATAA CTGATAAACC CAGTTTTCTC GGCTGCAGAA

8881  TTGAAGCAGG ACGGCAGTTA GTCCCCAATC GCGACCGTAT TCTGGCTGCT CTTGCATATC

8941  ATATGAAGGC GCAGAACGCC TCAGAGTATT ATGCGTCCGC TGCCGCAATT CTGATGGATT

9001  CGTGTGCTTG CATTGACCAT GACCCCGAGT GGTATGAGGA CCTTATCTGC GGCATCGCCC

9061  GGTGTGCTCG CCAGGACGGT TACCGTTTTC CAGGCCCGGC ATTTTTCATG TCCATGTGGG

9121  AGAAGCTGAA AAGTCATAAC GAAGGGAAGA AATGCCGTCA CTGCGGCATC TGCGACGCCA

9181  AAGCCGACTA TGCGTCCGCC TGTGGACTTG ATTTGTGTTT GTTCCATTCA CACTTTCATC

9241  AACACTGCCC AGTCACTCTG AGCTGTGGCC ACCATGCCGG TTCAAAGGAA TGTTCGCAGT

9301  GTCAGTCACC TGTCGGGGCT GGCAAATCCC CCCTTGACGC TGTGCTGAAA CAAATCCCGT

9361  ACAAACCTCC TCGTACCATT ATCATGAAGG TGGACAACAA AACAACGACC CTTGACCCGG

9421  GAAGATATCA GTCCCGTCGA GGTCTTGTTG CAGTCAAAAG AGGTATTGCA GGTAATGAGG

9481  TTGATCTTTC TGATGGAGAC TACCAAGTGG TGCCTCTTTT GCCGACTTGC AAAGACATAA

9541  ACATGGTGAA GGTGGCTTGC AACGTACTAC TCAGCAAGTT TATAGTAGGG CCGCCAGGTT

9601  CCGGAAAAAC CACCTGGCTA CTGAACCAAG TCCAGGACGA TGATGTCATT TACACACCTA

9661  CTCATCAGAC AATGTTTGAC ATAGTCAGTG CTCTTAAAGT TTGCAGGTAT TCCATCCCAG

9721  GAGCCTCAGG ACTCCCTTTT CCACCACCTG CCAGGTCCGG GCCGTGGGTT AGGCTCATCG

9781  CCAGCGGACA TGTCCCTGGC CGAGTGTCAT ATCTCGATGA GGCAGGATAT TGCAATCATC

9841  TAGACATTCT AAGGCTGCTT TCCAAAACAC CCCTTGTGTG TTTGGGTGAC CTTCAGCAAC

9901  TTCACCCGGT CGGCTTTGAT TCCTATTGTT ATGTGTTCGA TCAGATGCCT CAGAAGCAGC

9961  TGACCACCAT TTATAGATTT GGCCCTAACA TCTGTGCAGC CATCCAGCCT TGTTACAGGG

10021 AGAAACTTGA ATCCAAGGCC AGGAACACCA GAGTGGTTTT CACCACCCGG CCTGTGGCCT

10081 TTGGTCAGGT CCTGACACCG TACCACAAAG ATCGTACCGG CTCTGCAATA ACTATAGATT

10141 CATCCCAGGG GGCGACCTTC GACATTGTGA CATTGCATCT ACCATCGCCA AAGTCCCTAA

10201 ACAAATCCCG AGCACTTGTA GCCATCACTC GGGCAAGACA TGGGTTGTTC ATTTATGACC
```

```
10261 CTCATGACCA ACTCCAGGAG TTTTTCAACT TAACCCCGA GCGCACTGAT TGTAACCTTG

10321 CGTTCAGCCG TGGGGATGAG CTGGTTGTTT TGAATGTGGA TAATGCGGTC ACAACTGTAG

10381 CGAAGGCCCT AGAGACAGGT TCACCCCGAT TTCGAGTATC GGACCCGAGG TGCAAGTCTC

10441 TCTTAGCCGC TTGTTCGGCC AGTCTAGAAG GGAGCTGCAT GCCACTACCA CAAGTAGCAC

10501 ATAACCTGGG GTTTTACTTT TCCCCGGACA GCCCAGCTTT TGCACCCCTG CCAAAAGAGC

10561 TGGCGCCACA TTGGCCAGTG GTCACCCACC AGAATAATCG AGCGTGGCCT GATCGACTTG

10621 TCGCTAGTAT GCGCCCAATT GATGCCCGCT ACAGCAAGCC AATGGTCGGT GCAGGGTATG

10681 TGGTCGGGCC ATCCATTTTT CTTGGCACTC CTGGTGTGGT GTCATACTAT CTCACATTAT

10741 ACATCGGGGG CGAGCCTCAG GCCCTGCCAG AAACACTCGT TTCAACAGGA CGTATAGCCA

10801 CAGATTGTCG GAATATCTC GACGCGGCTG AGGAAGAGGC AGCGAGAGAA CTTCCCCACG

10861 CATTTATTGG CGATGTCAAA GGCACTACGG TCGGGGGGTG TCACCACATT ACATCGAAAT

10921 ACCTACCTAG GTCCCTGCCT AAAGACTCTG TTGCTGTGGT TGGGGTGAGT TCGCCCGGTA

10981 GGGCTGCTAA AGCCGTGTGC ACTCTCACCG ATGTGTACCT CCCCGAACTC CGACCATATT

11041 TGCAACCGGA GACGGCATCA AAATGCTGGA AACTTAAACT GGATTTCAGG GATGTTCGAC

11101 TGATGGTCTG GAAAGGCGCA CAGCCTATT TCCAGTTGGA AGGGCTGACA TGGTCAGCGC

11161 TGCCCGATTA TGCTAGGTTC ATTCAGCTAC CAAGGATGC CGTTGTGTAC ATCGATCCGT

11221 GTATAGGGCC GGCAACAGCC AATCGCAAGG TTGTGCGAAC CACAGACTGG CGGGCCGACC

11281 TGGCAGTGAC ACCGTATGAT TACGGTGCTC AGGTCATTTT GACAACAGCC TGGTTCGAGG

11341 ACCTTGGGCC GCAGTGGAAG ATTTTGGGGT GCAGCCTTT CAGACGAACA TTTGGCTTTG

11401 AGAACACTGA AGATTGGGCA ATTCTCGCAC GCCGTATGAA TGACGGCAAA GATTACACTG

11461 ACTATAATTG GCATTGTGTA CGAGAACGCC CACACGCAAT TTACGGGCGC GCCCGTGACC

11521 ATACGTATCA TTTTGCCCTT GGCACTGAAC TGCAAGTAGA GCTGGGCAGA CCCCGGCTGC

11581 CTCCTGAGCA AGTGCCGTGA

SEQ ID NO: 29 Nucleotide encoding parental PRRSV 94881 ORF2
11611 ATGCAATGGG TTCACTGTGG AGTAAAATCA

11641 GTCAGTTGTT CGTGGATGCC TTCACTGAGT TCCTTGTTAG TGTGGTTGAC ATTGTCATCT

11701 TTCTCGCCAT ATTGTTTGGG TTCACTGTTG CAGGCTGGTT ATTGGTCTTC CTTCTCAGAG

11761 TGGTTTGCTC CGCGTTTCTC CGTTCGCGCT CTGCCATTCA CTCTCCCGAA CTATCGAAGG

11821 TCCTATGAGG GCTTGCTACC CAACTGCAGA CCGGATGTCC CACAATTCGC AGTTAAGCAC

11881 CCGTTGGGTA TACTTTGGCA TATGCGAGTC TCCCACCTAA TTGACGAAAT GGTCTCTCGC

11941 CGCATTTACC GGACCATGGA ACATTCGGGT CAAGCGGCCT GGAAGCAGGT TGTTAGTGAA

12001 GCCACTCTCA CAAAACTGTC AAGGCTTGAC GTAGTCACTC ATTTCCAACA CCTGGCCGCA

12061 GTGGAGGCTG ATTCTTGCCG CTTCCTTAGC TCACGACTCG CGATGCTGAA AAACCTTGCC

12121 GTTGGCAATG TGAGCCTGGA GTACAACACT ACTTTGGACC GCGTTGAGCT CATCTTTCCC

12181 ACACCAGGTA CGAGGCCCAA GTTGACCGAT TTTAGGCAAT GGCTTATCAG CGTGCACGCT

12241 TCCATCTTCT CCTCTGTGGC TTCGTCTGTT ACCTTGTTCA CAGTGCTTTG GCTTCGAATT

12301 CCAGCTCTAC GCTATGTTTT TGGTTTCCAT GGCCCACGG CAACACATCA TTCGAACTAA

SEQ ID NO: 30 Nucleotide encoding parental PRRSV 94881 ORF3
12219           AT GGCTTATCAG CGTGCACGCT

12241 TCCATCTTCT CCTCTGTGGC TTCGTCTGTT ACCTTGTTCA CAGTGCTTTG GCTTCGAATT

12301 CCAGCTCTAC GCTATGTTTT TGGTTTCCAT GGCCCACGG CAACACATCA TTCGAACTAA

12361 CTATCAATTA CACTATATGT AAGCCATGCC CTACCAGTCA AGCTGCCCAA CAAAGACTCG
```

```
12421 AGCCTGGCCG TAACGTGTGG TGCAAAATAG GGCACGACAG GTGTGAGGAA CGTGACCATG

12481 ATGAGTTGTC AATGTCCATT CCGTCCGGGT ACGACAACCT CAAACTTGAG GGTTATTATG

12541 CTTGGCTGGC TTTTTTGTCC TTTTCCTACG CGGCCCAATT CCATCCGGAG CTGTTCGGAA

12601 TAGGAAACGT GTCGCGCGTC TTTGTGGATA AGCGACACCA GTTCATTTGC GCCGAGCATG

12661 ATGGACAAAA TTCAACCATA TCTGCCAGAC ACAACATCTC CGCGTCGTAT GCGGTGTATT

12721 ACCATCATCA AATAGACGGG GGCAATTGGT TTCATTTGGA ATGGCTGCGA CCATTCTTTT

12781 CCTCCTGGCT GGTGCTCAAC ATCTCATGGT TTCTGAGGCG TTCGCCTGCA AGCCCTGCTT

12841 CTCGACGCAT CTATCAGATA TTAAGACCAA CACGACCGCG GCTGCCGGTT TCATGGTCCT

12901 TCAGAACATC AATTGTTTCC AATCTCACAG GGCCTCAACA GCGCAAGGTA CCACTCCCCT

12961 CAGGAGGTCG TCCCAATGTC GTGAAGCCGT CGGCATTCCC CAGTACATCA CGATAA

SEQ ID NO: 31 Nucleotide encoding parental PRRSV 94881 ORF4
12761 ATGGCTGCGA CCATTCTTTT

12781 CCTCCTGGCT GGTGCTCAAC ATCTCATGGT TTCTGAGGCG TTCGCCTGCA AGCCCTGCTT

12841 CTCGACGCAT CTATCAGATA TTAAGACCAA CACGACCGCG GCTGCCGGTT TCATGGTCCT

12901 TCAGAACATC AATTGTTTCC AATCTCACAG GGCCTCAACA GCGCAAGGTA CCACTCCCCT

12961 CAGGAGGTCG TCCCAATGTC GTGAAGCCGT CGGCATTCCC CAGTACATCA CGATAACGGC

13021 TAATGTGACC GATGAATCGT ATTTGTACAA CGCGGACTTG CTGATGCTTT CCGCGTGCCT

13081 TTTCTACGCC TCGGAAATGA GCGAGAAAGG CTTCAAAGTC ATCTTTGGGA ATATTTCTGG

13141 CGTTGTTTCC GCTTGTGTTA ATTTCACAGA TTATGTGGCC CATGTGACCC AACACACTCA

13201 GCAGCACCAT TTGGTAATTG ATCACATTCG GTTACTACAC TTCTTGACAC CGTCTACGAT

13261 GAGGTGGGCT ACAACCATTG CTTGTTTGTT TGCCATTCTT TTGGCGGTAT GA

SEQ ID NO: 32 Nucleotide encoding parental PRRSV 94881 ORF5
13309                                                AT GAAATGTTCT

13321 TGCAAGTTGG GGCATTTCTT GACTCCTCAC TCTTGCTTCT GGTGGCTTTT TTTGCTGTGT

13381 ACCGGCTTGT CTTGGTCCTT TGTCGATGGC AACGACAACA GCTCGACATC CCAATACATA

13441 TATAATTTGA CGATATGCGA GCTGAATGGG ACCGAATGGT TGTCCGGTCA TTTTGATTGG

13501 GCAGTCGAAA CCTTTGTGCT TTACCCAGTT GCCACTCATA TCATTTCACT GGGTTTTCTC

13561 ACAACAAGCC ATTTCCTTGA TGCGCTCGGT CTCGGCGCTG TGTCCGCCAC AGGATTCATT

13621 GGCGAGCGGT ATGTACTTAG CAGCATGTAC GGCGTTTGCG CCTTCGCGGC GCTCGTATGT

13681 TTTGTCATCC GTGCTGCTAA AAATTGCATG GCTTGCCGCT ATGCCCGCAC CCGGTTTACC

13741 AACTTCATCG TGGACGACCG GGGAAGAATC CATCGATGGA AGTCTTCAAT AGTGGTGGAG

13801 AAATTGGGCA AGCTGAAGT CGGTGGTGAC CTTGTCAACA TTAAGCATGT TGTCCTCGAA

13861 GGGGTTAAAG CTCAACCCTT GACGAGGACT TCGGCTGAGC AATGGGAAGC CTAG

SEQ ID NO: 33 Nucleotide encoding parental PRRSV 94881 ORF6
13902    ATGGGAAGC CTAGACGACT

13921 TTTGCAACGA TCCCACCGCC GCACAAAAAC TCGTGCTGGC CTTTAGCATC ACATATACAC

13981 CCATAATGAT ATACGCCCTT AAGGTGTCAC GCGGCCGACT CCTGGGGCTG TTGCACATCT

14041 TGATATTTCT GAATTGTTCC TTTACTTTTG GGTACATGAC ATATGTGCAT TTTCAATCCA

14101 CCAACCGTGT CGCACTCACT CTGGGGGCTG TAGTCGCCCT TTTGTGGGGT GTTTACAGCC

14161 TCACAGAGTC ATGGAAGTTC ATCACTTCCA GATGCAGATT GTGTTGCCTA GGCCGGCGAT

14221 ACATTCTGGC CCCTGCCCAT CACGTAGAAA GTGCTGCAGG CCTCCATTCA ATCCCAGCGT

14281 CTGGTAACCG AGCATACGCT GTGAGAAAGC CCGGACTAAC ATCAGTGAAC GGCACTCTAG
```

-continued

```
14341 TACCTGGGCT TCGGAGCCTC GTGCTGGGCG GCAAACGAGC TGTTAAACGA GGAGTGGTTA

14401 ACCTCGTCAA GTATGGCCGG TAA

SEQ ID NO: 34 Nucleotide encoding parental PRRSV 94881 ORF7
14413     ATGGCCGG TAAGAACCAG AGCCAGAAGA AAAGAAGAAA TGCAGCTCCG

14461 ATGGGGAAAG GCCAGCCAGT CAATCAACTG TGCCAGTTGC TGGGTACAAT GATAAAGTCC

14521 CAGCGCCAGC AATCTAGGGG AGGACAGGCC AAAAAGAAGA AGCCTGAGAA GCCACATTTT

14581 CCCCTAGCTG CTGAAGATGA CATTCGGCAC CATCTCACCC AGGCCGAACG TTCCCTCTGC

14641 TTGCAATCGA TCCAGACGGC TTTCAATCAA GGCGCAGGAA CTGCGTCGCT TTCATCCAGC

14701 GGGAAGGTCA GTTTCCAGGT TGAGTTCATG CTGCCGGTTG CTCATACAGT GCGCCTGATT

14761 CGCGTGACTT CTACATCCGC CAGTCAGGGT GCAAATTAA
```

---

The invention claimed is:

1. A Porcine Reproductive and Respiratory Syndrome (PRRS) virus having an RNA nucleotide sequence that is at least 95% homologous with the DNA sequence set forth in either SEQ ID NO: 1 or SEQ ID NO: 10, passaged at least 36 times in cell culture to modify the virus such that when the modified virus is administered to a swine or other mammal prone to PRRS, it fails to cause clinical signs of PRRS disease but is capable of inducing an immune response that immunizes the swine or other mammal against pathogenic forms of PRRS.

2. A PRRS virus according to claim 1, wherein said PRRS virus has an RNA nucleotide sequence that corresponds to the DNA sequence set forth in either SEQ ID NO:1 or SEQ ID NO:10.

3. A vaccine for the production of pigs against a PRRS virus infection, comprising a PRRS virus according to claim 1 and a pharmaceutically acceptable carrier, wherein said PRRS virus has an RNA nucleotide sequence that corresponds to the DNA sequence set forth in SEQ ID NO:1 or is an attenuated PRRS virus that that has an RNA nucleotide sequence that is at least 95% homologous with the DNA sequence set forth in SEQ ID NO:1.

4. The vaccine according to claim 3, which further comprises one or more non-PRRS virus attenuated or inactivated pathogens or antigenic material thereof.

5. The vaccine according to claim 4, wherein said non-PRRS virus pathogens are selected from Pseudorabies virus, Porcine Influenza virus, Porcine Parvovirus, Transmissible gastroenteritis virus, *Escherichia coli, Erysipelo rhusiopathiae, Bordetella bronchiseptica, Salmonella cholerasuis, Haemophilus parasuis, Pasterella multocida, Streptococcus suis, Mycoplasma hypopneumoniae* and *Actinobacillus pleuopneumoniae.*

* * * * *